United States Patent
Zucherman et al.

(10) Patent No.: US 8,349,013 B2
(45) Date of Patent: Jan. 8, 2013

(54) SPINE DISTRACTION IMPLANT

(75) Inventors: James F. Zucherman, San Francisco, CA (US); Ken Y. Hsu, San Francisco, CA (US); Charles J. Winslow, Walnut Creek, CA (US); Henry A. Klyce, Piedmont, CA (US); Scott A. Yerby, Montara, CA (US); John J. Flynn, Walnut Creek, CA (US); Steven T. Mitchell, Pleasant Hill, CA (US); John A. Markwart, Castro Valley, CA (US)

(73) Assignee: Kyphon Sarl, Neuchatel (CH)

( * ) Notice: Subject to any disclaimer, the term of this patent is extended or adjusted under 35 U.S.C. 154(b) by 341 days.

(21) Appl. No.: 12/821,077

(22) Filed: Jun. 22, 2010

(65) Prior Publication Data

US 2010/0262243 A1 Oct. 14, 2010

Related U.S. Application Data

(60) Division of application No. 11/788,763, filed on Apr. 19, 2007, now abandoned, which is a continuation-in-part of application No. 11/092,862, filed on Mar. 29, 2005, now Pat. No. 7,621,939, which is a division of application No. 09/842,819, filed on Apr. 26, 2001, now Pat. No. 7,201,751, which is a continuation-in-part of application No. 09/579,039, filed on May 26, 2000, now Pat. No. 6,451,019, which is a continuation-in-part of application No. 09/473,173, filed on Dec. 28, 1999, now Pat. No. 6,235,030, which is a continuation of application No. 09/179,570, filed on Oct. 27, 1998, now Pat. No. 6,048,342, which is a continuation-in-part of application No. 08/958,281, filed on Oct. 27, 1997, now Pat. No. 5,860,977, which is a continuation-in-part of application No. 08/778,093, filed on Jan. 2, 1997, now Pat. No. 5,836,948, said application No. 11/788,763 is a continuation-in-part of application No. 10/684,847, filed on Oct. 14, 2003, now Pat. No. 7,306,628, said application No. 11/788,763 is a continuation-in-part of application No. 11/003,555, filed on Dec. 3, 2004, now abandoned, said application No. 11/788,763 is a continuation-in-part of application No. 11/389,002, filed on Mar. 24, 2006.

(60) Provisional application No. 60/421,921, filed on Oct. 29, 2002, provisional application No. 60/565,910, filed on Apr. 28, 2004, provisional application No. 60/672,402, filed on Apr. 18, 2005.

(51) Int. Cl.
*A61F 2/44* (2006.01)

(52) U.S. Cl. .................. 623/17.12; 623/17.16; 606/247

(58) Field of Classification Search ............... 606/86 A, 606/246, 247, 248, 249, 279, 914; 623/17.11, 623/17.16; 128/898
See application file for complete search history.

(56) References Cited

U.S. PATENT DOCUMENTS 624,969 A 5/1899 Peterson
(Continued)

FOREIGN PATENT DOCUMENTS

DE 2821678 A1 11/1979
(Continued)

OTHER PUBLICATIONS

Benzel et al., "Posterior Cervical Interspinous Compression Wiring and Fusion for Mid to Low Cervical Spinal Injuries," J. Neurosurg., Jun. 1989, pp. 893-899, vol. 70.
(Continued)

*Primary Examiner* — Pedro Philogene
(74) *Attorney, Agent, or Firm* — Coats and Bennett, P.L.L.C.

(57) ABSTRACT

A method for stabilizing at least one spinal motion segment includes an expandable spacer in a collapsed state into the interspinous space between superior and inferior vertebrae such that the spacer extends through the sagittal plane defined by the spinous processes of the superior and inferior vertebrae. The spacer has a flexible membrane defining an interior cavity. The method includes expanding the spacer to an expanded state by forcing a fill material in a fluid state into the cavity with the spacer disposed in the interspinous space, and thereafter solidifying the fill material to a solid state in the cavity. The method may be performed through a percutaneous penetration in the patient's skin and may cause the first and second vertebrae to be distracted.

4 Claims, 118 Drawing Sheets

U.S. PATENT DOCUMENTS

| | | | |
|---|---|---|---|
| 1,153,797 A | 9/1915 | Kegreisz |
| 1,516,347 A | 11/1924 | Pataky |
| 1,870,942 A | 8/1932 | Beatty |
| 2,077,804 A | 4/1937 | Morrison |
| 2,299,308 A | 10/1942 | Creighton |
| 2,485,531 A | 10/1949 | Dzus et al. |
| 2,607,370 A | 8/1952 | Anderson |
| 2,677,369 A | 5/1954 | Knowles |
| 2,685,877 A | 8/1954 | Dobelle |
| 3,065,659 A | 11/1962 | Eriksson et al. |
| 3,108,595 A | 10/1963 | Overment |
| 3,397,699 A | 8/1968 | Kohl |
| 3,426,364 A | 2/1969 | Lumb |
| 3,648,691 A | 3/1972 | Lumb et al. |
| 3,779,239 A | 12/1973 | Fischer et al. |
| 3,867,728 A | 2/1975 | Stubstad et al. |
| 4,011,602 A | 3/1977 | Rybicki et al. |
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |
| 4,327,736 A | 5/1982 | Inoue |
| 4,401,112 A | 8/1983 | Rezaian |
| 4,499,636 A | 2/1985 | Tanaka |
| 4,519,100 A | 5/1985 | Wills et al. |
| 4,553,273 A | 11/1985 | Wu |
| 4,554,914 A | 11/1985 | Kapp et al. |
| 4,573,454 A | 3/1986 | Hoffman |
| 4,592,341 A | 6/1986 | Omagari et al. |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,721,103 A | 1/1988 | Freedland |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 4,969,888 A | 11/1990 | Scholten et al. |
| 5,000,166 A | 3/1991 | Karpf |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,171,280 A | 12/1992 | Baumgartner |
| 5,201,734 A | 4/1993 | Cozad et al. |
| 5,267,999 A | 12/1993 | Olerud |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,316,422 A | 5/1994 | Coffman |
| 5,356,423 A | 10/1994 | Tihon et al. |
| 5,360,430 A | 11/1994 | Lin |
| 5,366,455 A | 11/1994 | Dove |
| 5,370,697 A | 12/1994 | Baumgartner |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,456,689 A | 10/1995 | Kresch et al. |
| 5,458,641 A | 10/1995 | Ramirez Jimenez |
| 5,480,442 A | 1/1996 | Bertagnoli |
| 5,496,318 A | 3/1996 | Howland et al. |
| 5,518,498 A | 5/1996 | Lindenberg et al. |
| 5,549,679 A | 8/1996 | Kuslich |
| 5,554,191 A | 9/1996 | Lahille et al. |
| 5,562,662 A | 10/1996 | Brumfield et al. |
| 5,562,735 A | 10/1996 | Margulies |
| 5,562,736 A | 10/1996 | Ray et al. |
| 5,571,189 A * | 11/1996 | Kuslich ............... 623/17.12 |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,597 A | 7/1997 | Krapiva |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,685,826 A | 11/1997 | Bonutti |
| 5,690,649 A | 11/1997 | Li |
| 5,693,100 A | 12/1997 | Pisharodi |
| 5,702,395 A | 12/1997 | Hopf |
| 5,702,452 A | 12/1997 | Argenson et al. |
| 5,702,454 A | 12/1997 | Baumgartner |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,755,797 A | 5/1998 | Baumgartner |
| 5,800,547 A | 9/1998 | Schafer et al. |
| 5,800,549 A | 9/1998 | Bao et al. |
| 5,810,815 A | 9/1998 | Morales |
| 5,827,289 A * | 10/1998 | Reiley et al. ............... 606/86 R |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,941,881 A | 8/1999 | Barnes |
| 5,964,730 A | 10/1999 | Williams et al. |
| 5,976,186 A | 11/1999 | Bao et al. |
| 5,980,523 A | 11/1999 | Jackson |
| 6,022,376 A | 2/2000 | Assell et al. |
| 6,048,342 A | 4/2000 | Zucherman et al. |
| 6,066,154 A * | 5/2000 | Reiley et al. ............... 606/192 |
| 6,068,630 A | 5/2000 | Zucherman et al. |
| 6,074,390 A | 6/2000 | Zucherman et al. |
| 6,102,922 A | 8/2000 | Jakobsson et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,149,652 A * | 11/2000 | Zucherman et al. ......... 606/86 A |
| 6,190,413 B1 | 2/2001 | Sutcliffe |
| 6,190,414 B1 | 2/2001 | Young |
| 6,214,037 B1 | 4/2001 | Mitchell et al. |
| 6,214,050 B1 | 4/2001 | Huene |
| 6,235,043 B1 * | 5/2001 | Reiley et al. ............... 606/192 |
| 6,245,107 B1 | 6/2001 | Ferree |
| 6,280,444 B1 * | 8/2001 | Zucherman et al. ......... 606/86 A |
| 6,293,949 B1 | 9/2001 | Justis et al. |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,402,750 B1 | 6/2002 | Atkinson et al. |
| 6,402,751 B1 | 6/2002 | Hoeck et al. |

| | | | | | |
|---|---|---|---|---|---|
| 6,419,703 B1 | 7/2002 | Fallin et al. | 2004/0010316 A1 | 1/2004 | William et al. |
| 6,419,704 B1 | 7/2002 | Ferree | 2004/0083002 A1 | 4/2004 | Belef et al. |
| 6,432,130 B1 | 8/2002 | Hanson | 2004/0087947 A1 | 5/2004 | Lim et al. |
| 6,440,169 B1 | 8/2002 | Elberg et al. | 2004/0097931 A1 | 5/2004 | Mitchell |
| 6,447,513 B1 | 9/2002 | Griggs | 2004/0106995 A1 | 6/2004 | LeCoudeic et al. |
| 6,451,019 B1 | 9/2002 | Zucherman et al. | 2004/0117017 A1 | 6/2004 | Pasquet et al. |
| 6,500,178 B2 | 12/2002 | Zucherman et al. | 2004/0133204 A1 | 7/2004 | Davies |
| 6,511,508 B1 | 1/2003 | Shahinpoor et al. | 2004/0133280 A1 | 7/2004 | Trieu |
| 6,514,256 B2 | 2/2003 | Zucherman et al. | 2004/0158248 A1 | 8/2004 | Ginn |
| 6,520,991 B2 | 2/2003 | Huene | 2004/0167625 A1 | 8/2004 | Beyar et al. |
| 6,554,833 B2 | 4/2003 | Levy | 2004/0199255 A1 | 10/2004 | Mathieu et al. |
| 6,582,433 B2 | 6/2003 | Yun | 2004/0260397 A1 | 12/2004 | Lambrecht et al. |
| 6,582,467 B1 | 6/2003 | Teitelbaum et al. | 2005/0010293 A1 | 1/2005 | Zucherman et al. |
| 6,592,585 B2 | 7/2003 | Lee et al. | 2005/0015140 A1 | 1/2005 | deBeer |
| 6,626,944 B1 | 9/2003 | Taylor | 2005/0033434 A1 | 2/2005 | Berry |
| 6,645,207 B2 | 11/2003 | Dixon et al. | 2005/0049708 A1 | 3/2005 | Atkinson et al. |
| 6,669,729 B2 | 12/2003 | Chin | 2005/0056292 A1 | 3/2005 | Cooper |
| 6,685,742 B1 | 2/2004 | Jackson | 2005/0085814 A1 | 4/2005 | Sherman et al. |
| 6,695,842 B2 | 2/2004 | Zucherman et al. | 2005/0143827 A1 | 6/2005 | Globerman et al. |
| 6,699,246 B2 | 3/2004 | Zucherman et al. | 2005/0165398 A1 | 7/2005 | Reiley |
| 6,709,435 B2 | 3/2004 | Lin | 2005/0203512 A1 | 9/2005 | Hawkins et al. |
| 6,723,126 B1 | 4/2004 | Berry | 2005/0203519 A1 | 9/2005 | Harms et al. |
| 6,730,126 B2 | 5/2004 | Boehm, Jr. et al. | 2005/0203624 A1 | 9/2005 | Serhan et al. |
| 6,733,531 B1 | 5/2004 | Trieu | 2005/0228391 A1 | 10/2005 | Levy et al. |
| 6,733,533 B1 | 5/2004 | Lozier | 2005/0245937 A1 | 11/2005 | Winslow |
| 6,733,534 B2 | 5/2004 | Sherman | 2005/0261768 A1 | 11/2005 | Trieu |
| 6,736,818 B2 | 5/2004 | Perren et al. | 2005/0267579 A1 | 12/2005 | Reiley et al. |
| 6,743,257 B2 | 6/2004 | Castro | 2005/0273166 A1 | 12/2005 | Sweeney |
| 6,758,863 B2 | 7/2004 | Estes et al. | 2005/0288672 A1 | 12/2005 | Ferree |
| 6,761,720 B1 | 7/2004 | Senegas | 2006/0004447 A1 | 1/2006 | Mastrorio et al. |
| 6,770,096 B2 | 8/2004 | Bolger et al. | 2006/0004455 A1 | 1/2006 | Leonard et al. |
| 6,783,530 B1 | 8/2004 | Levy | 2006/0015181 A1 | 1/2006 | Elberg |
| 6,796,983 B1 * | 9/2004 | Zucherman et al. ........ 606/86 A | 2006/0047282 A1 | 3/2006 | Gordon |
| 6,835,205 B2 | 12/2004 | Atkinson et al. | 2006/0064165 A1 | 3/2006 | Zucherman et al. |
| 6,902,580 B2 | 6/2005 | Fallin et al. | 2006/0084983 A1 | 4/2006 | Kim |
| 6,905,512 B2 | 6/2005 | Paes et al. | 2006/0084985 A1 | 4/2006 | Kim |
| 6,946,000 B2 | 9/2005 | Senegas et al. | 2006/0084987 A1 | 4/2006 | Kim |
| 6,958,077 B2 | 10/2005 | Suddaby | 2006/0084988 A1 | 4/2006 | Kim |
| 6,969,404 B2 | 11/2005 | Ferree | 2006/0085069 A1 | 4/2006 | Kim |
| 6,981,975 B2 | 1/2006 | Michelson | 2006/0085070 A1 | 4/2006 | Kim |
| 7,011,685 B2 | 3/2006 | Arnin et al. | 2006/0085074 A1 | 4/2006 | Raiszadeh |
| 7,041,136 B2 | 5/2006 | Goble et al. | 2006/0089654 A1 | 4/2006 | Lins et al. |
| 7,048,736 B2 | 5/2006 | Robinson et al. | 2006/0089719 A1 | 4/2006 | Trieu |
| 7,070,598 B2 | 7/2006 | Lim et al. | 2006/0095136 A1 | 5/2006 | McLuen |
| 7,081,120 B2 | 7/2006 | Li et al. | 2006/0106381 A1 | 5/2006 | Ferree et al. |
| 7,087,055 B2 | 8/2006 | Lim et al. | 2006/0106397 A1 | 5/2006 | Lins |
| 7,087,083 B2 | 8/2006 | Pasquet et al. | 2006/0111728 A1 | 5/2006 | Abdou |
| 7,097,648 B1 | 8/2006 | Globerman et al. | 2006/0116690 A1 | 6/2006 | Pagano |
| 7,097,654 B1 | 8/2006 | Freedland | 2006/0122620 A1 | 6/2006 | Kim |
| 7,101,375 B2 | 9/2006 | Zucherman et al. | 2006/0129239 A1 | 6/2006 | Kwak |
| 7,163,558 B2 | 1/2007 | Senegas et al. | 2006/0136060 A1 | 6/2006 | Taylor |
| 7,201,751 B2 | 4/2007 | Zucherman et al. | 2006/0142858 A1 | 6/2006 | Colleran et al. |
| 7,217,293 B2 | 5/2007 | Branch, Jr. | 2006/0149242 A1 | 7/2006 | Kraus et al. |
| 7,238,204 B2 | 7/2007 | Le Couedic et al. | 2006/0182515 A1 | 8/2006 | Panasik et al. |
| 7,306,628 B2 | 12/2007 | Zucherman et al. | 2006/0184247 A1 | 8/2006 | Edidin et al. |
| 7,335,203 B2 | 2/2008 | Winslow et al. | 2006/0184248 A1 | 8/2006 | Edidin et al. |
| 7,377,942 B2 | 5/2008 | Berry | 2006/0195102 A1 | 8/2006 | Malandain |
| 7,431,735 B2 | 10/2008 | Liu et al. | 2006/0217726 A1 | 9/2006 | Maxy et al. |
| 7,442,208 B2 | 10/2008 | Mathieu et al. | 2006/0224159 A1 | 10/2006 | Anderson |
| 7,442,210 B2 | 10/2008 | Segal et al. | 2006/0224241 A1 | 10/2006 | Butler et al. |
| 7,445,637 B2 | 11/2008 | Taylor | 2006/0235387 A1 | 10/2006 | Peterman |
| 7,458,981 B2 | 12/2008 | Fielding et al. | 2006/0235532 A1 | 10/2006 | Meunier et al. |
| 7,582,106 B2 | 9/2009 | Teitelbaum et al. | 2006/0241601 A1 | 10/2006 | Trautwein et al. |
| 7,604,652 B2 | 10/2009 | Arnin et al. | 2006/0241613 A1 | 10/2006 | Bruneau et al. |
| 7,611,316 B2 | 11/2009 | Panasik et al. | 2006/0241643 A1 | 10/2006 | Lim et al. |
| 7,621,950 B1 | 11/2009 | Globerman et al. | 2006/0241757 A1 | 10/2006 | Anderson |
| 7,658,752 B2 | 2/2010 | Labrom et al. | 2006/0247623 A1 | 11/2006 | Anderson et al. |
| 7,749,252 B2 | 7/2010 | Zucherman et al. | 2006/0247640 A1 | 11/2006 | Blackwell et al. |
| 7,771,456 B2 | 8/2010 | Hartman et al. | 2006/0264938 A1 | 11/2006 | Zucherman et al. |
| 7,862,615 B2 | 1/2011 | Carli et al. | 2006/0271044 A1 | 11/2006 | Petrini et al. |
| 7,901,430 B2 | 3/2011 | Matsuura et al. | 2006/0271049 A1 | 11/2006 | Zucherman et al. |
| 2001/0016743 A1 | 8/2001 | Zucherman et al. | 2006/0271061 A1 | 11/2006 | Beyer et al. |
| 2002/0082600 A1 | 6/2002 | Shaolian et al. | 2006/0282075 A1 | 12/2006 | Labrom et al. |
| 2002/0143331 A1 | 10/2002 | Zucherman et al. | 2006/0282079 A1 | 12/2006 | Labrom et al. |
| 2003/0040746 A1 | 2/2003 | Mitchell et al. | 2006/0293662 A1 | 12/2006 | Boyer, II et al. |
| 2003/0045940 A1 | 3/2003 | Eberlein et al. | 2006/0293663 A1 | 12/2006 | Walkenhorst et al. |
| 2003/0065330 A1 | 4/2003 | Zucherman et al. | 2007/0005064 A1 | 1/2007 | Anderson et al. |
| 2003/0153915 A1 | 8/2003 | Nekozuka et al. | 2007/0010813 A1 | 1/2007 | Zucherman et al. |
| 2004/0010312 A1 | 1/2004 | Enayati | 2007/0032790 A1 | 2/2007 | Aschmann et al. |

| | | | |
|---|---|---|---|
| 2007/0043362 A1 | 2/2007 | Malandain et al. | |
| 2007/0043363 A1 | 2/2007 | Malandain et al. | |
| 2007/0073289 A1 | 3/2007 | Kwak et al. | |
| 2007/0100340 A1 | 5/2007 | Lange et al. | |
| 2007/0123861 A1 | 5/2007 | Dewey et al. | |
| 2007/0142915 A1 | 6/2007 | Altarac et al. | |
| 2007/0151116 A1 | 7/2007 | Malandain | |
| 2007/0162000 A1 | 7/2007 | Perkins | |
| 2007/0162136 A1 | 7/2007 | O'Neil et al. | |
| 2007/0167945 A1 | 7/2007 | Lange et al. | |
| 2007/0173822 A1 | 7/2007 | Bruneau et al. | |
| 2007/0173823 A1 | 7/2007 | Dewey et al. | |
| 2007/0191833 A1 | 8/2007 | Bruneau et al. | |
| 2007/0191834 A1 | 8/2007 | Bruneau et al. | |
| 2007/0191837 A1 | 8/2007 | Trieu | |
| 2007/0191838 A1 | 8/2007 | Bruneau et al. | |
| 2007/0198091 A1 | 8/2007 | Boyer et al. | |
| 2007/0225807 A1 | 9/2007 | Phan et al. | |
| 2007/0233068 A1 | 10/2007 | Bruneau et al. | |
| 2007/0233074 A1 | 10/2007 | Anderson et al. | |
| 2007/0233076 A1 | 10/2007 | Trieu | |
| 2007/0233081 A1 | 10/2007 | Pasquet et al. | |
| 2007/0233089 A1 | 10/2007 | DiPoto et al. | |
| 2007/0250060 A1 | 10/2007 | Anderson et al. | |
| 2007/0270823 A1 | 11/2007 | Trieu et al. | |
| 2007/0270824 A1 | 11/2007 | Lim et al. | |
| 2007/0270825 A1 | 11/2007 | Carls et al. | |
| 2007/0270826 A1 | 11/2007 | Trieu et al. | |
| 2007/0270827 A1 | 11/2007 | Lim et al. | |
| 2007/0270828 A1 | 11/2007 | Bruneau et al. | |
| 2007/0270829 A1 | 11/2007 | Carls et al. | |
| 2007/0270834 A1 | 11/2007 | Bruneau et al. | |
| 2007/0270874 A1 | 11/2007 | Anderson | |
| 2007/0272259 A1 | 11/2007 | Allard et al. | |
| 2007/0276368 A1 | 11/2007 | Trieu et al. | |
| 2007/0276369 A1 | 11/2007 | Allard et al. | |
| 2007/0276493 A1 | 11/2007 | Malandain et al. | |
| 2007/0276496 A1 | 11/2007 | Lange et al. | |
| 2007/0276497 A1 | 11/2007 | Anderson | |
| 2007/0282443 A1 | 12/2007 | Globerman et al. | |
| 2008/0021457 A1 | 1/2008 | Anderson et al. | |
| 2008/0021460 A1 | 1/2008 | Bruneau et al. | |
| 2008/0058934 A1 | 3/2008 | Malandain et al. | |
| 2008/0097446 A1 | 4/2008 | Reiley et al. | |
| 2008/0114357 A1 | 5/2008 | Allard et al. | |
| 2008/0114358 A1 | 5/2008 | Anderson et al. | |
| 2008/0114456 A1 | 5/2008 | Dewey et al. | |
| 2008/0147190 A1 | 6/2008 | Dewey et al. | |
| 2008/0161818 A1 | 7/2008 | Kloss et al. | |
| 2008/0167685 A1 | 7/2008 | Allard et al. | |
| 2008/0183209 A1 | 7/2008 | Robinson et al. | |
| 2008/0183211 A1 | 7/2008 | Lamborne et al. | |
| 2008/0183218 A1 | 7/2008 | Mueller et al. | |
| 2008/0195152 A1 | 8/2008 | Altarac et al. | |
| 2008/0215094 A1 | 9/2008 | Taylor | |
| 2008/0221685 A9 | 9/2008 | Altarac et al. | |
| 2008/0234824 A1 | 9/2008 | Youssef et al. | |
| 2008/0262617 A1 | 10/2008 | Froehlich et al. | |
| 2008/0281360 A1 | 11/2008 | Vittur et al. | |
| 2008/0281361 A1 | 11/2008 | Vittur et al. | |
| 2009/0062915 A1 | 3/2009 | Kohm et al. | |
| 2009/0099610 A1 | 4/2009 | Johnson et al. | |
| 2009/0105766 A1 | 4/2009 | Thompson et al. | |
| 2009/0105773 A1 | 4/2009 | Lange et al. | |
| 2009/0234389 A1 | 9/2009 | Chuang et al. | |
| 2009/0240283 A1 | 9/2009 | Carls et al. | |
| 2009/0270918 A1 | 10/2009 | Attia et al. | |
| 2010/0121379 A1 | 5/2010 | Edmond | |
| 2010/0204732 A1 | 8/2010 | Aschmann et al. | |
| 2010/0211101 A1 | 8/2010 | Blackwell et al. | |

FOREIGN PATENT DOCUMENTS

| | | |
|---|---|---|
| DE | 3922044 A1 | 2/1991 |
| DE | 4012622 C1 | 7/1991 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 B1 | 10/2001 |
| EP | 1148851 B1 | 10/2001 |
| EP | 1302169 A1 | 4/2003 |
| EP | 1330987 A1 | 7/2003 |
| EP | 1552797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| JP | 2003079649 | 3/2003 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | WO 99/26562 | 6/1999 |
| WO | WO 99/59669 | 11/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | 2004/084743 A1 | 10/2004 |
| WO | WO 2004/084768 A2 | 10/2004 |
| WO | 2004/110300 A2 | 12/2004 |
| WO | WO 2005/002474 A1 | 1/2005 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | WO 2007052975 A1 | 5/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," Spine, 2005, pp. S73-S78, vol. 30, No. 16S.

Cousin Biotech, Dispositif Intervertébral Amortissant, Jun. 1998, pp. 1-4.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Duff, "Methyl Methacrylate in Spinal Stabilization," Techniques in Spinal Fusion and Stabilization, Hitchon et al., eds., 1995, pp. 147-151, Ch. 14, Thieme, New York.

Ebara et al., "Inoperative Measurement of Lumbar Spinal Instability," Spine, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," Spine, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Kramer et al., "Intervetertebral Disk Diseases: Causes, Diagnosis, Treatment and Prophylaxis," pp. 244-249, Medical, 1990.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," Spine, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," Spine, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," Spine, 2005, pp. 744-749, vol. 30, No. 7.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," Spine, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-5169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Taylor et al., "Analyse d'une expérience clinique d'un implant postérieur amortissant," Rachis Revue de Pathologie Vertébrate, Oct./Nov. 1999, vol. 11, No. 4-5, Gieda Inter Rachis.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiese!, ed., Jun. 1994, pp. 116-123, vol. 6, No. 2.

Zdeblick et al., "Two-Point Fixation of the Lumbar Spine Differential Stability in Rotation," Spine, 1991, pp. S298-S301, vol. 16, No. 6, Supplement.

Zucherman et al., "Clinical Efficacy of Spinal Instrumentation in Lumbar Degenerative Disc Disease," Spine, Jul. 1992, pp. 834-837, vol. 17, No. 7.

Anasetti et al., "Spine Stability After Implantation of an Interspinous Device: An In Vitro and Finite Element Biomechanical Study," J. Neurosurg. Spine, Nov. 2010, vol. 13, pp. 568-575.

Bellini et al., "Biomechanics of the Lumbar Spine Afer Dynamic Stabilization," J. Spinal Discord Tech., 2006, vol. 00, No. 00, pp. 1-7.

Buric et al., "DIAM Device for Low Back Pain in Degenerative Disc Disease 24 Months Follow-up," Advances in Minimally Invasive Surgery and Therapy for Spine and Nerves, Alexandre et al., eds., 2011, pp. 177-182, Spinger-Verlat/Wien.

Phillips et al., "Biomechanics of Posterior Dynamic Stabiling Device (DIAM) After Facetectomy and Disectomy," The Spine Journal, 2006, vol. 6, pp. 714-722.

Taylor et al., "Device for Intervertebral Assisted Motion: Technique and Intial Results," 22 Neurosurg. Focus, Jan. 2007, vol. 22, No. 1, pp. 1-6.

Wilke et al., "Biomedical Effect of Different Lumbar Interspinous Implants on Flexibilty and Intradiscal Pressure," Eur Spine J., Vo. 17, published online Jun. 27, 2008, pp. 1049-1056.

Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.

* cited by examiner

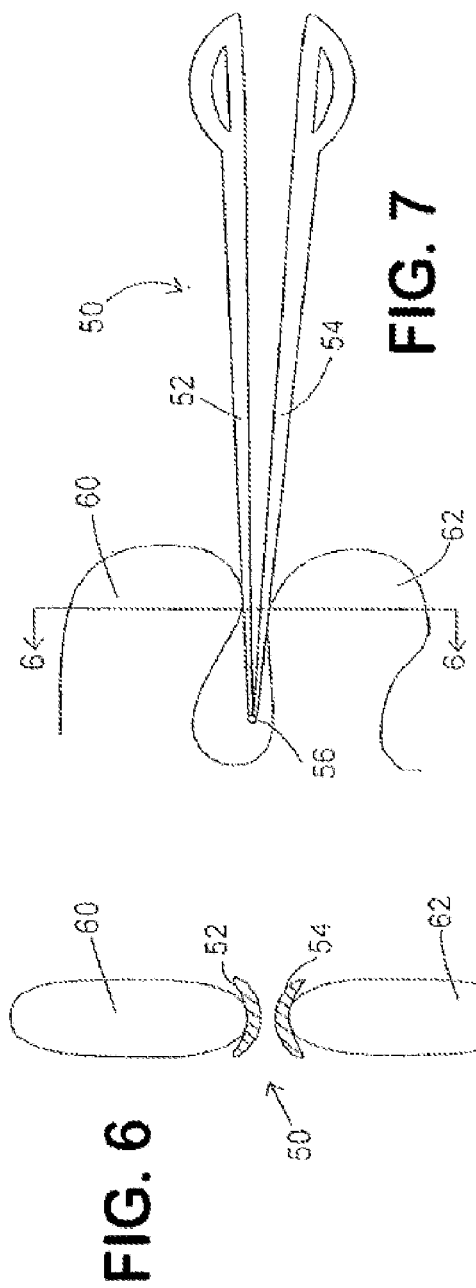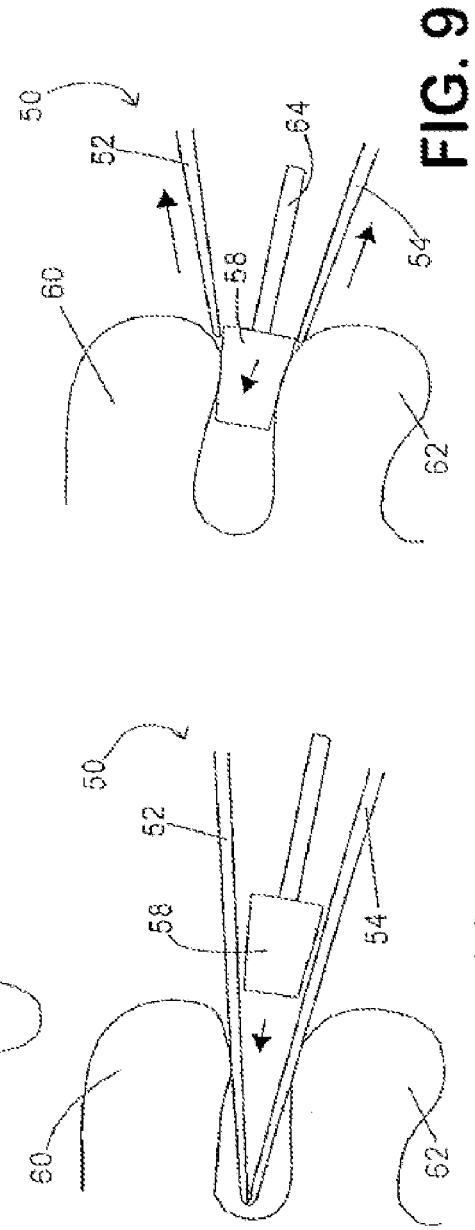

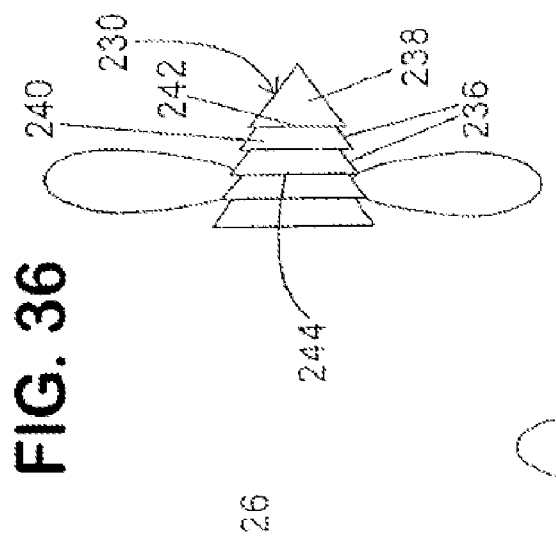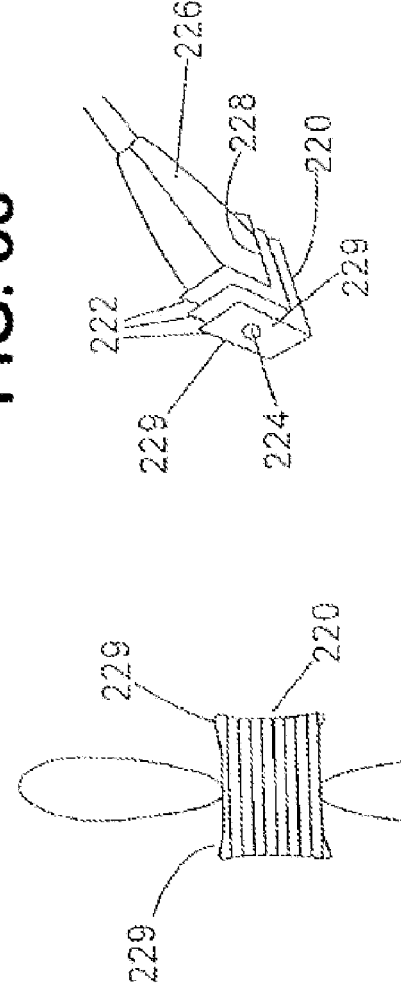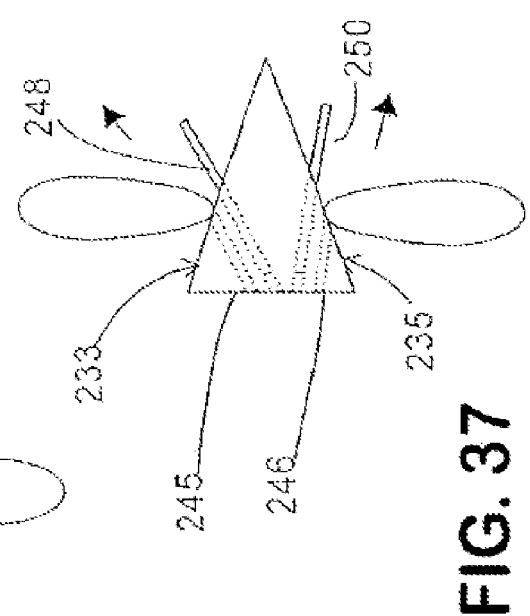

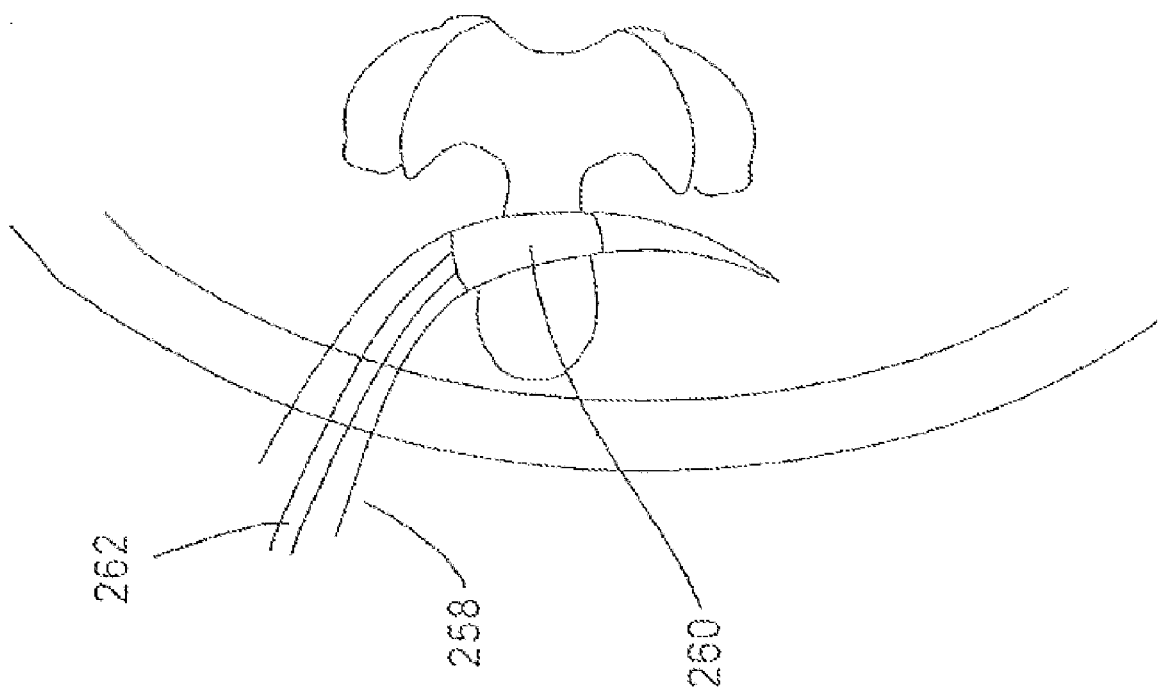

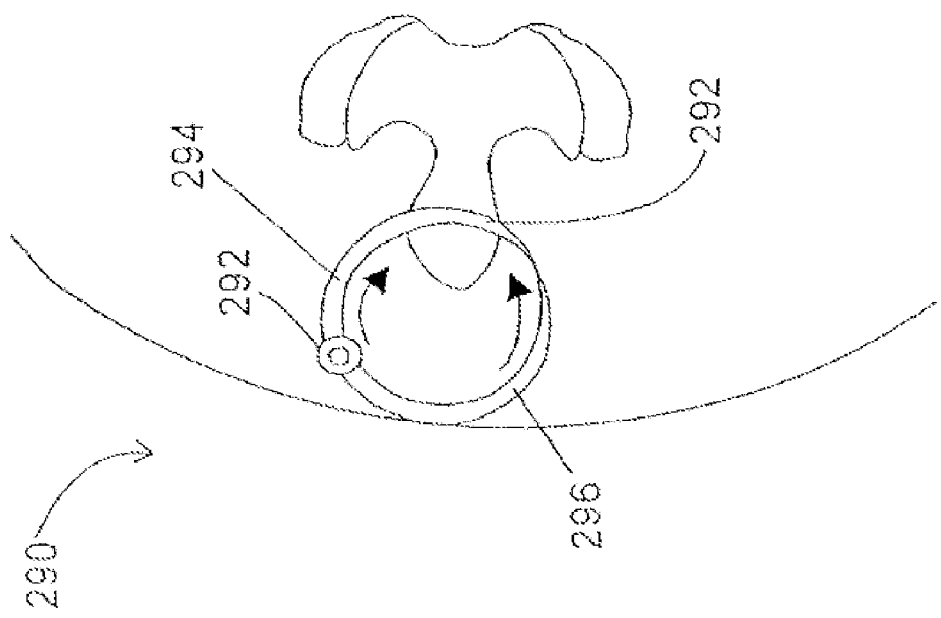

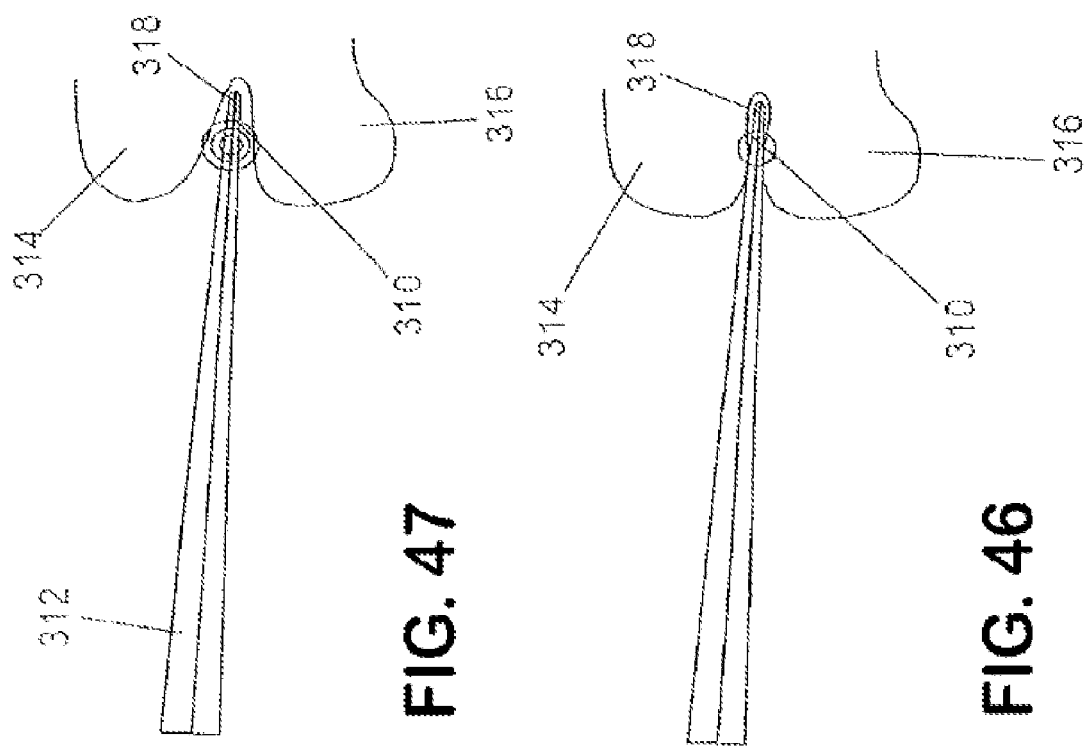
FIG. 47
FIG. 46
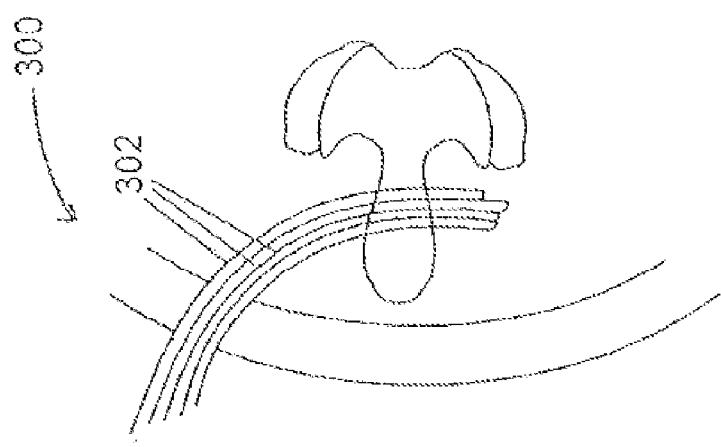
FIG. 45

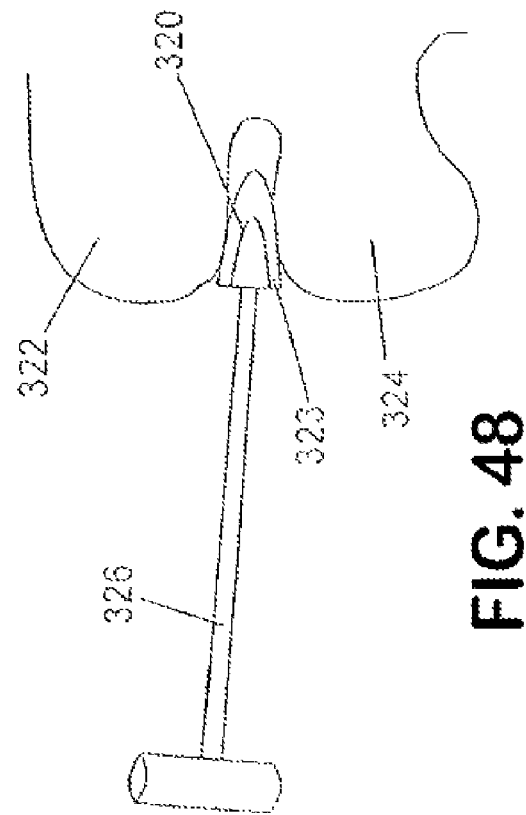
FIG. 48
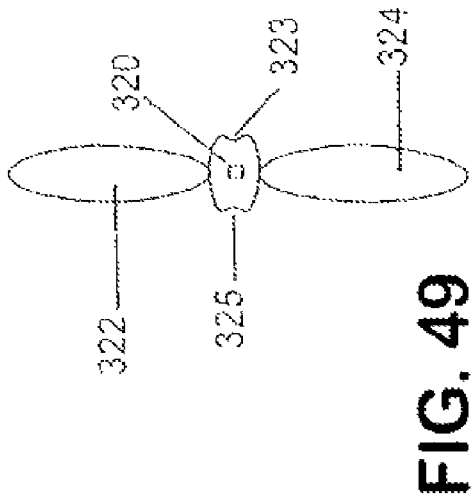
FIG. 49
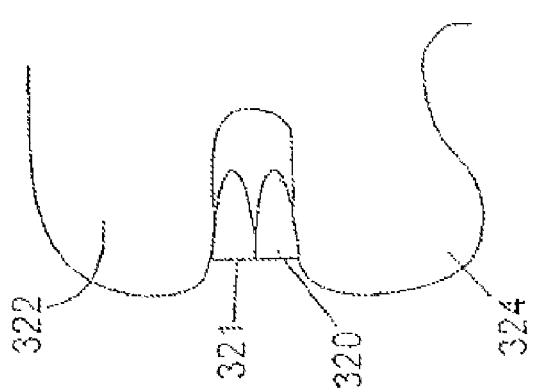
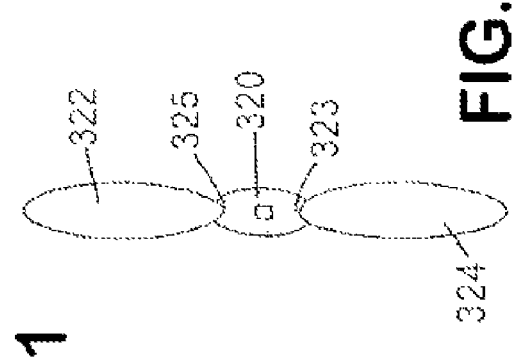
FIG. 50
FIG. 51

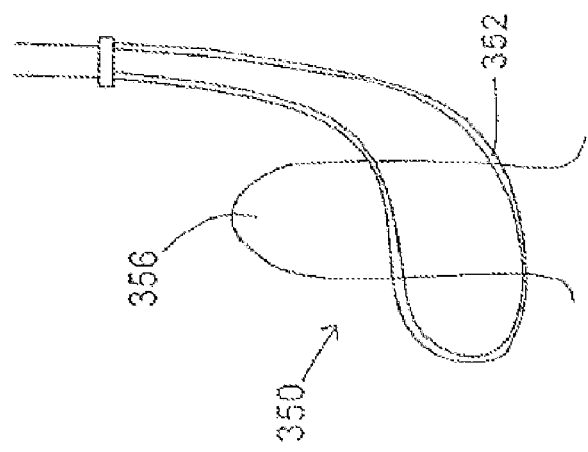
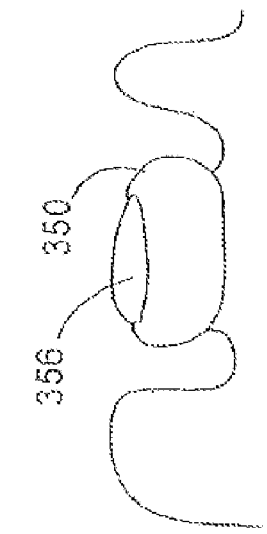
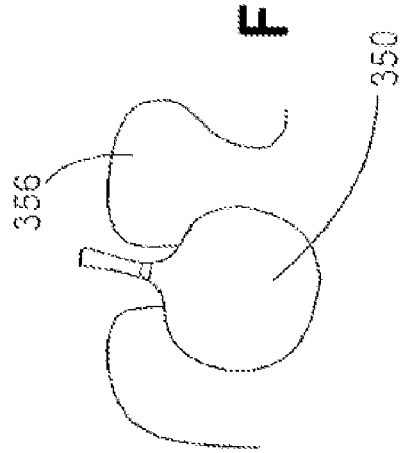

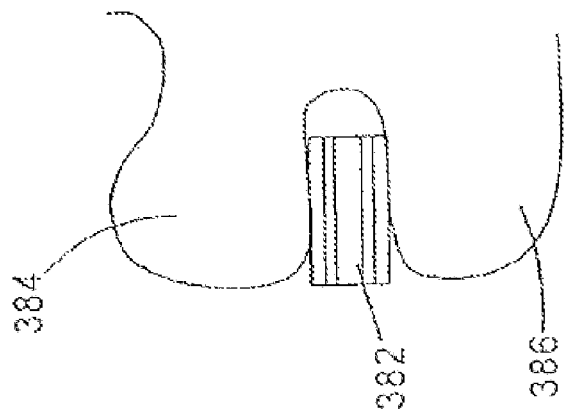
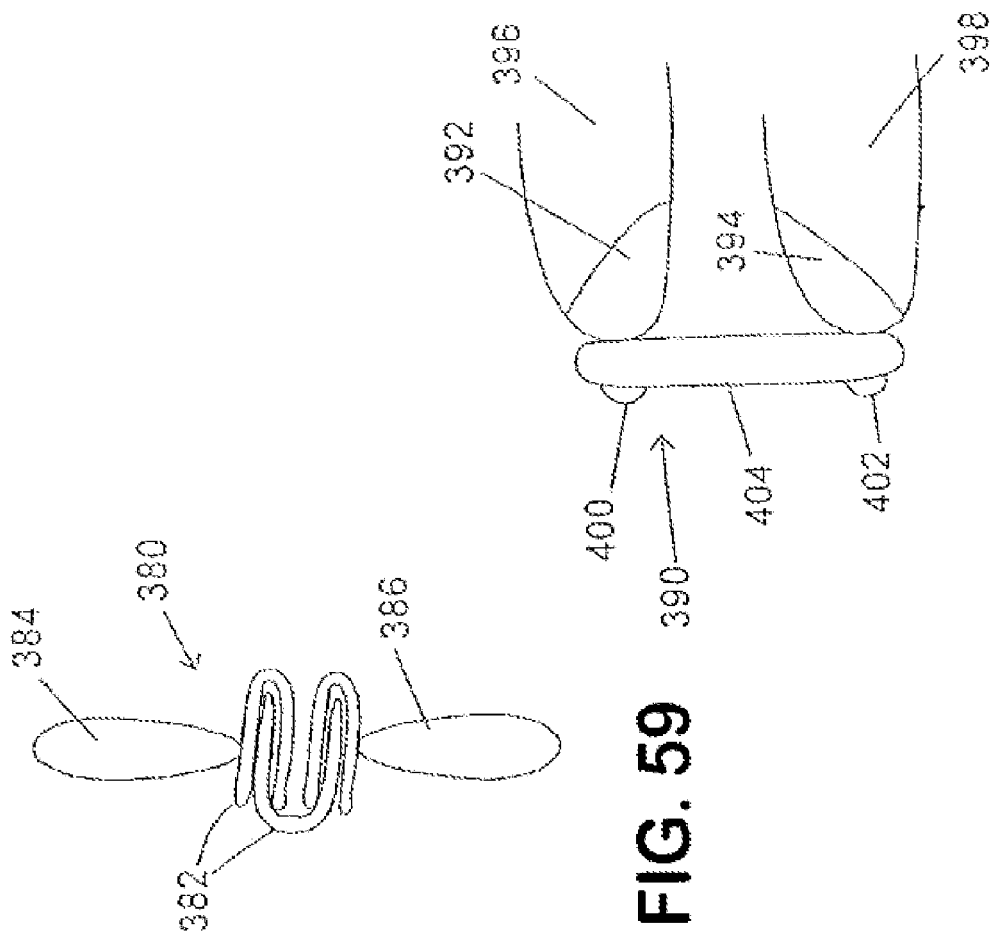

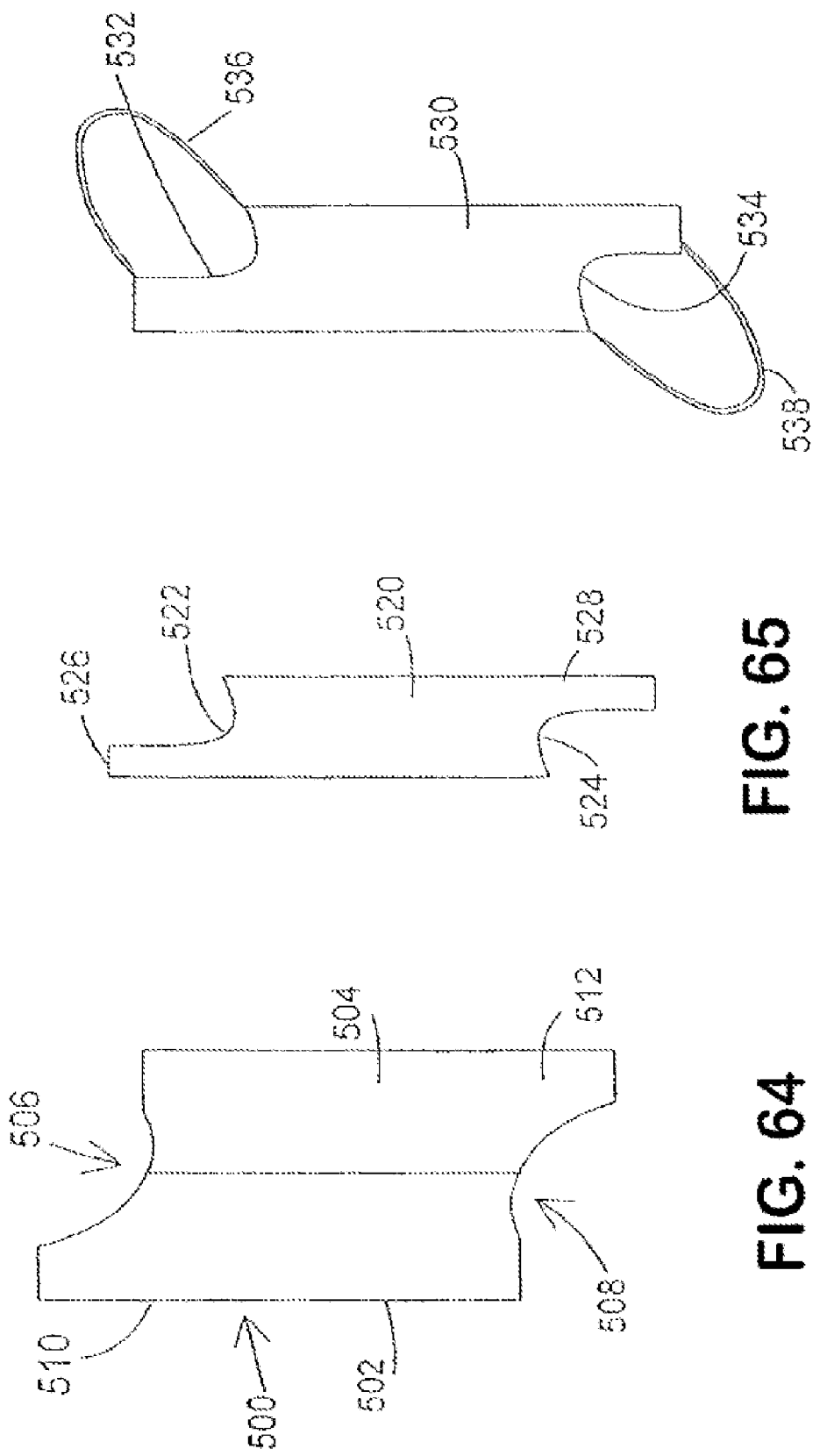

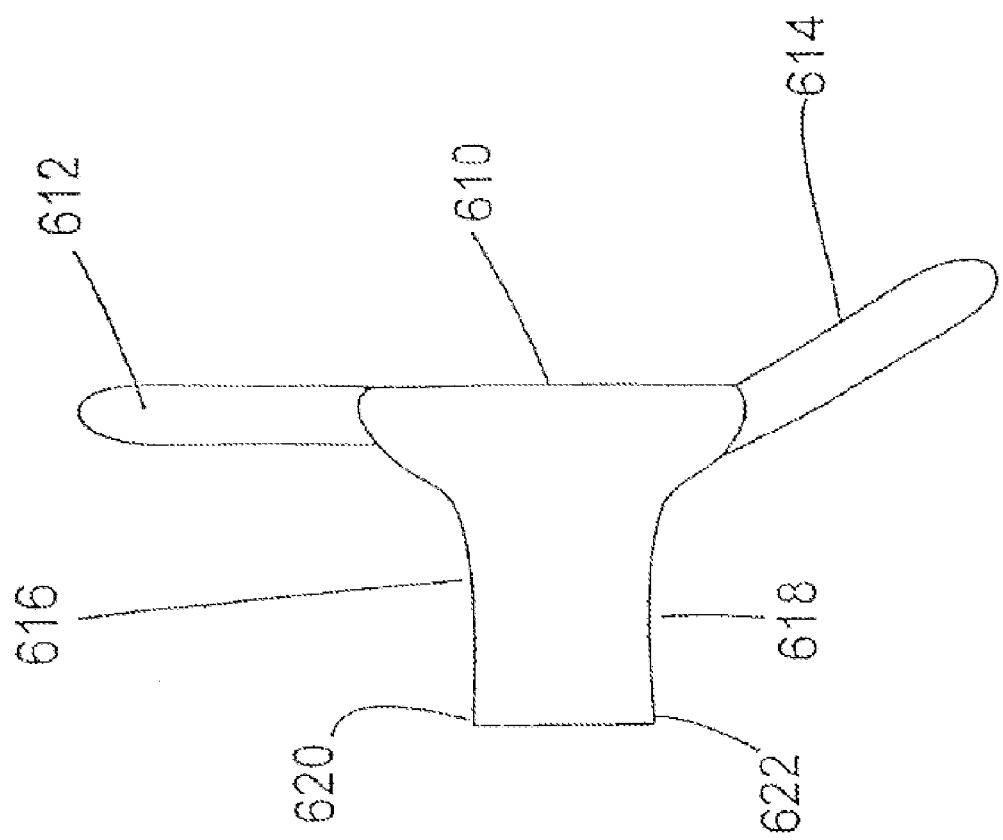

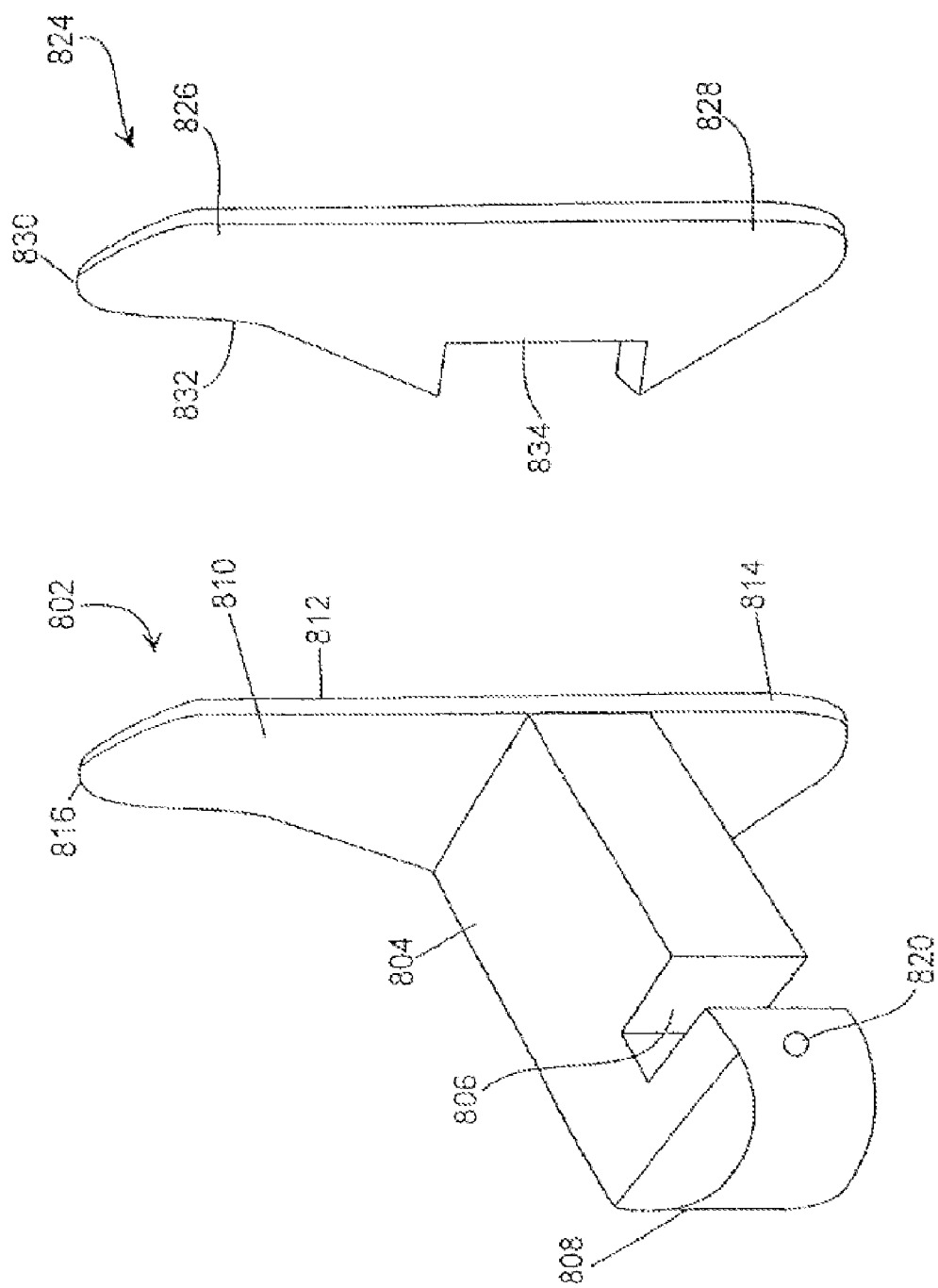

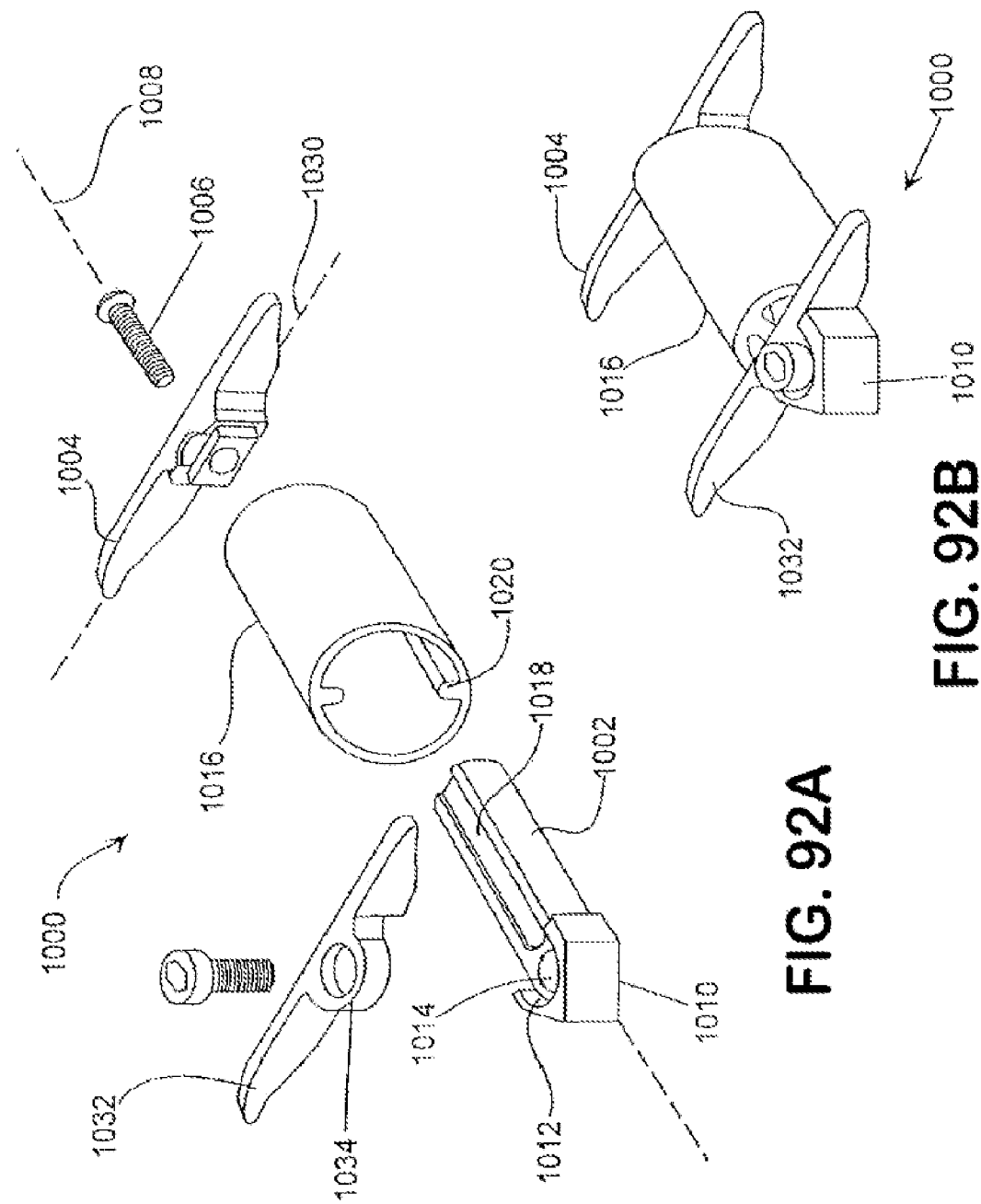

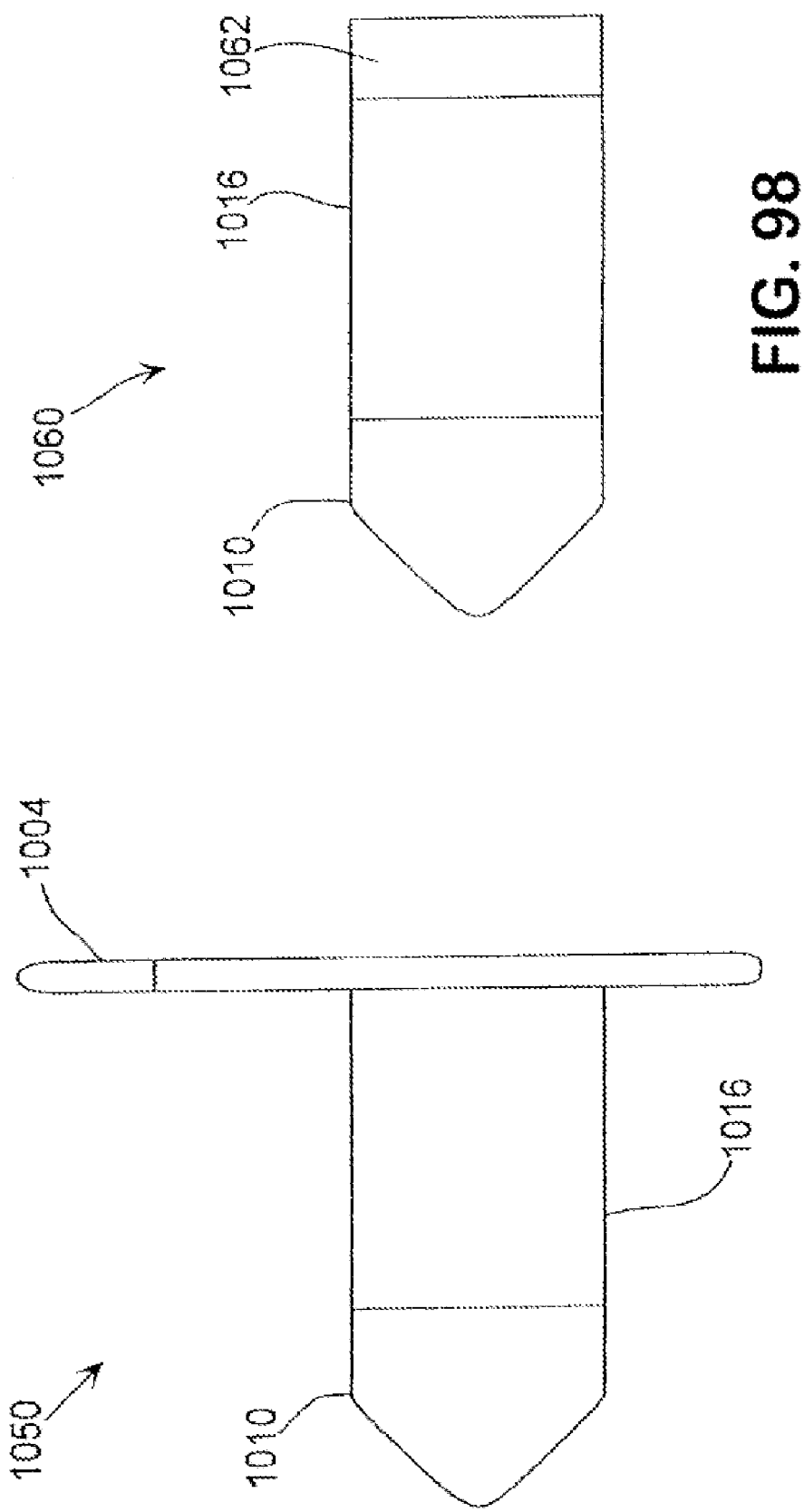

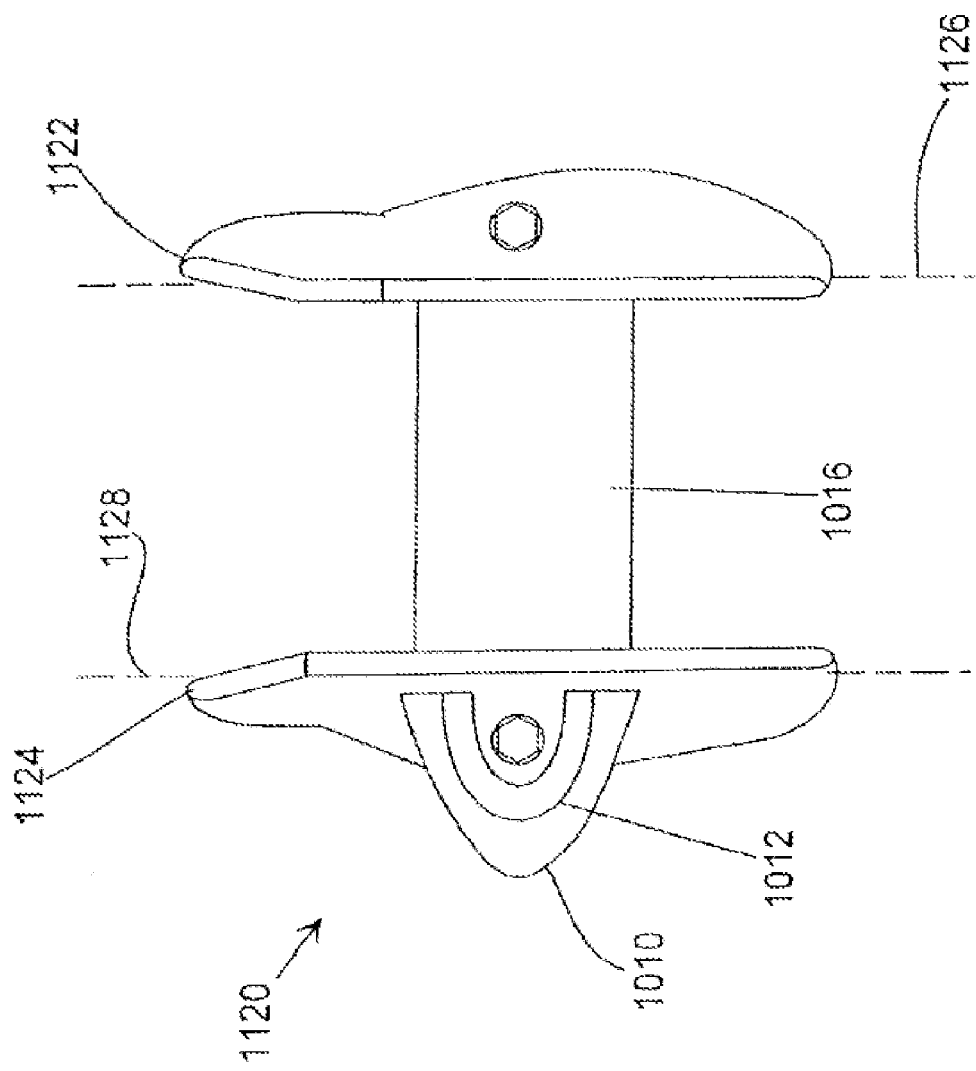

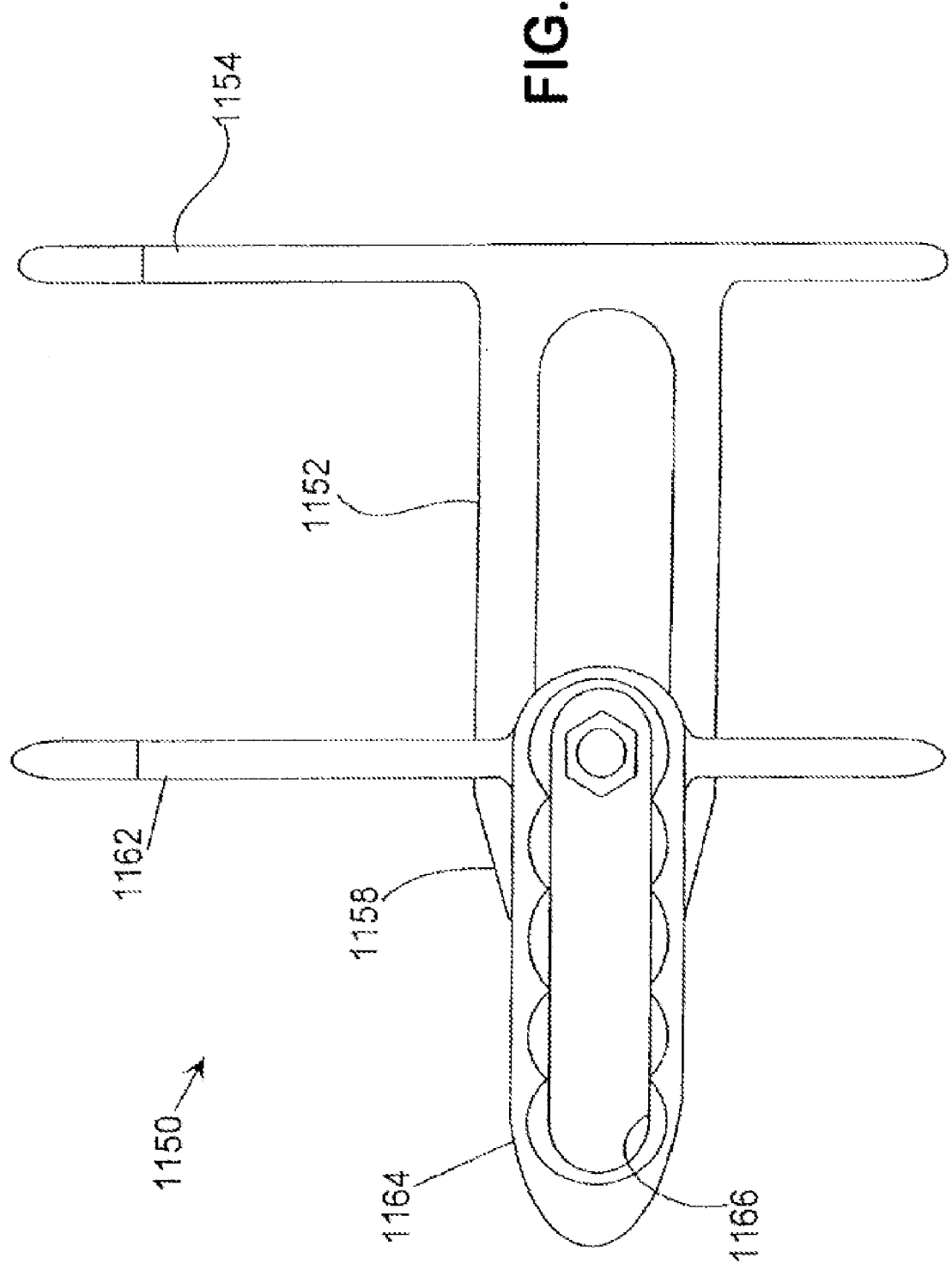

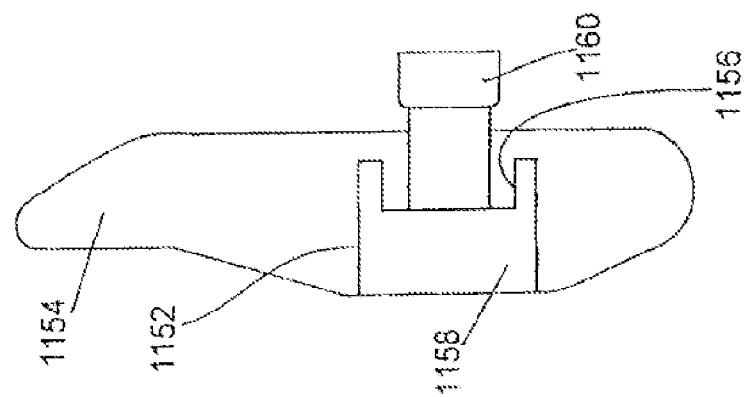
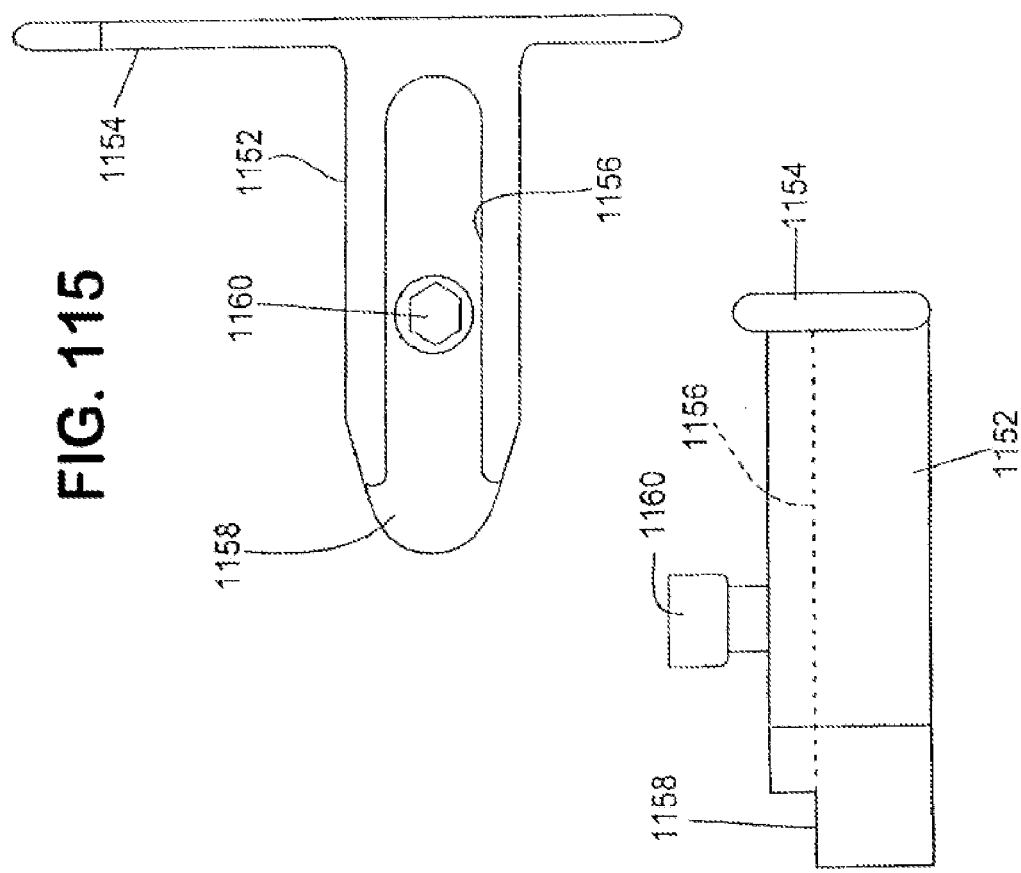
FIG. 115
FIG. 116
FIG. 117

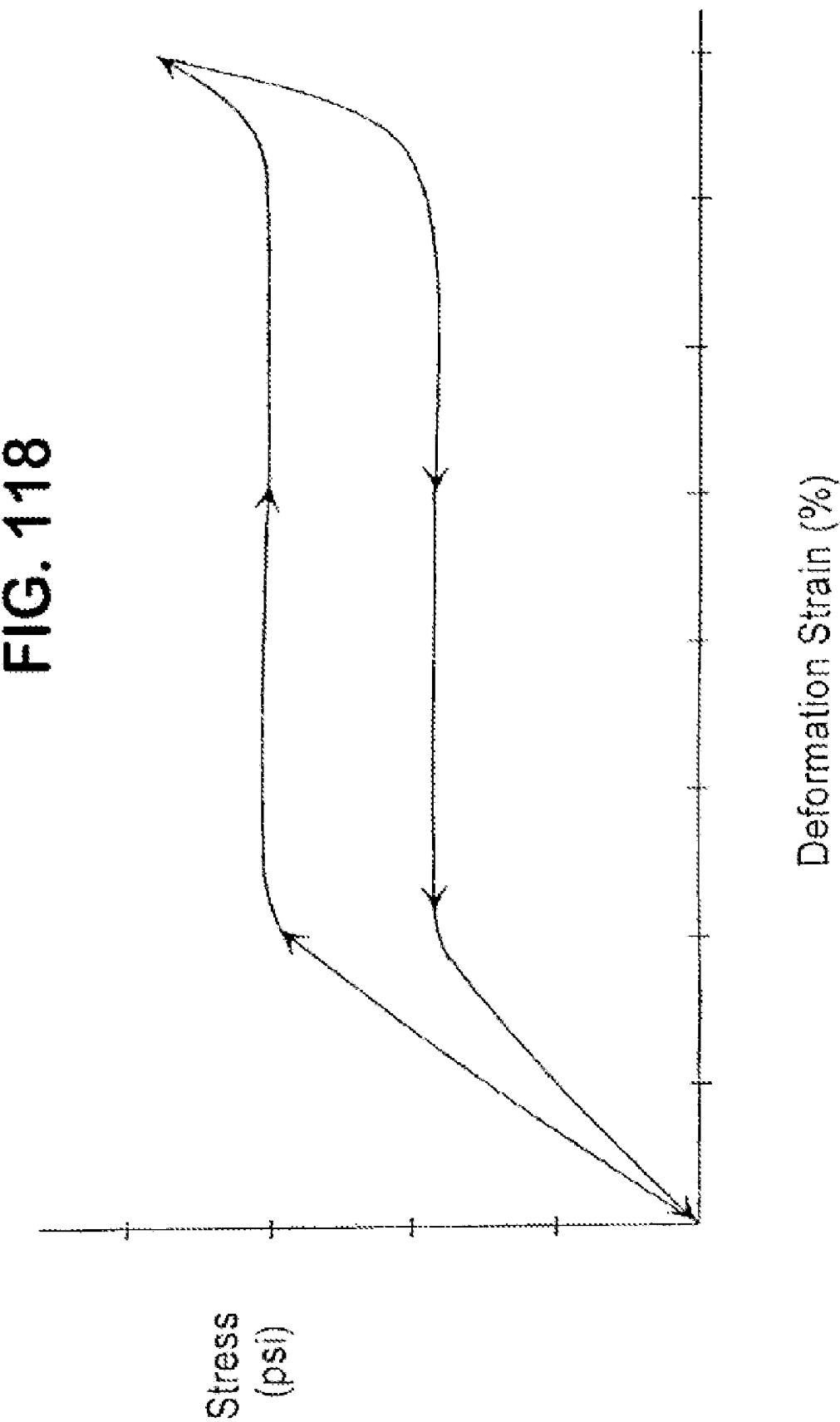

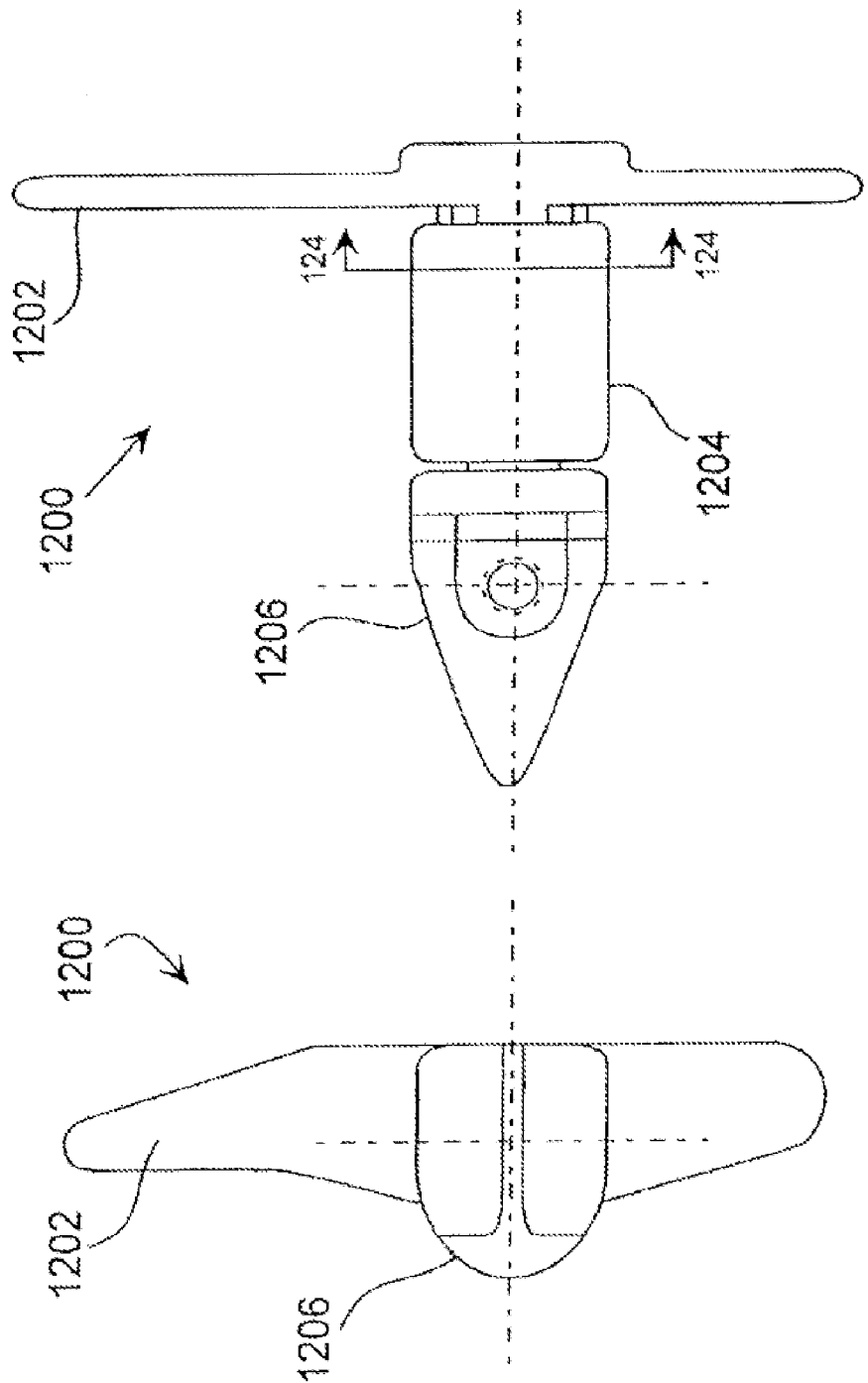

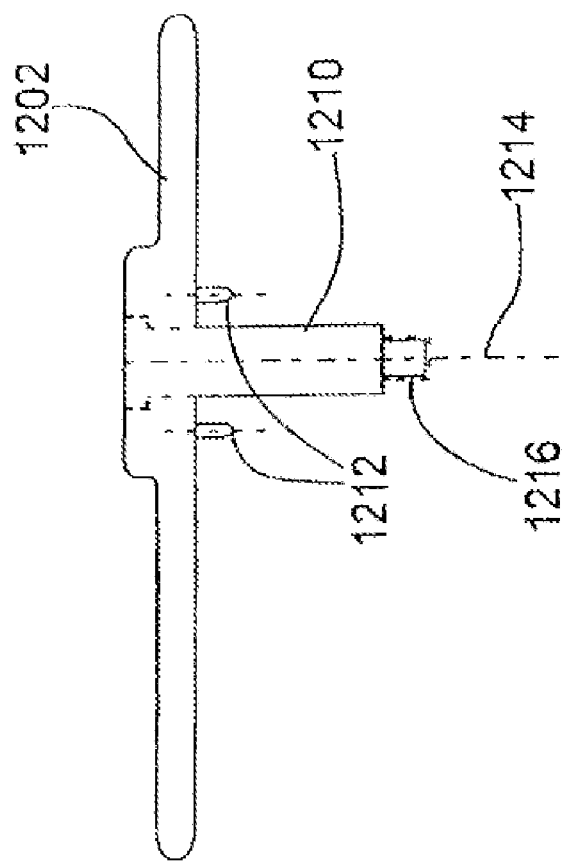
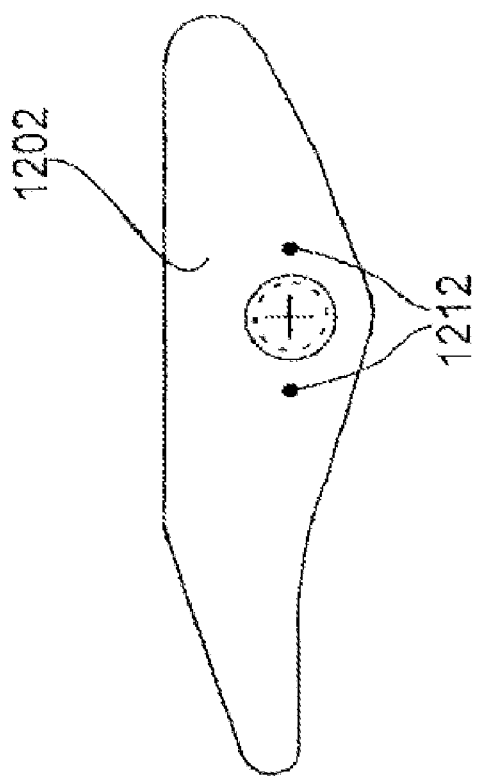
FIG. 121B
FIG. 121A

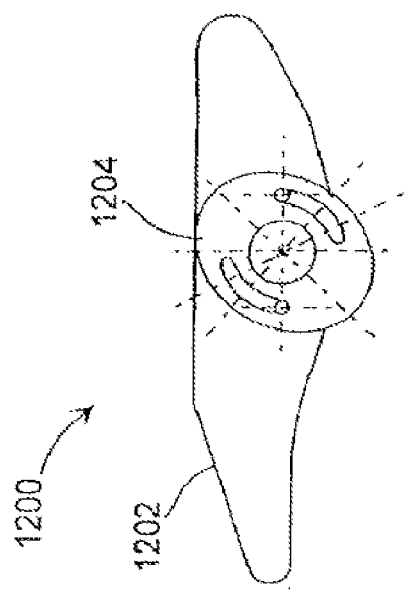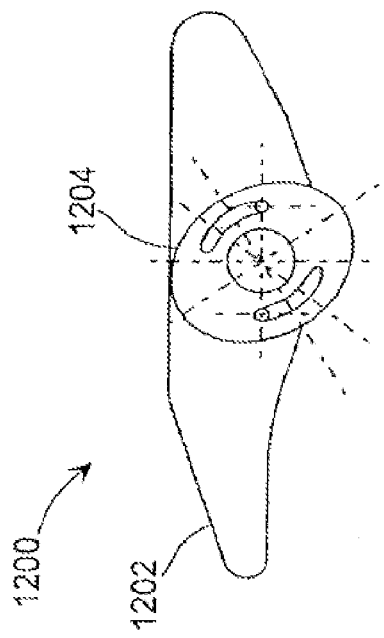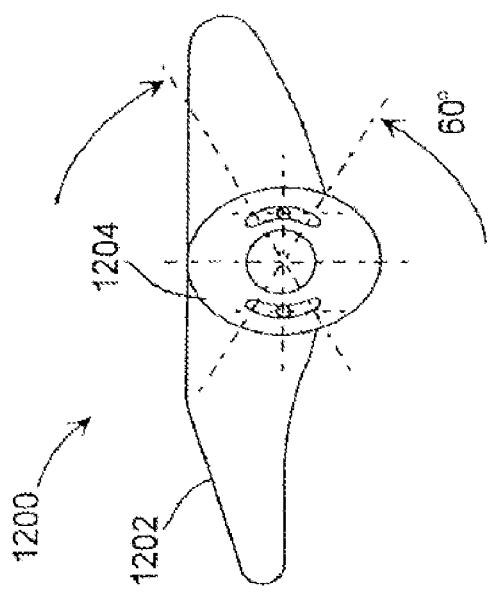
FIG. 124A
FIG. 124B
FIG. 124C

SPINE DISTRACTION IMPLANT

CROSS-REFERENCES TO RELATED APPLICATIONS

This application is a divisional of co-pending U.S. patent application Ser. No. 11/788,763, filed Apr. 19, 2007, which is a continuation-in-part of U.S. patent application Ser. No. 11/092,862, filed on Mar. 29, 2005, now issued as U.S. Pat. No. 7,621,939; which is a divisional of U.S. patent application Ser. No. 09/842,819, filed on Apr. 26, 2001, now issued as U.S. Pat. No. 7,201,751; which is a continuation-in-part of U.S. patent application Ser. No. 09/579,039, filed on May 26, 2000, now U.S. Pat. No. 6,451,019; which is a continuation-in-part of U.S. patent application Ser. No. 09/473,173, filed on Dec. 28, 1999, now U.S. Pat. No. 6,235,030; which is a continuation of U.S. patent application Ser. No. 09/179,570, filed on Oct. 27, 1998, now U.S. Pat. No. 6,048,342; which is a continuation-in-part of U.S. patent application Ser. No. 08/958,281, filed on Oct. 27, 1997, now U.S. Pat. No. 5,860,977; which is a continuation-in-part of U.S. patent application Ser. No. 08/778,093, filed on Jan. 2, 1997 now U.S. Pat. No. 5,836,948.

The present application is also a continuation-in-part of U.S. patent application Ser. No. 10/684,847, filed on Oct. 14, 2003; which claims priority to U.S. Provisional Application No. 60/421,921, filed on Oct. 29, 2002; both entitled "Interspinous Process Apparatus and Method with a Selectably Expandable Spacer."

The present application is also a continuation-in-part of U.S. patent application Ser. No. 11/003,555, filed on Dec. 3, 2004; which claims priority to U.S. Provisional Application No. 60/565,910, filed on Apr. 28, 2004.

The present application is also a continuation-in-part of U.S. patent application Ser. No. 11/389,002, filed on Mar. 24, 2006; which claims benefit to U.S. Provisional Application No. 60/672,402, filed Apr. 18, 2005; both entitled "Interspinous Process Implant Having Deployable Wings and Method of Implantation."

All of the above-listed references are incorporated herein by reference in their entirety.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The spinal column is a bio-mechanical structure composed primarily of ligaments, muscles, vertebrae and intervertebral disks. The bio-mechanical functions of the spine include: (1) support of the body, which involves the transfer of the weight and the bending movements of the head, trunk, and arms to the pelvis and legs, (2) complex physiological motion between these parts, and (3) protection of the spinal cord and the nerve roots.

As the present society ages, it is anticipated that there will be an increase in adverse spinal conditions which are characteristic of older people. By way of example, with aging comes increases in spinal stenosis (including but not limited to central canal and lateral stenosis), the thickening of the bones which make up the spinal column and facet arthropathy. Spinal stenosis results in a reduction foraminal area (i.e., the available space for the passage of nerves and blood vessels) which compresses the cervical nerve roots and causes radicular pain. Humpreys, S. C. et al., Flexion and traction effect on C5-C6 foraminal space, Arch. Phys. Med. Rehabil., vol. 79 at 1105 (September 1998). Another symptom of spinal stenosis is myelopathy, which results in neck pain and muscle weakness. Id. Extension and ipsilateral rotation of the neck further reduces the foraminal area and contributes to pain, nerve root compression and neural injury. Id.; Yoo, J. U. et al., Effect of cervical spine motion on the neuroforaminal dimensions of human cervical spine, Spine, vol. 17 at 1131 (Nov. 10, 1992). In contrast, neck flexion increases the foraminal area. Humpreys, S. C. et al., at 1105.

Spinal stenosis is characterized by a reduction in the available space for the passage of blood vessels and nerves. Pain associated with such stenosis can be relieved by medication and/or surgery. Of course, it is desirable to eliminate the need for major surgery for all individuals and in particular for the elderly.

Accordingly, there needs to be developed procedures and implants for alleviating such condition which are minimally invasive, can be tolerated by the elderly and can be performed preferably on an outpatient basis.

This invention also relates to an apparatus and method for adjustably distracting the spinous process of adjacent vertebrae.

In addition, there are a variety of other ailments that can cause back pain in patients of all ages. For these ailments it is also desirable to eliminate such pain without major surgery.

Accordingly, there is a need for a method for alleviating such conditions that is minimally invasive, can be tolerated by patients of all ages (in particular, the elderly), can be performed on an out-patient basis, and allows adjustments both during and after surgery to minimize patient discomfort. There is a further need for an apparatus with which to apply the method.

BRIEF SUMMARY OF THE INVENTION

The present invention is directed to providing a minimally invasive implant and method for alleviating discomfort associated with the spinal column.

The present invention provides for apparatus and method for relieving pain by relieving the pressure and restrictions on the aforementioned blood vessels and nerves. Such alleviation of pressure is accomplished in the present invention through the use of an implant and method which distract the spinous process of adjacent vertebra in order to alleviate the problems caused by spinal stenosis and facet arthropathy and the like. While the implant and method particularly address the needs of the elderly, the invention can be used with individuals of all ages and sizes where distraction of the spinous process would be beneficial.

In one aspect of the invention, an implant is provided for relieving pain comprising a device positioned between a first spinous process and a second spinous process. The device includes a spinal column extension stop and a spinal column flexion non-inhibitor.

In another aspect of the invention, the implant is positioned between the first spinous process and the second spinous process and includes a distraction wedge that can distract the first and second spinous processes as the implant is positioned between the spinous processes.

In yet another aspect of the present invention, the implant includes a device which is adapted to increasing the volume of the spinal canal and/or the neural foramen as the device is positioned between adjacent spinous processes.

In yet a further aspect of the present invention, a method is presented for relieving pain due to the development of, by way of example only, spinal stenosis and facet arthropathy. The method is comprised of the steps of accessing adjacent first and second spinal processes of the spinal column and distracting the processes a sufficient amount in order to increase the volume of the spinal canal in order to relieve pain. The method further includes implanting a device in order to maintain the amount of distraction required to relieve such pain.

In yet a further aspect of the invention, the method includes implanting a device in order to achieve the desired distraction and to maintain that distraction.

In yet a further aspect of the invention, the implant includes a first portion and a second portion. The portions are urged together in order to achieve the desired distraction. In still a further aspect of the invention, the implant includes a distracting unit and a retaining unit. The distracting unit includes a body which can be urged between adjacent spinous processes. The body includes a slot. After the distracting unit is positioned, the retaining unit can fit into the slot of the retaining unit and be secured thereto.

In yet a further aspect of the invention, the implant includes a first unit with a central body. A sleeve is provided over the central body and is at least partially spaced from the central body in order to allow for deflection toward the central body.

In a further aspect of the invention, the implant includes a first unit having a central body with a guide and a first wing, with the first wing located at first end of the body. The guide extends from a second end of the body located distally from the first wing. The implant further includes a sleeve provided over said central body. The sleeve is at least partially spaced from the central body in order to allow for deflection of the sleeve toward the central body. The implant further includes a second wing and a device for securing the second wing to the first unit, wherein the sleeve is located between the first and second wings.

In yet another aspect of the invention, an implant system includes a cylindrical sleeve which is inwardly deflectable. The system further includes an insertion tool which includes an insertion guide, a central body, a stop and a handle. The guide and the stop extend from opposite sides of the central body and the handle extend from the stop. A sleeve fits over the guide and against the stop preparatory to being positioned between the two adjacent vertebrae with the insertion tool.

In yet a further aspect of the invention, the implant includes central body and first and second wings and a means for selectively positioning one of the first and second wings relative to the other in order to accommodate spinous processes of different sizes.

In yet still a further aspect of the invention, the implant includes a sleeve which is rotatable relative to the wings of the implant in order to be able to accommodate the anatomical structure of spinous processes.

In yet still a further aspect of the invention, the sleeve is formed from bar stock comprised of a super-elastic material.

Other implants and methods within the spirit and scope of the invention can be used to increase the volume of the spinal canal thereby alleviating restrictions on vessels and nerves associated therewith, and pain.

BRIEF DESCRIPTION OF THE DRAWINGS

FIG. 1 depicts the implant in a more extended configuration than does FIG. 2.

FIGS. 6, 7, 8, 9, and 10 depict apparatus and method for another embodiment of the present invention for creating distraction between adjacent spinous processes.

FIGS. 16, 16a, and 17 depict yet another embodiment of the present invention.

FIGS. 34 and 35 depict yet another apparatus and method of the present invention.

FIGS. 36, 37, and 38 depict three different embodiments of the present invention.

FIGS. 39 and 40 depict yet another apparatus and method of an embodiment of the present invention.

FIG. 44 is still a further embodiment of an implant of the invention.

FIG. 45 is yet another depiction of an apparatus and method of the invention.

FIGS. 46 and 47 depict still a further apparatus and method of an embodiment of the invention.

FIGS. 48, 49, 50, and 51 depict yet a further apparatus and method of the invention.

FIGS. 52, 53, 54, 55a, and 55b depict another apparatus and method of the invention.

FIGS. 59 and 60 depict still a further embodiment of the invention.

FIG. 61 depict another embodiment of the invention.

FIGS. 64 and 65 depict still a further embodiment of the present invention.

FIG. 66 depicts another embodiment of the invention.

FIGS. 69, 70, 71, and 71a depict a further embodiment of the present invention.

FIGS. 79, 80, 80a, 81, 82, 83, 83a, 84, 85, 86, and 87 depict still a further embodiment of the present invention.

FIGS. 92, 92a, 92b, 93, 93a, 93b, 93c, 93d, 94, 94a, 94b, 95, 95a, and 96, depict still a further embodiment of the present invention wherein a sleeve is provided which is capable of deflecting response to relative motion between the spinous processes.

FIG. 97 depicts still another embodiment of the present invention.

FIG. 98 depicts yet a further embodiment of the present invention.

FIGS. 108, 109, and 110 depict still another embodiment of the present invention.

FIGS. 111, 112, 113, 114, 115, 116, and 117 depict yet another embodiment of the present invention.

FIG. 118 depicts a graph showing characteristics of a preferred material usable with several of the embodiments of the present invention.

FIGS. 119a and 119b depict side and plan views of still a further embodiment of the present invention.

FIGS. 121a and 121b depict side and plan views of the first wing and central body of the embodiment of the invention depicted in FIGS. 119a and 119b.

FIGS. 124a, 124b, and 124c depict a view of the embodiment of the invention of FIGS. 119a and 119b taken through line 124-124 in FIG. 119b shown in with the sleeve in various positions relative to a first wing.

FIG. 128 is still a further embodiment of the invention as depicted in FIG. 93a.

DETAILED DESCRIPTION OF THE INVENTION

Figure 1:
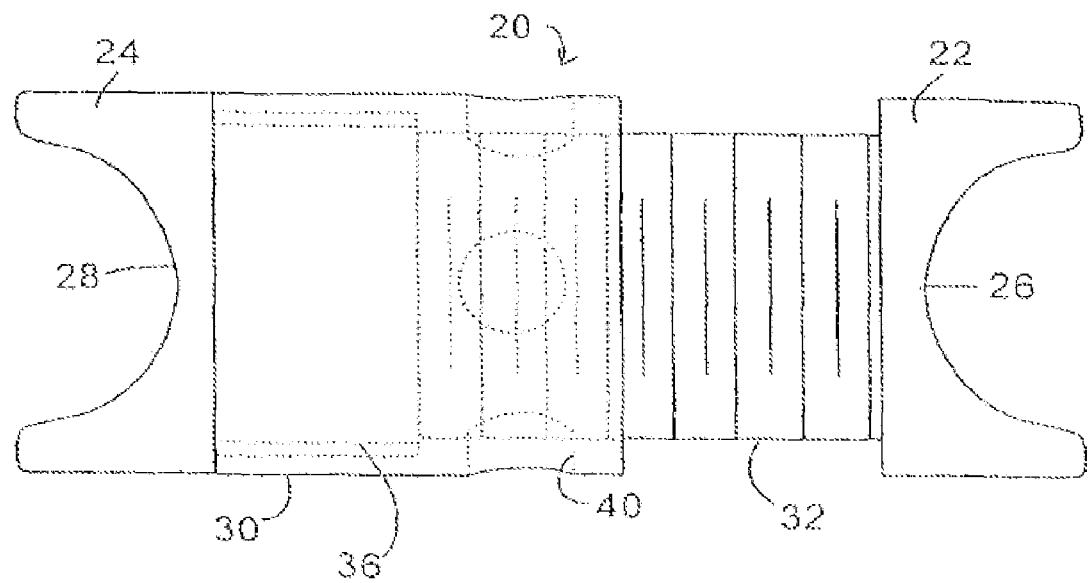
FIGS. 1 and 2 depict an embodiment of an implant of the invention which is adjustable in order to select the amount of distraction required.

A first embodiment of the invention is shown in FIGS. 1-5a, 5b. Implant 20 includes first and second forked ends 22 and 24, each defining a saddle 26, 28 respectively. The forked ends 22, 24 are mated using an interbody piece 30. As can be seen in FIGS. 3a, 3b, the first forked end 22 includes a threaded shaft 32 which projects rearwardly from the saddle 26. The threaded shaft 32 fits into the threaded bore 34 (FIG. 4a) of the interbody piece 30.

The second forked end 24 (FIGS. 5a, 5b) includes a smooth cylindrical shaft 36 which can fit into the smooth bore 38 of the interbody piece 30.

Figure 2:
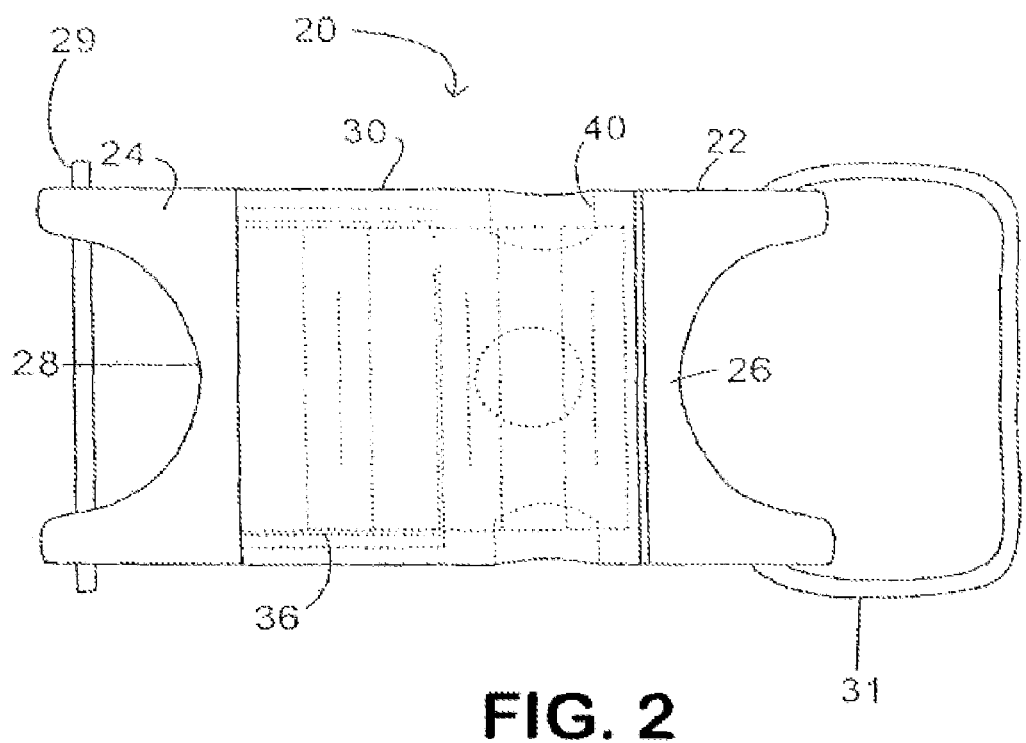
Figure 3A:
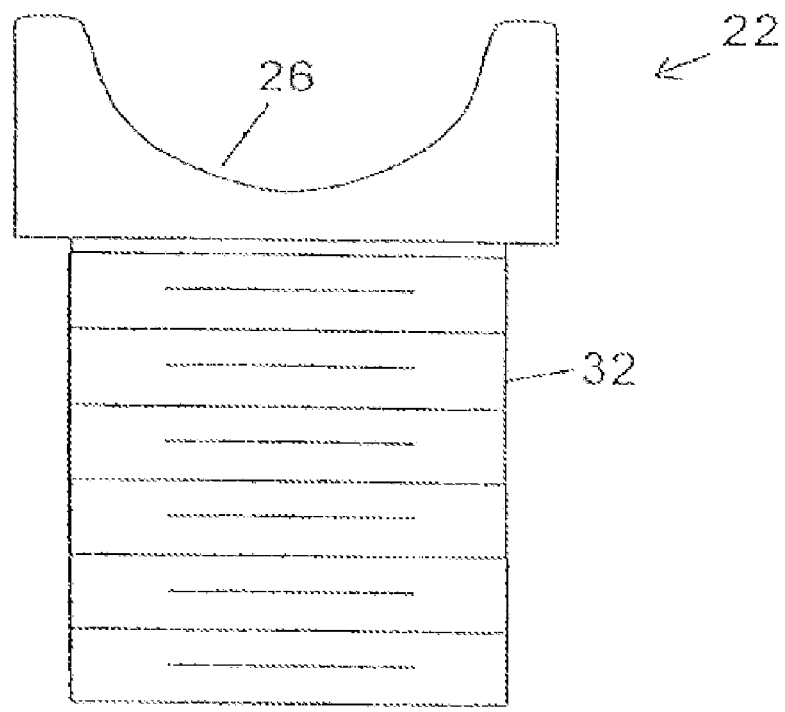
FIGS. 3a and 3b depict side and end views of a first forked and of the embodiment of FIG. 1.
Figure 3B:
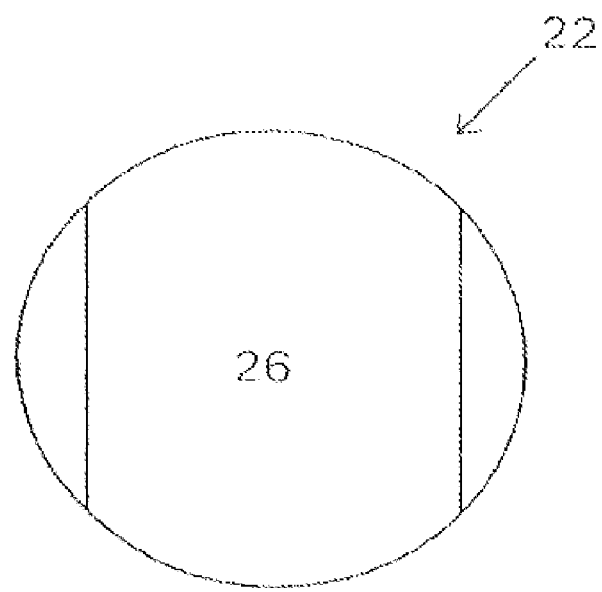
Figure 4A:
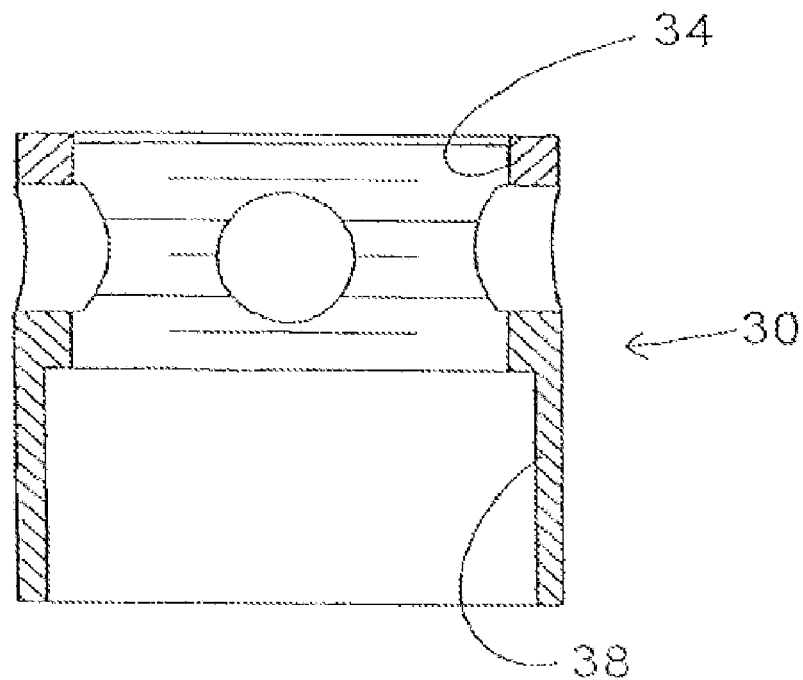
FIGS. 4a and 4b depict side sectioned and end views of an interbody piece of the implant of FIG. 1.
Figure 4B:
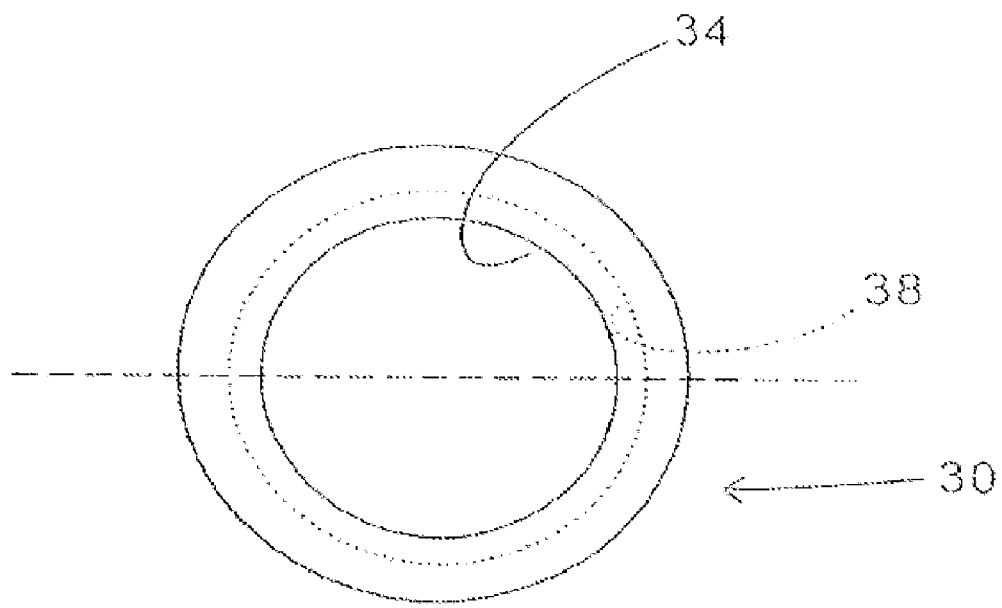
Figure 5A:
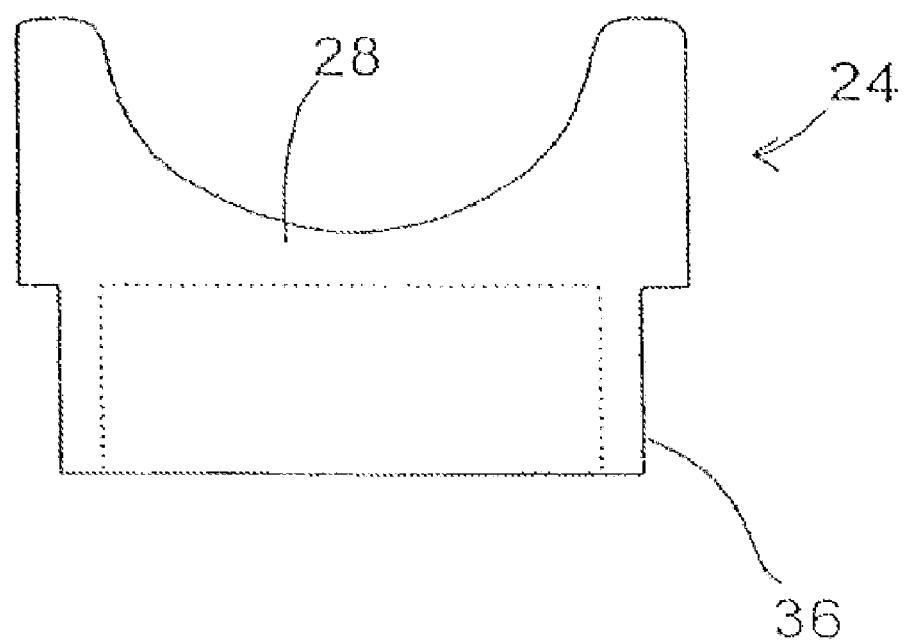
FIGS. 5a and 5b depict side and end views of a second forked end of the embodiment of FIG. 1.
Figure 5B:
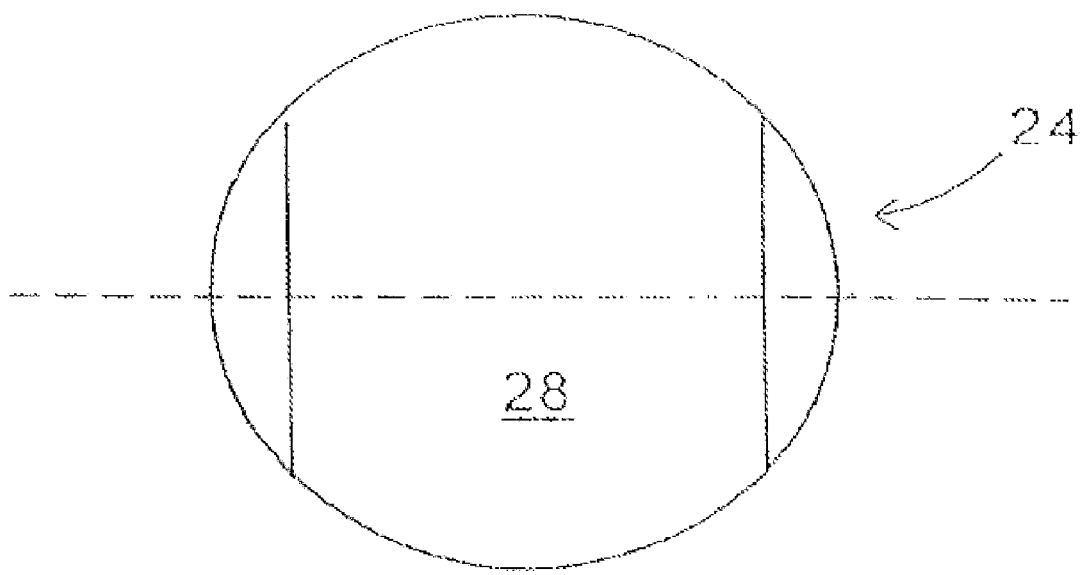

FIG. 1 shows the implant 20 in a fully extended position, while FIG. 2 shows the implant in an unextended position. In the unextended position, it can be seen that the threaded shaft 32 of the first forked end 22 fits inside the hollow cylindrical shaft 36 of the second forked end 24.

For purposes of implantation between adjacent first and second spinous processes of the spinal column, the implant 20 is configured as shown in FIG. 2. The first and second spinous processes are exposed using appropriate surgical techniques and thereafter, the implant 20 is positioned so that saddle 26 engages the first spinous process, and saddle 28 engages the second spinous process. At this point, the interbody piece 30 can be rotated by placing an appropriate tool or pin into the cross holes 40 and upon rotation, the saddle 26 is moved relative to the saddle 28. Such rotation spreads apart or distracts the spinous processes with the resultant and beneficial effect of enlarging the volume of the spinal canal in order to alleviate any restrictions on blood vessels and nerves.

It is noted that this implant as well as the several other implants described herein act as an extension stop. That means that as the back is bent backwardly and thereby placed in extension the spacing between adjacent spinous processes cannot be reduced to a distance less than the distance between the lowest point of saddle 26 and the lowest point of saddle 28. This implant, however, does not inhibit or in any way limit the flexion of the spinal column, wherein the spinal column is bent forward.

Preferably, such a device provides for distraction in the range of about 5 mm to about 15 mm. However, devices which can distract up to and above 22 mm may be used depending on the characteristics of the individual patient.

With all the ligaments (such as the superspinous ligament) and tissues associated with the spinous processes left intact, the implant 20 can be implanted essentially floating in position in order to gain the benefits of the aforementioned extension stop and flexion non-inhibitor. If desired, one of the saddles 26 can be laterally pinned with pin 29 to one of the spinous processes and the other saddle can be loosely associated with the other spinous processes by using a tether 31 which either pierces or surrounds the other spinous process and then is attached to the saddle in order to position the saddle relative to the spinous process. Alternatively, both saddles can be loosely tethered to the adjacent spinous process in order to allow the saddles to move relative to the spinous processes.

The shape of the saddles, being concave, gives the advantage of distributing the forces between the saddle and the respective spinous process. This ensures that the bone is not resorbed due to the placement of the implant 20 and that the structural integrity of the bone is maintained.

The implant 20 in this embodiment can be made of a number of materials, including but not limited to, stainless steel, titanium, ceramics, plastics, elastics, composite materials or any combination of the above. In addition, the modulus of elasticity of the implant can be matched to that of bone, so that the implant 20 is not too rigid. The flexibility of the implant can further be enhanced by providing additional apertures or perforations throughout the implant in addition to the holes 40 which also have the above stated purpose of allowing the interbody piece 30 to be rotated in order to expand the distance between the saddle 26, 28.

In the present embodiment, it is understood that the spinous processes can be accessed and distracted initially using appropriate instrumentation, and that the implant 20 can be inserted and adjusted in order to maintain and achieve the desired distraction. Alternatively, the spinous process can be accessed and the implant 20 appropriately positioned. Once positioned, the length of the implant can be adjusted in order to distract the spinous processes or extend the distraction of already distracted spinous processes. Thus, the implant can be used to create a distraction or to maintain a distraction which has already been created.

The placement of implants such as implant 20 relative to the spinous process will be discussed hereinbelow with other embodiments. However, it is to be noted that ideally, the implant 20 would be placed close to the instantaneous axis of rotation of the spinal column so that the forces placed on the implant 20 and the forces that the implant 20 places on the spinal column are minimized.

Further, it is noted that during the actual process of installing or implanting the implant 20, that the method uses the approach of extending the length of the implant 20 a first amount and then allowing the spine to creep or adjust to this distraction. Thereafter, implant 20 would be lengthened another amount, followed by a period where the spine is allowed to creep or adjust to this new level of distraction. This process could be repeated until the desired amount of distraction has been accomplished. This same method can be used with insertion tools prior to the installation of an implant. The tools can be used to obtain the desired distraction using a series of spinal distraction and spine creep periods before an implant is installed.

Figure 10:
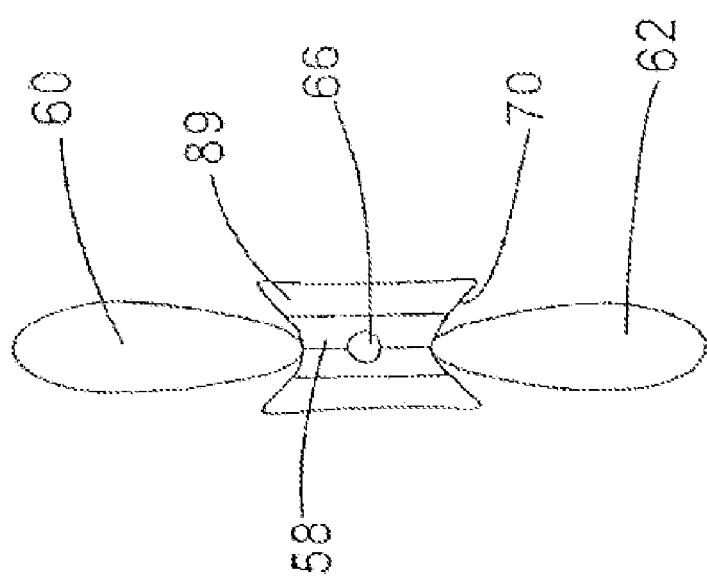

The embodiment of the invention shown in the above FIGS. 6, 7, 8, 9 and 10 includes distraction or spreader tool 50 which has first and second arms 52, 54. Arms 52, 54 are pivotal about pivot point 56 and releasable from pivot point 56 in order to effect the implantation of implant 58. As can be seen in FIG. 6, in cross-section, the arms 52, 54 are somewhat concave in order to cradle and securely hold the first spinous process 60 relative to arm 52 and the second spinous process 62 relative to arm 54. The distraction tool 50 can be inserted through a small incision in the back of the patient in order to address the space between the first spinous process 60 and the second spinous process 62. Once the tool 50 is appropriately positioned, the arms 52, 54 can be spread apart in order to distract the spinous processes. After this has occurred, an implant 58 as shown in FIGS. 8 and 9, or of a design shown in other of the embodiments of this invention, can be urged between the arms 52, 54 and into position between the spinous processes. After this occurs, the arms 52, 54 can be withdrawn from the spinous processes leaving the implant 58 in place. The implant 58 is urged into place using a tool 64 which can be secured to the implant 58 through a threaded bore 66 in the back of the implant. As can be seen in FIG. 10, the implant 58 includes saddles 68 and 70 which cradle the upper and lower spinous processes 60, 62 in much the same manner as the above first embodiment and also in much the same manner as the individual arms of the tool 50. The saddles as described above tend to distribute the load between the implant and the spinous processes and also assure that the spinous process is stably seated at the lowest point of the respective saddles.

Figure 11:
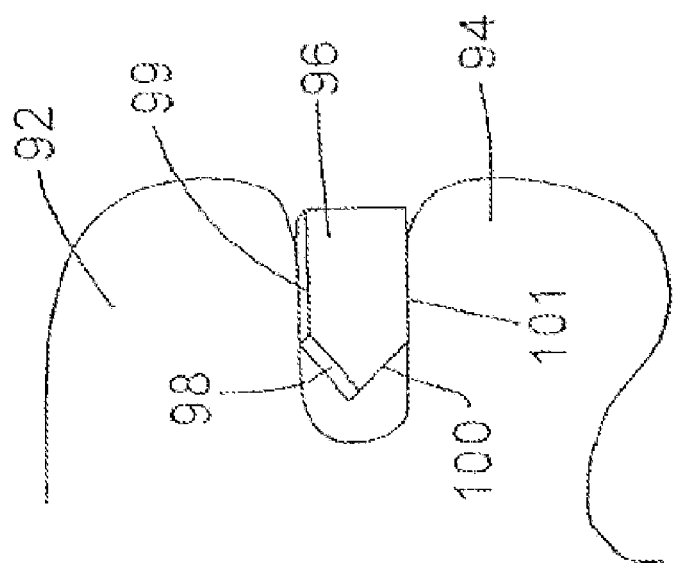
FIGS. 11, 12, and 13 depict yet a further embodiment of the invention for creating distraction between adjacent spinous processes.
Figure 12:
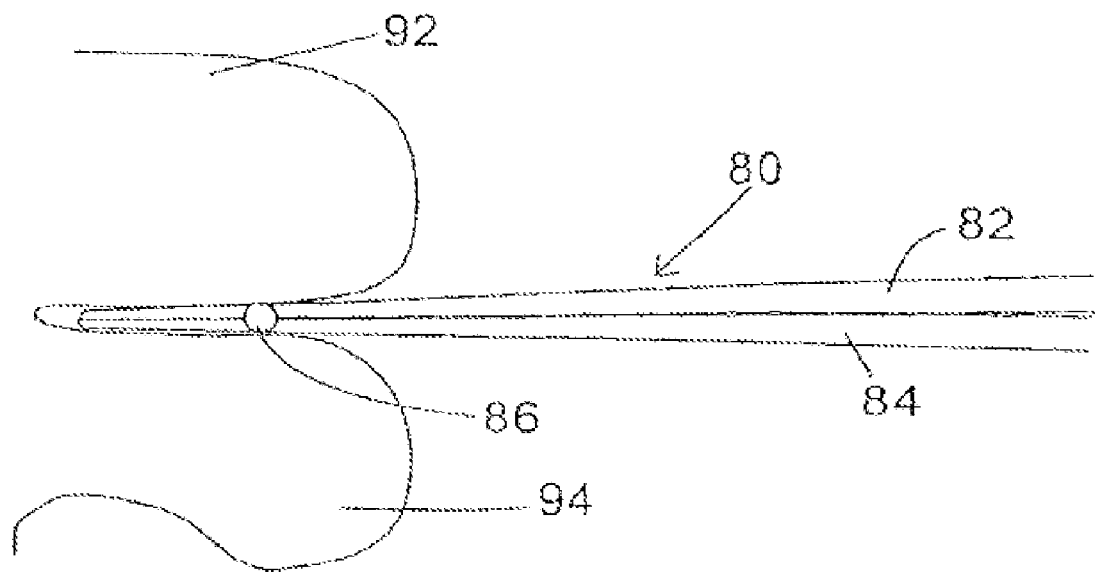
Figure 13:
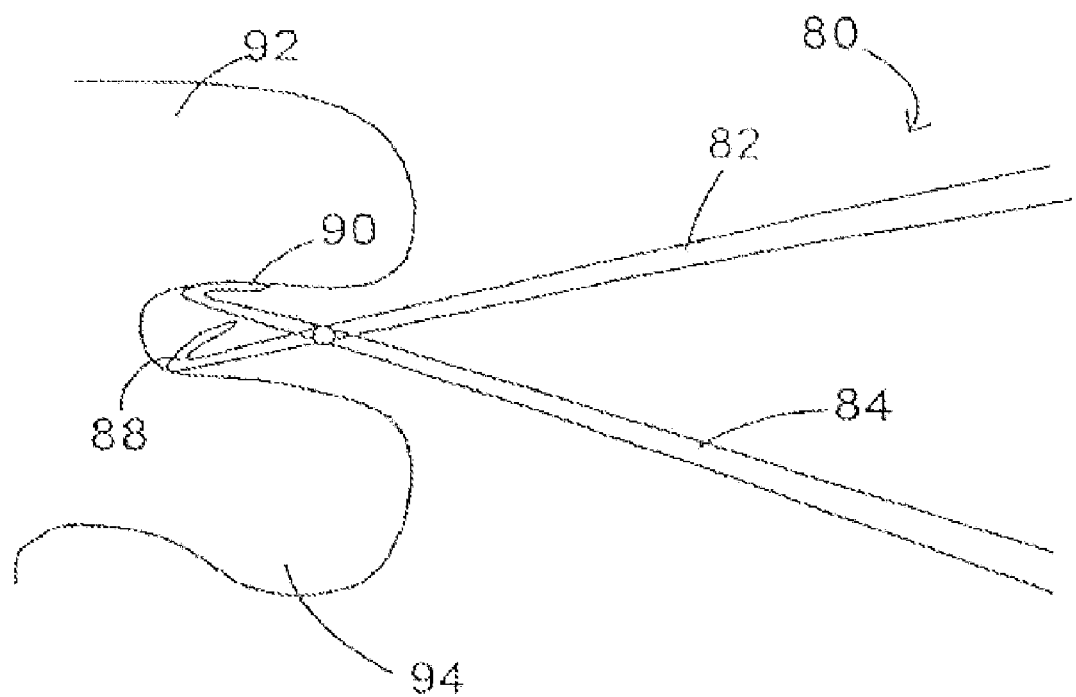

Another embodiment of the apparatus and method of the invention is shown in FIGS. 11, 12 and 13. In this embodiment, the spreader or distraction tool 80 includes first and second arms 82, 84 which are permanently pivoted at pivot point 86. The arms include L-shaped ends 88, 90. Through a small incision, the L-shaped ends 88, 90 can be inserted between the first and second spinous processes 92, 94. Once positioned, the arms 82, 84 can be spread apart in order to distract the spinous processes. The implant 96 can then be urged between the spinous processes in order to maintain the distraction. It is noted that implant 96 includes wedged surfaces or ramps 98, 100. As the implant 96 is being urged between the spinous processes, the ramps further cause the spinous processes to be distracted. Once the implant 96 is fully implanted, the full distraction is maintained by the planar surfaces 99, 101 located rearwardly of the ramps. It is to be understood that the cross-section of the implant 96 can be similar to that shown for implant 58 or similar to other implants in order to gain the advantages of load distribution and stability.

Figure 14:
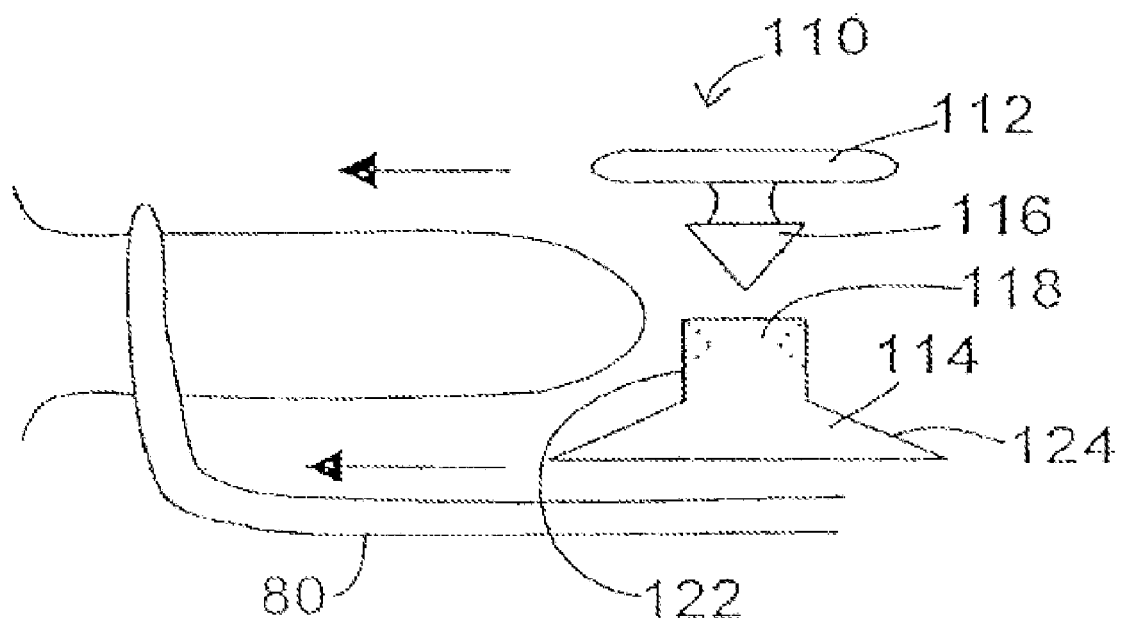
FIGS. 14 and 15 depict a further apparatus and method of an embodiment of the invention for creating distraction.
Figure 15:
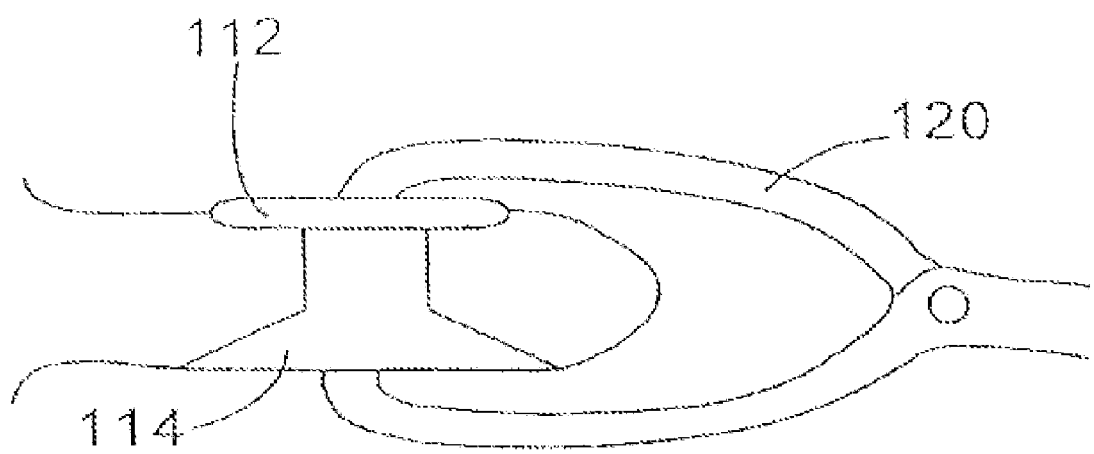

In FIGS. 14 and 15, yet another embodiment of the invention is depicted. In this embodiment, the implant 110 includes first and second conically shaped members 112, 114. Member 112 includes a male snap connector 116 and member 114 includes a female snap connector 11S. With male snap connector 116 urged into female snap connector 118, the first member 112 is locked to the second member 114. In this embodiment, a distraction or spreader tool 80 could be used. Once the spinous process has been spread apart, an implantation tool 120 can be used to position and snap together the implant 110. The first member 112 of implant 110 is mounted on one arm and second member 114 is mounted on the other arm of tool 120. The member 112, 114 are placed on opposite sides of the space between adjacent spinous processes. The members 112, 114 are urged together so that the implant 110 is locked in place between the spinous processes as shown in FIG. 15. It is to be noted that the implant 110 can also be made more self-distracting by causing the cylindrical surface 122 to be more conical, much as surface 124 is conical, in order to hold implant 110 in place relative to the spinous processes and also to create additional distraction.

Figure 16:
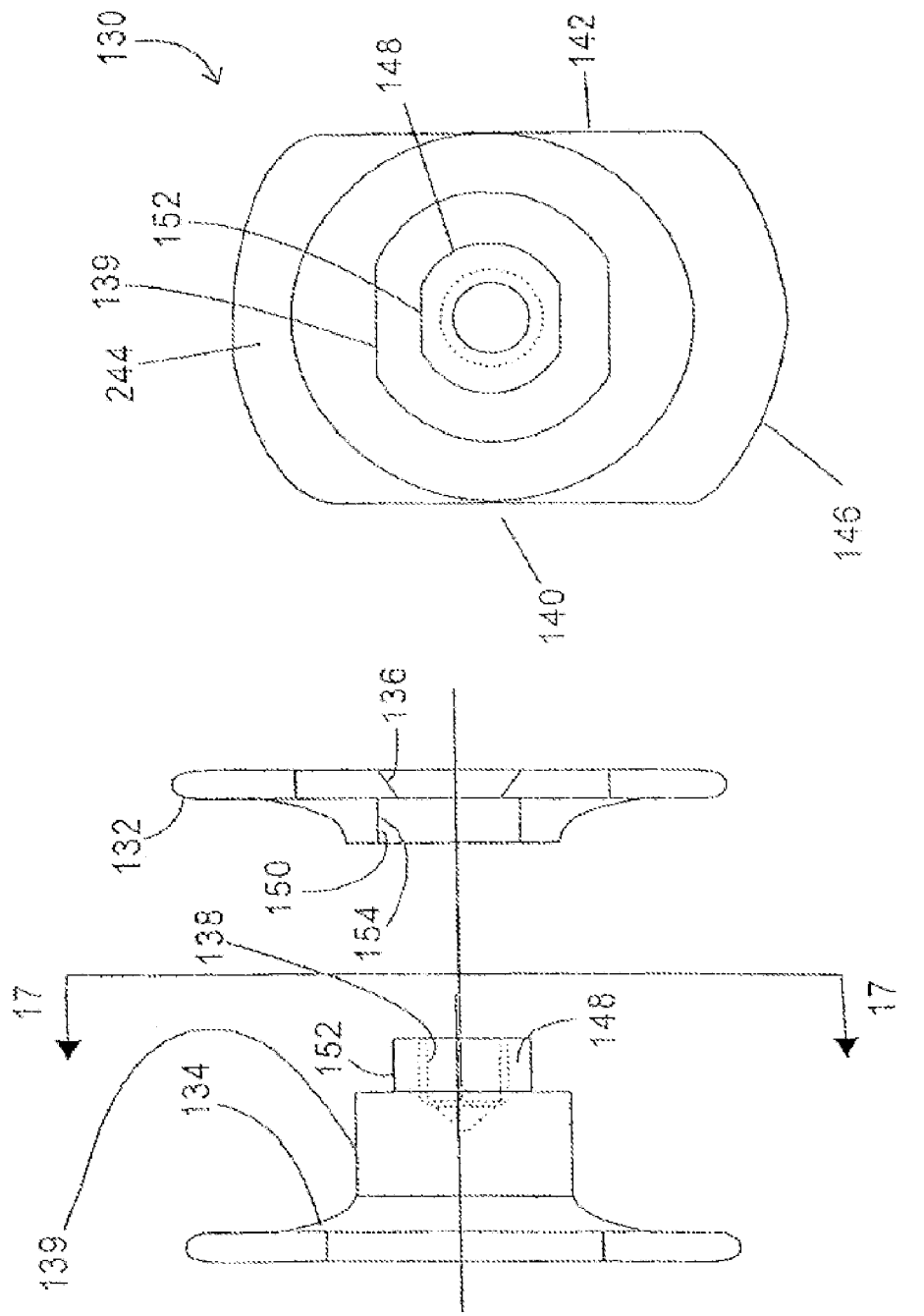
Figure 17:
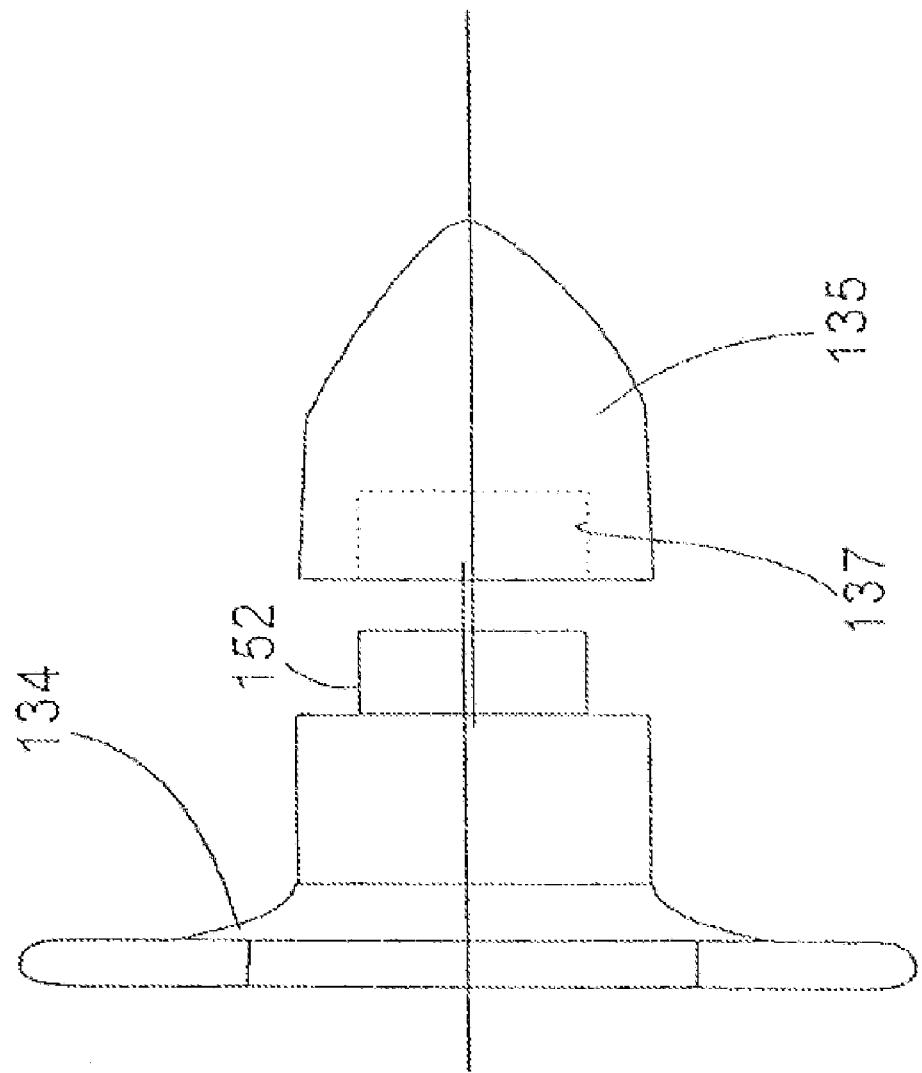

An alternative embodiment of the implant can be seen in FIGS. 16 and 17. This implant 130 includes first and second members 132, 134. In this particular embodiment, the implants are held together using a screw (not shown) which is inserted through countersunk bore 136 and engages a threaded bore 138 of the second member 134. Surfaces 139 are flattened (FIG. 17) in order to carry and spread the load applied thereto by the spinous processes.

The embodiment of implant 130 is not circular in overall outside appearance, as is the embodiment 110 of FIGS. 14 and 15. In particular, with respect to the embodiment of implant 130 of FIGS. 16 and 17, this embodiment is truncated so that the lateral side 140, 142 are flattened with the upper and lower sides 144, 146 being elongated in order to capture and create a saddle for the upper and lower spinous processes. The upper and lower sides, 144, 146 are rounded to provide a more anatomical implant which is compatible with the spinous processes.

If it is desired, and in order to assure that the first member 132 and the second member 134 are aligned, key 148 and keyway 150 are designed to mate in a particular manner. Key 148 includes at least one flattened surface, such as flattened surface 152, which mates to an appropriately flattened surface 154 of the keyway 150. In this manner, the first member is appropriately mated to the second member in order to form appropriate upper and lower saddles holding the implant 130 relative to the upper and lower spinous processes.

FIG. 16a depicts second member 134 in combination with a rounded nose lead-in plug 135. Lead-in plug 135 includes a bore 137 which can fit snugly over key 148. In this configuration, the lead-in plug 135 can be used to assist in the placement of the second member 134 between spinous processes. Once the second member 134 is appropriately positioned, the lead-in plug 135 can be removed. It is to be understood that the lead-in plug 135 can have other shapes such as pyramids and cones to assist in urging apart the spinous processes and soft tissues in order to position the second member 134.

Figure 18:
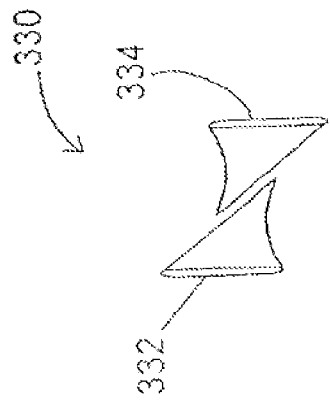
FIGS. 18, 19, and 20 depict yet a further apparatus and method of the present embodiment.
Figure 19:
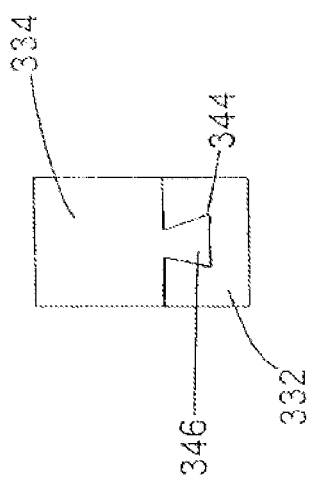
Figure 20:
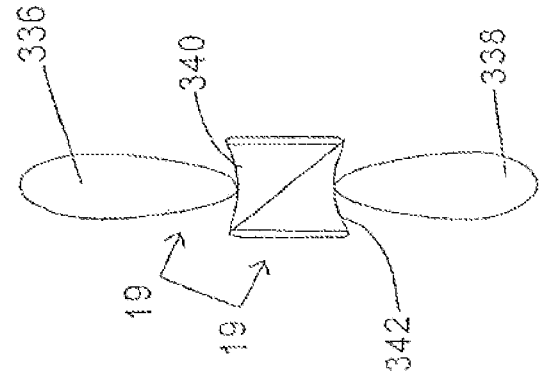

The implant 330 as shown in FIG. 18 is comprised of first and second mating wedges 332 and 334. In order to implant these wedges 332, 334, the spinous processes are accessed from both sides and then a toot is used to push the wedges towards each other. As the wedges are urged towards each other, the wedges move relative to each other so that the combined dimension of the implant 330 located between the upper and lower spinous processes 336, 338 (FIG. 20), increases, thereby distracting the spinous processes. It is noted that the wedges 332, 334 include saddle 340, 342, which receiving the spinous processes 336, 338. These saddles have the advantages as described hereinabove.

The first or second wedges 332, 334 have a mating arrangement which includes a channel 344 and a projection of 346 which can be urged into the channel in order to lock the wedges 332, 334 together. The channel 334 is undercut in order to keep the projection from separating therefrom. Further, as in other devices described herein, a detent can be located in one of the channel and the projection, with a complimentary recess in the other of the channel and the projection. Once these two snap together, the wedges are prevented from sliding relative to the other in the channel 344.

While the above embodiment was described with respect to wedges, the wedges could also have been designed substantially as cones with all the same features and advantages.

Figure 21:
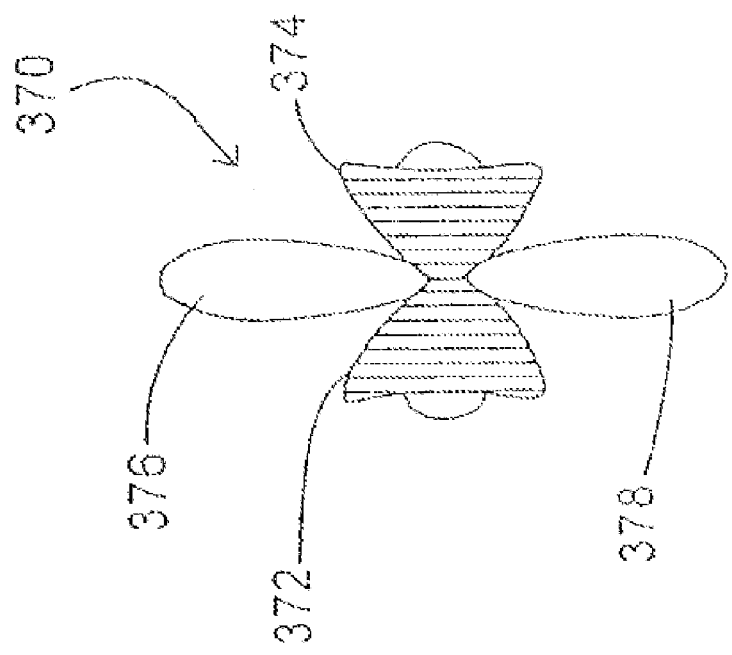
FIGS. 21 and 22 depict still a further embodiment of the present invention.
Figure 22:
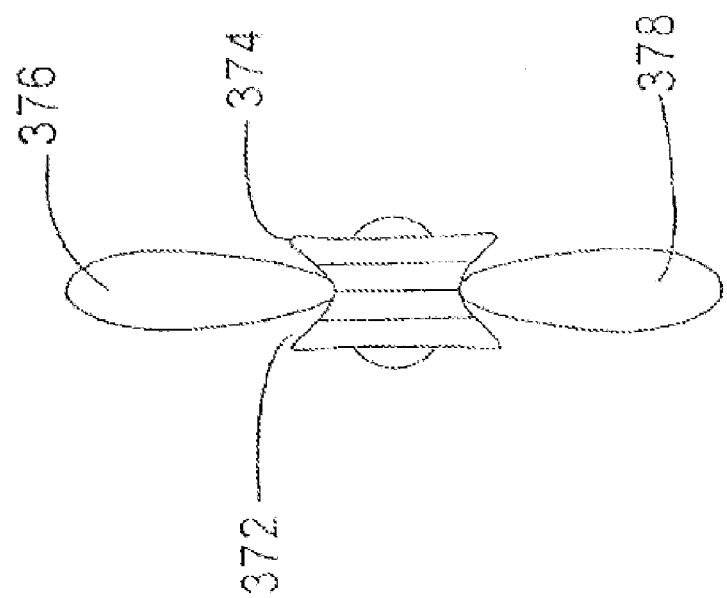

The implant 370 is comprised of first and second distraction cone 372, 374. These cones are made of a flexible material. The cones are positioned on either side of the spinous processes 376, 378 as shown in FIG. 21. Using appropriate tool as shown hereinabove, the distraction cones 372, 374 are urged together. As they are urged together, the cones distract the spinous processes as shown in FIG. 22. Once this has occurred, an appropriate screw or other type of fastening mechanism 380 can be used to maintain the position of the distraction cones 372, 374. The advantage of this arrangement is that the implant 370 is self-distracting and also that the implant, being flexible, molds about the spinous processes as shown in FIG. 22.

Figure 24:
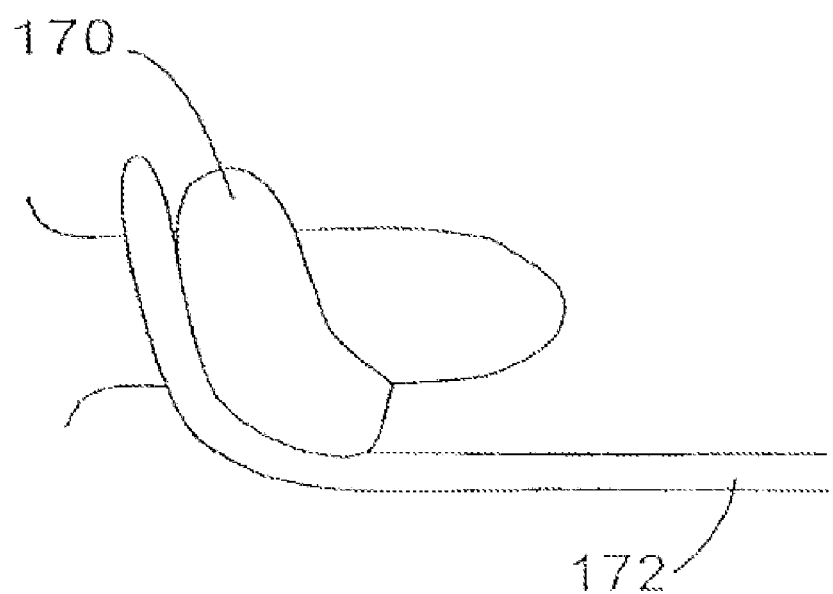
FIGS. 23, 24, and 25 depict another embodiment of the present invention.
Figure 23:
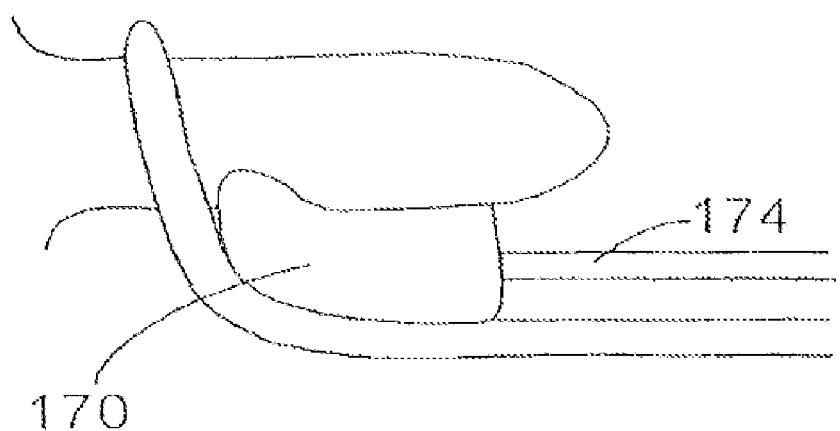

In FIGS. 23 and 24, another embodiment of the implant 170 is depicted. This implant is guided in place using an L-shaped guide 172 which can have a concave cross-section such as the cross-section 52 of retraction tool 50 in FIG. 6 in order to cradle and guide the implant 170 in position. Preferably a small incision would be made into the back of the patient and the L-shaped guide tool 172 inserted between the adjacent spinous processes. The implant 170 would be mounted on the end of insertion tool 174 and urged into position between the spinous processes. The act of urging the implant into position could cause the spinous processes to be further distracted if that is required. Prior to the insertion of the L-shaped guide tool 172, a distraction tool such as shown in FIG. 13 could be used to initially distract the spinous processes.

Implant 170 can be made of a deformable material so that it can be urged into place and so that it can somewhat conform to the shape of the upper and lower spinous processes. This deformable material would be preferably an elastic material. The advantage of such a material would be that the load forces between the implant and the spinous processes would be distributed over a much broader surface area. Further, the implant would mold itself to an irregular spinous process shape in order to locate the implant relative to spinous processes.

Figure 25:
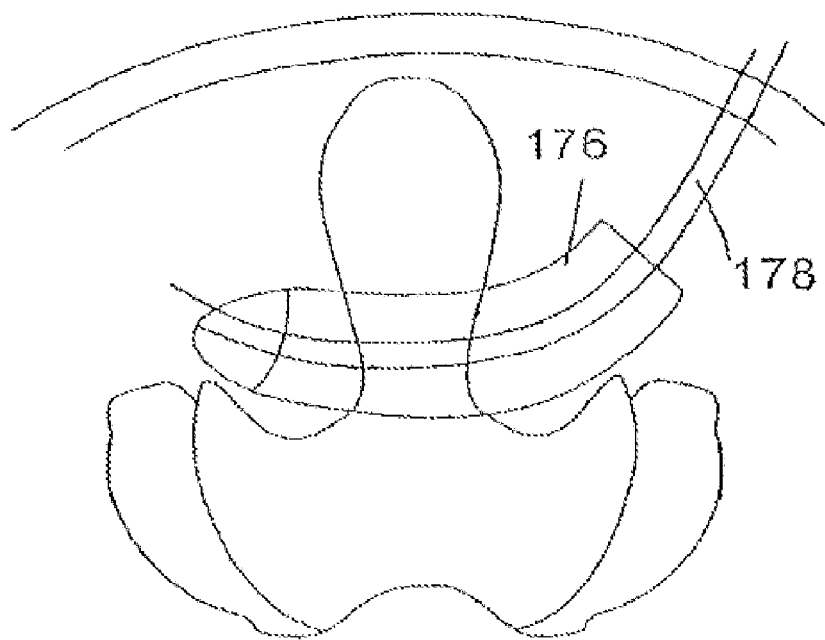
Figure 26:
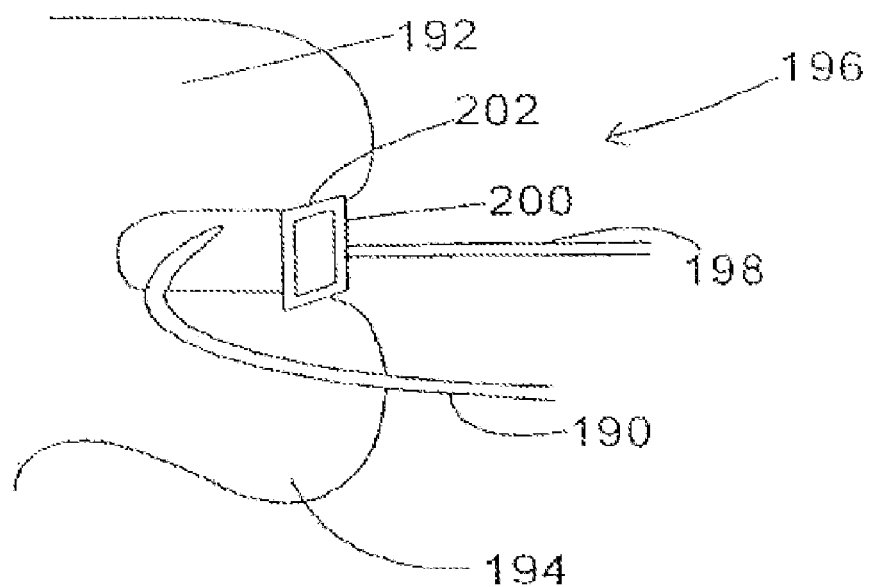
FIGS. 26, 27, and 28 depict another embodiment of the invention.

With respect to FIG. 25, this implant 176 can be inserted over a guide wire, guide tool or stylet 178. Initially, the guide wire 178 is positioned through a small incision to the back of the patient to a position between the adjacent spinous processes. After this has occurred, the implant is threaded over the guide wire 178 and urged into position between the spinous processes. This urging can further distract the spinous processes if further distraction is required. Once the implant is in place, the guide tool 178 is removed and the incision closed. The insertion tools of FIGS. 23 and 24 can also be used if desired.

Figure 28:
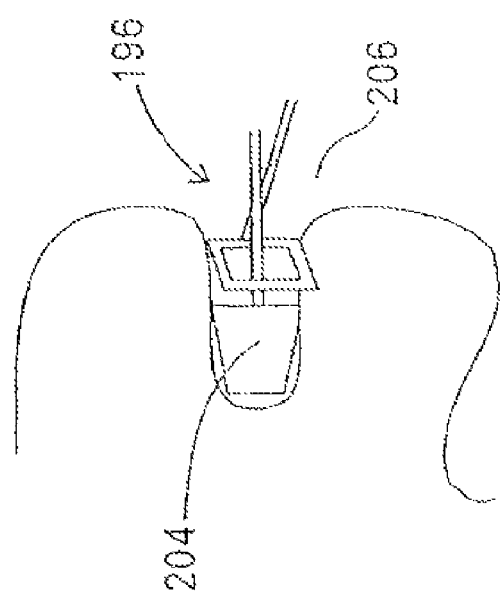
Figure 30:
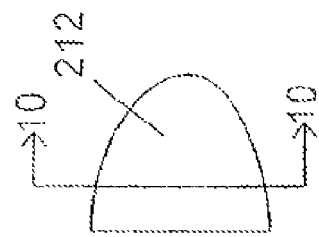
FIGS. 29 and 30 depict side elevational views of differently shaped implants of embodiments of the present invention.
Figure 27:
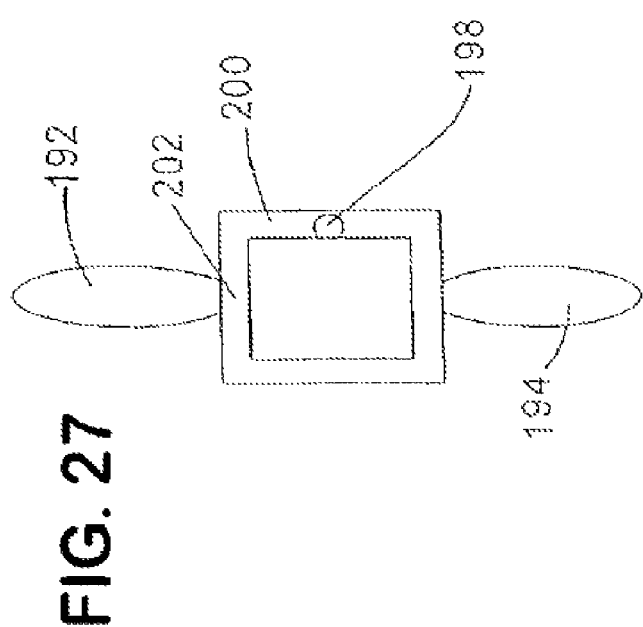
Figure 29:
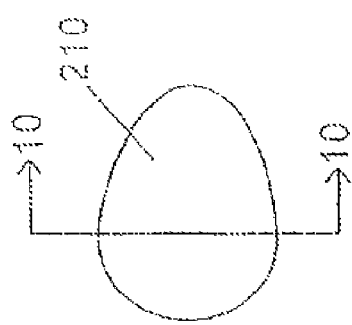

As can be seen in FIGS. 29 and 30, the implants 210, 212, can have different shapes when viewed from the side. These implants are similar to the above-referenced implants 58 (FIG. 8) and 204 (FIG. 28). These implants have cross-sections similar to that shown in FIG. 10 which includes saddles in order to receive and hold the adjacent spinous processes.

Figure 33:
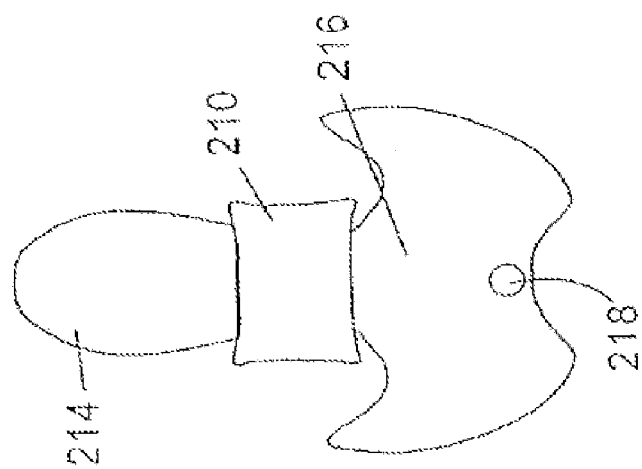
FIGS. 31, 32, and 33 depict various implant positions of an apparatus of the present invention.
Figure 32:
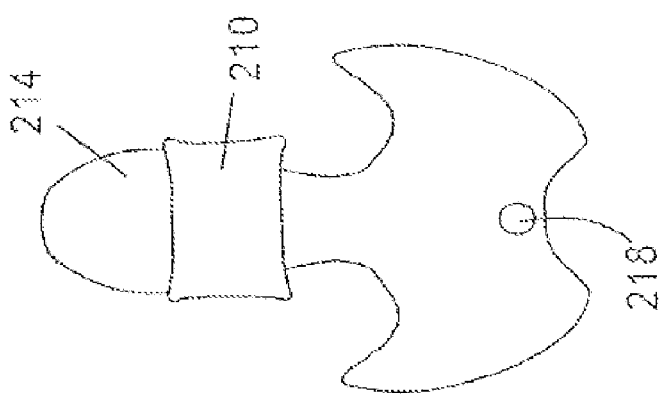
Figure 31:
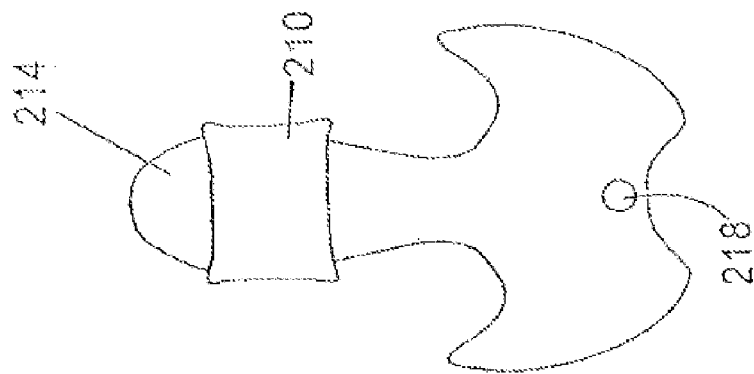

As can be seen in FIGS. 31, 32 and 33, these implants can be placed in different positions with respect to the spinous process 214. Preferably as shown in FIG. 33, the implant 210 is placed closest to the lamina 216. Being so positioned, the implant 210 is close to the instantaneous axis of rotation 218 of the spinal column, and the implant would experience least forces caused by movement of the spine. Thus, theoretically, this is the optimal location for the implant.

As can be seen in FIGS. 31 and 32, the implant can be placed midway along the spinous process (FIG. 32) and towards the posterior aspect of the spinous process (FIG. 31). As positioned shown in FIG. 31, the greatest force would be placed on the implant 210 due to a combination of compression and extension of the spinal column.

Another embodiment of the invention is shown in FIGS. 34 and 35. In these figures, implant 220 is comprised of a plurality of individual leaves 222 which are substantially V-shaped. The leaves include interlocking indentations or detents 224. That is, each leaf includes an indentation with a corresponding protrusion such that a protrusion of one leaf mates with an indentation of an adjacent leaf. Also associated with this embodiment is an insertion tool 226 which has a blunt end 228 which conforms to the shape of an individual leaf 222. For insertion of this implant into the space between the spinous processes as shown in FIG. 29, the insertion tool 226 first insert a single leaf 220. After that has occurred, the insertion tool then inserts a second leaf with the protrusion 224 of the second leaf snapping into corresponding indentation made by the protrusion 224 of the first leaf. This process would reoccur with third and subsequent leaves until the appropriate spacing between the spinous processes was built up. As can be seen in FIG. 29, the lateral edges 229 of the individual leaves 222 are slightly curved upwardly in order to form a saddle for receiving the upper and lower spinous processes.

The embodiments of FIGS. 36, 37 and 38 which include implants 230, 232, and 234 respectively, are designed in such a manner so the implant locks itself into position once it is properly positioned between the spinous processes. Implant 220 is essentially a series of truncated cones and includes a plurality of ever expanding steps 236. These steps are formed by the conical bodies starting with the nose body 238 followed there behind by conical body 240. Essentially, the implant 234 looks like a fir tree placed on its side.

The implant 230 is inserted laterally throughout the opening between upper and lower spinous processes. The first body 238 causes the initial distraction. Each successive conical body distracts the spinous processes a further incremental amount. When the desired distraction has been reached, the spinous processes are locked into position by steps 236. At this point, if desired, the initial nose body 238 of the implant and other bodies 240 can be broken, snapped or sawed off if desired in order to minimize the size of the implant 230. In order for a portion of the implant 230 to be broken or snapped off, the intersection between bodies such as body 238 and 240, which is intersection line 242, would be somewhat weaken with the appropriate removal of material. It is noted that only the intersection lines of the initial conical bodies need to be so weakened. Thus, intersection line 244 between the bodies which remain between the spinous processes would not need to be weaker, as there would be no intention that the implant would be broken off at this point.

FIG. 37 shows implant 232 positioned between upper and lower spinous processes. This implant is wedge-shaped or triangular shaped in cross-sectioned and includes bore pluralities 245 and 246. Through these bores can be placed locking pins 248 and 250. The triangular or wedged-shaped implant can be urged laterally between and thus distract the upper and lower spinous processes. Once the appropriate distraction is reached, pins 248, 250 can be inserted through the appropriate bores of the bore pluralities 245 and 246 in order to lock the spinous processes in a V-shaped valley formed by pins 248, 250 on the one hand and the ramped surface 233, 235 on the other hand.

Turning to FIG. 38, the implant 234 has a triangular-shaped or wedge-shaped body similar to that shown in FIG. 32. In this embodiment, tab 252, 254 are pivotally mounted to the triangular shaped body 234. Once the implant 234 is appropriately positioned in order to distract the spinous processes to the desired amount, the tabs 252, 254 rotate into position in order to hold the implant 234 in the appropriate position.

Figure 40:
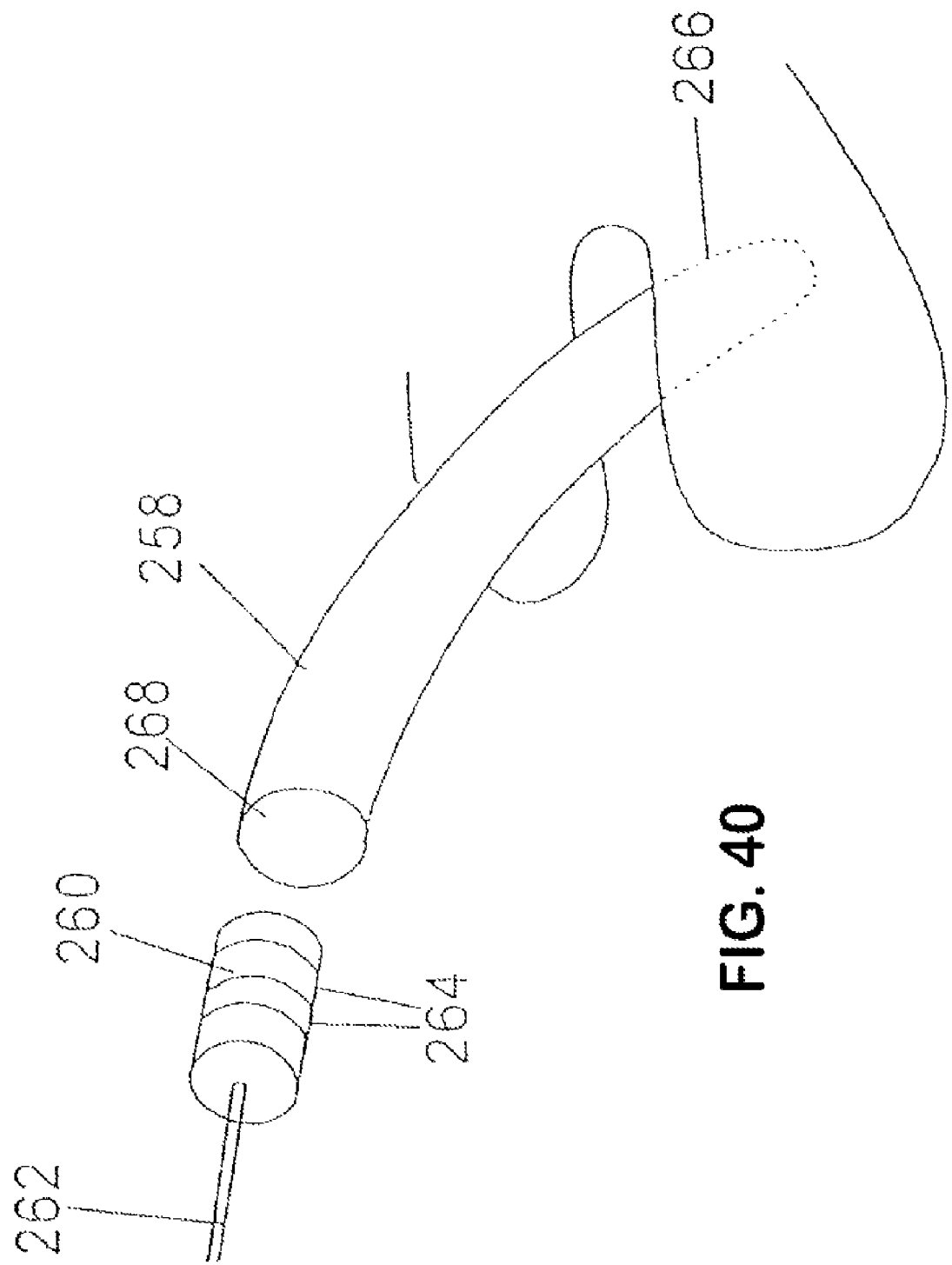

In the embodiment of FIGS. 39 and 40, cannula 258 is inserted through a small incision to a position between upper and lower spinous processes. Once the cannula is properly inserted, an implant 260 is pushed through the cannula 258 using an insertion tool 262. The implant 260 includes a plurality of ribs or indentation 264 that assist in positioning the implant 2260 relative to the upper and lower spinal processes.

Once the implant 260 is in position, the cannula 258 is withdrawn so that the implant 260 comes in contact with and wedges between the spinous processes. The cannula 258 is somewhat conical in shape with the nose end 266 being somewhat smaller than the distal end 268 in order to effect the insertion of the cannula into the space between the spinous processes.

Further, a plurality of cannula can be used instead of one, with each cannula being slightly bigger than one before. In the method of the invention, the first smaller cannula would be inserted followed by successively larger cannula being placed over the previous smaller cannula. The smaller cannula would then be withdrawn from the center of the larger cannula. Once the largest cannula is in place, and the opening of the skin accordingly expanded, the implant, which is accommodated by only the larger cannula, is inserted through the larger cannula and into position.

Figure 43:
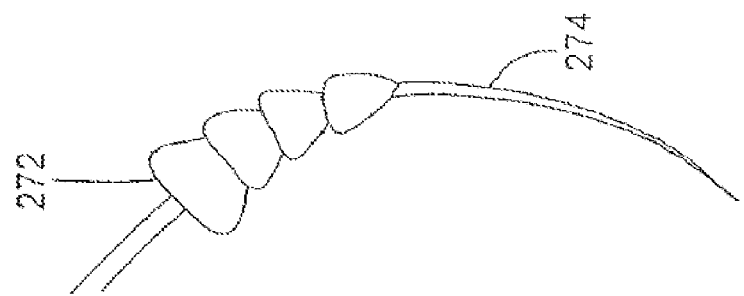
FIGS. 41, 42, and 43 depict yet further embodiments of an apparatus and method of the present invention.
Figure 42:
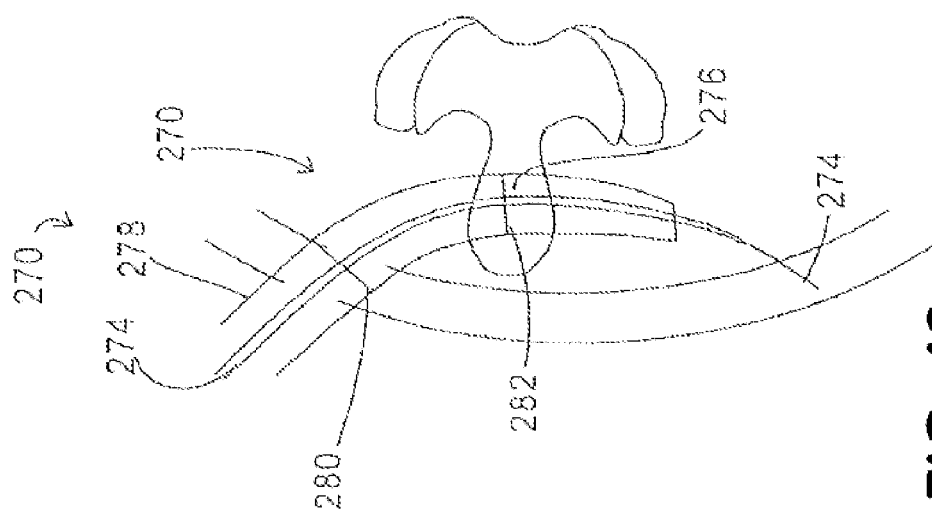
Figure 41:
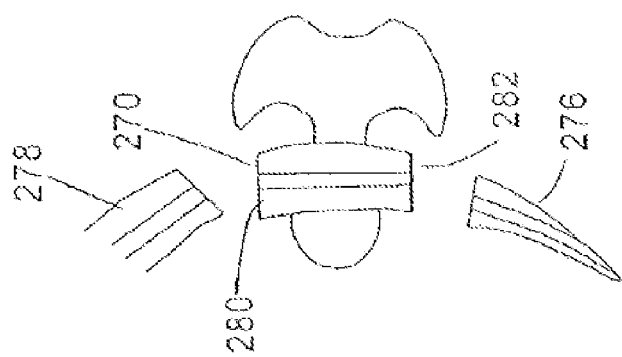
Figure 58:
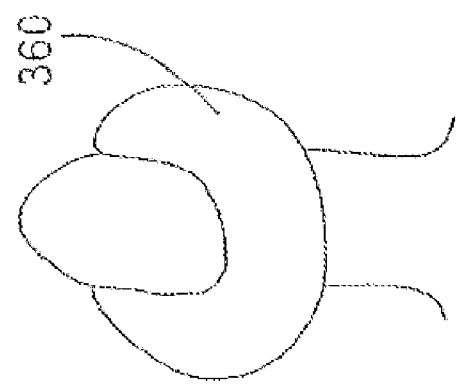
FIGS. 56, 57, and 58 depict yet a further apparatus and method of the invention.
Figure 57:
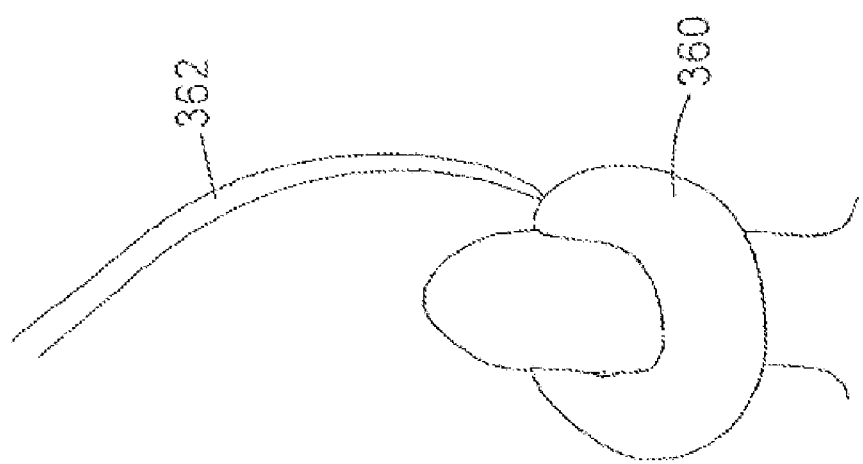

The precurved implant 270 in FIGS. 41 and 42, and precurved implant 272 in FIG. 43 have common introduction techniques which includes a guide wire, guide tool, or stylet 274. For both embodiments, the guide wire 274 is appropriately positioned through the skin of the patient and into the space between the spinous processes. After this is accomplished, the implant is directed over the guide wire and into position between the spinous processes. The precurved nature of the implant assist in (1) positioning the implant through a first small incision in the patient's skin on one side of the space between two spinous processes and (2) guiding the implant toward a second small incision in the patient's skin on the other side of the space between the two spinous processes. With respect to the implant 270, the implant includes a conical introduction nose 276 and a distal portion 278. As the nose 276 is inserted between the spinous processes, this causes distraction of the spinous processes. Break lines 280, 282 are established at opposite sides of the implant 270. Once the implant is properly positioned over the guide wire between the spinous processes, the nose portion 276 and the distal portion 278 can be broken off along the break lines, through the above two incisions, in order to leave the implant 270 in position.

Although only two break lines 280, 282 are depicted, multiple break lines can be provided on implant 270 so that the implant can continue to be fed over the guide wire 278 until the appropriate width of the implant 270 creates the desired amount of distraction. As described hereinabove, the break lines can be created by perforating or otherwise weakening the implant 270 so that the appropriate portions can be snapped or sawed off.

With respect to the precurved implant 272, this implant is similar in design to the implant 230 shown in FIG. 36. This implant 272 in FIG. 47, however, is precurved and inserted over a guide wire 274 to a position between the spinous processes. As with implant 230 in FIG. 43, once the appropriate level of this distraction has been reached and if desired, sections of the implant 272 can be broken, snapped or sawed off as described hereinabove in order to leave a portion of the implant wedged between the upper and lower spinous processes.

A further embodiment of the invention is shown in FIG. 44. This embodiment includes a combination insertion tool and implant 290. The insertion tool and implant 290 is in the shape of a ring which is hinged at point 292. The ring is formed by a first elongated and conically shaped member 294 and a second elongated and conically shaped member 296. Members 294 and 296 terminate in points and through the use of hinge 292 are aligned and meet. Through similar incisions on both sides of the spinous processes, first member and second member are inserted through the skins of the patient and are mated together between the spinous processes. After this has occurred, the implant 290 is rotated, for example clockwise, so that increasingly widening portions of the first member 292 are used to distract the first and second spinous processes. When the appropriate level of distraction has occurred, the remainder of the ring before and after the section which is located between the spinous processes can be broken off as taught hereinabove in order to maintain the desired distraction. Alternatively, with a small enough ring, the entire ring can be left in place with the spinous processes distracted.

In FIG. 45, the implant 300 is comprised of a plurality of rods or stylets 302 which are inserted between the upper and lower spinous processes. The rods are designed much as described hereinabove so that they may be broken, snapped or cut off. Once these are inserted and the appropriate distraction has been reached, the stylets are broken off and a segment of each stylet remains in order to maintain distraction of the spinous process.

Implant 310 of FIGS. 46 and 47 is comprised of a shape memory material which coils upon being released. The material is straightened out in a delivery tool 312. The delivery tool is in position between upper and lower spinous processes 314, 316. The material is then pushed through the delivery tool. As it is released from the delivery end 318 of the delivery tool, the material coils, distracting the spinous processes to the desired amount. Once this distraction has been achieved, the material is cut and the delivery tool removed.

As can be seen in FIG. 48, the implant 320 is delivered between upper and lower spinous processes 322 and 324, by delivery tool 326. Once the implant 320 is in place between the spinous processes, the delivery tool is given a 90.degree. twist so that the implant goes from the orientation as shown in FIG. 49, with longest dimension substantially perpendicular to the spinous processes, to the orientation shown in FIG. 50 where the longest dimension is in line with and parallel to the spinous processes. This rotation causes the desired distraction between the spinous processes. Implant 320 includes opposed recesses 321 and 323 located at the ends thereof. Rotation of the implant 320 causes the spinous processes to become lodged in these recesses.

Alternatively, the insertion tool 326 can be used to insert multiple implants 320, 321 into the space between the spinous processes 322, 324 (FIG. 51). Multiple implants 320, 321 can be inserted until the appropriate amount of distraction is built up. It is to be understood in this situation that one implant would lock to another implant by use of, for example, a channel arrangement wherein a projection from one of the implants would be received into and locked into a channel of the other implant. Such a channel arrangement is depicted with respect to the other embodiment.

The embodiment of FIGS. 52 through 55b is comprised of a fluid-filled dynamic distraction implant 350. This implant includes a membrane 352 which is placed over pre-bent insertion rod 354 and then inserted through an incision on one side of the spinous process 356. The bent insertion rod, with the implant 350 thereover, is guided between appropriate spinous processes. After this occurs, the insertion rod 354 is removed leaving the flexible implant in place. The implant 350 is then connected to a source of fluid (gas, liquid, gel and the like) and the fluid is forced into the implant causing it to expand as shown in FIG. 54, distracting the spinal processes to the desired amount. Once the desired amount of distraction has occurred, the implant 350 is closed off as is shown in FIG. 55a. The implant 350 being flexible, can mold to the spinous processes which may be of irregular shape, thus assuring positioning. Further, implant 350 acts as a shock absorber, damping forces and stresses between the implant and the spinous processes.

A variety of materials can be used to make the implant and the fluid which is forced into the implant. By way of example only, viscoelastic substances such as methylcellulose, or hyaluronic acid can be used to fill the implant. Further, materials which are initially a fluid, but later solidify, can be inserted in order to cause the necessary distraction. As the materials solidify, they mold into a custom shape about the spinous processes and accordingly are held in position at least with respect to one of two adjacent spinous processes. Thus, it can be appreciated that using this embodiment and appropriate insertion tools the implant can be formed about one spinous process in such a manner that the implant stays positioned with respect to that spinous process (FIG. 55b). With such an embodiment, a single implant can be used as an extension stop for spinous process located on either side, without restricting flexion of the spinal column.

It is to be understood that many of the other implants disclosed herein can be modified so that they receive a fluid in order to establish and maintain a desired distraction such in the manner as implant 350 receives a fluid.

Figure 56:
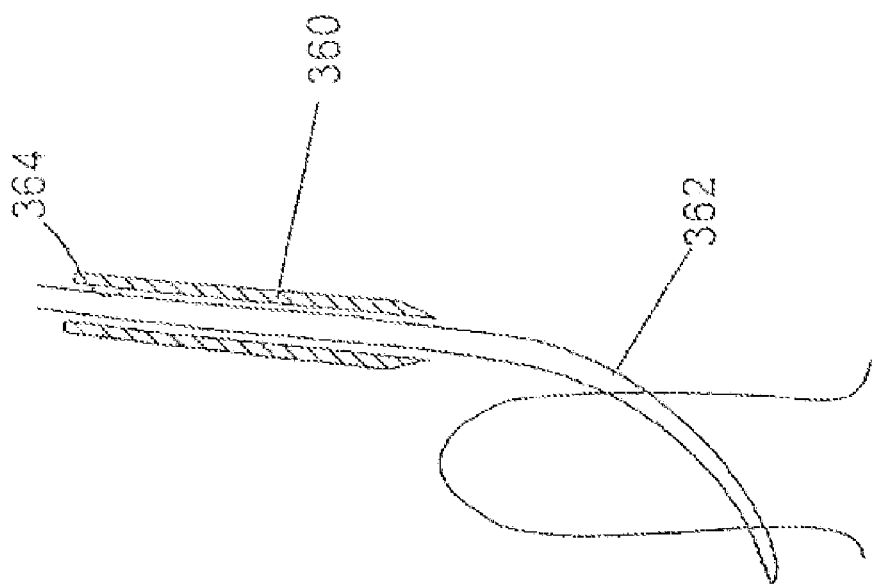

The implant 360 as shown in FIG. 56 is comprised of a shape memory material such as a plastic or a metal. A curved introductory tool 362 is positioned between the appropriate spinous processes as described hereinabove. Once this has occurred, bore 364 of the implant is received over the tool. This act can cause the implant to straighten out. The implant is then urged into position and thereby distracts the spinous processes. When this has occurred, the insertion tool 362 is removed, allowing the implant to assume its pre-straightened configuration and is thereby secured about one of the spinous processes. Such an arrangement allows for an implant that is an extension stop and does not inhibit flexion of the spinous column. Alternatively, the implant can be temperature sensitive. That is to say that the implant would be more straightened initially, but become more curved when it was warmed by the temperature of the patient's body.

In this embodiment, the implant 380 is comprised of a plurality of interlocking leaves 382. Initially, a first leaf is positioned between opposed spinous processes 384, 386. Then subsequently, leafs 382 are interposed between the spinous processes until the desired distraction has been built up. The leaves are somewhat spring-like in order to absorb the shock and can somewhat conform to the spinous processes.

The implant 390 of FIG. 61 includes the placement of shields 392, 394 over adjacent spinous processes 396, 398. The shields are used to prevent damage to the spinous processes. These shields include apertures which receives a self-tapping screw 4400, 402. In practice, the shields are affixed to the spinous processes and the spinous processes are distracted in the appropriate amount. Once this has occurred, a rod 404 is used to hold the distracted position by being screwed into each of the spinous processes through the aperture in the shields using the screws as depicted in FIG. 61.

Figure 62:
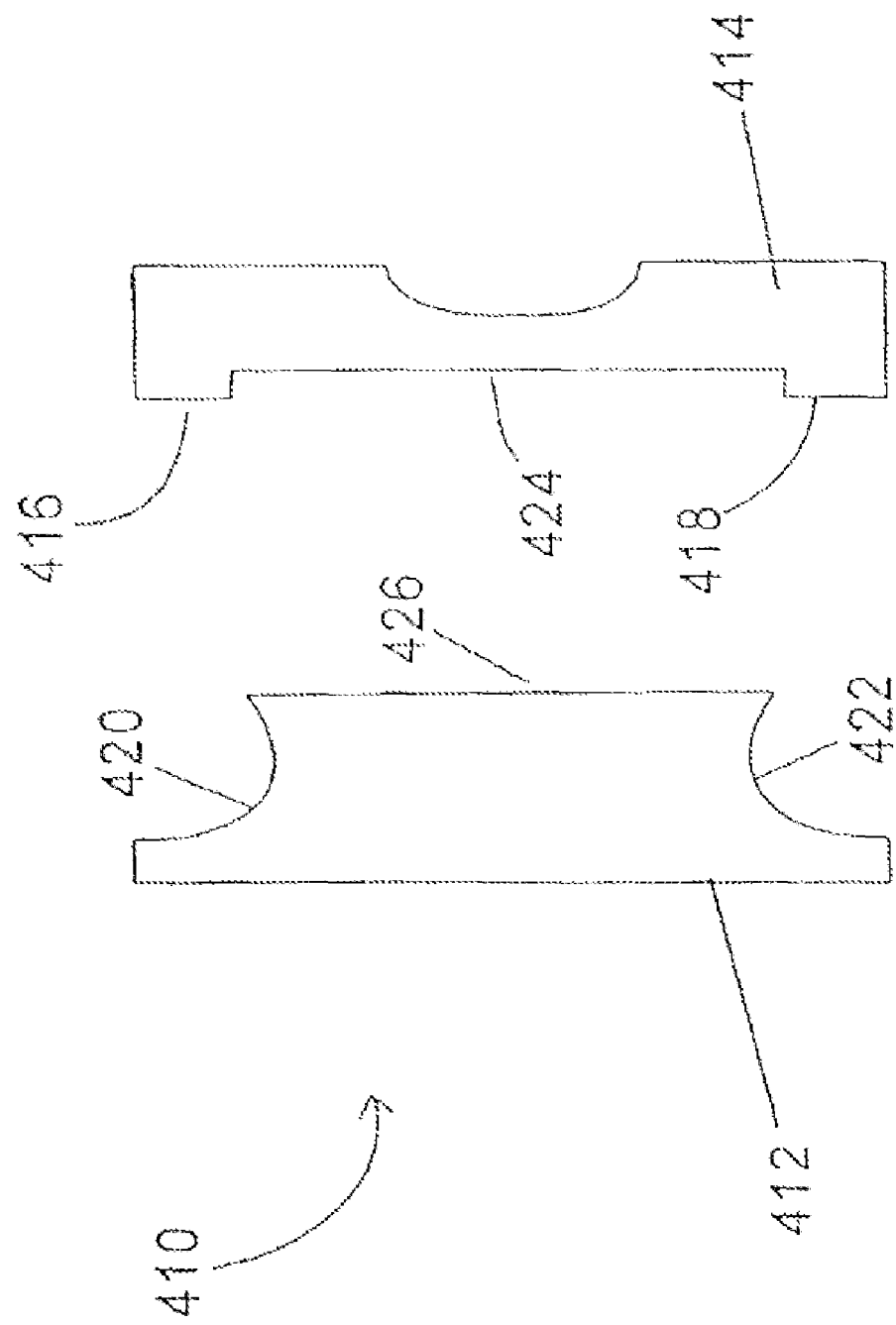
FIGS. 62 and 63 depict yet another embodiment of the present invention.
Figure 63:
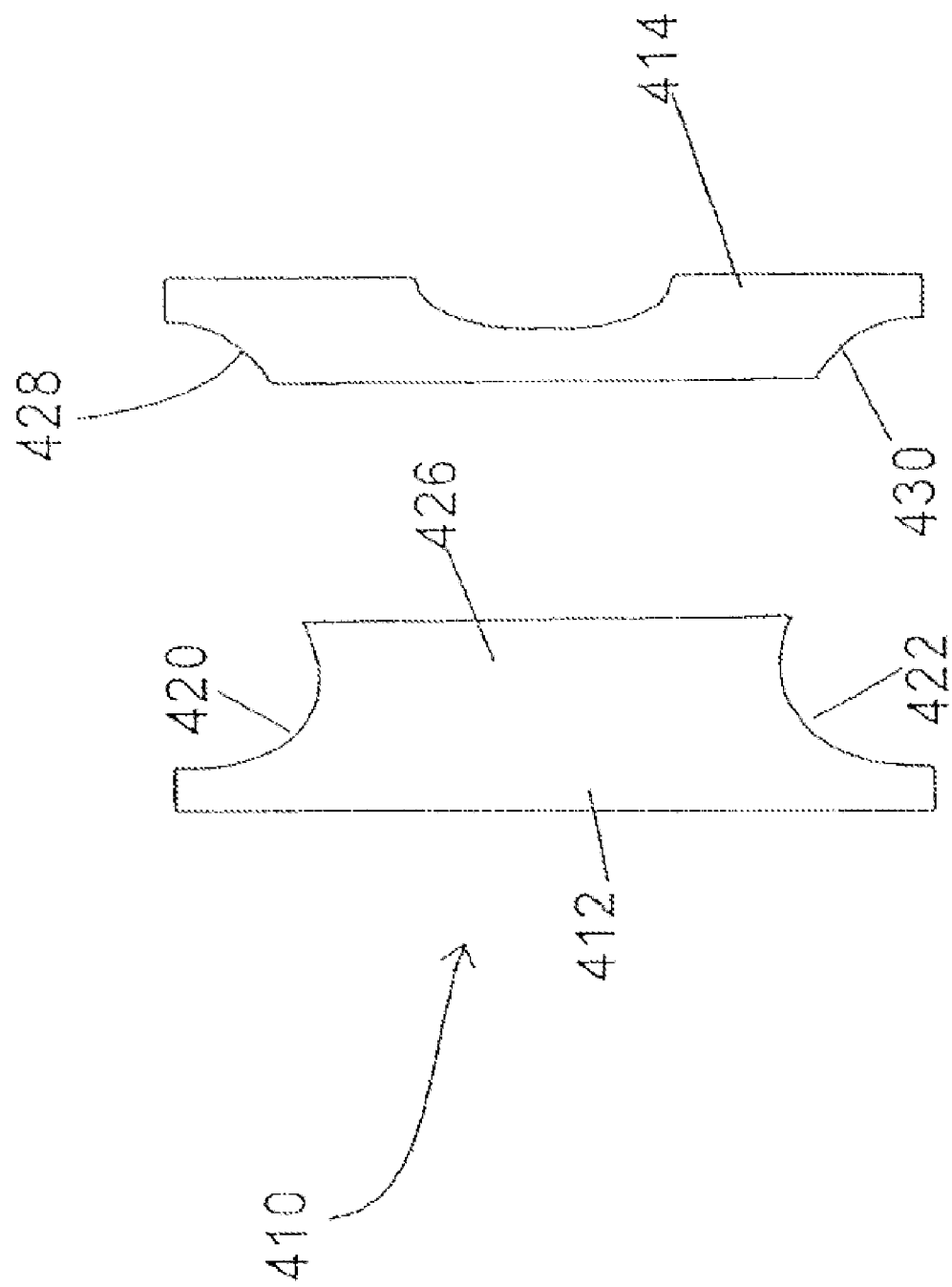

Implant 410 of FIGS. 62, 63 is comprised of first and second members 412, 414 which can be mated together using an appropriate screw and threaded bore arrangement to form the implant 410. Main member 412 and mating member 414 form implant 410. Accordingly, the implant 410 would have a plurality of members 414 for use with a standardized first member 412. FIGS. 62 and 64 show different types of mating members 414. In FIG. 62, the mating member 414 includes projections 416 and 418 which act like shims. These projections are used to project into the space of saddles 420, 422 of the first member 412. These projections 416, 418 can be of varying lengths in order to accommodate different sizes of spinous processes. A groove 424 is placed between the projections 416, 418 and mates with an extension 426 of the first member 412.

As shown in FIG. 63, the projections of the embodiment shown in FIG. 62 are removed and recesses 428, 430 are substituted therefor. These recesses expand the area of the saddles 420, 422 in order to accommodate larger spinous processes.

The embodiments of FIGS. 64, 65 and 66 are similar in design and concept to the embodiment of FIGS. 62 and 63. In FIG. 64, the implant 500 includes the first and second members 502, 504. These members can be secured together with appropriate screws or other fastening means as taught in other embodiments. Implant 500 includes first and second saddles 506, 508 which are formed between the ends of first and second members 502, 504. These saddles 506, 508 are used to receive and cradle the adjacent spinous processes. As can be seen in FIG. 64, each saddle 506, 508 is defined by a single projection or leg 510, 512, which extends from the appropriate first and second members 502, 504. Unlike the embodiment found in FIGS. 62 and 63, each of the saddles is defined by only a single leg as the ligaments and other tissues associated with the spinous processes can be used to ensure that the implant is held in an appropriate position. With the configuration of FIG. 64, it is easier to position the implant relative to the spinous processes as each saddle is defined by only a single leg and thus the first and second members can be more easily worked into position between the various tissues.

In the embodiment of FIG. 65, the implant 520 is comprised of a single piece having saddles 522 and 524. The saddles are defined by a single leg 526, 528 respectively. In order for this implant 520 to be positioned between the spinous processes, an incision is made between lateral sides of adjacent spinous processes. The single leg 526 is directed through the incision to a position adjacent to an opposite lateral side of the spinous process with the spinous process cradled in the saddle 522. The spinous processes are then urged apart until saddle 524 can be pivoted into position into engagement with the other spinous process in order to maintain the distraction between the two adjacent spinous processes.

The embodiment of FIG. 66 is similar to that of FIG. 65 with an implant 530 and first and second saddles 532 and 534. Associated with each saddle is a tether 536, 538 respectively. The tethers are made of flexible materials known in the trade and industry and are positioned through bores in the implant 530. Once appropriately positioned, the tethers can be tied off. It is to be understood that the tethers are not meant to be used to immobilize one spinous process relative to the other, but are used to guide motion of the spinous processes relative to each other so that the implant 530 can be used as an extension stop and a flexion non-inhibitor. In other words, the saddles 532, 534 are used to stop spinal column backward bending and extension. However, the tethers do not inhibit forward bending and spinal column flexion.

Figure 68:
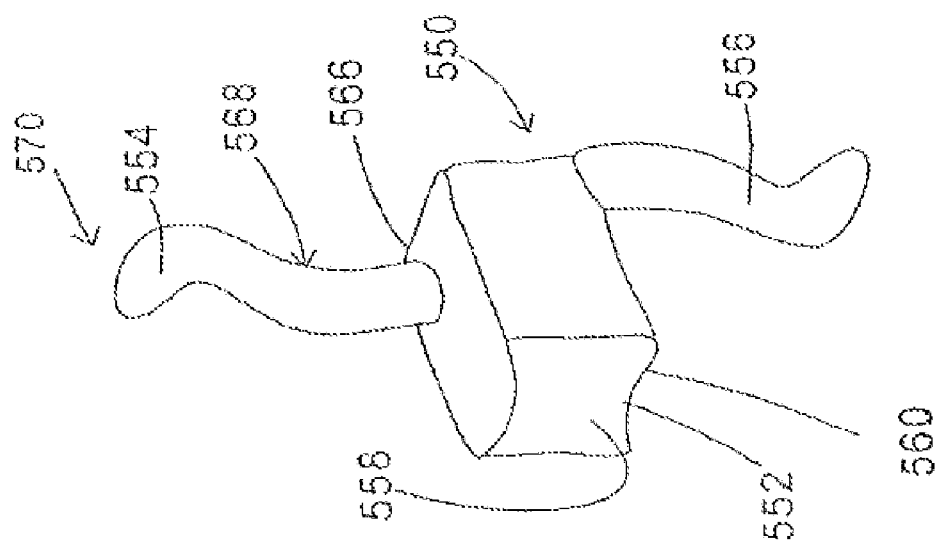
FIGS. 67 and 68 depict yet another embodiment of the present invention.
Figure 67:
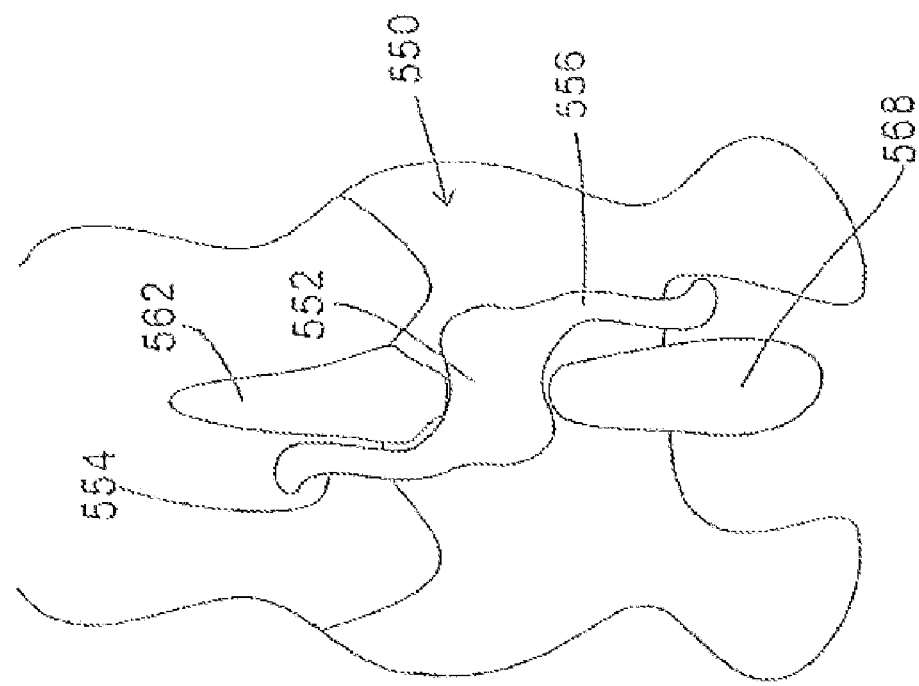

The implant 550 is Z-shaped and includes a central body 552 and first and second arms 554, 556, extending in opposite directions therefrom. The central body 552 of the implant 550 includes first and second saddles 558 and 560. The first and second saddles 558 and 560 would receive upper and lower spinous processes 562, 568. The arms 554, 556 are accordingly located adjacent the distal end 566 (FIG. 68) of the central body 552. The first and second arms 554, 556, act to inhibit forward movement, migration or slippage of the implant 550 toward the spinal canal and keep the implant in place relative to the first and second spinal processes. This prevents the implant from pressing down on the ligamentum flavum and the dura. In a preferred embodiment, the central body would have a height of about 10 mm with each of the arms 554, 556 have a height of also about 10 mm. Depending on the patient, the height of the body could vary from about less than 10 mm to about greater than 24 mm. As can be seen in FIGS. 67 and 68, the first and second arms 554, 556 are additionally contoured in order to accept the upper and lower spinous processes 556, 558. In particular, the arms 554, 556 as can be seen with respect to arm 554 have a slightly outwardly bowed portion 568 (FIG. 68) with a distal end 570 which is slightly inwardly bowed. This configuration allows the arm to fit about the spinous process with the distal end 570 somewhat urged against the spinous process in order to guide the motion of the spinous process relative to the implant. These arms 554, 556 could if desired to be made more flexible than the central body 552 by making arms 554, 556 thin and/or with perforations, and/or other material different than that of the central body 550. As with the last embodiment, this embodiment can be urged into position between adjacent spinous processes by directing an arm into a lateral incision so that the central body 552 can be finally positioned between spinous processes.

Figure 71:
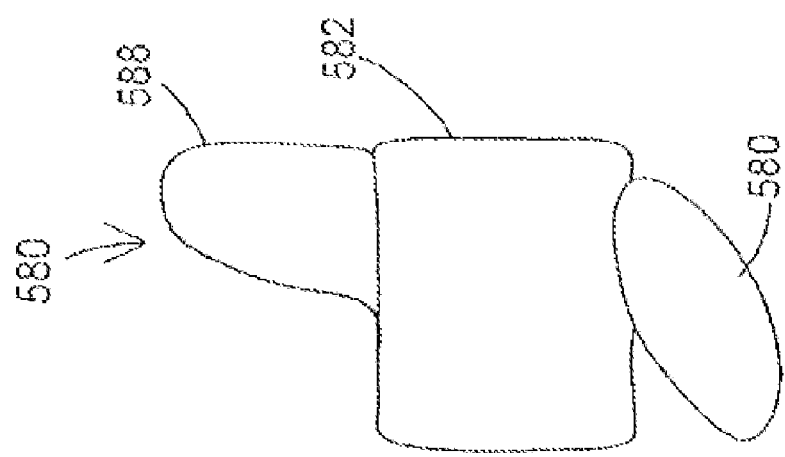
Figure 70:
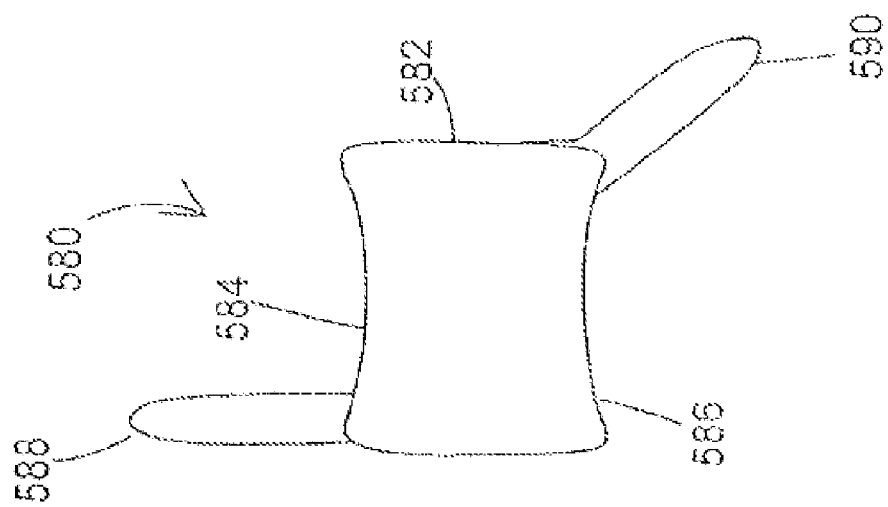
Figure 69:
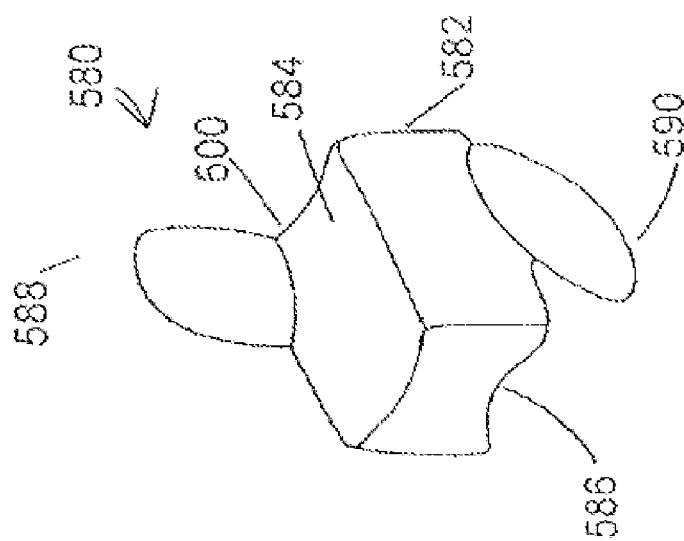

FIGS. 69, 70 and 71 are perspective front, end, and side views of implant 580 of the invention. This implant includes a central body 582 which has first and second saddles 584, 586 for receiving adjacent spinous processes. Additionally, the implant 580 includes first and second arms 588 and 590. The arms, as with the past embodiment, prevent forward migration or slippage of the implant toward the spinal canal. First arm 588 projects outwardly from the first saddle 584 and second arm 590 projects outwardly from the second saddle 586. In a preferred embodiment, the first arm 588 is located adjacent to the distal end 600 of the central body 582 and proceeds only partly along the length of the central body 582. The first arm 588 is substantially perpendicular to the central body as shown in FIG. 70. Further, the first arm 588, as well as the second arm 590, is anatomically rounded.

The second arm 590, projecting from second saddle 586, is located somewhat rearward of the distal end 600, and extends partially along the length of the central body 582. The second arm 590 projects at a compound angle from the central body 582. As can be seen in FIGS. 70 and 71, the second arm 590 is shown to be at about an angle of 45.degree. from the saddle 586 (FIG. 70). Additionally, the second arm 590 is at an angle of about 45.degree. relative to the length of the central body 580 as shown in FIG. 71. It is to be understood that other compound angles are within the spirit and scope of the invention as claimed.

In a preferred embodiment, the first and second arms 588, 590 have a length which is about the same as the width of the central body 582. Preferably, the length of each arm is about 10 mm and the width of the central body is about 10 mm. However, the bodies with the widths of 24 mm and greater are within the spirit and scope of the invention, along with first and second arms ranging from about 10 mm to greater than about 24 mm. Further, it is contemplated that the embodiment could include a central body having a width of about or greater than 24 mm with arms being at about 10 mm.

It is to be understood that the embodiment of FIGS. 69, 70 and 71 as well as the embodiment of FIGS. 67 and 68 are designed to preferably be positioned between the L4-L5 and the L5-S1 vertebral pairs. The embodiment of FIGS. 69, 70, 71 is particularly designed for the L5-S1 position with the arms being designed to conform to the sloping surfaces found therebetween. The first and second arms are thus contoured so that they lie flat against the lamina of the vertebra which has a slight angle.

The embodiment of FIGS. 69, 70, and 71 as with the embodiment of FIGS. 67 and 68 is Z-shaped in configuration so that it may be inserted from one lateral side to a position between adjacent spinous processes. A first arm, followed by the central body, is guided through the space between the spinous processes. Such an arrangement only requires that a incision on one side of the spinous process be made in order to successfully implant the device between the two spinous processes.

The implant 610 of FIG. 71a is similar to that immediately, above with the first arm 612 located on the same side of the implant as the second arm 614. The first and second saddle 616, 618 are slightly modified in that distal portion 620, 622 are somewhat flattened from the normal saddle shape in order to allow the implant to be positioned between the spinous processes from one side. Once in position, the ligaments and tissues associated with the spinous processes would hold the implant into position. Tethers also could be used if desired.

Figure 72:
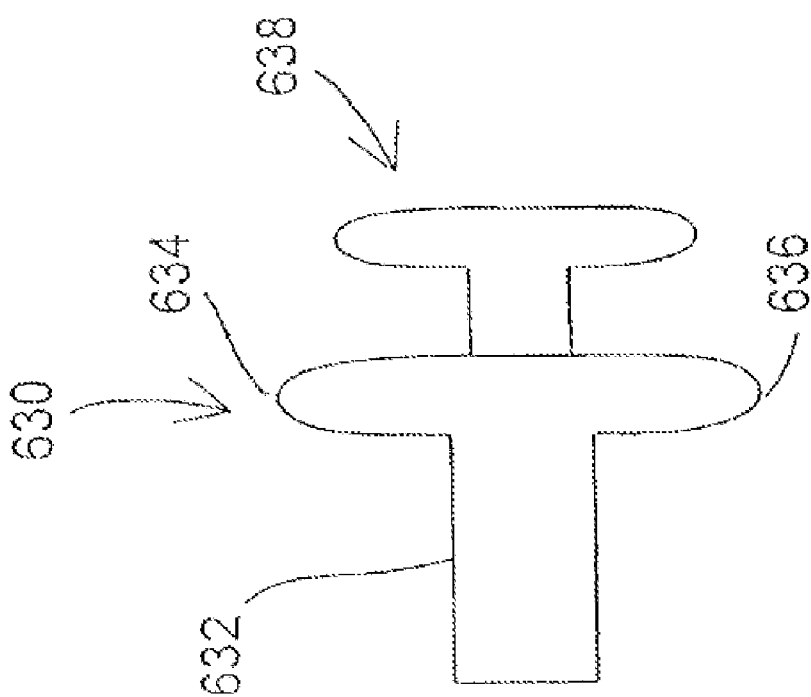
FIGS. 72 and 73 depict still another embodiment of the invention.
Figure 73:
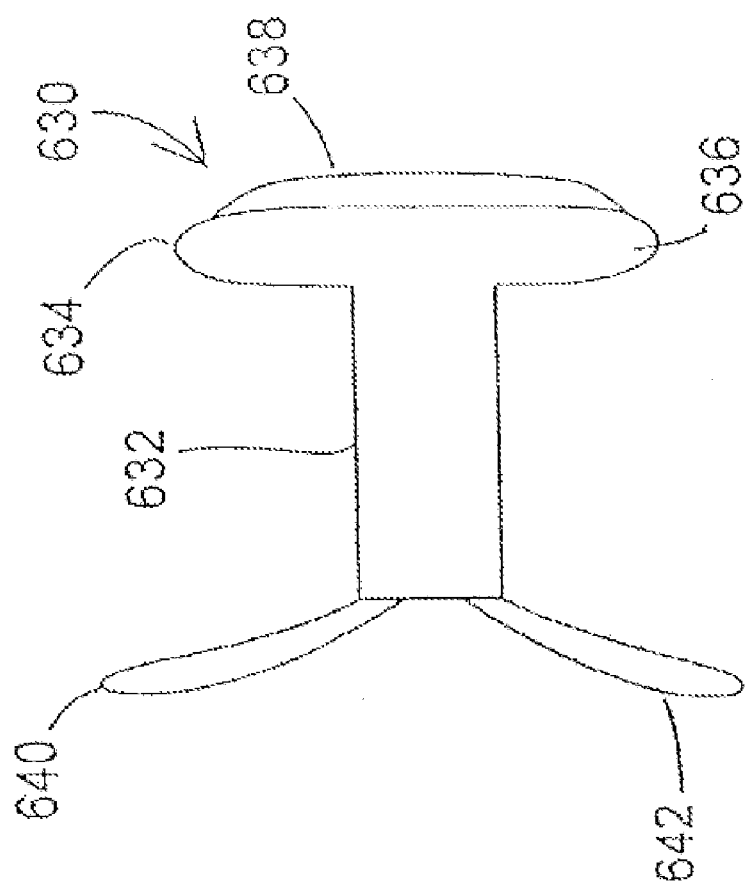

Implant 630 is also designed so that it can be inserted from one side of adjacent spinous processes. This insert 630 includes a central body 632 with the first and second arms 634, 636 extending on either side thereof. As can be seen in FIG. 72, a plunger 638 is positioned to extend from an end of the central body 632. As shown in FIG. 72, the plunger 638 is fully extended and as shown in FIG. 73, the plunger 638 is received within the central body 632 of the implant 630. With the plunger received into the implant 632, the third and fourth arms or hooks 640, 642 can extend outwardly from the central body 632. The third and fourth arms or hooks 640, 642 can be comprised of a variety of materials, such as for example, shape memory metal materials or materials which have a springy quality.

For purposes of positioning the implant 630 between adjacent spinous processes, the plunger 638 is pulled outwardly as shown in FIG. 72. The central body 632 is then positioned between adjacent spinous processes and the plunger 638 is allowed to move to the position of FIG. 73 so that the third and fourth arms 640, 642 can project outwardly from the central body 632 in order to hold the implant 630 in position between the spinous processes.

Plunger 638 can be spring biased to the position as shown in FIG. 73 or can include detents or other mechanisms which lock it into that position. Further, the third and fourth arms themselves, as deployed, can keep the plunger in the position as shown in FIG. 73.

Figure 74:
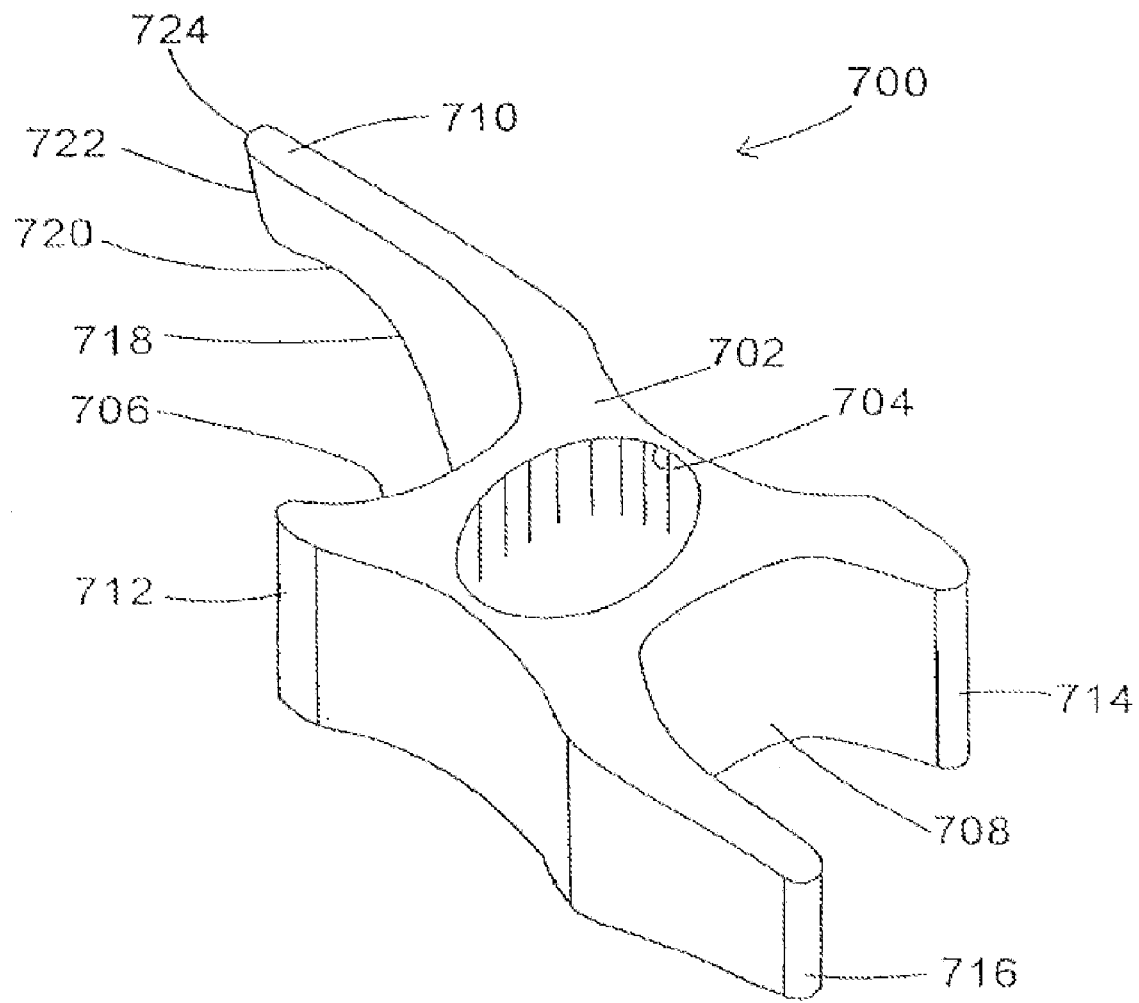
FIGS. 74, 75, 76, 77, and 78 depict still other embodiments of the invention.
Figure 75:
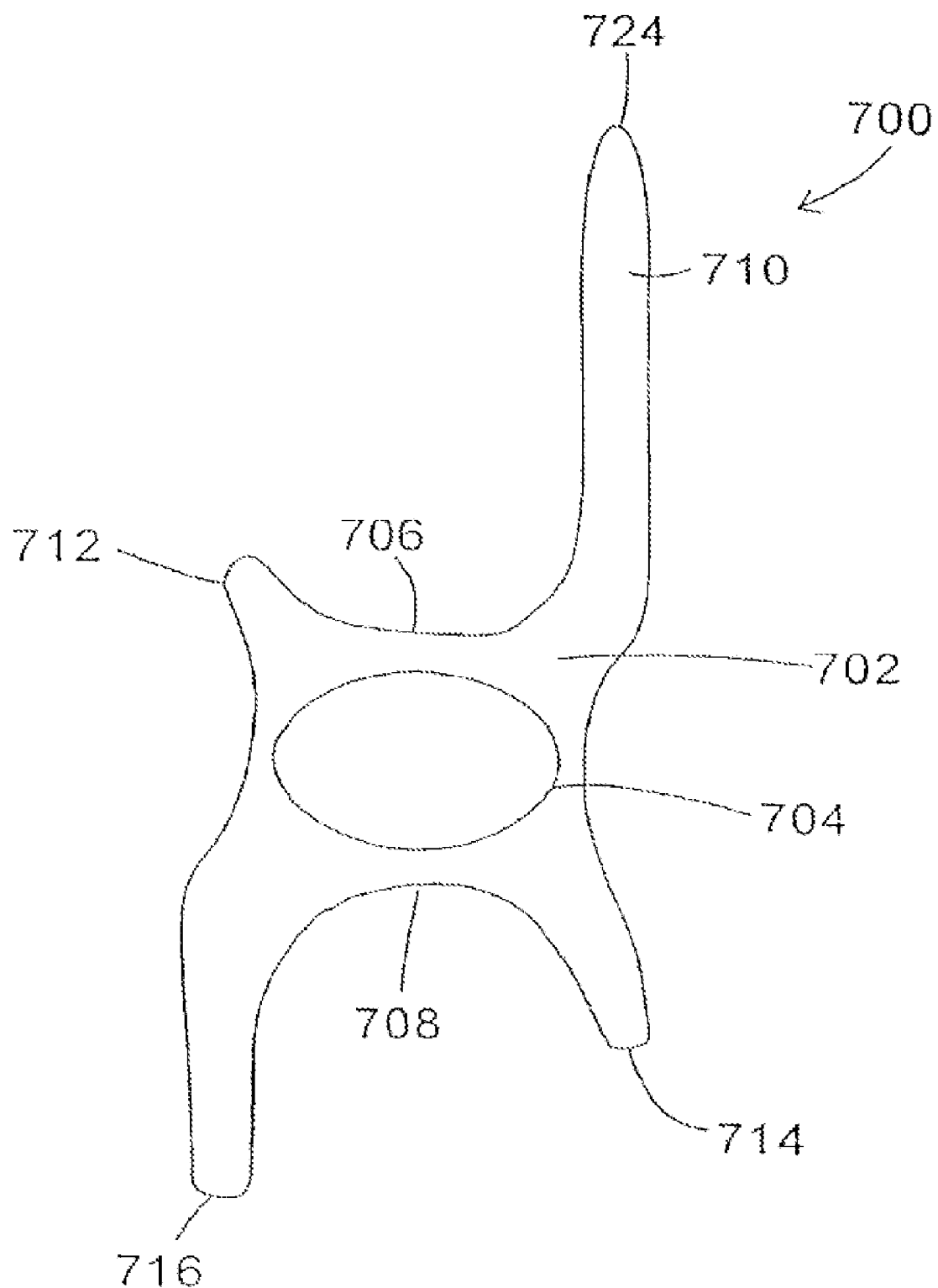
Figure 76:
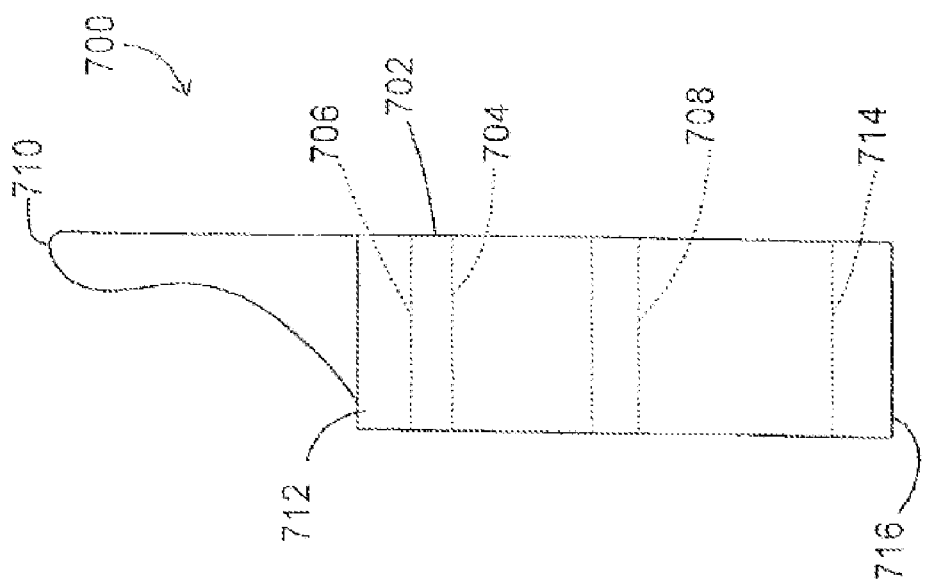

Other embodiments of the invention are shown in FIGS. 74 through 78. FIGS. 74, 75 and 76 disclose implant 700. Implant 700 is particularly suited for implantation between the L4-L5 and L5-S1 vertebra. As can be seen in FIG. 74, the implant 700 includes a central body 702 which has a bore 704 provided therein. Bore 704 is used in order to adjust the modulus of elasticity of the implant so that it is preferably approximately two times the anatomical load placed on the vertebra in extension. In other words, the implant 700 is approximately two times stiffer than the normal load placed on the implant. Such an arrangement is made in order to ensure that the implant is somewhat flexible in order to reduce potential resorption of the bone adjacent to the implant. Other modulus values can be used and be within the spirit of the invention.

Implant 700 includes first and second saddle 706, 708 which are used to receive and spread the load from the upper and lower spinous processes. The saddle 706 is defined by first and second arms 710 and 712. The second saddle 708 is defined by third and fourth arms 714 and 716. As can be seen in FIG. 74, the first arm 710, in a preferred embodiment, is approximately two times the length of the body 702 with the second arm being approximately less than a quarter length of the body. Third arm 714 is approximately one times the length of the body 702 with the fourth arm 716 being, in this preferred embodiment, approximately one and a half times the length of the body 702. The arms are designed in such a way that the implant (1) can be easily and conveniently inserted between the adjacent spinous processes, (2) will not migrate forwardly toward the spinal canal, and (3) will hold its position through flexion and extension as well as lateral bending of the spinal column.

Figure 77:
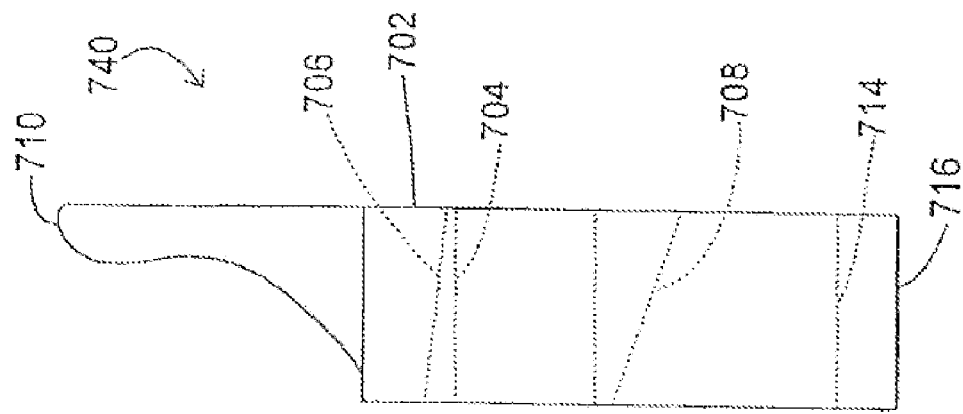
Figure 78:
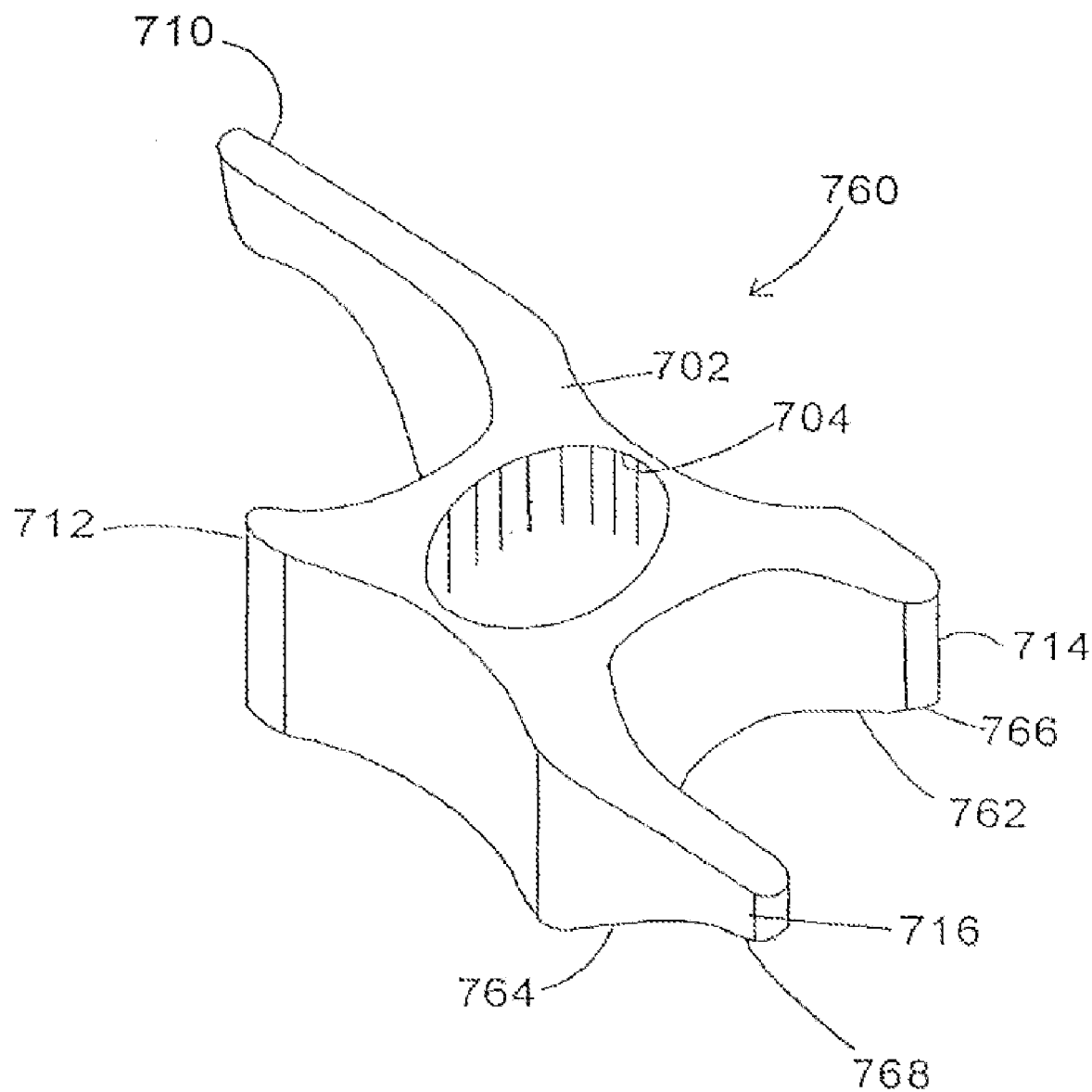
Figure 81:
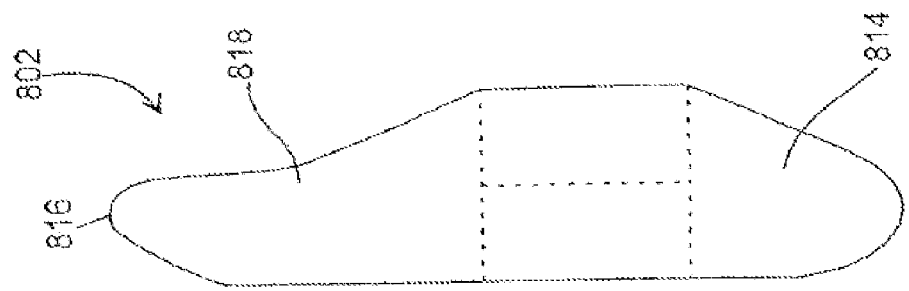

First arm 710 is in addition designed to accommodate the shape of the vertebra. As can be seen in FIG. 74, the first arm 710 becomes narrower as it extends away from the body 702. The first arm 710 includes a sloping portion 718 followed by a small recess 720 ending in a rounded portion 722 adjacent to the end 724. This design is provided to accommodate the anatomical form of for example the L4 vertebra. It is to be understood that these vertebra have a number of surfaces at roughly 30.degree. angles and that the sloping surfaces of this embodiment and the embodiments shown in FIGS. 77 and 78 are designed to accommodate these surfaces. These embodiments can be further modified in order to accommodate other angles and shapes.

The second arm 712 is small so that it is easy to insert between the spinous processes, yet still define the saddle 706. The fourth arm 716 is larger than the third arm 714, both of which are smaller than the first arm 710. The third and fourth arms are designed so that they define the saddle 706, guide the spinous processes relative to the implant 700 during movement of the spinal column, and yet are of a size which makes the implant easy to position between the spinous processes.

The procedure, by way of example only, for implanting the implant 700 can be to make an incision laterally between two spinous processes and then initially insert first arm 710 between the spinous processes. The implant and/or appropriate tools would be used to distract the spinous processes allowing the third leg 714 and the central body 702 to fit through the space between the spinous processes. The third leg 714 would then come to rest adjacent the lower spinous processes on the opposite side with the spinous processes resting in the first and second saddle 706, 708. The longer fourth leg 716 would then assist in the positioning of the implant 700.

FIG. 77 includes an implant 740 which is similar to implant 700 and thus have similar numbering. The saddle 706, 708 of implant 740 have been cantered or sloped in order to accommodate the bone structure between, by way of example, the L4-L5 and the L5-S1 vertebra. As indicated above, the vertebra in this area have a number of sloping surfaces in the range of about 30.degree. Accordingly, saddle 706 is sloped at less than 30.degree. and preferably about 20.degree. while saddle 708 is sloped at about 30.degree. and preferably more than 30.degree.

The implant 760 as shown in FIG. 78 is similar to implant 700 in FIG. 74 and is similarly numbered. Implant 760 includes third and fourth legs 714, 716 which have sloping portions 762, 764 which slope toward ends 766, 768 of third and fourth arm 714, 716 respectively. The sloping portions accommodate the form of the lower vertebra against which they are positioned. In the preferred embodiment, the sloping portions are of about 30.degree. However, it is to be understood that sloping portions which are substantially greater and substantially less than 30.degree. can be included and be within the spirit and scope of the invention.

Figure 80:
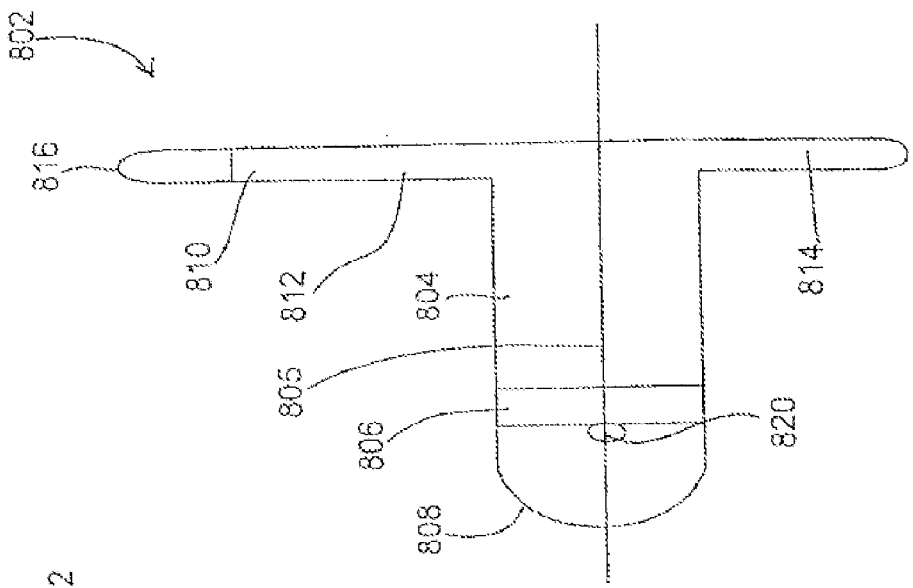
Figure 79:
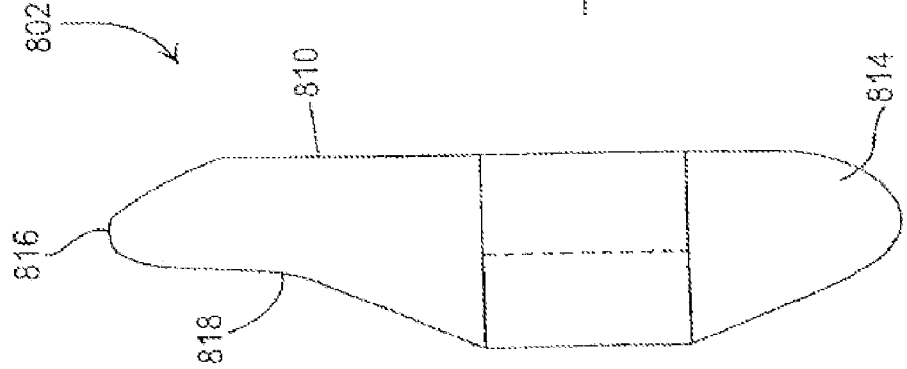
Figure 86:
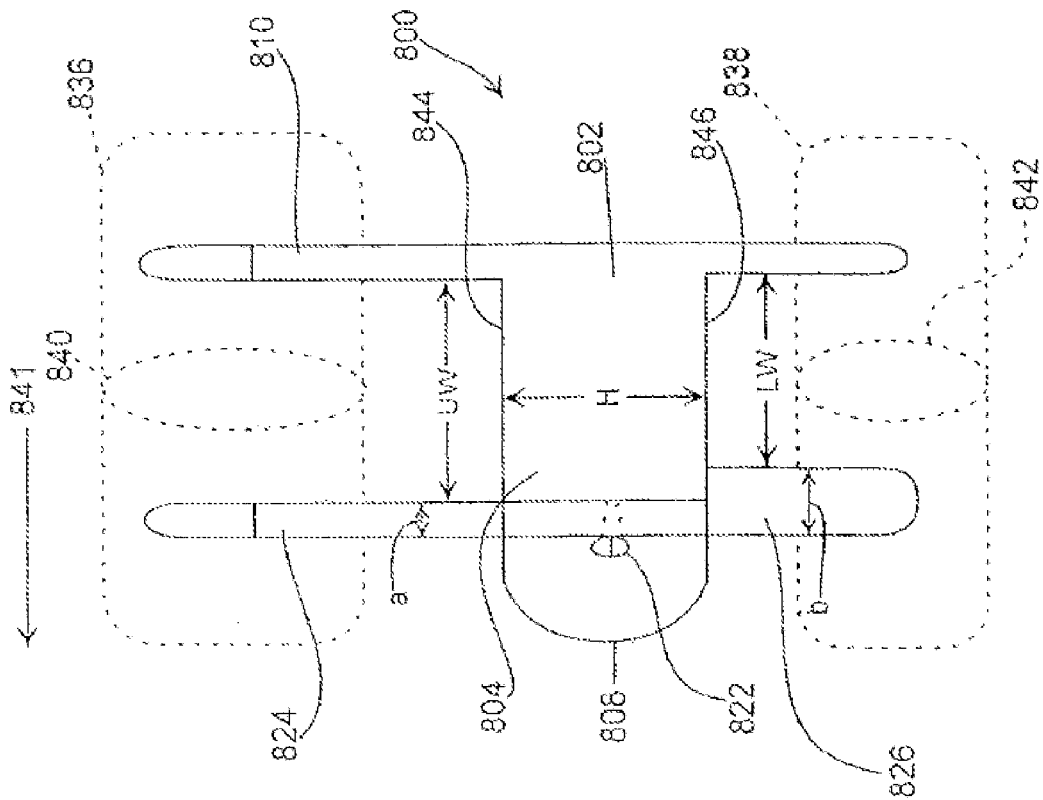

Another embodiment of the invention is shown in FIGS. 79-87 and includes implant 800 (FIG. 86). Implant 800 includes a distracting unit 802 which is shown in left side, plan, and right side views of FIGS. 79, 80 and 81. A perspective view of the distraction unit is shown in FIG. 84. The distracting unit as can be seen in FIG. 80 includes a distracting body 804, with longitudinal axis 805, which body 804 has a groove 806 and a rounded or bulbous end 808 which assist in the placement of the distracting body between adjacent spinous process so that an appropriate amount of distraction can be accomplished. Extending from the distracting body 804 is a first wing 810 which in FIG. 80 is substantially perpendicular to the distracting body 804. Such wings which are not perpendicular to the body are within the spirit and scope of the invention. First wing 810 includes a upper portion 812 and a lower portion 814. The upper portion 810 (FIG. 79) includes a rounded end 816 and a small recess 818. The rounded end 816 and the small recess 818 in the preferred embodiment are designed to accommodate the anatomical form or contour of the L4 (for a L4-L5 placement) or L5 (for a L5-S1 placement) superior lamina of the vertebra. It is to be understood that the same shape or variations of this shape can be used to accommodate other lamina of any vertebra. The lower portion 814 is also rounded in order to accommodate in the preferred embodiment in order to accommodate the vertebrae. The distracting unit further includes a threaded bore 820 which in this embodiment accepts a set screw 822 (FIG. 86) in order to hold a second wing 824 (FIGS. 82, 83) in position as will be discussed hereinbelow.

The threaded bore 820 in this embodiment slopes at approximately 45.degree. angle and intersects the slot 806. With the second wing 824 in position, the set screw 822 when it is positioned in the threaded bore 820 can engage and hold the second wing 824 in position in the slot 806.

Figure 83A:
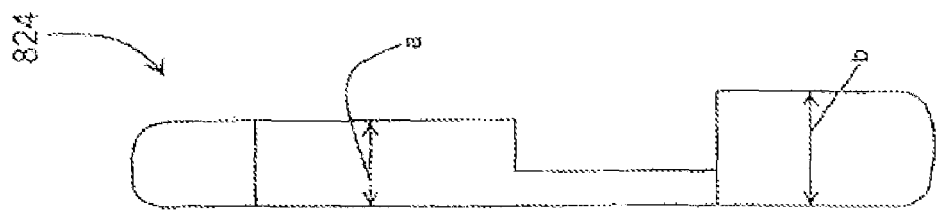
Figure 83:
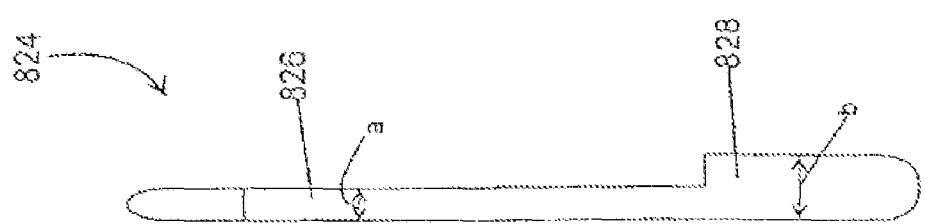
Figure 82:
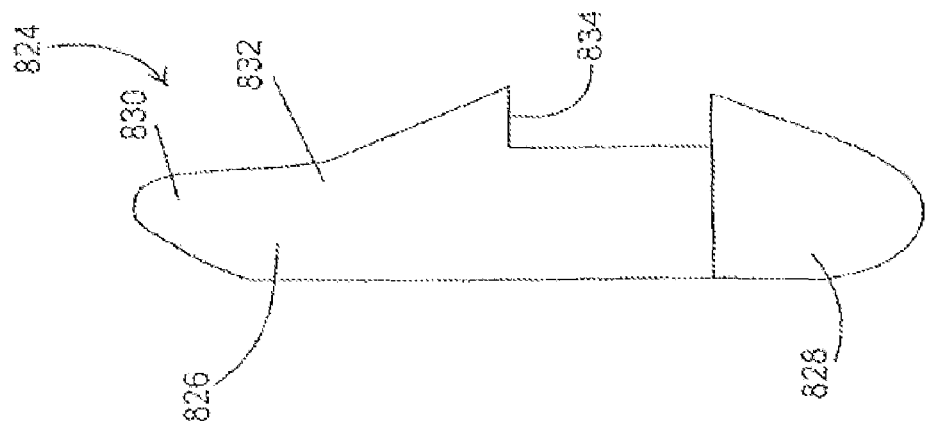

Turning to FIGS. 82, 83 and 85, left side, plan and perspective views of the second wing 824 are depicted. The second wing 824 is similar in design to the first wing. The second wing includes an upper portion 826 and a lower portion 828. The upper portion includes a rounded end 830 and a small recess 832. In addition, the second wing 824 includes a slot 834 which mates with the slot 806 of the distracting unit 802. The second wing 824 is the retaining unit of the present embodiment.

As can be seen in FIGS. 83 and 86, the second wing or retaining unit 824 includes the upper portion 826 having a first width "a" and the lower portion 828 having a second width "b". In the preferred embodiment, the second width "b" is larger than first width "a" due to the anatomical form or contour of the L4-L5 or L5-S1 laminae. As can be seen in FIG. 83a in second wing or retaining unit 824, the widths "a" and "b" would be increased in order to, as described hereinbelow, accommodate spinous processes and other anatomical forms or contours which are of different dimensions. Further, as appropriate, width "a" can be larger than width "b". Thus, as will be described more fully hereinbelow, the implant can include a universally-shaped distracting unit 802 with a plurality of retaining units 824, with each of the retaining units having different widths "a" and "b". During surgery, the appropriately sized retaining unit 824, width with the appropriate dimensions "a" and "b" can be selected to match to the anatomical form of the patient.

FIG. 86 depicts an assembled implant 800 positioned adjacent to upper and lower laminae 836, 838 (which are shown in dotted lines) of the upper and lower vertebrae. The vertebrae 836, 838 are essentially below the implant 800 as shown in FIG. 86. Extending upwardly from the vertebrae 836, 838, and between the first and second wings 810, 824, are the upper and lower spinous processes 840, 842. It is to be understood that in a preferred embodiment, the fit of the implant between the spinous processes can be such that the wings do not touch the spinous processes, as shown in FIG. 86, and be within the spirit and scope of the invention.

Figure 87:
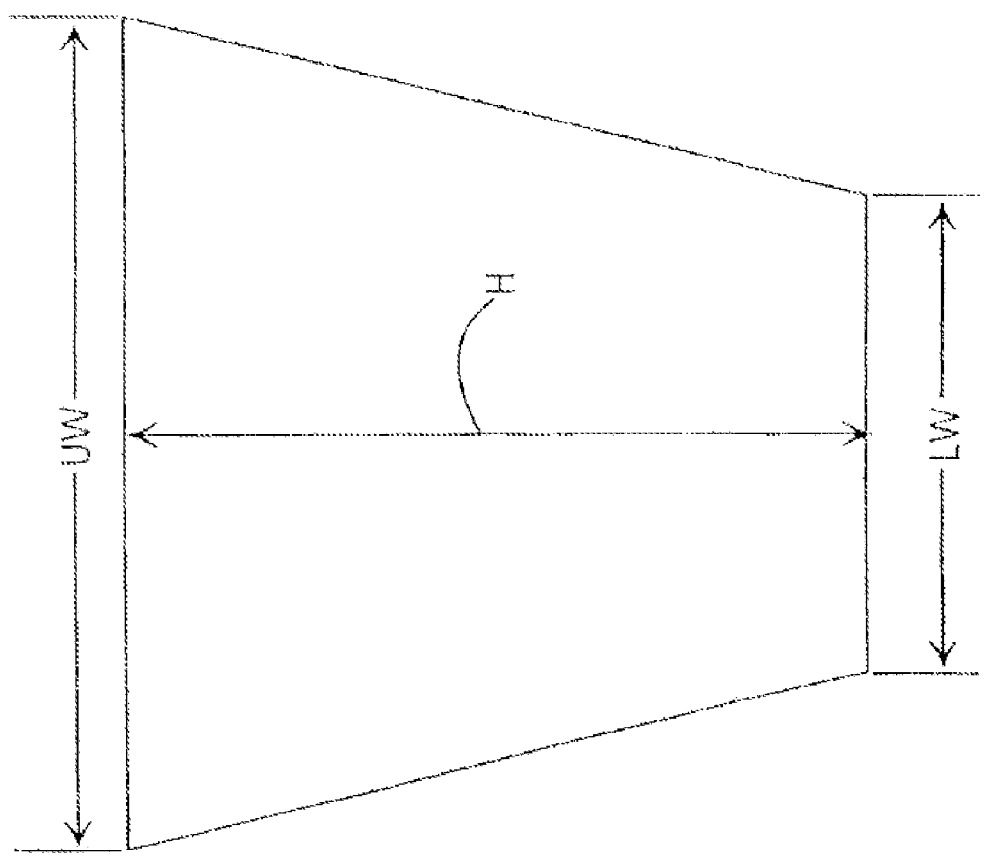
Figure 88:
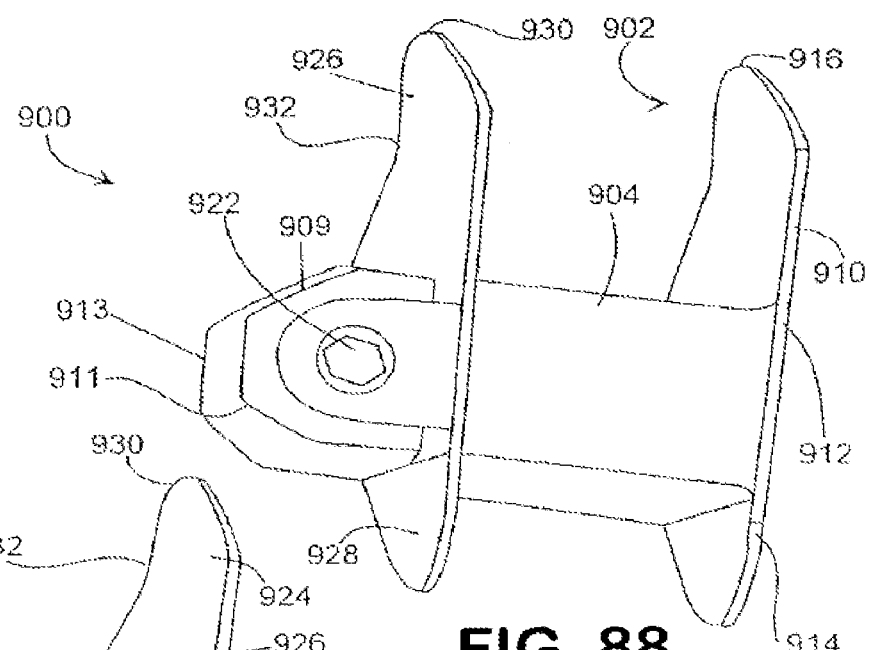
FIGS. 88, 89, 90, and 91 depict yet another embodiment of the present invention.

The implant 800 includes, as assembled, an upper saddle 844 and the lower saddle 846. The upper saddle 844 has an upper width identified by the dimension "UW". The lower saddle 846 has a lower width identified by the dimension "LW". In a preferred embodiment, the upper width is greater than the lower width. In other embodiments, the "UW" can be smaller than the "LW" depending on the anatomical requirements. The height between the upper and lower saddles 844, 846 is identified by the letter "h". These dimensions are carried over into FIG. 87 which is a schematic representation of the substantially trapezoidal shape which is formed between the upper and lower saddles. The table below gives sets of dimensions for the upper width, lower width, and height as shown in FIG. 87. This table includes dimensions for some variations of this embodiment.

TABLE

| Variation | 1 | 2 | 3 |
|---|---|---|---|
| Upper width | 8 | 7 | 6 |
| Lower width | 7 | 6 | 5 |
| Height | 10 | 9 | 8 |

For the above table, all dimensions are given in millimeters.

For purposes of surgical implantation of the implant 800 into a patient, the patient is preferably positioned on his side (arrow 841 points up from an operating table) and placed in a flexed (tucked) position in order to distract the upper and lower vertebrae.

In a preferred procedure, a small incision is made on the midline of the spinous processes. The spinous processes are spread apart or distracted with a spreader. The incision is spread downwardly toward the table, and the distracting unit 802 is preferably inserted upwardly between the spinous processes 840 and 842 in a manner that maintains the distraction of spinous processes. The distracting unit 802 is urged upwardly until the distracting or bulbous end 808 and the slot 806 are visible on the other wide of the spinous process. Once this is visible, the incision is spread upwardly away from the table and the retaining unit or second wing 824 is inserted into the slot 806 and the screw 822 is used to secure the second wing in position. After this had occurred, the incisions can be closed.

An alternative surgical approach requires that small incisions be made on either side of the space located between the spinous processes. The spinous processes are spread apart or distracted using a spreader placed through the upper incision. From the lower incision, the distracting unit 802 is preferably inserted upwardly between the spinous processes 840 and 842 in a manner that urges the spinous processes apart. The distracting unit 802 is urged upwardly until the distracting or bulbous end 808 and the slot 806 are visible through the second small incision in the patient's back. Once this is visible, the retaining unit or second wing 824 is inserted into the slot 806 and the screw 822 is used to secure the second wing in position. After this has occurred, the incisions can be closed.

The advantage of either of the above present surgical procedures is that a surgeon is able to observe the entire operation, where he can look directly down onto the spinous processes as opposed to having to view the procedure from positions which are to the right and to the left of the spinous processes. Generally, the incision is as small as possible and the surgeon is working in a bloody and slippery environment. Thus, an implant that can be positioned directly in front of a surgeon is easier to insert and assemble than an implant which requires the surgeon to shift from side to side. Accordingly, a top-down approach, as an approach along a position to anterior line is preferred so that all aspects of the implantation procedure are fully visible to the surgeon at all times. This aides in the efficient location of (i) the distracting unit between the spinous processes, (ii) the retaining unit in the distracting unit, and (iii) finally the set screw in the distracting unit.

Figure 80A:
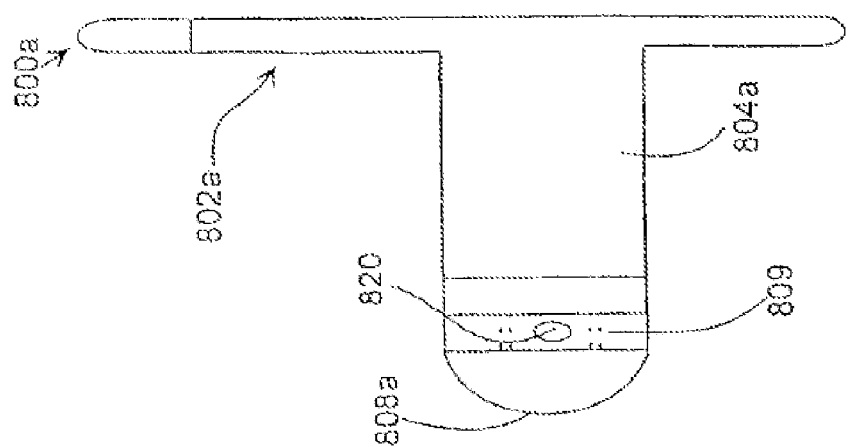

FIG. 80a shows an alternative embodiment of the distracting unit 802a. This distracting unit 802a is similar to distracting unit 802 in FIG. 80 with the exception that the bulbous end 808a is removable from the rest of the distracting body 804a as it is screwed into the threaded bore 809. The bulbous end 808a is removed once the distracting unit 802a is positioned in the patient in accordance with the description associated with FIG. 86. The bulbous end 808a can extend past the threaded bore 820 by about 1 cm in a preferred embodiment.

Another embodiment of the invention is shown in FIGS. 88, 89, 90 and 91. In this embodiment, the implant is identified by the number 900. Other elements of implant 900 which are similar to implant 800 are similarly numbered but in the 900 series. For example, the distracting unit is identified by the number 902 and this is in parallel with the distracting unit 802 of the implant 800. The distracting body is identified by the number 904 in parallel with the distracting body 804 of the implant 800. Focusing on FIG. 90, the distracting unit 902 is depicted in a perspective view. The distracting unit includes slot 906 which is wider at the top than at the bottom. The reason for this is that the wider upper portion of the slot 906, which is wider than the second wing 924 (FIG. 89), is used to allow the surgeon to easily place the second wing 924 into the slot 906 and allow the wedge-shaped slot 906 to guide the second wing 924 to its final resting position. As can be see in FIG. 91, in the final resting position, the largest portion of the slot 906 is not completely filled by the second wing 924.

The end 908 of implant 900 is different in that it is more pointed, having sides 909 and 911 which are provided at about 45.degree. angles (other angles, such as by way of example only, from about 30.degree. to about 60.degree. are within the spirit of the invention), with a small flat tip 913 so that the body 904 can be more easily urged between the spinous processes.

The distracting unit 902 further includes a tongue-shaped recess 919 which extends from the slot 906. Located in the tongue-shaped recess is a threaded bore 920.

Figure 89:
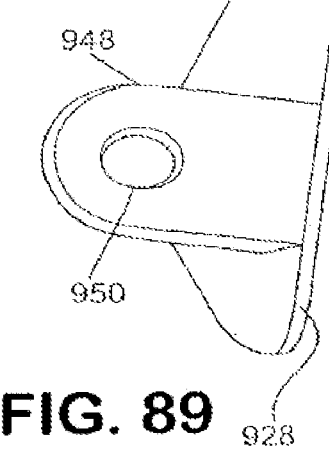
Figure 90:
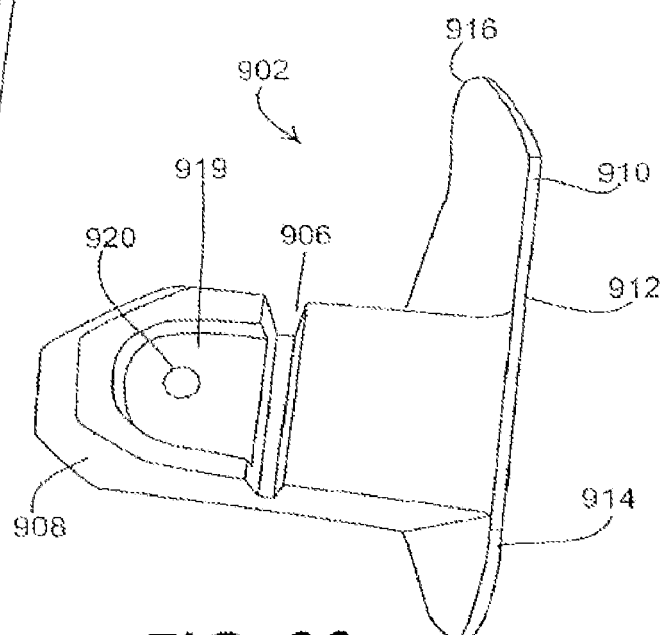
Figure 91:
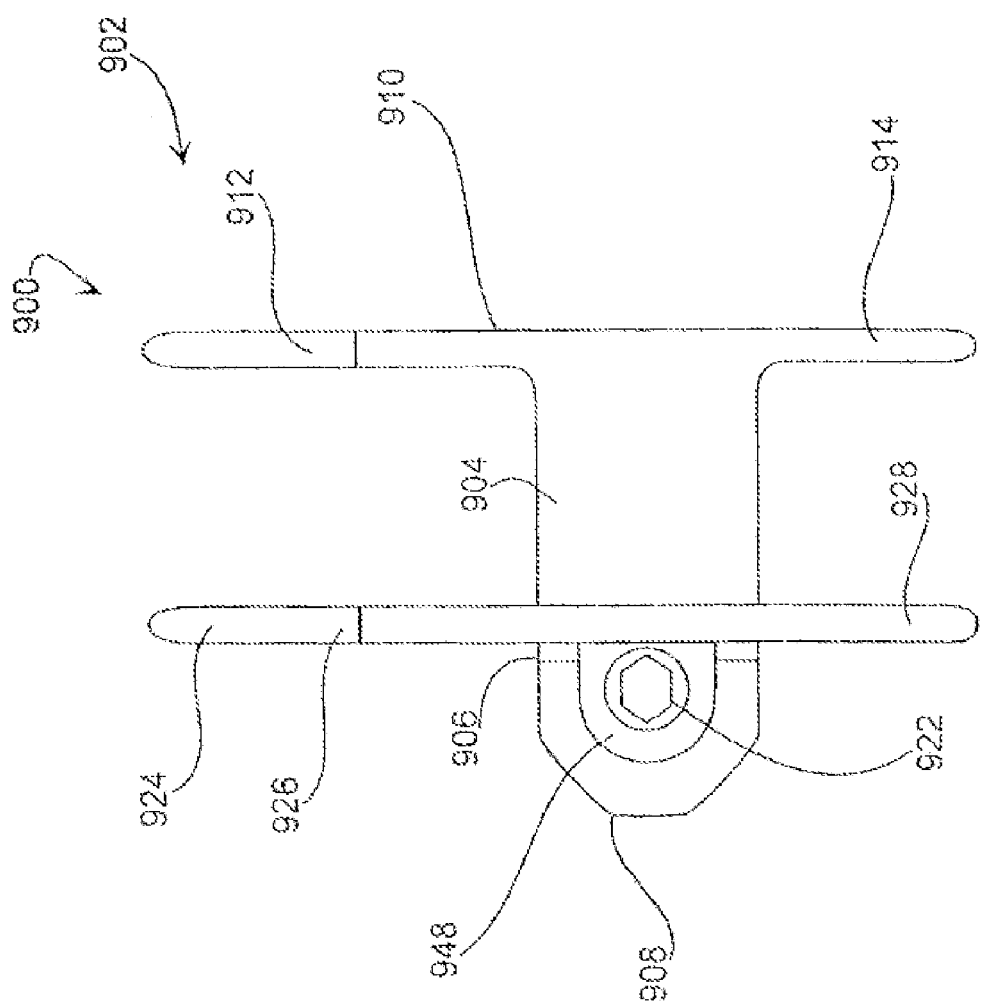

As can be seen in FIG. 89, a second wing 924 includes a tongue 948 which extends substantially perpendicular thereto and between the upper and lower portions 926, 928. The tab 948 includes a bore 4950. With the second wing 924 positioned in the slot 906 of the distracting unit 902 and tab 948 positioned in recess 919, a threaded set screw 922 can be positioned through the bore 4950 and engage the threaded bore 920 in order to secure the second wing or retaining unit 924 to the distracting unit 902. The embodiment 900 is implanted in the same manner as embodiment 800 previously described. In addition, as the bore 922 is substantially perpendicular to the distracting body 904 (and not provided at an acute angle thereto), the surgeon can even more easily secure the screw in place from a position directly behind the spinous processes.

Figure 92:
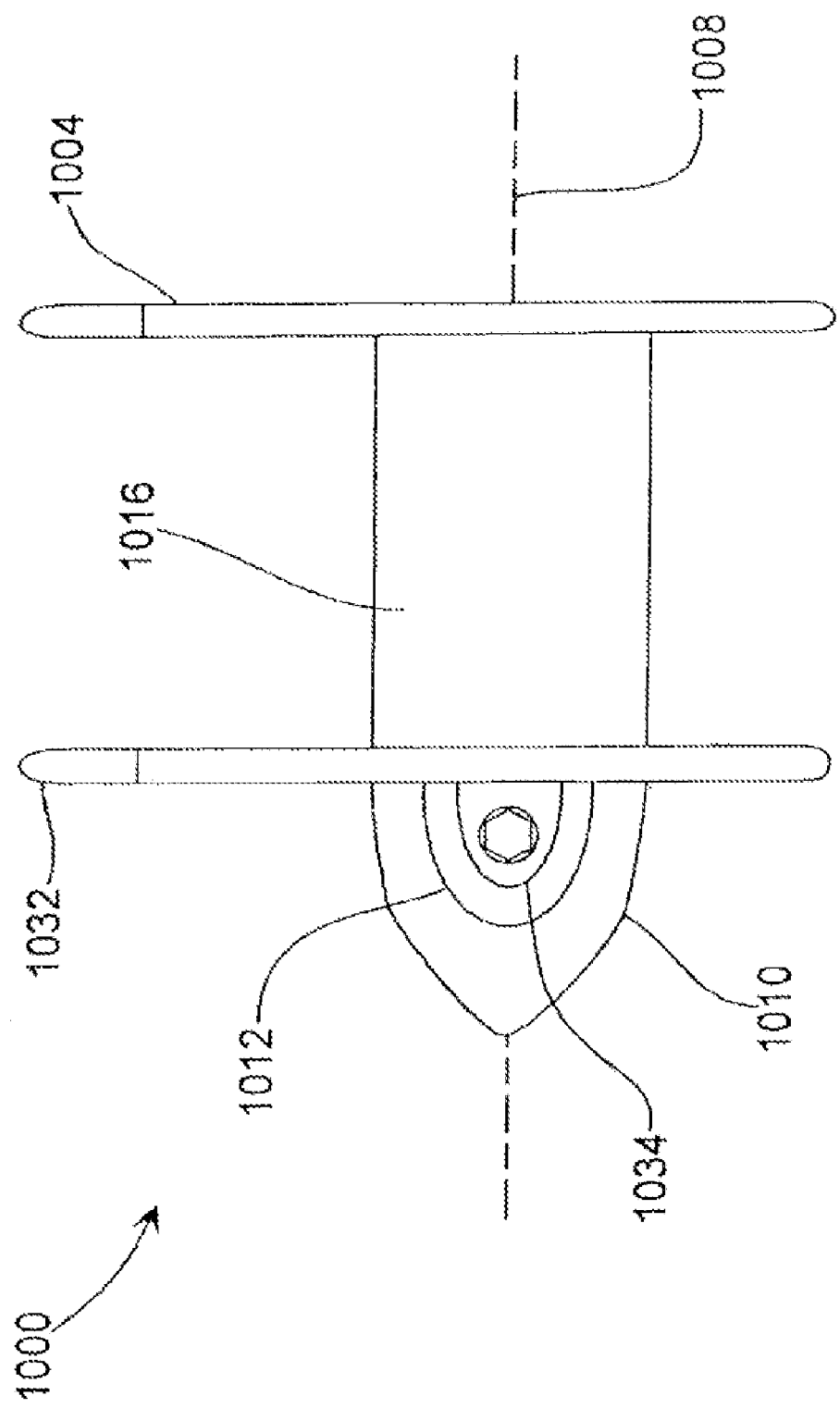

Still a further embodiment of the invention is depicted in FIGS. 92, and 92a. In this embodiment, the implant 1000 as can be seen in FIG. 92a includes a central elongated body 1002 which has positioned at one end thereof a first wing 1004. Wing 1004 is similar to the first wing previously described with respect to the embodiment of FIG. 88. Bolt 1006 secures wing 1004 to body 1002 in this embodiment. Bolt 1006 is received in a bore of the body 1002 which is along the longitudinal axis 1008 of body. It is to be understood that in this embodiment, the first unit is defined by the central body 1002, the first wing 1004, and the guide 1010.

Figure 93A:
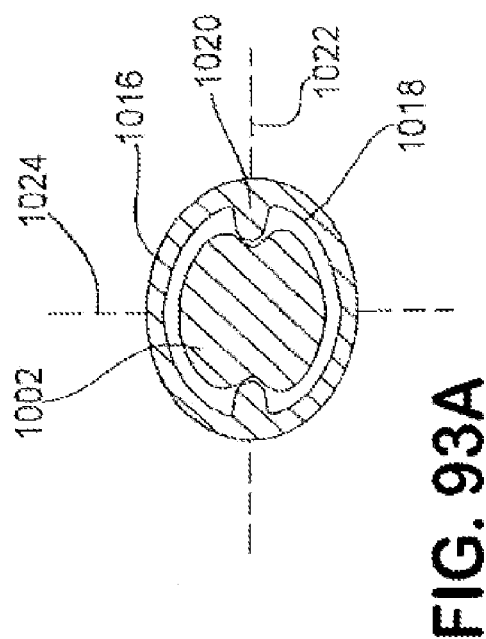
Figure 93B:
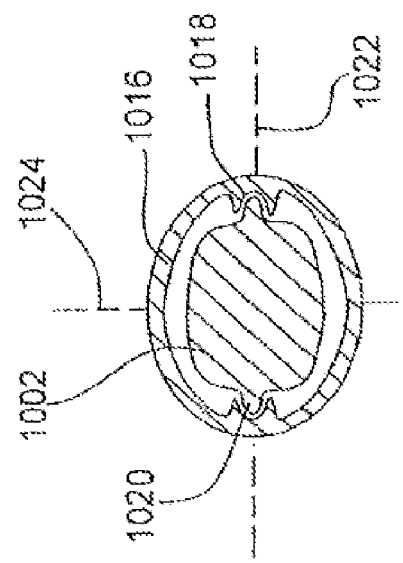
Figure 93:
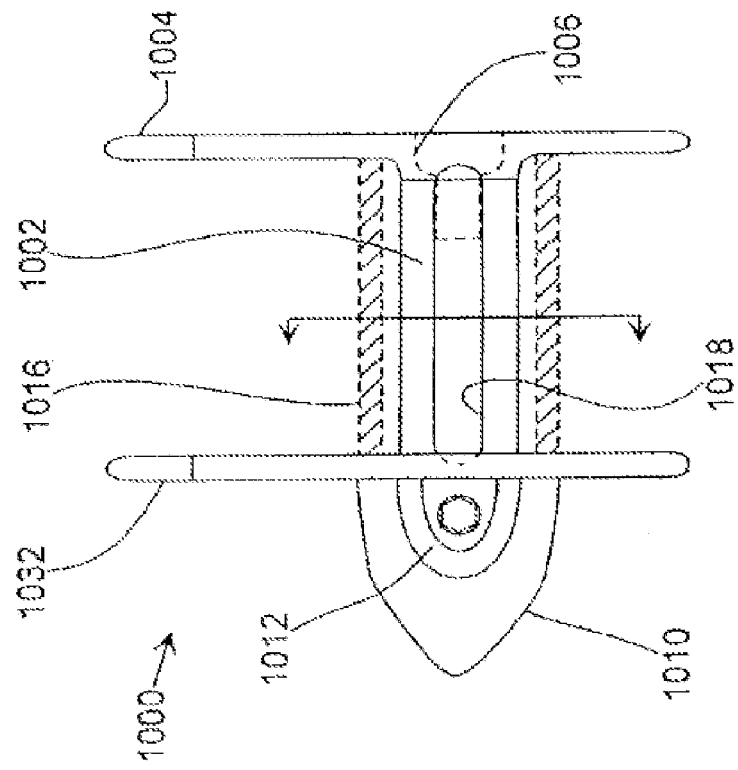
Figure 93C:
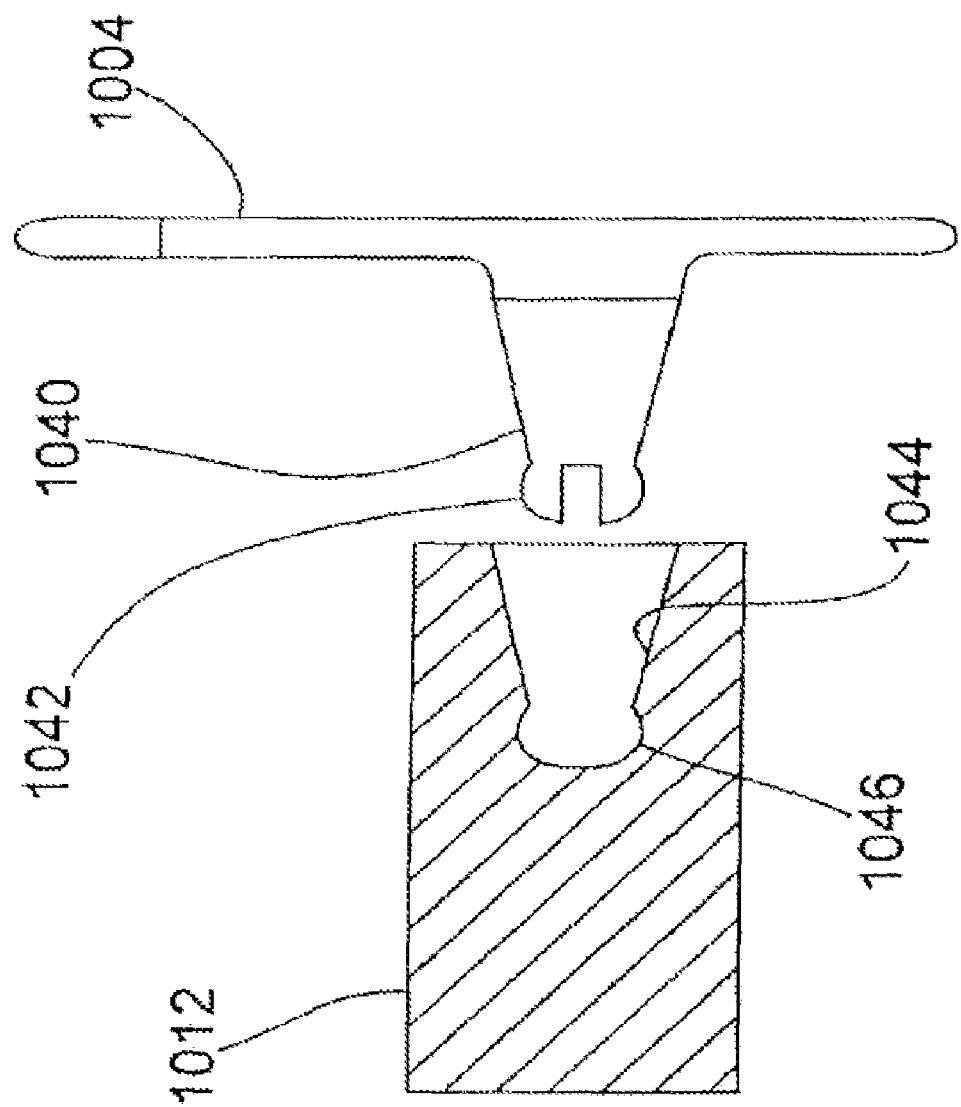

Alternatively, the first wing can be secured to the central body with a press fit and detent arrangement as seen in FIG. 93c. In this arrangement, the first wing has a protrusion 1040 extending preferably about perpendicularly from the first wing, with a flexible catch 1042. The protrusion and flexible catch are press fit into a bore 1044 of the central body with the catch received in a detent 1046.

Figure 93D:
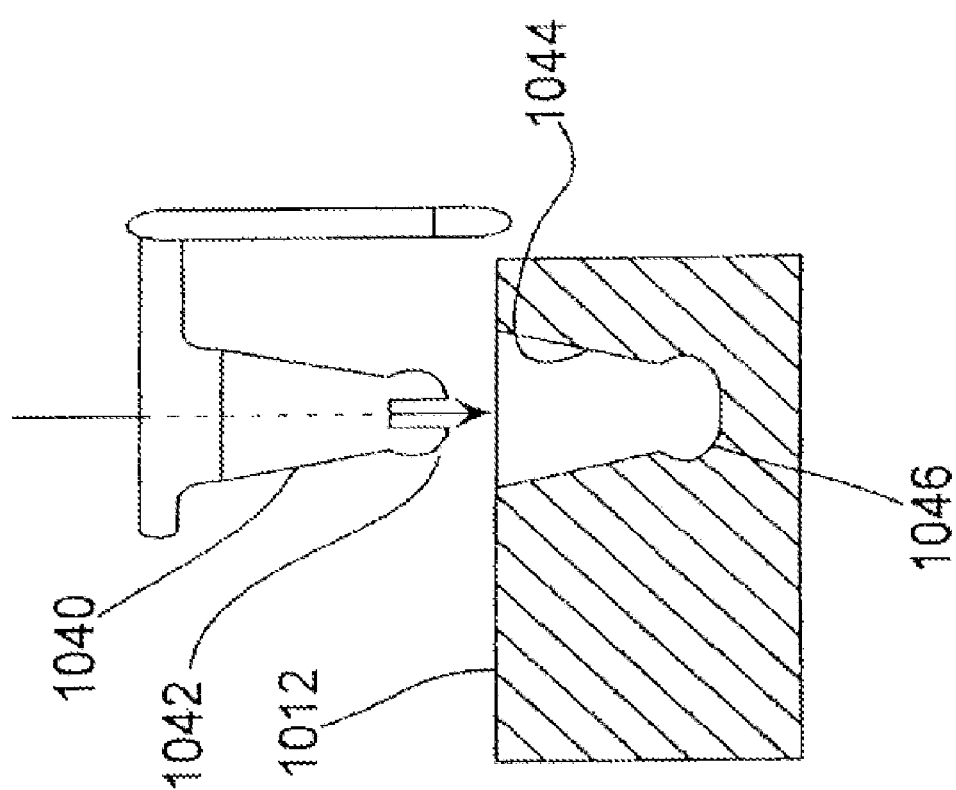

In yet another alternative embodiment, the first wing can be designed as shown in FIG. 93d with the protrusion directed substantially parallel to the first wing from a member that joins the first wing to the protrusion. Thus in this embodiment, the first wing is inserted into the body along the same direction as the second wing is inserted.

Positioned at the other end of the central body 1002 is a guide 1010. In this particular embodiment, guide 1010 is essentially triangularly-shaped so as to be a pointed and arrow-shaped guide. Alternatively, guide 1010 could be in the shape of a cone with lateral truncated sides along the longitudinal axis 1008. Guide 1010 includes a recess 1012 having a threaded bore 1014. Recess 1012 is for receiving a second wing 1032 as will be described hereinbelow.

Additionally, it is also to be understood that the guide 1010 can be bulbous, cone-shaped, pointed, arrow-shaped, and the like, in order to assist in the insertion of the implant 1000 between adjacent spinous processes. It is advantageous that the insertion technique disturb as little of the bone and surrounding tissue or ligaments as possible in order to (1) reduce trauma to the site and facilitate early healing, and (2) not destabilize the normal anatomy. It is to be noted that with the present embodiment, there is no requirement to remove any of the bone of the spinous processes and depending on the anatomy of the patient, there may be no requirement to remove or sever ligaments and tissues immediately associated with the spinous processes.

The implant 1000 further includes a sleeve 1016 which fits around and is at least partially spaced from the central body 1002. As will be explained in greater detail below, while the implant may be comprised of a bio-compatible material such as titanium, the sleeve is comprised preferably of a super-elastic material which is by way of example only, a nickel titanium material (NiTi), which has properties which allow it to withstand repeated deflection without fatigue, while returning to its original shape. The sleeve could be made of other materials, such as for example titanium, but these materials do not have the advantages of a super-elastic material.

FIG. 93a is a cross-section through the implant 1000 depicting the central body 1002 and the sleeve 1016. As can be seen from the cross-section of FIG. 93a in a preferred embodiment, both the central body 1002 and the sleeve 1016 are substantially cylindrical and oval or ecliptically-shaped. An oval or elliptical shape allows more of the spinous process to be supported by the sleeve, thereby distributing the load between the bone and the sleeve more evenly. This reduces the possibility of fracture to the bone or bone resorption. Additionally, an oval or elliptical shape enhances the flexibility of the sleeve as the major axis of the sleeve, as described below, is parallel to the longitudinal direction of the spinous process. However, other shapes such as round cross-sections can come within the spirit and scope of the invention.

In this particular embodiment, the central body 1002 includes elongated grooves 1018, along axis 1008, which receives elongated spokes 1020 extending from the internal surface of the cylinder 1016.

In a preferred embodiment, both the cross-section of the central body and the sleeve have a major dimension along axis 1022 and a minor dimensional along axis 1024 (FIG. 93*a*). The spokes 1020 are along the major dimension so that along the minor dimension, the sleeve 1016 can have its maximum inflection relative to the central body 1002. It is to be understood that the central body along the minor dimension 1024 can have multiple sizes and can, for example, be reduced in thickness in order to increase the ability of the sleeve 1016 to be deflected in the direction of the central body 1002.

Alternatively as can be seen in FIG. 93*b*, the central body 1002 can include the spokes 1020 and the sleeve 1016 can be designed to include the grooves 1018 in order to appropriately space the sleeve 1016 from the central body 1002.

In other embodiments, the sleeve can have minor and major dimensions as follows:

| Minor Dimension | Major Dimension |
| --- | --- |
| 6 mm | 10 mm |
| 8 mm | 10.75 mm |
| 12 mm | 14 mm |
| 6 mm | 12.5 mm |
| 8 mm | 12.5 mm |
| 10 mm | 12.5 mm |

In one preferred embodiment, said sleeve has a cross-section with a major dimension and a minor dimension and said major dimension is greater than said minor dimension and less than about two times said minor dimension. In said embodiment, said guide has a cross-section which is adjacent to said sleeve with a guide major dimension about equal to said sleeve major dimension and a guide minor dimension about equal to said sleeve minor dimension. Further in said embodiment, said guide extends from said central body with a cross-section which reduces in size in a direction away from said central body.

In another preferred embodiment, said guide is cone-shaped with a base located adjacent to said sleeve. Further, said guide has a base cross-section about the same as the oval cross-section of said sleeve.

Thus, from the above, it is evident that preferably a major dimension of the sleeve correspond with a major dimension of the central body and a minor dimension of the sleeve corresponds with a minor dimension of the central body. Additionally, it is evident that the major dimension of the sleeve 1016 is substantially perpendicular to a major dimension of the first wing 1004 along longitudinal axis 1030 (FIG. 92*a*). This is so that as discussed above, when the implant 1000 is properly positioned between the spinous processes, a major portion of the sleeve comes in contact with both the upper and lower spinous processes in order to distribute the load of the spinous processes on the sleeve 1016 during spinal column extension.

As indicated above, the preferred material for the sleeve 1016 is a super-elastic material and more preferably one comprised of an alloy of nickel and titanium. Such materials are available under the trademark Nitinol. Other super-elastic materials can be used as long as they are bio-compatible and have the same general characteristics of super-elastic materials. In this particular embodiment, a preferred super-elastic material is made up of the following composition of nickel, titanium, carbon, and other materials as follows:

| | |
| --- | --- |
| Nickel | 55.80% by weight |
| Titanium | 44.07% by weight |
| Carbon | <0.5% by weight |
| Oxygen | <0.5% by weight |

In particular, this composition of materials is able to absorb about 8% recoverable strain. Of course, other materials which can absorb greater and less than 8% can come within the spirit and scope of the invention. This material can be repeatably deflected toward the central body and returned to about its original shape without fatigue. Preferably and additionally, this material can withstand the threshold stress with only a small amount of initial deforming strain and above the threshold stress exhibit substantial and about instantaneous deformation strain which is many times the small amount of initial deforming strain. Such a characteristic is demonstrated in FIG. 118 where it is shown that above a certain threshold stress level, deformation strain is substantially instantaneous up to about 8%. FIG. 118 shows a loading and unloading curve between stress and deformation strain for a typical type of super-elastic material as described above.

Preferably, the above super-elastic material is selected to allow deformation of up to about, by way of example only, 8%, at about 20 lbs. to 50 lbs. force applied between a spinous processes. This would cause a sleeve to deflect toward the central body absorbing a substantial amount of the force of the spinous processes in extension. Ideally, the sleeves are designed to absorb 20 lbs. to 100 lbs. before exhibiting the super-elastic effect (threshold stress level) described above. Further, it is possible, depending on the application of the sleeve and the anatomy of the spinal column and the pairs of spinous processes for a particular individual, that the sleeve can be designed for a preferable range of 20 lbs. to 500 lbs. of force before the threshold stress level is reached. Experimental results indicate that with spinous processes of an older individual, that at about 4400 pounds force, the spinous process may fracture. Further, such experimental results also indicate that with at least 100 pounds force, the spinous process may experience some compression. Accordingly, ideally the super-elastic material is designed to deform or flex at less than 100 pounds force.

In a preferred embodiment, the wall thickness of the sleeve is about 1 mm or $40/1000$ of an inch (0.040 in.). Preferably the sleeve is designed to experience a combined 1 mm deflection. The combined 1 mm deflection means that there is ½ mm of deflection at the top of the minor dimension and a ½ mm deflection at the bottom of the minor dimension. Both deflections are toward the central body.

In a particular embodiment where the sleeve is more circular in cross-section, with an outer dimension of 0.622 in. and a wall thickness of 0.034 in., a 20 lb. load causes a 0.005 in. deflection and a 60 lb. load causes a 0.020 in. deflection (approximately ½ mm). A 100 lb. load would cause a deflection of about 0.04 in. or approximately 1 mm.

Thus in summary, the above preferred super-elastic material means that the sleeve can be repeatedly deflected and returned to about its original shape without showing fatigue. The sleeve can withstand a threshold stress with a small amount of deforming strain and at about said threshold stress exhibit about substantially instantaneous deformation strain which is many times the small amount of the forming strain. In other words, such super-elastic qualities mean that the material experiences a plateau stress where the material supports a constant force (stress) over very large strain range as exhibited in FIG. 118.

It is to be understood that for this particular embodiment, bar stock of the super-elastic material is machined into the appropriate form and then heat treated to a final temperature to set the shape of the material by increasing the temperature of the material to 932° F. and holding that temperature for five (5) minutes and then quickly quenching the sleeve in water. It is also to be understood that preferably the present nickel titanium super-elastic alloy is selected to have a transition temperature $A_r$ of about 59° Fahrenheit (15° C.). Generally for such devices the transition temperature can be between 15° C. to 65° C. (59° F. to 149° F.), and more preferably 10° C. to 40° C. (50° F. to 104° F.). Preferably, the material is maintained in the body above the transition temperature in order to exhibit optimal elasticity qualities.

Alternatively, and preferably, the sleeve can be fabricated by wire Electrical Discharge Machining (EDM) rather than machined. Additionally, the sleeve can be finished using a shot blast technique in order to increase the surface strength and elasticity of the sleeve.

Figure 94B:
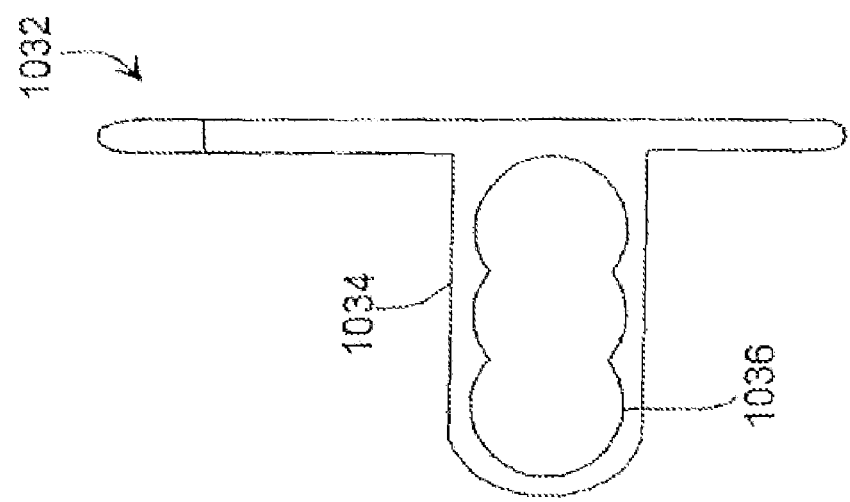
Figure 94A:
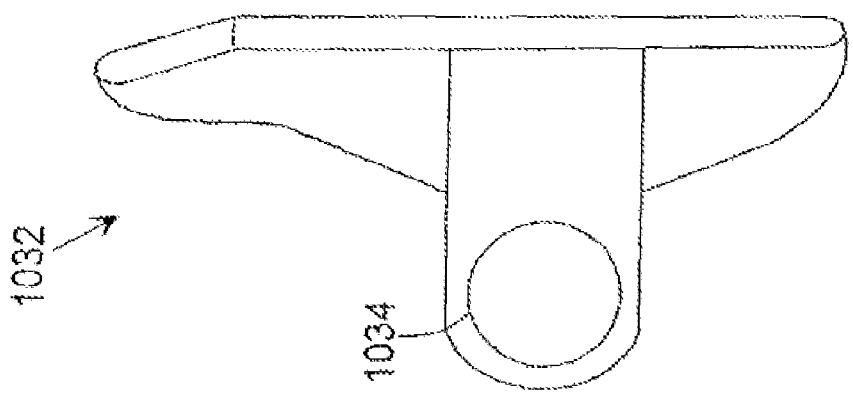
Figure 94:
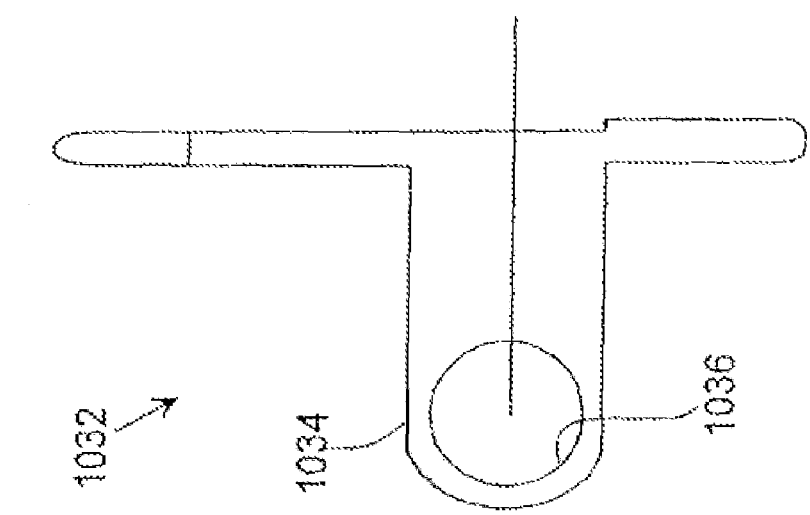
Figure 96:
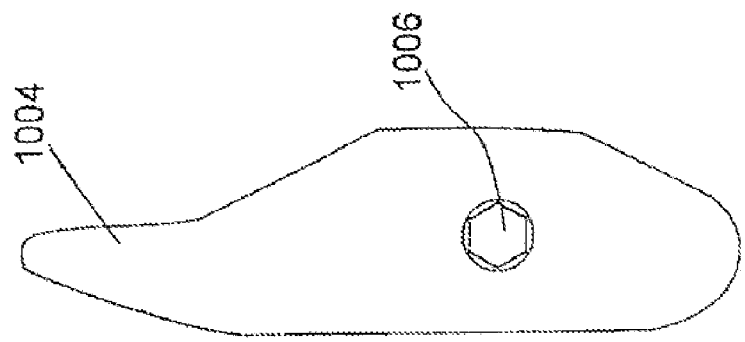
Figure 95A:
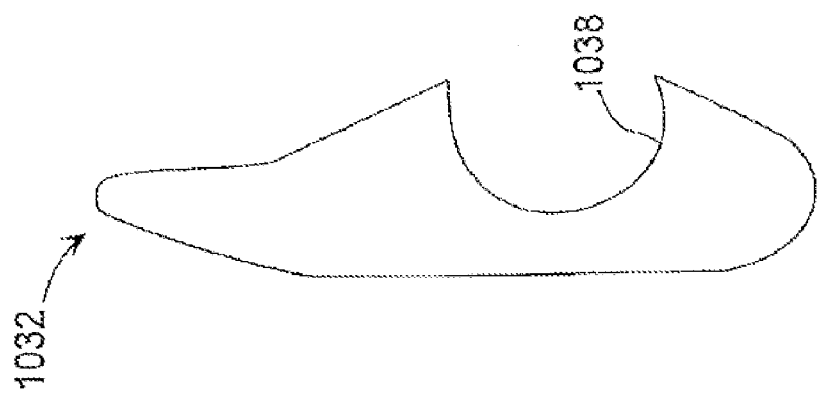
Figure 95:
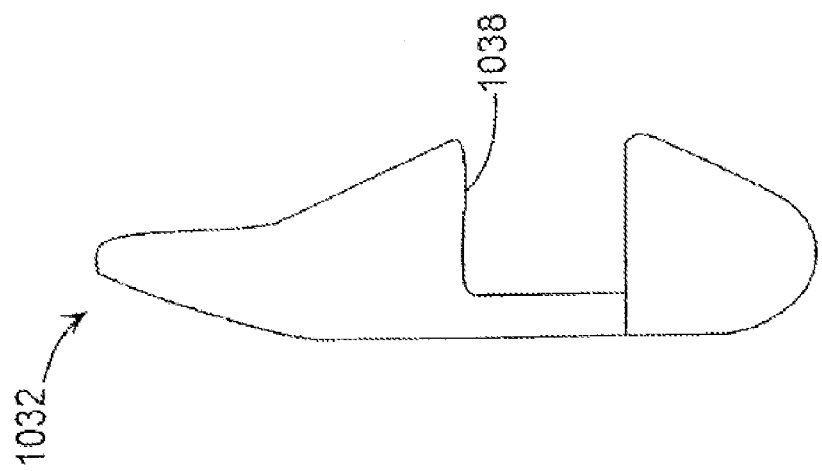

Top and side views of the second wing 1032 are shown in FIGS. 94 and 95. Second wing 1032 as in several past embodiments includes a tab 1034 with a bore 1036 which aligns with the bore 1014 of the guide 1010. In this particular embodiment, the second wing 1032 includes a cut-out 1038 which is sized to fit over the guide 1010, with the tab 1034 resting in the recess 1012 of the guide 1010.

An alternative configuration of the second wing 1032 is depicted in FIG. 94a. In this configuration, the second wing 1032 is held at acute angle with respect to the tab 1034. This is different from the situation in the embodiment of FIGS. 94 and 95 where the second wing is substantially perpendicular to the tab. For the embodiment of the second wing in FIG. 94a, such embodiment will be utilized as appropriate depending on the shape of the spinous processes.

With respect to the alternative second wing 1032 depicted in FIGS. 94b and 95a, elongated tab 1034 has a plurality of closely positioned bores 1036. The bores, so positioned, appear to form a scallop shape. Each individual scallop portion of the bore 1036 can selectively hold the bolt in order to effectively position the second wing 1032 in three different positions relative to the first wing 1004. The cut-out 1038 (FIG. 95a of this alternative embodiment) is enlarged over that of FIG. 95 as in a position closest to the first wing 1004, the second wing 1032 is immediately adjacent and must conform to the shape of the sleeve 1016.

Implant 1050 of FIG. 97 is similar to the implant 1000 in FIG. 92 with the major difference being that a second wing is not required. The implant 1050 includes a central body as does implant 1000. The central body is surrounded by a sleeve 1016 which extends between a first wing 1004 and a guide 1010. The guide 1010 in this embodiment is substantially cone-shaped without any flats and with no bore as there is no need to receive a second wing. The sleeve and the central body as well as the first wing and guide act in a manner similar to those parts of the implant 1000 in FIG. 92. It is to be understood a cross-section of this implant 1050 through sleeve 1016 can preferably be like FIG. 93a. This particular embodiment would be utilized in a situation where it was deemed impractical or unnecessary to use a second wing. This embodiment has the significant advantages of the sleeve being comprised of super-elastic alloy materials as well as the guide being utilized to guide the implant between spinous processes while minimizing damage to the ligament and tissue structures found around the spinous processes.

Implant 1060 is depicted in FIG. 98. This implant is similar to the implants 1000 of FIG. 92 and the implant 1050 of FIG. 97, except that this implant does not have either first or second wings. Implant 1060 includes a sleeve 1016 which surrounds a central body just as central body 1002 of implant 1000 in FIG. 93. It is to be understood that a cross-section of this implant 1060 through sleeve 1016 can preferably be like FIG. 93a. Implant 1060 includes a guide 1010 which in this preferred embodiment is cone-shaped. Guide 1010 is located at one end of the central body. At the other end is a stop 1062. Stop 1062 is used to contain the other end of the sleeve 1016 relative to the central body. This embodiment is held together with a bolt such as bolt 1006 of FIG. 93 that is used for the immediate above two implants. For the implant 1060 of FIG. 98, such a device would be appropriate where the anatomy between the spinous processes was such that it would be undesirable to use either a first or second wing. However, this embodiment affords all the advantageous described hereinabove (FIGS. 92 and 97) with respect to the guide and also with respect to the dynamics of the sleeve.

Figure 99:
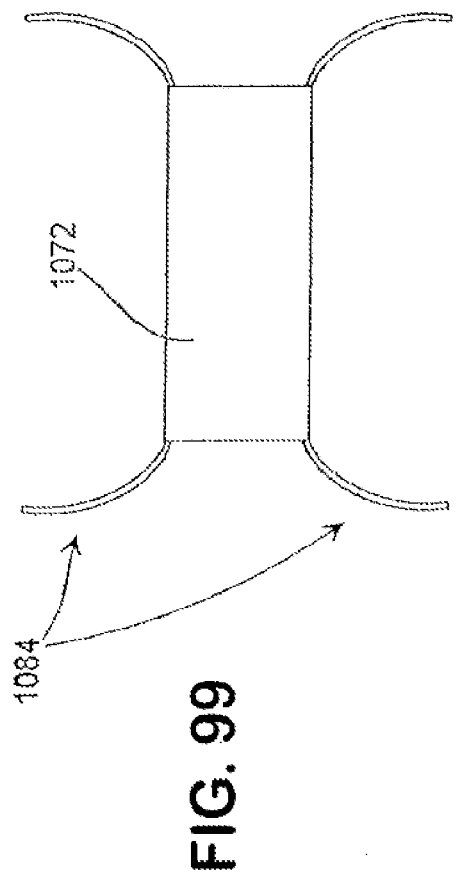
FIGS. 99 and 100 depict still another embodiment of the present invention including an insertion tool.
Figure 100:
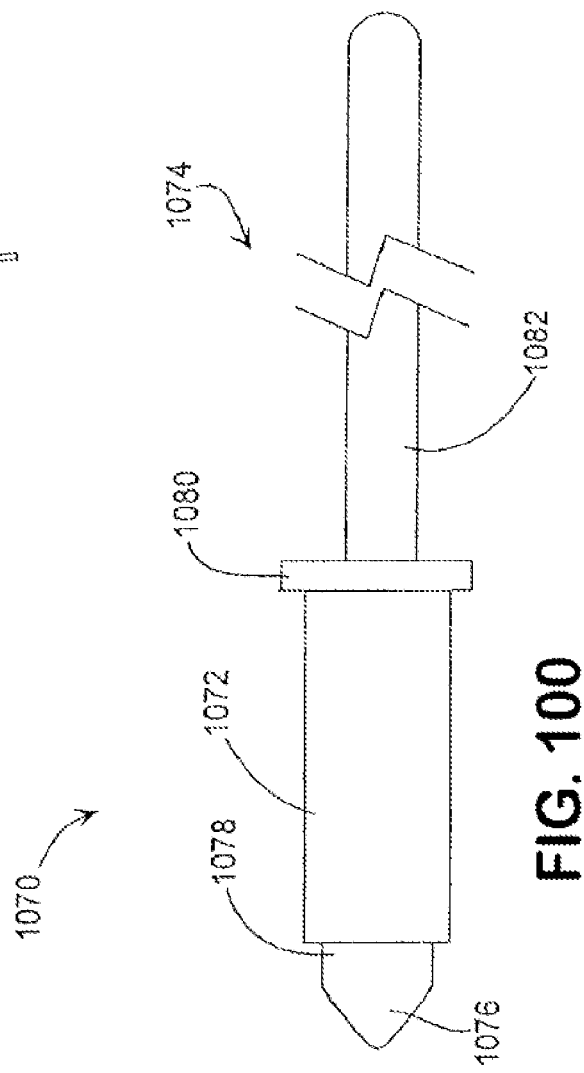

FIGS. 99 and 100 depict an implant system 1070. Implant system 1070 includes a sleeve 1072 which is similar to and has the advantageous of sleeve 1016 of the embodiment in FIG. 92. Sleeve 1072 does not, however, have any spokes. Additionally, implant system 1070 includes an insertion tool 1074. Insertion tool 1074 includes a guide 1076 which in a preferred embodiment is substantially cone-shaped. Guide 1076 guides the insertion of the sleeve 1072 and the insertion tool 1074 between adjacent spinous processes. The insertion tool 1074 further includes a central body 1078, a stop 1080, and a handle 1082. The guide 1076 at its base has dimensions which are slightly less than the internal dimensions of the sleeve 1074 so that the sleeve can fit over the guide 1076 and rest against the stop 1080. The tool 1074 with the guide 1076 is used to separate tissues and ligaments and to urge the sleeve 1072 in the space between the spinous processes. Once positioned, the guide insertion tool 1074 can be removed leaving the sleeve 1072 in place. If desired, after the sleeve is positioned, position maintaining mechanisms such as springy wires 1084 made out of appropriate material such as the super-elastic alloys and other materials including titanium, can be inserted using a cannula through the center of the sleeve 1072. Once inserted, the ends of the retaining wires 1084 (FIG. 99) extend out of both ends of the sleeve 1072, and due to this springy nature, bent at an angle with respect to the longitudinal axis of the sleeve 1072. These wires help maintain the position of the sleeve relative to the spinous processes.

Figure 101:
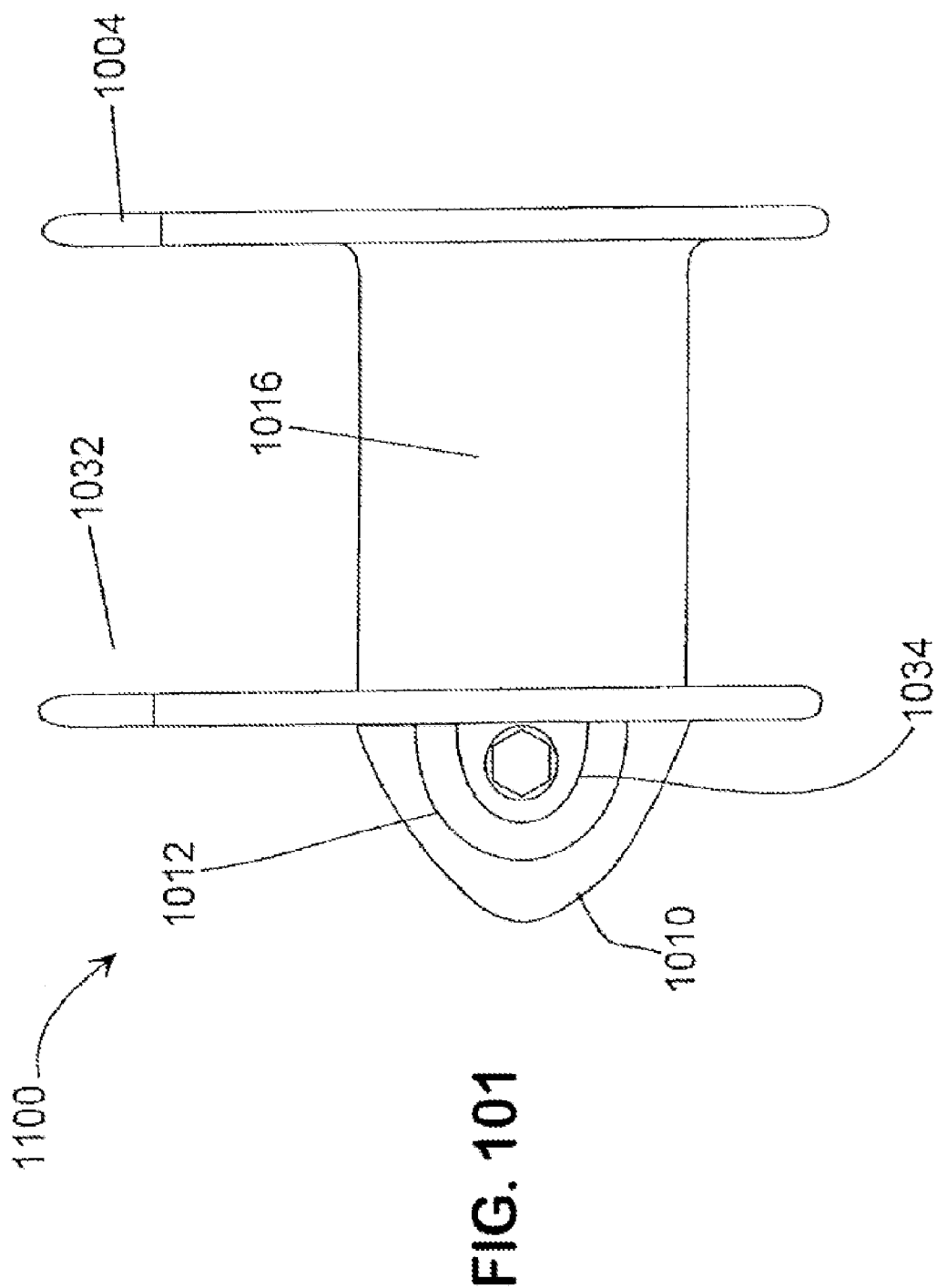
FIGS. 101, 102, 102a, 103, 104, 105, 106, and 107 depict still a further embodiment of the present invention.

Another embodiment of the invention can be seen in FIG. 101 which includes implant 1100. Implant 1100 has many similar features that are exhibited with respect to implant 1000 in FIG. 92. Accordingly, elements with similar features and functions would be similarly numbered. Additionally, features that are different from implant 1100 can be, if desired, imported into and become a part of the implant 1000 of FIG. 92.

As with implant 1000, implant 1100 includes a central body 1002 (FIG. 102) with a first wing 1004 and a bolt 1006 which holds the first wing and the central body together. In this particular embodiment, the central body is made in two portions. The first portion 1102 is in the shape of a truncated cone with an oval or elliptical base and a second portion 1104 includes a cylindrical central portion with a distal end in the shape of a truncated cone 1103 with an oval or elliptical base. In addition, in this particular embodiment, formed with the central body is the guide 1010 which has an oval or elliptical base. Bolt 1006 is used to secure the first wing through the second portion 1104 with the first portion 1102 held in-between. In this particular embodiment, the guide 1010 in addition to including recess 1012 and bore 1014 includes a groove 1106 which receives a portion of the second wing 1032.

Figure 102A:
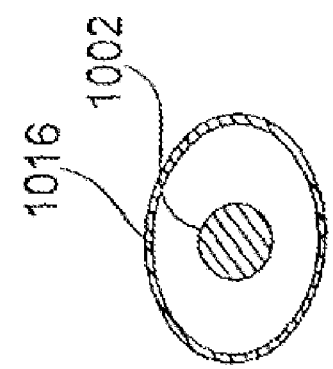
Figure 102:
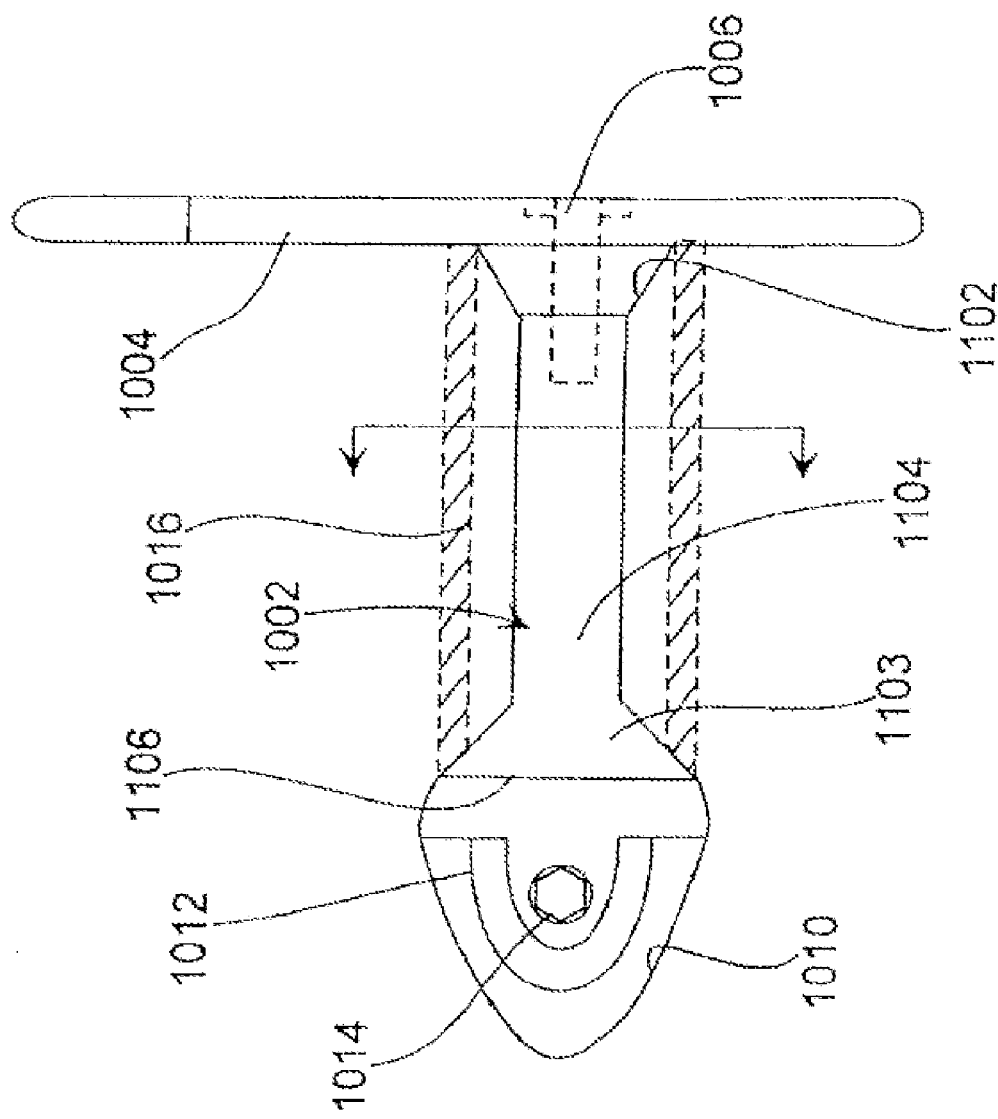

In this particular embodiment, the sleeve 1016 is preferably oval or elliptical in shape as can be seen in FIG. 102a. The central body can be oval, elliptical or circular in cross-section, although other shapes are within the spirit and scope of the invention. The sleeve 1016 held in position due to the fact that the truncated conical portion 1102 and the corresponding truncated conical portion 1103 each have a base that is elliptical or oval in shape. Thus, the sleeve is held in position so that preferably the major dimension of the elliptical sleeve is substantially perpendicular to the major dimension of the first wing. It is to be understood that if the first wing is meant to be put beside the vertebrae so that the first wing is set at an angle other than perpendicular with respect to the vertebrae and that the sleeve may be held in a position so that the major dimension of the sleeve is at an angle other than perpendicular to the major dimension of the first wing and be within the spirit and scope of the invention. This could be accomplished by tightening bolt 1006 with the first wing 1004 and sleeve 1016 so positioned. In such a configuration, the major dimension of the sleeve would be preferably positioned so that it is essentially parallel to the length of the adjacent spinous processes. So configured, the elliptical or oval shape sleeve would bear and distribute the load more evenly over more of its surface.

It is to be understood that the sleeve in this embodiment has all the characteristics and advantages described hereinabove with respect to the above-referenced super-elastic sleeves.

Figure 105:
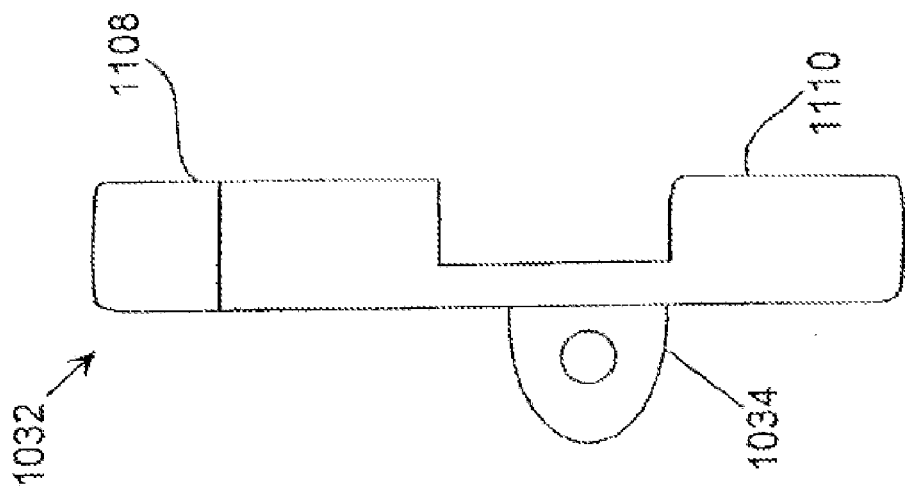
Figure 104:
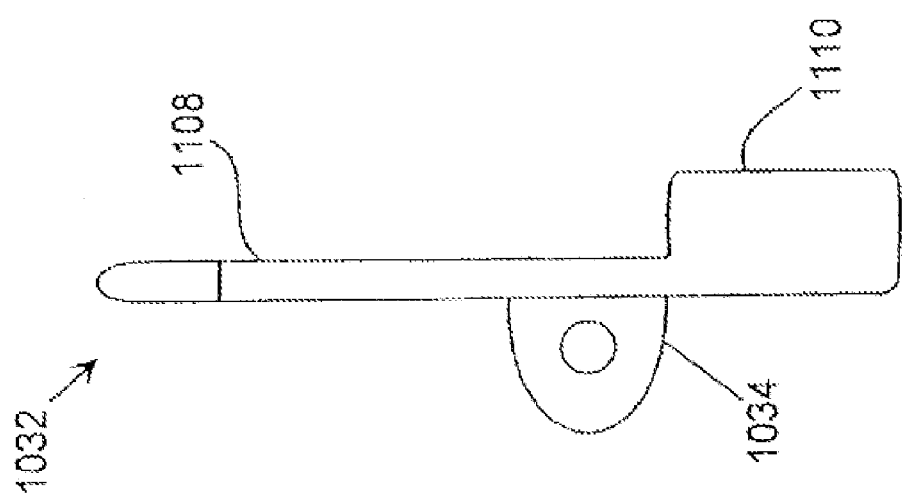
Figure 103:
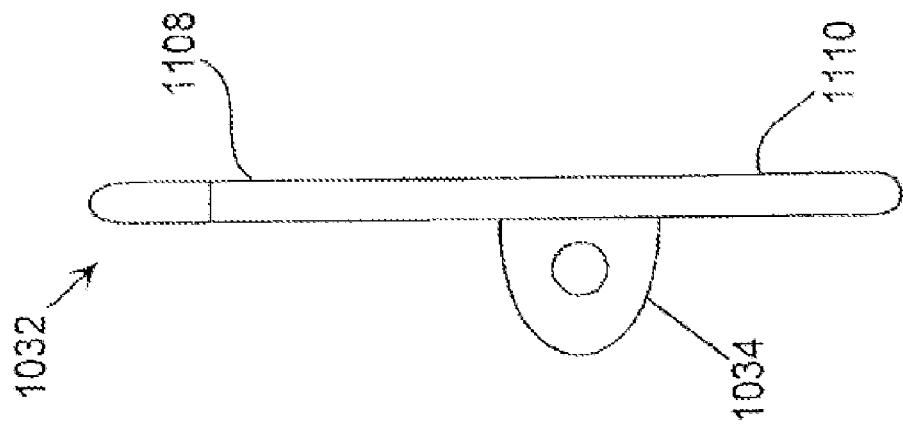

The second wing as discussed above, can come in a variety of shapes in order to provide for variations in the anatomical form of the spinous processes. Such shapes are depicted in FIGS. 103, 104, 105, 106, and 107. In each configuration, the second wing 1032 has a upper portion 1108 and a lower portion 1110. In FIG. 104, the lower portion is thicker than the upper portion in order to accommodate the spinous process, where the lower spinous process is thinner than the upper spinous process. In FIG. 105, both the upper and lower portions are enlarged over the upper and lower portions of FIG. 103 to accommodate both the upper and lower spinous processes being smaller. That is to say that the space between the upper and lower portions of the first and second wings are reduced due to the enlarged upper and lower portions of the second wing.

Figure 107:
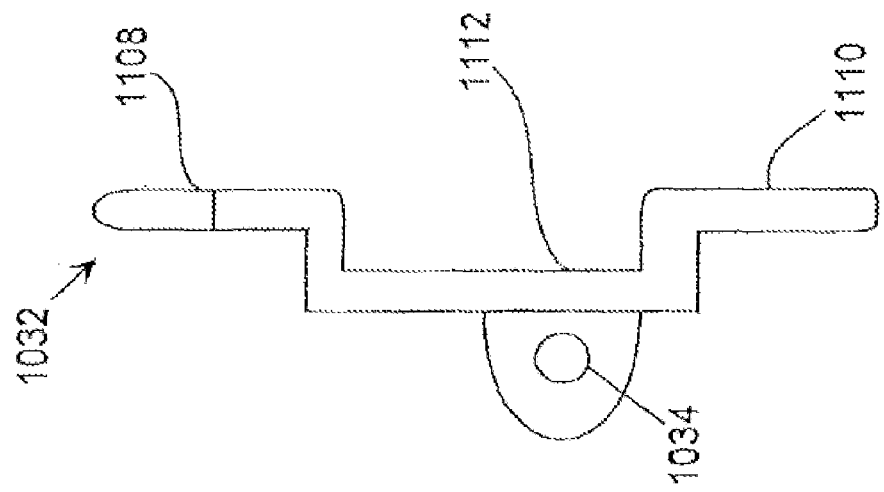
Figure 106:
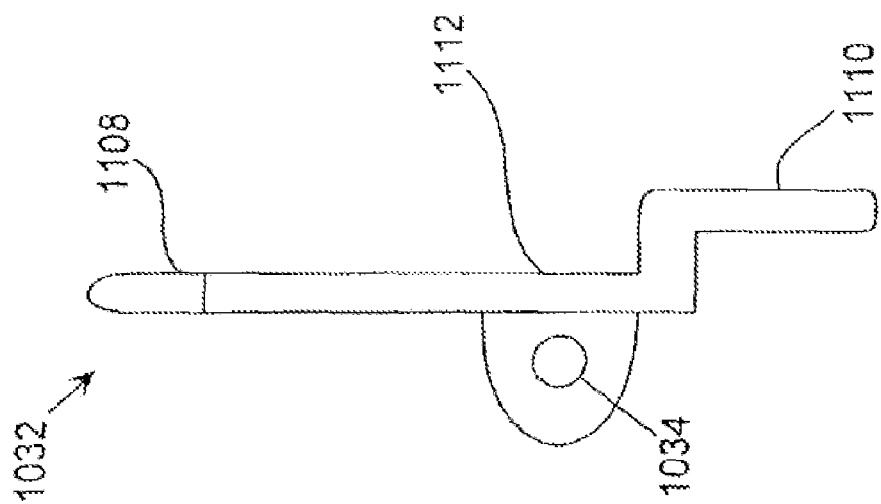

Alternative embodiments of second wings, as shown in FIGS. 104 and 105, are depicted in FIGS. 106 and 107. In these FIGS. 106 and 107, the second wing 1032 accommodates the same anatomical shape and size of the spinous processes as does the second wing in FIGS. 104 and 105 respectively. However, in the embodiments of the second wing 1032 of FIGS. 106 and 107, substantial masses have been removed from the wings. The upper and lower portions 1108 and 1110 are essentially formed or bent in order to extend from the central portion 1112 of the second wing 1032.

It is to be understood that in this embodiment, if desired, the second wing may not have to be used, depending on the anatomy of the spinal column of the body, and this embodiment still has the significant advantages attributable to the guide 1010 and the functionality of the sleeve 1016.

Figure 109:
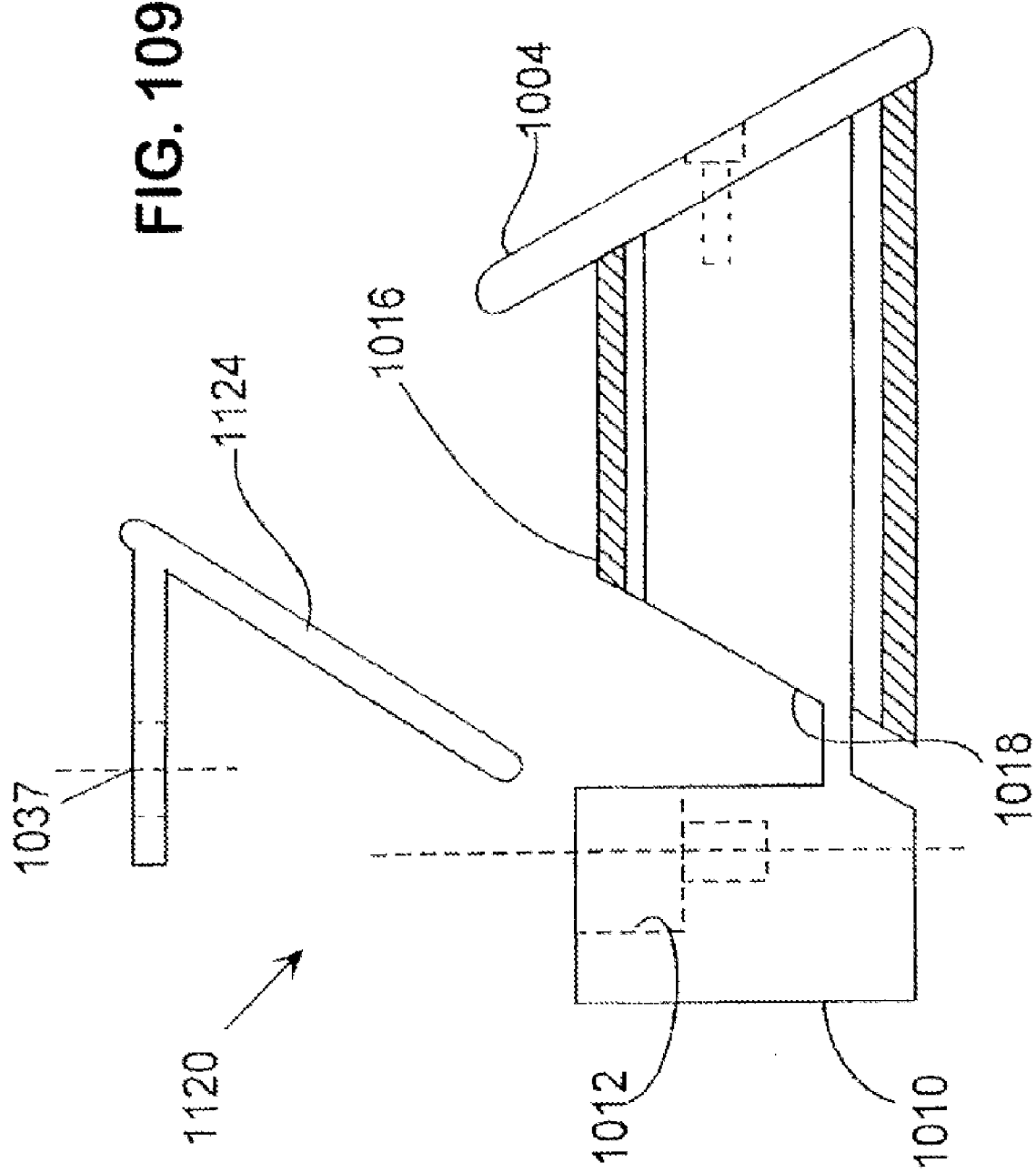
Figure 110:
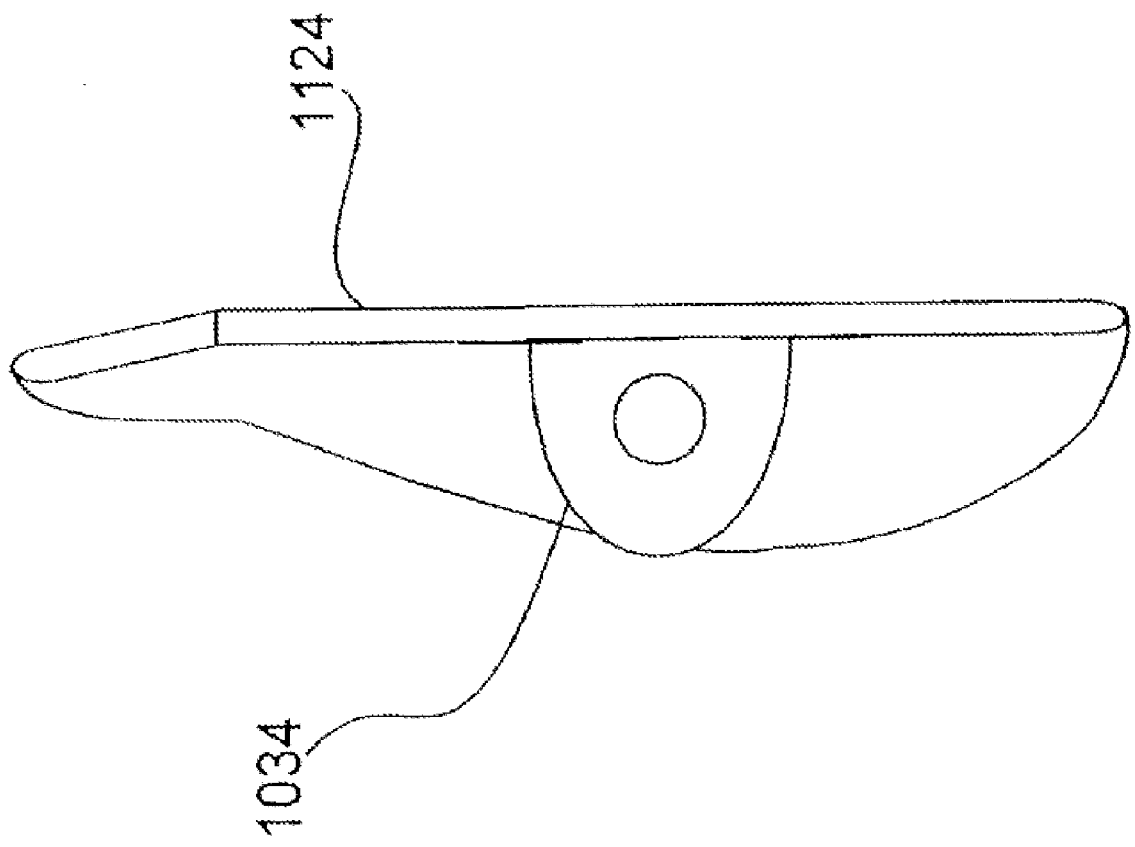

The implant 1120 as shown in FIGS. 108 and 109, is similar to implant 1100 which is in turn similar to implant 1000. Such similar details have already been described above and reference here is made to the unique orientation of the first and second wings 1122 and 1124. These wings have longitudinal axis 1126 and 1128 respectfully. As can be seen in these figures, the first and second wings 1122, 1124 have been rotated so that they both slope inwardly and if they were to continue out of the page of the drawing of FIG. 108, they would meet to form an A-frame structure as is evident from the end view of FIG. 109. In this particular embodiment, as can be seen in FIGS. 109 and 110, the tab 1034 is provided an acute angle to the remainder of the second wing 1124. Further, the groove 1018 formed in the implant is sloped in order to accept the second wing 1124. Accordingly, this present implant 1120 is particularly suited for an application where the spinous process is wider adjacent to the vertebral body and then narrows in size at least some distance distally from the vertebral body. It is to be understood that a cross-section of this implant 1120 through sleeve 1016 can preferably be like FIG. 93a.

Figure 111:
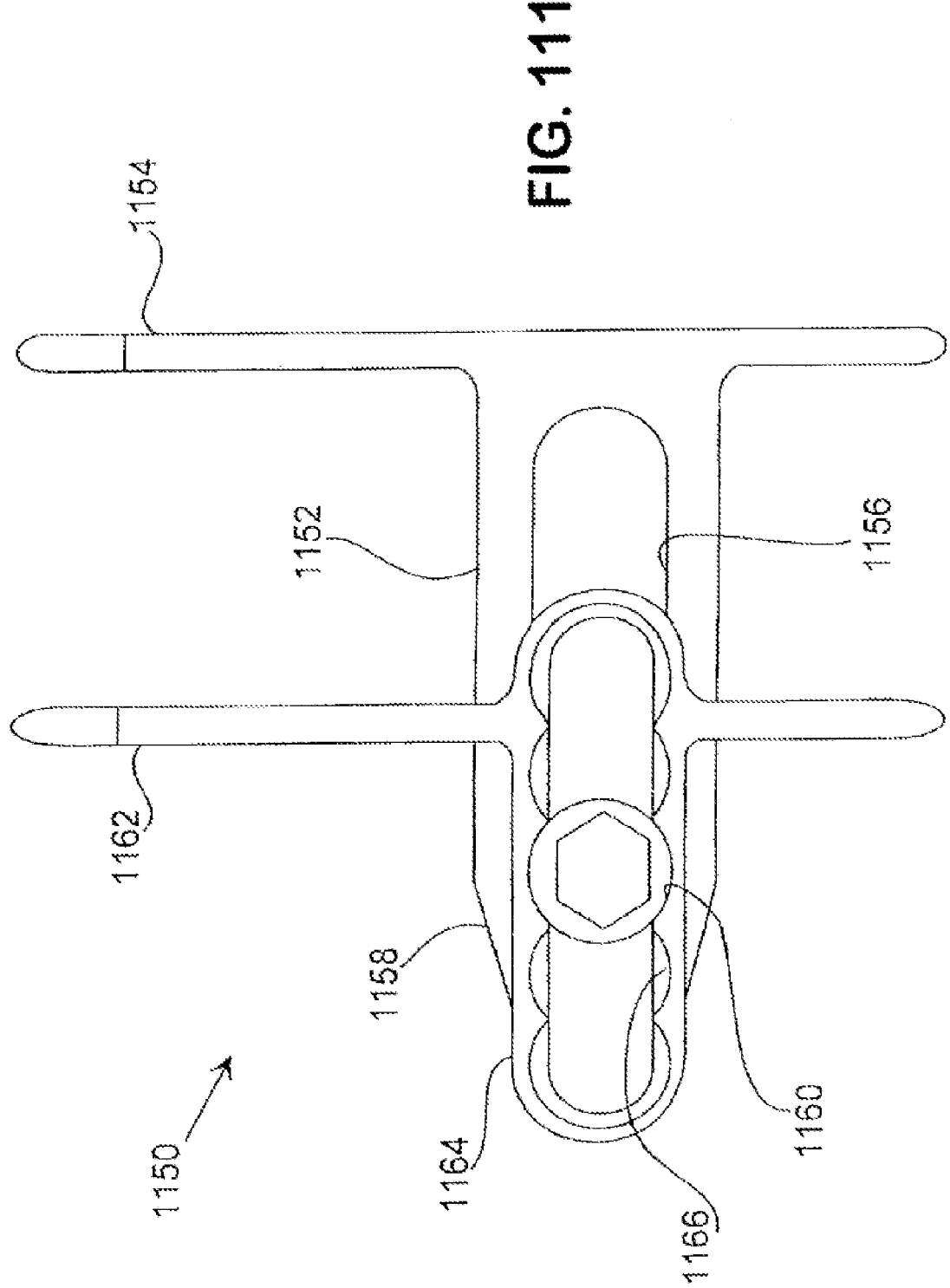

An additional embodiment of the implant 1150 is shown in FIG. 111. Implant 1150 has features similar to those described with respect to FIG. 94b.

Implant 1150 includes a central body 1152 with a first wing 1154, where central body 1152 includes elongated groove 1156 which extends to the guide 1158. A screw 1160 is received in a threaded bore located in the elongated groove 1156.

The second wing 1162 includes a central body 1164 which is substantially perpendicular to the second wing 1162.

Figure 114:
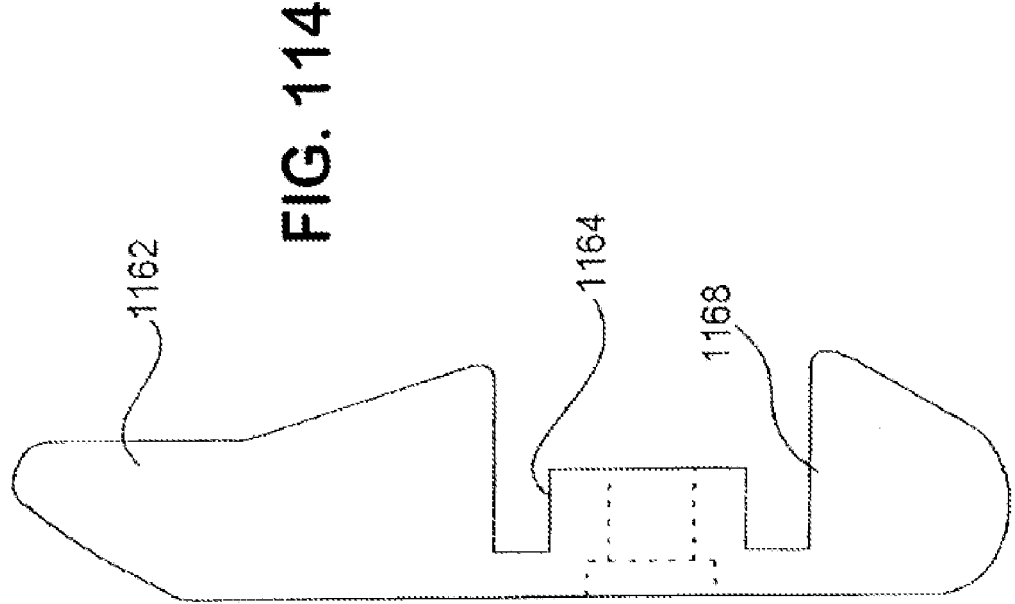
Figure 113:
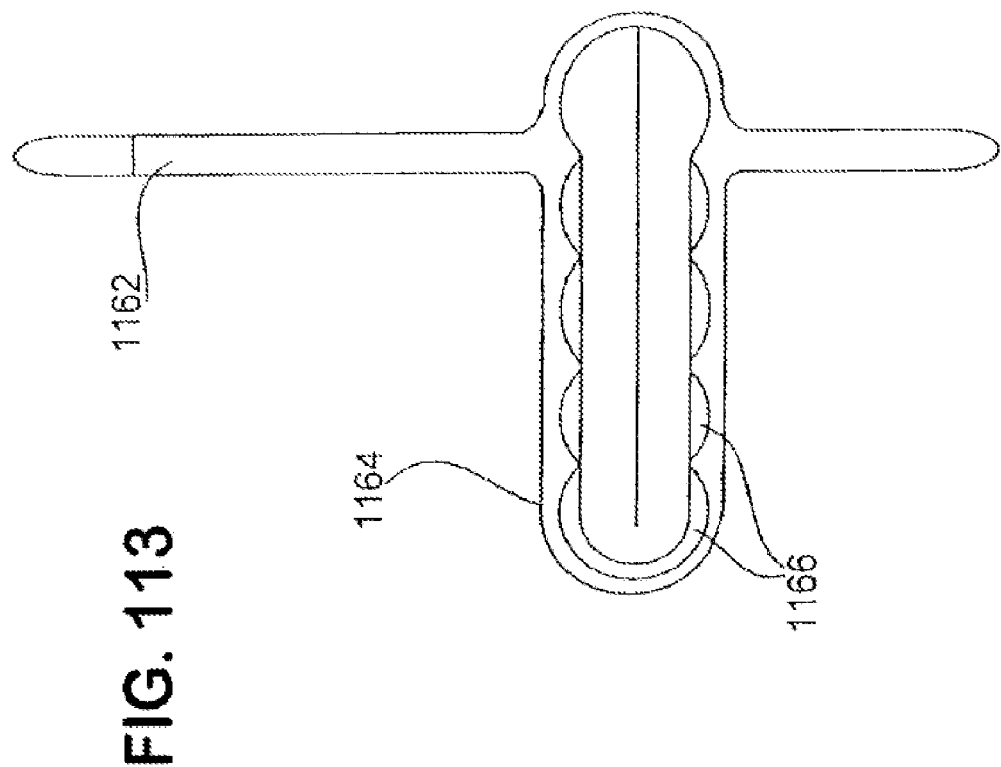

The central body 1164 includes a plurality of bores 1166 provided therein. These bores are formed adjacent to each other in order to define a plurality of scallops, each scallop capable of retaining bolt 1160 therein. As can be seen in FIG. 114, the second wing includes a cut-out 1168 such that with the central body 1164 of the second wing received in the groove 1156 of the central body associated with the first wing, the remainder of the second wing is received over the central body 1152 of the implant 1150. With this implant 1150, the distance between the first and second wings can be adjusted by selectively placing the bolt 1160 through one of the five specified bores defined by the scalloped plurality of bores 1166. Accordingly, FIG. 112 depicts the implant where the first and second wings are widest apart in order to accommodate spinous processes of greater thickness. FIG. 111 shows the middle position between the first and second wings in order to accommodate average size spinous processes.

It is to be understood that preferably during the surgical process, the central body 1152 is urged between spinous processes. After this has occurred, the second wing is guided by the other sides of the spinous processes from a path which causes the plane of the second wing to move substantially parallel to the plane of the first wing until the central body 1164 associated with the second wing 1162 is received in the groove of 1156 of the central body 1152 associated with the first wing 1154. After this has occurred, the bolt 1160 is positioned through aligned bores associated with the second wing 1162 and the central body 1152 in order to secure the second wing to the central body.

While embodiment 1150 does not depict a sleeve such as sleeve 1016, such a sleeve 1016 could be placed over body 1152 and be within the spirit of the invention.

Figure 120B:
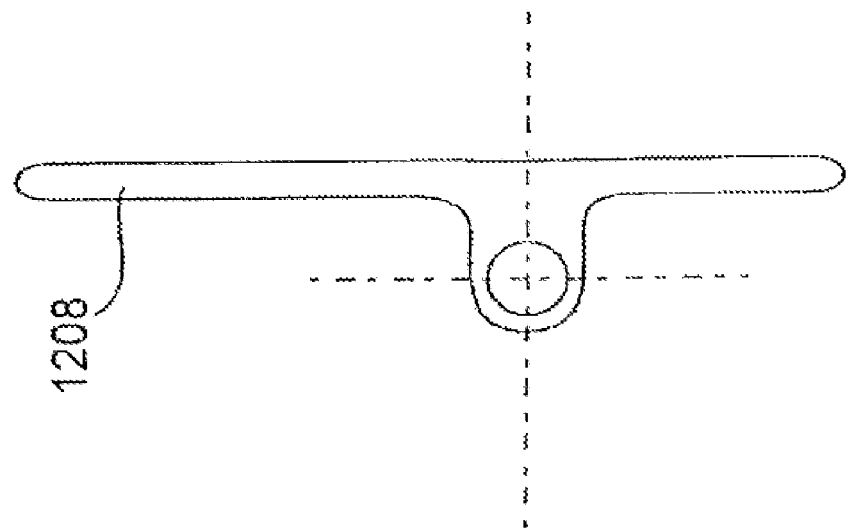
FIGS. 120a and 120b depict side and plan views of the second wing which can be used in conjunction with the embodiment of the invention of FIGS. 119a and 119b.
Figure 120A:
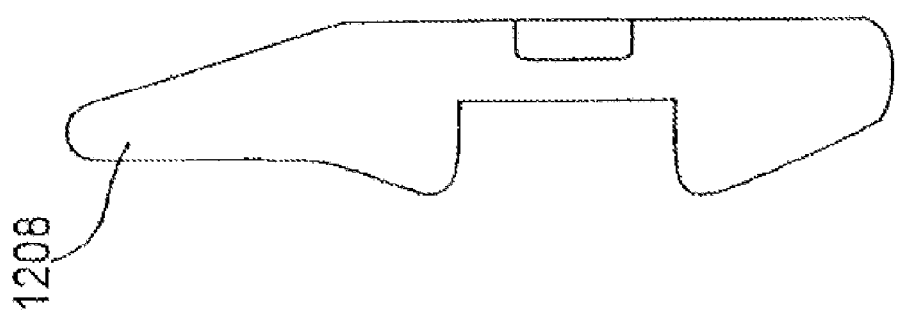

Implant 1200 of the invention is depicted in FIGS. 119a and 119b. This implant Includes the first wing 1202 and sleeve 1204 and a guide 1206. An alternative to this embodiment further includes, as required, second wing 1208 as depicted in FIGS. 120a and 120b.

As can be seen in FIGS. 121a and 121b, the first wing 1202 includes a bore which receives a central body 1210. Preferably, the central body is pressed fit through the bore of the first wing although it is to be understood that other securing mechanisms such as through the use of threads and still other mechanisms can be used to accomplish this task. Additionally, in this particular embodiment first and second pins 1212 extend from the first wing 1202, each along an axis which is substantially parallel to the longitudinal axis 1214 of the central body 1210. In this particular embodiment, the distal end 1216 of the central body 1210 is threaded in order to be coupled to the guide 1206.

Figure 122C:
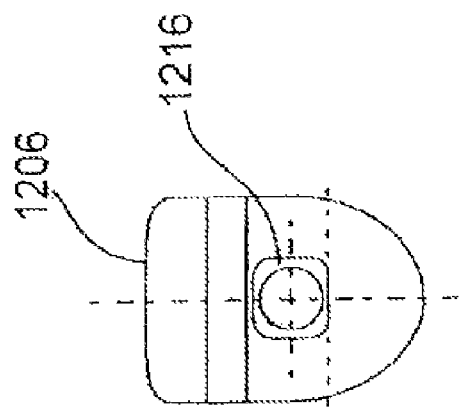
FIGS. 122a, 122b, and 122c depict top, side and end views of a guide which is a portion of the embodiment of the invention of FIGS. 119a and 119b.
Figure 122B:
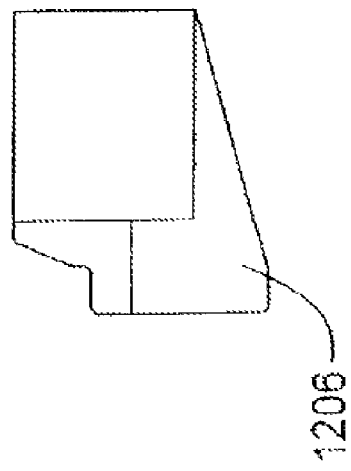
Figure 122A:
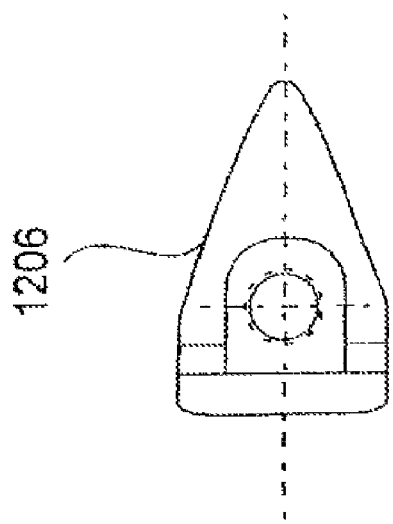

As can be seen in FIGS. 122*a*, 122*b* and 122*c*, the guide 1206 in this particular embodiment is pointed in order to allow the implant to be inserted between, and if necessary distract, adjacent spinous processes. The guide 206 includes a threaded bore 1218 which is designed to accept the threaded end 1216 of the central body 1210 in order to secure the guide to the central body and additionally for purposes of retaining the sleeve between the guide 1206 and the first wing 1202.

Figure 123B:
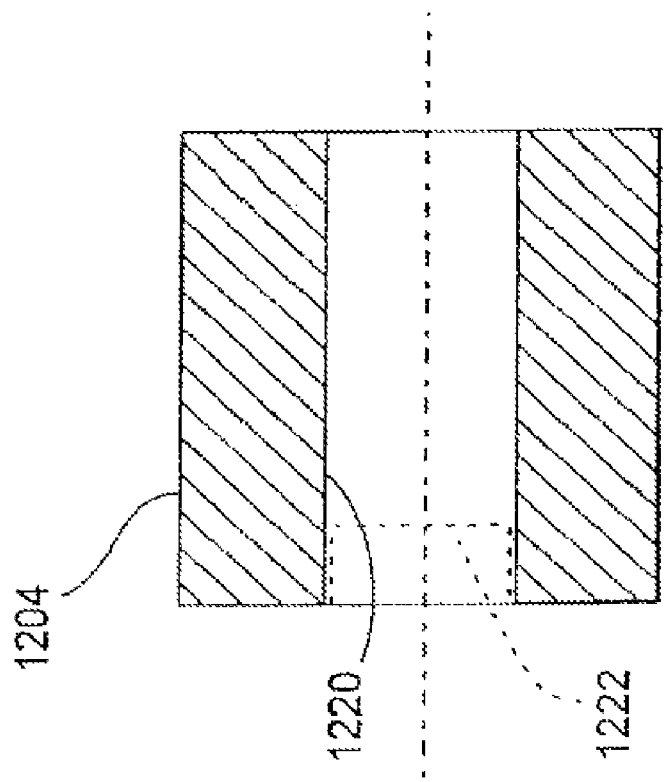
FIGS. 123a and 123b depict an end view and a cross-sectioned view respectfully of the sleeve of the embodiment of the invention of FIGS. 119a and 119b.
Figure 123A:
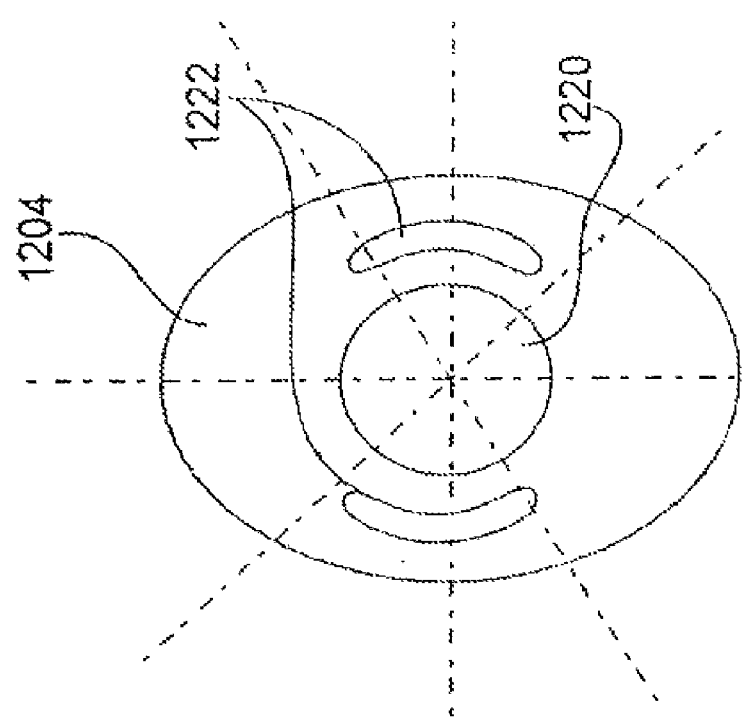

As can be seen in FIG. 123*a* the sleeve 1204 is preferably cylindrical, and oval or elliptical in shape in cross-section. It is to be understood that sleeve 1204 can have other shapes as described throughout the specification and be within the spirit and scope of the invention. In this particular embodiment, sleeve 1204 has at least one major diameter and one minor diameter in cross-section. Sleeve 1204 includes a central bore 1220 which extends the length of sleeve 1204 and curve grooves 1222 which are formed about central bore 1220 and extend only part way into the body of the sleeve. In this particular embodiment, the curved grooves 1222 describe an arc of about 60.degree. It is to be understood that in other embodiment, this arc can be less than 60.degree. and extend past 120.degree.

The sleeve 1204 is received over the central body 1210 of the implant 1200 and can rotate thereon about the longitudinal axis 1214 of the central body 1210. When this particular embodiment is assembled, the grooves 1222 have received therein the pins 1212 that extend from the first wing 1202. Accordingly, the pins inserted in the grooves 1222 assist in the positioning of the sleeve relative to the remainder of the implant 1200. With the pins 1212 received in the curved grooves 1222, the pins limit the extent of the rotation of the sleeve about the central body and relative to the first wing.

As can be seen in FIGS. 124*a*, 124*b*, and 124*c*, the sleeve is free to rotate relative to the longitudinal axis of the central body 1210 and thus relative to the first wing 1202 of the embodiment shown in FIGS. 119*a* and 119*b*. The sleeve can rotate relative to a second wing 1208, when the second wing is utilized in conjunction with the embodiment of FIGS. 119*a* and 119*b*. The pins limit the rotation of the sleeve. In an alternative embodiment, the pins are eliminated so that the sleeve can rotate to any position relative to the first wing.

It is to be understood that the sleeve can be comprised of biologically acceptable material such as titanium. Additionally, it can be comprised of super-elastic material such as an alloy of nickel and titanium, much as described hereinabove with respect to other embodiments.

The great advantage of the use of the sleeve 1204 as depicted in the embodiment of FIGS. 119*a* and 119*b* is that the sleeve can be rotated and repositioned with respect to the first wing 1202, and/or the second wing 1208 should the second wing be used in the embodiment, in order to more optimally position the implant 1200 between spinous processes. It is to be understood that the cortical bone or the outer shell of the spinous processes is stronger at an anterior position adjacent to the vertebral bodies of the vertebra that at a posterior position distally located from the vertebral bodies. Accordingly, there is some advantage of having the implant 1200 placed as close to the vertebral bodies as is possible. In order to facilitate this and to accommodate the anatomical form of the bone structures, as the implant is inserted between the vertebral bodies and urged toward the vertebral bodies, the sleeve 1204 can be rotated relative to the wings, such as wing 1202, so that the sleeve is optimally positioned between the spinous processes, and the wing 1202 is optimally positioned relative to the spinous processes. Without this capability, depending on the anatomical form of the bones, it is possible for the wings to become somewhat less than optimally positioned relative to the spinous processes.

Figure 125:
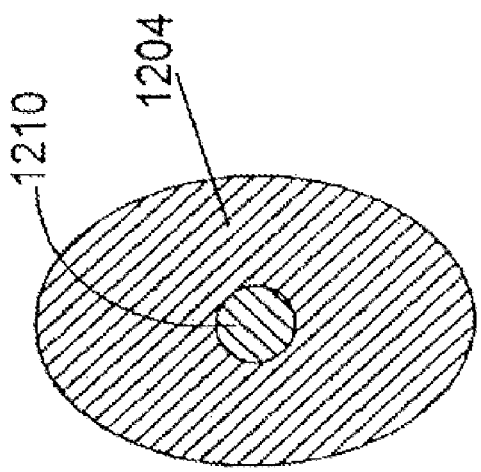
FIG. 125 depicts an alternative embodiment of the invention as depicted in FIGS. 119a and 119b.
Figure 126:
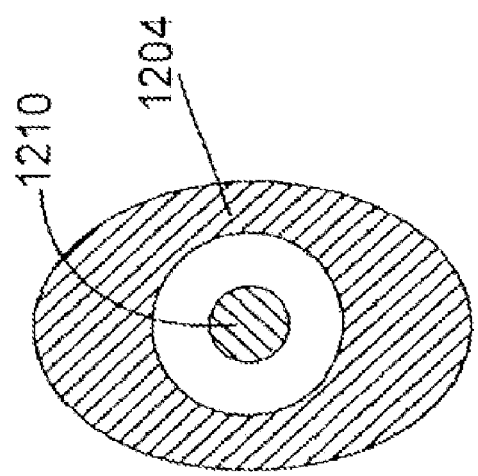
FIG. 126 depicts yet a further alternative embodiment of the invention depicted in FIGS. 119a and 119b.
Figure 127:
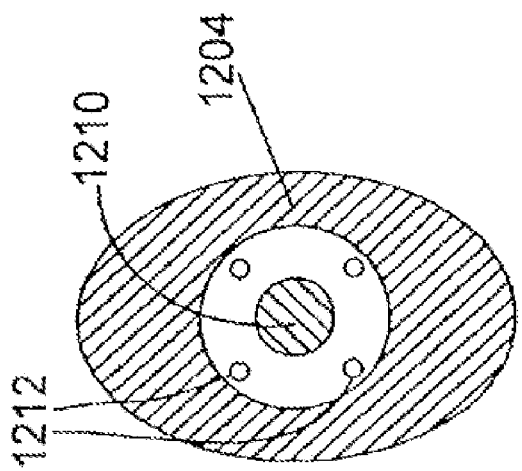
FIG. 127 depicts yet a further embodiment of the invention as depicted in FIGS. 119a and 119b.

FIGS. 125, 126 and 127 depict three alternative embodiments of the invention as can be seen through a line parallel to line 124-124 of FIG. 119*b*.

In FIG. 125, the sleeve 1204 is rotatable about central body 1210. In this embodiment, however, the sleeve 1204 design does not include the grooves 1222 as previously depicted in the embodiment shown in FIG. 123*a*. Thus, without pins, the sleeve is completely free to rotate about the central body 1210.

An alternative embodiment is shown in FIG. 126. In this embodiment, the sleeve 1204 is essentially a thin wall cylinder which is spaced from the central body 1210. Sleeve 1204 is free to move relative to central body 1210. Sleeve 1204 can rotate relative to central body 1210. In addition, sleeve 1204 can take a somewhat cocked or skewed position relative to central body 1210.

A further embodiment, it is shown in FIG. 127. This embodiment is somewhat similar to the embodiment shown in FIG. 126 except that in this case, several pins project from the first wing in order to somewhat limit and restrict the motion of the sleeve 1204. As shown in FIG. 127, four pins are depicted. It is to be understood however that such an embodiment can include one, two, three, four or more pins and be within the spirit and scope of the invention. It is to be understood that if the embodiment is used with a second wing, that similar pins can extend from the second wing. However, in the embodiment using a second wing, the pins-would preferably be somewhat flexible so that they could snap into the inside of the sleeve 1204 as the second wing is inserted relative to the central body and secured in place. In the embodiment shown in FIG. 127, the sleeve 1204 is free to rotate about the longitudinal axis of the central body 1210 and is somewhat restricted in this motion and its ability to become skewed relative to the longitudinal axis of the central body by the pins.

Figure 128:
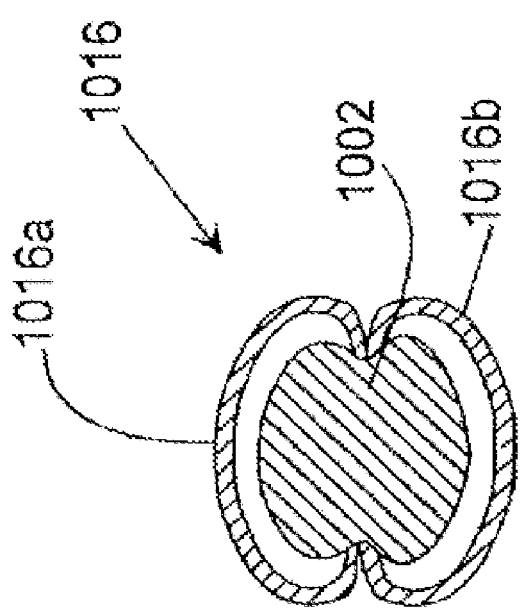

The embodiments of FIG. 128 is an advantageous alternative to that of FIG. 93*a*. In this embodiment, the central body 1002 is similar to that as shown in FIG. 93*a*. The sleeve 116 is comprised of two sleeve portions 1016*a* and 1016*b*. The sleeve portions are preferably formed from flat stock material which is substantially easier to form than having the sleeve formed or machined from solid bar stock material. A further advantage of the sleeve 1016, if formed of super-elastic material, is that the sleeve can be formed in a manner which optimizes the super-elastic characteristics of such material in order to enhance its ability to repeatedly deflect under load. In this particular embodiment, the sleeve portions 1016*a* and 1016*b* are somewhat C-shaped and then after being formed, are snapped into the grooves of the central body 1002.

Figure 129:
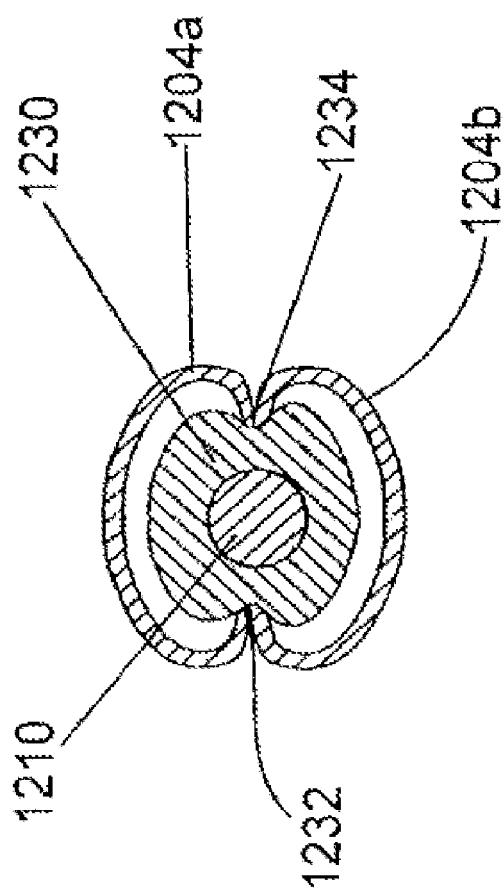
FIG. 129 depicts still a further embodiment of the invention as depicted in FIGS. 119a and 119b.

An alternative embodiment of the invention is shown in FIG. 129. This embodiment is most favorably used with the embodiment of FIGS. 119*a* and 119*b*. In this particular embodiment, the sleeve 1204 is designed to rotate about the central body 1210. Sleeve 1204 includes a central member 1230 which includes a bore that receives the central body 1210. The central member 1230 is rotatable about the central body 1210 of the implant 1200. The central member 1230 includes first and second grooves 1232 and 1234. These grooves can receive C-shaped sleeve members 1204*a* and 1204b. These C-shaped sleeve members are similar in construction and design to the C-shaped sleeve members shown above with respect to FIG. 128. These sleeve members can be snapped into position relative to the central member 1230 of the sleeve 1204. It is to be understood that other mechanisms can be used to secure the C-shaped sleeve member relative to the central member of the sleeve and be within the spirit and scope of the invention. Further, it is to be understood that the sleeve members 1204a and 1204b can be formed from a single flat stock material such that one of the grooves 1232 and 1234 receives continuous piece of flat material which has been appropriately bent and the other grooves receives two ends of the sleeve.

From the above, it is evident that the present invention can be used to relieve pain caused by spinal stenosis in the form of, by way of example only, central canal stenosis or foraminal (lateral) stenosis. These implants have the ability to flatten the natural curvature of the spine and open the neural foramen and the spacing between adjacent vertebra to relieve problems associated with the above-mentioned lateral and central stenosis. Additionally, the invention can be used to relieve pain associated with facet arthropathy. The present invention is minimally invasive and can be used on an outpatient basis.

The following description is presented to enable any person skilled in the art to make and use the invention. Various modifications to the embodiments described will be readily apparent to those skilled in the art, and the principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all patents and patent applications cited in this application are incorporated herein by reference.

Figure 130A:
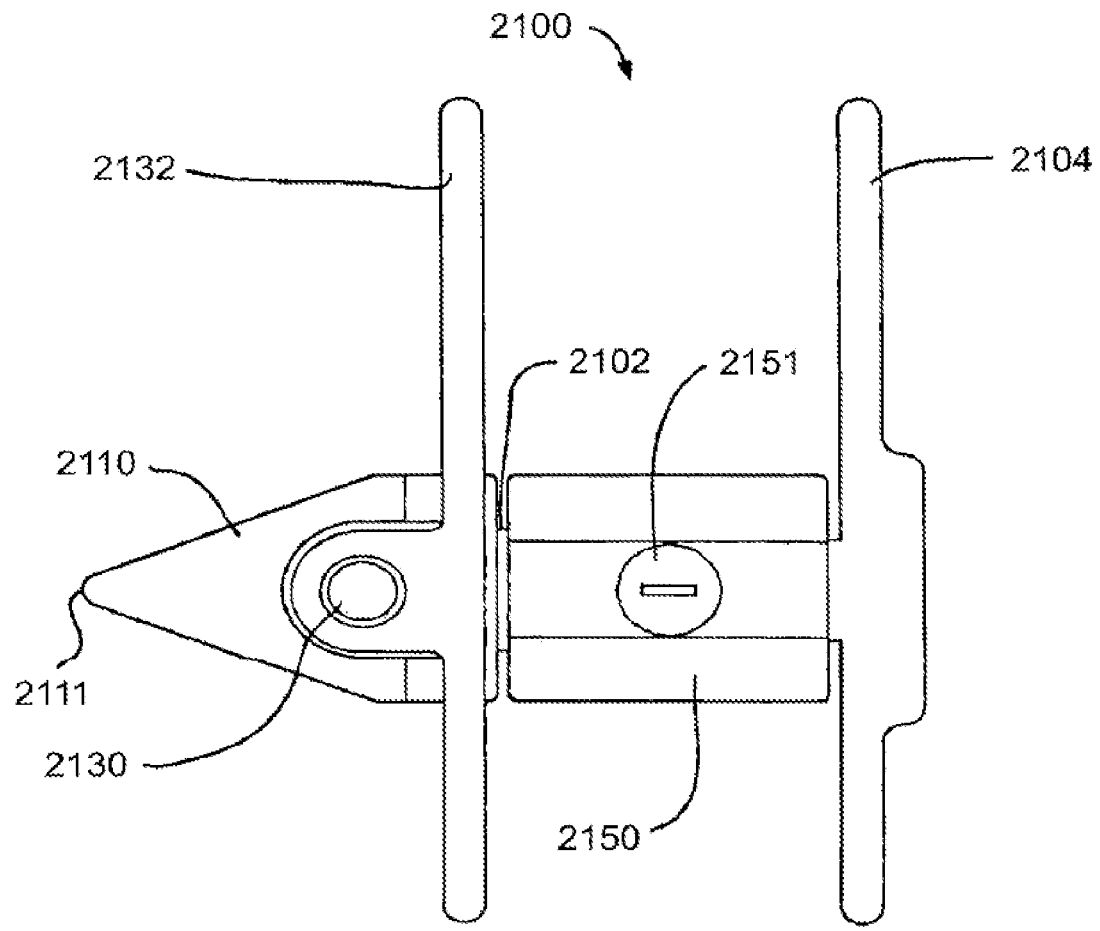
FIG. 130A is a front plan view of one embodiment of an apparatus with a selectably expandable spacer.
Figure 130B:
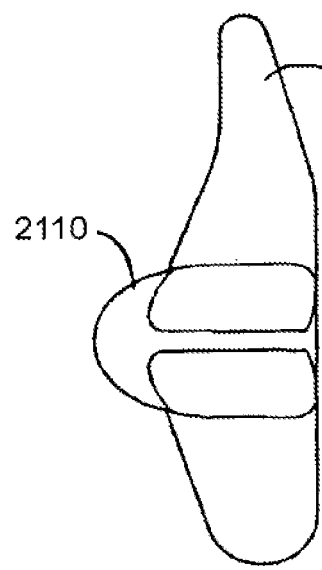
FIG. 130B is a left side view of the apparatus of FIG. 130A.
Figure 130C:
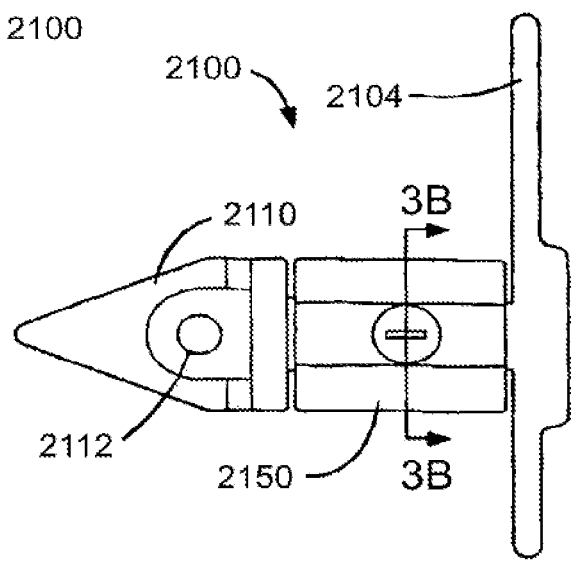
FIG. 130C is a front plan view of the apparatus of FIG. 130A including a selectably expandable spacer, a main body and a first wing.
Figure 130D:
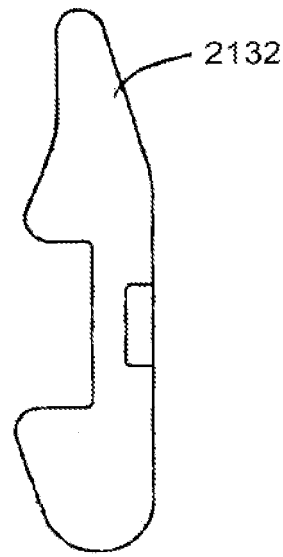
FIG. 130D is a left side view of the second wing of the apparatus of FIG. 130A.
Figure 130E:
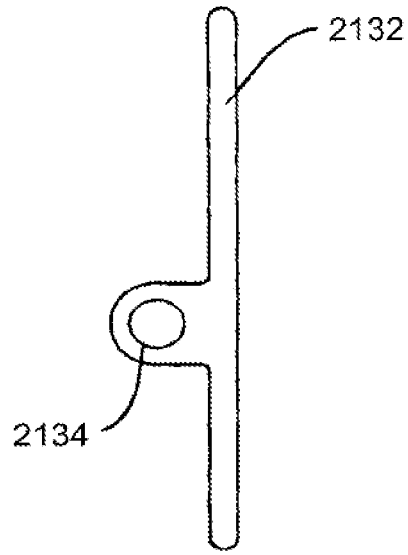
FIG. 130E is a front plan view of the second wing of the apparatus of FIG. 130A.
Figure 130F:
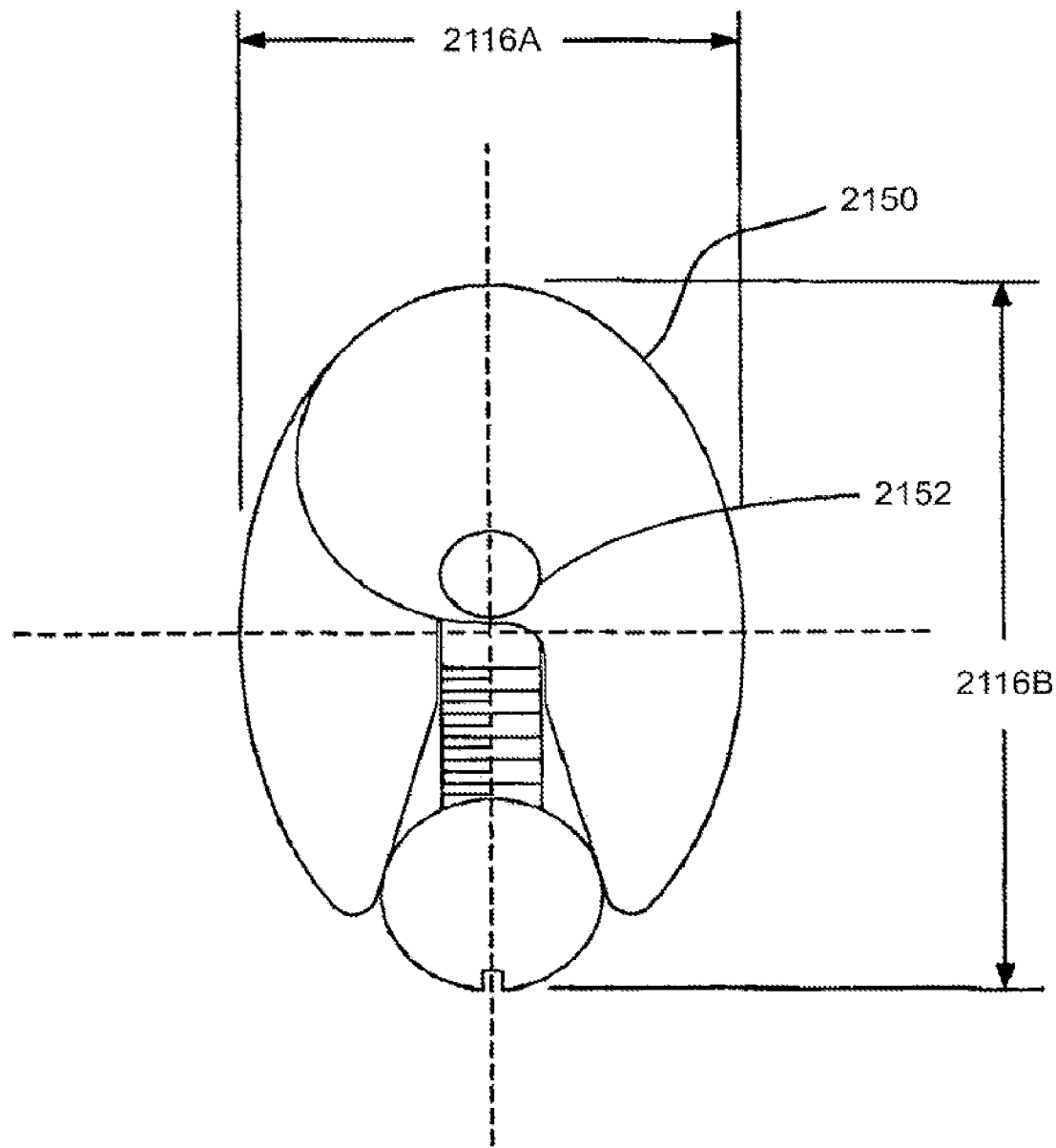
FIG. 130F is an end view of the selectably expandable spacer of the apparatus of FIG. 130A.

FIGS. 130A-130F illustrate an embodiment of an apparatus, or implant 2100, suitable for use with the method of this invention. The implant 2100 includes a first wing 2104, a selectably expandable spacer 2150 and a lead-in tissue expander or distraction guide 2110. The implant further includes, as required, a second wing 2132. As can be seen in FIG. 130A, a shaft 2102 extends from the first wing 2104 and is the body that connects the first wing to the distraction guide 2110. Also, as can be seen in FIGS. 130A and 130B, the guide 2110 in this particular embodiment is pointed in order to allow the implant to be inserted between, and, if necessary, to distract adjacent spinous processes. In this particular embodiment, the guide 2110 has a wedge-shaped cross-section, expanding from the distal end 2111 to the area where the second wing 2132 can be optionally secured to the guide. FIGS. 130B and 130C illustrate an embodiment of the implant 2100 with only a first wing 2104.

As required, implant 2100 can include a second wing 2132 which fits over the guide 2110 and is secured by a bolt 2130 placed through aperture 2134 of the second wing 2132 to the threaded bore 2112 located in the guide 2110. As implanted, the first wing 2104 is located adjacent to first sides of the spinous processes and the second wing 2132 is located adjacent to second sides of the same spinous processes.

The spacer 2150 is rotatably mounted about a shaft 2102. The spacer 2150 is positioned between the first wing 2104 and the guide 2110. The tissue expander 2110 guides the spacer 2150 into position between the spinous process of adjacent vertebrae. The spacer 2150 includes a slotted sphere 2151 that when rotated is positioned along a lead-screw, expanding or collapsing the spacer.

FIGS. 130F, 131A-B, 132A-B, and 133 illustrate a preferred embodiment of the spacer 2150 wherein the shape of the spacer 2150 is oval or elliptical in cross-section, although it can alternatively be circular or ovoid or race-track shaped in cross-section. It is to be understood that the spacer 2150 can have other shapes as described throughout the specification and be within the spirit and scope of the invention. In a preferred embodiment, the spacer 2150 includes a bore 2152 extending the length of the spacer 2150. The bore 2152 of the spacer 2150 is received over the shaft 2102 of the implant 2100 so that, as described above, the spacer can be rotated about the shaft 2102. In these embodiments, the spacer 2150 can have minor and major dimensions as follows:

| Minor Dimension (116a) | Major Dimension (116b) |
| --- | --- |
| 6 mm | 10 mm |
| 8 mm | 10.75 mm |
| 12 mm | 14 mm |
| 6 mm | 12.5 mm |
| 8 mm | 12.5 mm |
| 10 mm | 12.5 mm |

One advantage of the use of the spacer 2150, as depicted in the embodiment of FIG. 130A, is that the spacer 2150 can be partially rotated and repositioned with respect to the first wing 2104 in order to optimize positioning of the implant 2100 between spinous processes. It is to be understood that the cortical bone or the outer bone of the spinous processes is stronger at an anterior position adjacent to the vertebral bodies of the vertebra than at a posterior position distally located from the vertebral bodies. Also, biomechanically for load bearing, it is advantageous for the spacer 2150 to be close to the vertebral bodies. In order to facilitate this and to accommodate the anatomical form of the bone structures, as the implant is inserted between the spinous processes and/or urged toward the vertebral bodies, the spacer 2150 rotates relative to the wings, such as wing 2104, so that the spacer 2150 is optimally positioned between the spinous processes, and the wing 2104 is optimally positioned relative to the spinous processes.

In another embodiment, the spacer 2150 has a cross-section with a major dimension and a minor dimension, wherein the major dimension is greater than the minor dimension, and, for example, less than about two times the minor dimension. It is to be understood that the spacer 2150 can be fabricated from somewhat flexible and/or deflectable material.

In this embodiment the spacer is made out of a polymer, more specifically, the polymer is a thermoplastic. Still more specifically, the polymer is a polyketone known as polyetheretherketone (PEEK™). Still more specifically, the material is PEEK 450G, which is an unfilled PEEK approved for medical implantation available from Victrex of Lancashire, Great Britain. (Victrex is located at www.matweb.com or see Boedeker www.boedeker.com). Other sources of this material include Gharda located in Panoli, India (www.ghardapolymers.com).

The spacer 2150 can be formed by extrusion, injection, compression molding and/or machining techniques. This material has appropriate physical and mechanical properties and is suitable for carrying and spreading the physical toad between the spinous process. For example, in this embodiment, the PEEK has the following approximate properties:

| | |
|---|---|
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 Gpa |

It should be noted that the material selected may also be filled. For example, other grades of PEEK are also available and contemplated, such as 30% glass-filled or 30% carbon-filled, provided such materials are cleared for use in implantable devices by the FDA, or other regulatory body. Glass-filled PEEK reduces the expansion rate and increases the flexural modulus of PEEK relative to that which is unfilled. The resulting product is known to be ideal for improved strength, stiffness, or stability. Carbon-filled PEEK is known to enhance the compressive strength and stiffness of PEEK and lower its expansion rate. Carbon-filled PEEK offers wear resistance and load carrying capability.

In this embodiment, as described above, the spacer 2150 is manufactured from polyetheretherketone (PEEK™), available from Victrex. As will be appreciated, other suitable similarly biocompatibte thermoplastic or thermoplastic polycondensate materials that resist fatigue, have good memory, are flexible, and/or deflectable, have very low moisture absorption, and good wear and/or abrasion resistance, can be used without departing from the scope of the invention. The spacer can also be comprised of polyetherketoneketone (PEKK).

Other materials that can be used include polyetherketone (PEK), polyetherketoneetherketoneketone (PEKEKK), and polyetheretherketoneketone (PEEKK), and generally a polyaryletheretherketone. Further other polyketones can be used as well as other thermoplastics. The spacer can also be made of titanium.

Reference to appropriate polymers that can be used in the spacer can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials."

Other materials such as Bionate®, polycarbonate urethane, available from the Polymer Technology Group, of Berkeley, Calif., may also be appropriate because of the good oxidative stability, biocompatibility, mechanical strength and abrasion resistance. Other thermoplastic materials and other high molecular weight polymers can be used.

Figure 131A:
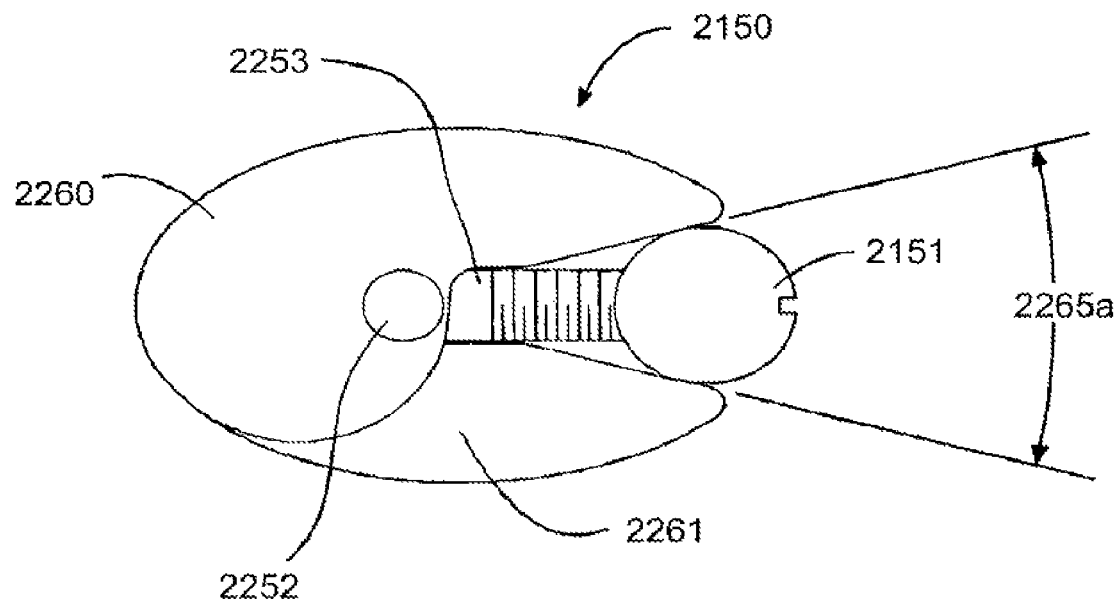
FIG. 131A is a right side view of an embodiment of the selectably adjustable spacer in an unexpanded position.

A preferred embodiment of the spacer is illustrated in FIGS. 131A-134A. In FIGS. 131A and 131B the spacer 2150 includes a first portion 2260 pivotably or rotatably coupled with a second portion 2261 by a hinge (shown in FIG. 133). Both the first portion 2260 and the second portion have tapered distal ends that form an acute angle between the two portions. FIG. 131A illustrates the acute angle 2265a formed when the spacer 2150 is in the unexpanded position. The first portion 2260 has a bore 2252 through which the shaft 2102, shown in FIG. 130A, is received, connecting the first wing 2104 with the guide 2110 and connecting the spacer 2150 with the implant 2100. The bore 2252 allows the spacer 2150 to partially rotate about the shaft 2102. The second portion 2261 of the spacer 2150 also has a bore that is located behind and aligned with the bore 2252, shown in FIG. 131A. This bore is also received on the shaft 2102 so that both the first and second portions of the spacer 2150 can rotate about the shaft 2102. A threaded screw 2253 protrudes through the angle 2265 a formed by the tapered distal ends of the portions. The end of the threaded screw 2253 also has a bore that aligns with the bores of the first and second portions of the spacer 2150 and is received on the shaft 2102 and can rotate about the shaft 2102. A slotted sphere 2151 is connected with the distal end of screw 2253. In the least expanded position, the slotted sphere 2151 is at the farthest point of travel away from the proximal end of the screw 2253, shown in FIG. 131A.

Figure 131B:
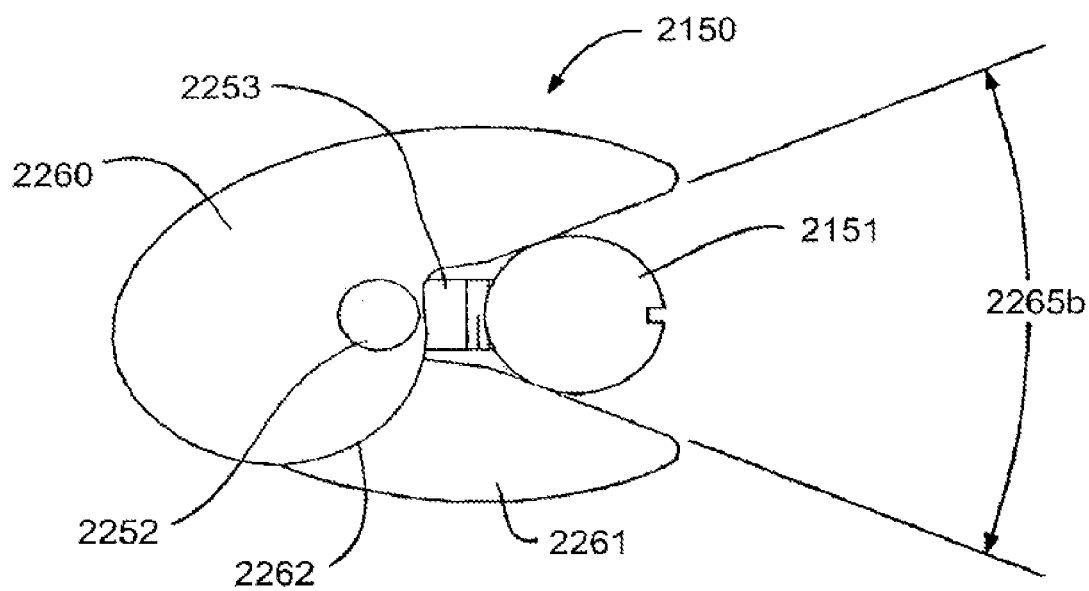
FIG. 131B is a right side view of an embodiment of the selectably adjustable spacer in a fully

FIG. 131B illustrates the acute angle 2265b formed when the spacer 2150 is in the fully expanded position. The slatted sphere 2151 is rotated such that the sphere travels toward the proximal end of the threaded screw 2253. As the slotted sphere 2151 travels toward the proximal end of the screw 2253, the sphere 2151 forces the tapered distal ends of the portions 2260, 2261 apart. As the distal ends of the portions are forced apart, the first portion 2260 and the second portion 2261 rotate in opposite directions about a common hinge 2463 (shown in FIG. 133), sliding along the contact surface 2262. As the acute angle formed by the distal ends of the portions increases, the height of the spacer 2150 expands.

Figure 132A:
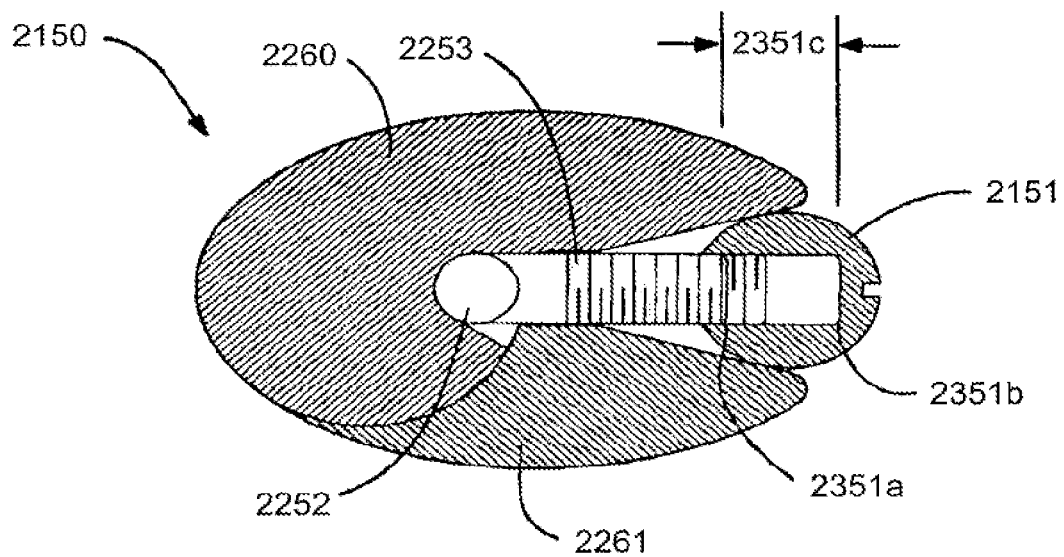
FIG. 132A is a right side cross-sectional view of an embodiment of the selectably adjustable spacer in an unexpanded position.
Figure 132B:
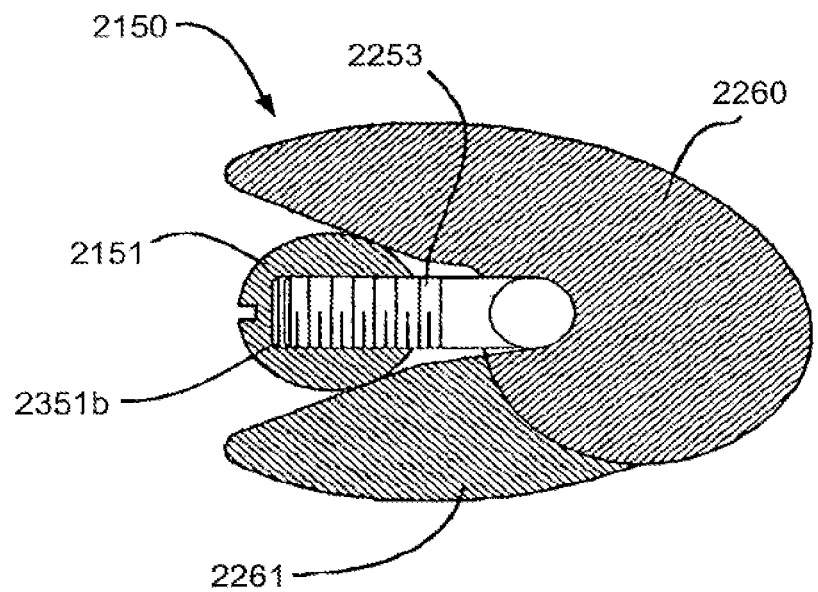
FIG. 132B is a left side cross-sectional view of an embodiment of the selectably adjustable spacer in a fully expanded position.

FIGS. 132A and 132B illustrate in cross-section the preferred embodiment of the selectably expandable spacer described in reference to FIGS. 131A and 131B. The slotted sphere 2151 has a threaded cavity for receiving the threaded screw 2253 when the sphere 2151 is rotated. The slotted sphere 2151 travels the distance 2351c such that the distal end of the screw 2253 moves from position 2351a to position 2351b along the threaded cavity of the sphere when adjusted from an unexpanded to a fully expanded position. When rotated in the opposite direction, the slotted sphere 2151 moves away from the proximal end of the screw 2253, collapsing the spacer 2150. FIG. 132B illustrates the spacer 2150 in a fully expanded position with the distal end of the screw 2253 at the maximum position 2351b in the threaded cavity of the slotted sphere 2151. It is to be understood that portions the 2260, 2261 of the spacer 2150 can be biased to the closed position shown in FIG. 132A. The biasing can be accomplished by a spring that is coiled in or about the bore of the spacer that receives the shaft 2102. Such a spring would be connected to both of the portions 2260, 2261 of the spacer 2150.

The first and second portions of the spacer 2150 in combination, can have a cross-section that is elliptical, oval, ovoid, football-shaped, circular-shaped, rectangular with rounded ends (where the cross-section has two somewhat flattened surfaces and two rounded surfaces similar to the effect of a flattened ellipse) or race-track shaped. Further, the first and second portions can have different cross-sectional shapes relative to each other. At least the minor dimension (the height) of the spacer is between 6 mm and 14 mm. Typically, the minor outer dimension is one of 6 mm, 8 mm, 10 mm, 12 mm, and 14 mm. The different sizes and selectable expandability enable the spacer to accommodate different sized patients.

As discussed above, the spacer 2150 and its components, including either the first or second portions, or both, can be made of a number of materials. Suitable materials can include polymers, such as; for example, polyetheretherketone (PEEK™), as well as other materials described above, including titanium. Such materials can be deflectable and flexible depending on the configuration of the spacer 2150.

Further, the deflectable or flexible material can have a graduated stiffness to help gradually distribute the load when the spinous processes place a force upon the exterior surface of the spacer. This can be accomplished by forming multiple layers of the deflectable or flexible material with decreasing stiffness or hardness from the center of the spacer outwardly. Alternatively, the material can have a higher stiffness or hardness in the center of the inner spacer.

Figure 133:
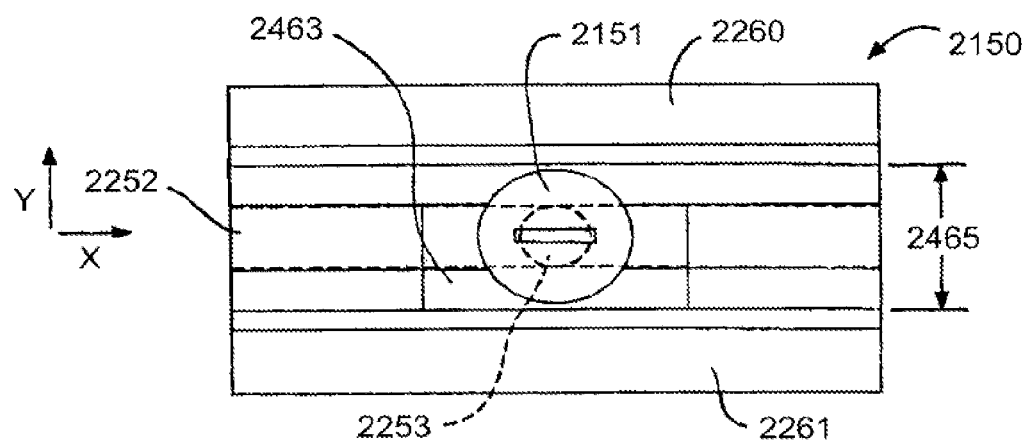
FIG. 133 is a front side view of an embodiment of the selectably adjustable spacer.

Referring to FIG. 133, the slotted sphere 2151 is positioned approximately equidistant from a first and second ends of the spacer 2150, distributing the parting force of the sphere 2151 so as not to create disproportionate stress on either side of the spacer 2150.

A hinge 2463 couples a first portion 2260 with a second portion 2261, such that the two portions pivot about the hinge 2463, expanding or collapsing the gap 2465.

Figure 134A:
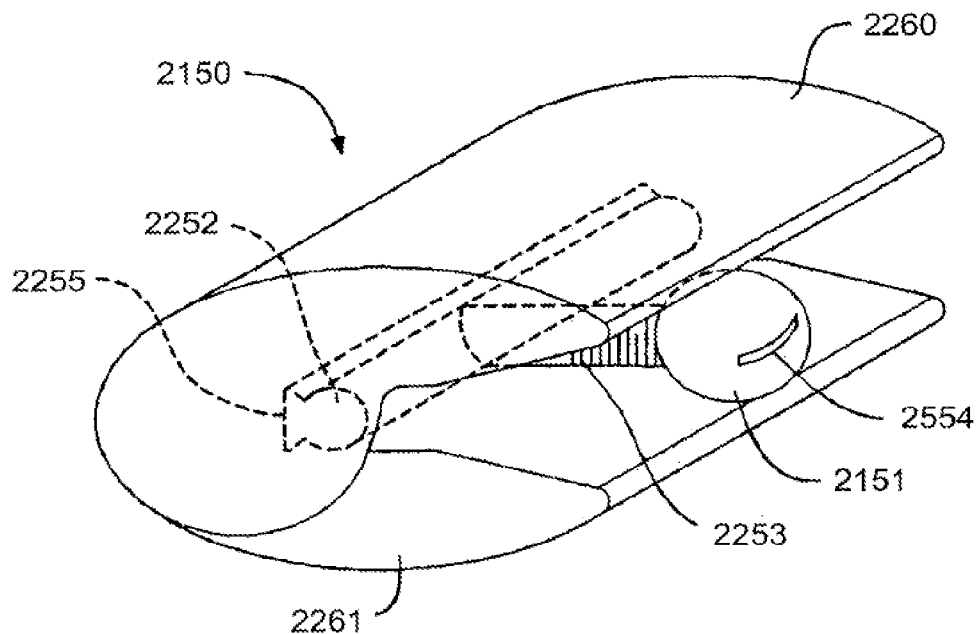
FIG. 134A is a perspective view of an embodiment of the selectably adjustable spacer.

A perspective view is provided in FIG. 134A, showing the clam-shape of the preferred embodiment of the spacer 2150. The implant 2100 is positioned between the adjacent vertebrae so as to permit access to the slot 2554 from a posterior direction both during and after surgery. Post-surgery adjustment is made using a cannula inserted through the patient's back. Convenient access to the slot 2554 is important for reducing patient discomfort and procedure complication.

The bore 2252 provides a sleeve for the shaft 2102, and also limits the rotation of the spacer 2150 about the shaft 2102. Limiting the rotation of the spacer 2150 can be accomplished, for example, by providing a slot 2255 in the bore 2252 and a key on the shaft 2102, or vice-versa. One of skill in the art can appreciate that different mechanisms and geometries can be used to limit spacer rotation. Reference is also made to a copending U.S. patent application Ser. No. 09/799,470, filed on Mar. 5, 2001, entitled "Spinal Implants, Insertion Instruments, and Methods of Use," which is incorporated herein by reference and which discloses an implant which has a spacer with a slot and an implantation tool that includes a probe that engages the slot in order to position the spacer relative to the implantation tool for desirable initial positioning of the space relative to the spinous processes. Such a mechanism can be used by itself or in addition to the above discussed keyway and key for purposes of positioning the sphere 2151 so that the height of the spacer 2150 can be selectively adjusted during the initial surgical procedure or, thereafter, should such adjustment be desirable due, for example, to the need for more distraction between the spinous processes.

Figure 134B:
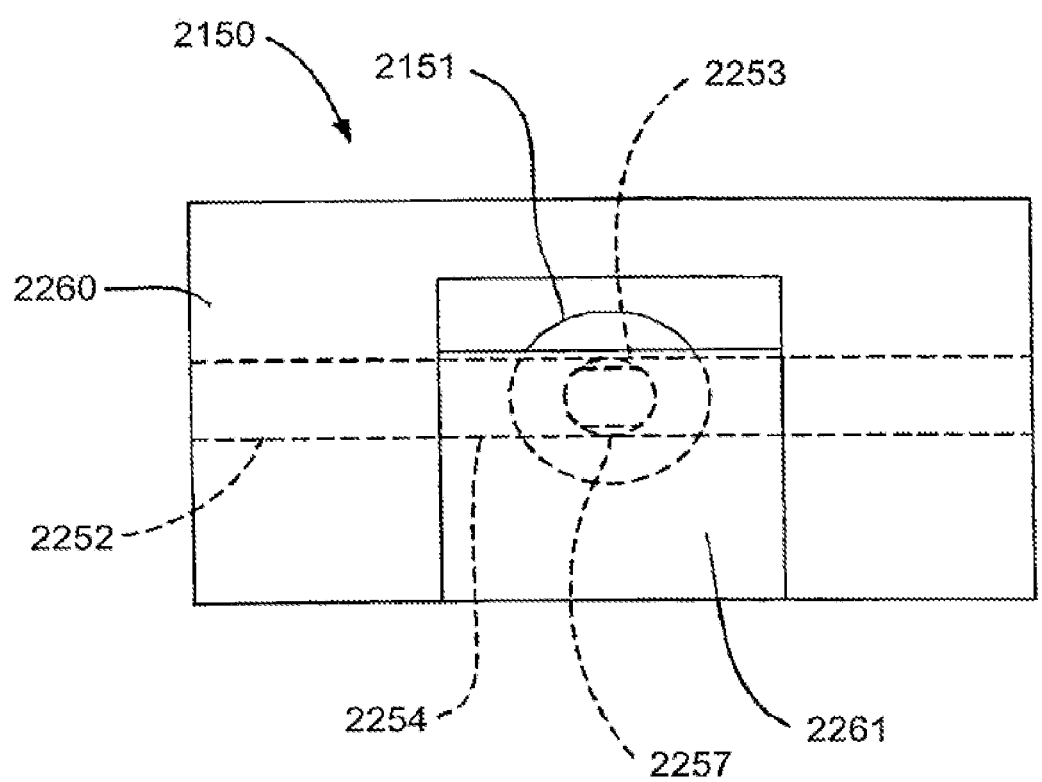
FIG. 134B is a back view of another embodiment of the spacer similar to that shown in FIG. 134A with a mechanism for allowing the spacer to expand.

FIG. 134B depicts the back of another embodiment of the spacer 2150 of the implant 2100 of the invention. FIG. 134B is similar to a back view of the embodiment depicted in FIG. 133. In FIG. 134B, the spacer 2150 includes the first and second portions 2260, 2261, respectively. The first portion includes a bore 2252 that receives the shaft 2102 and the second portion includes bore 2254 that also receives the shaft 2102. In addition, the screw 2253 is shown with a portion of the sphere 2151 that is used to adjust the height of the spacer 2150. The screw 2253 includes a bore 2257 that also receives the shaft 2102. Thus, the first and second portions of the spacer and the screw are rotatable about the shaft.

Figure 135A:
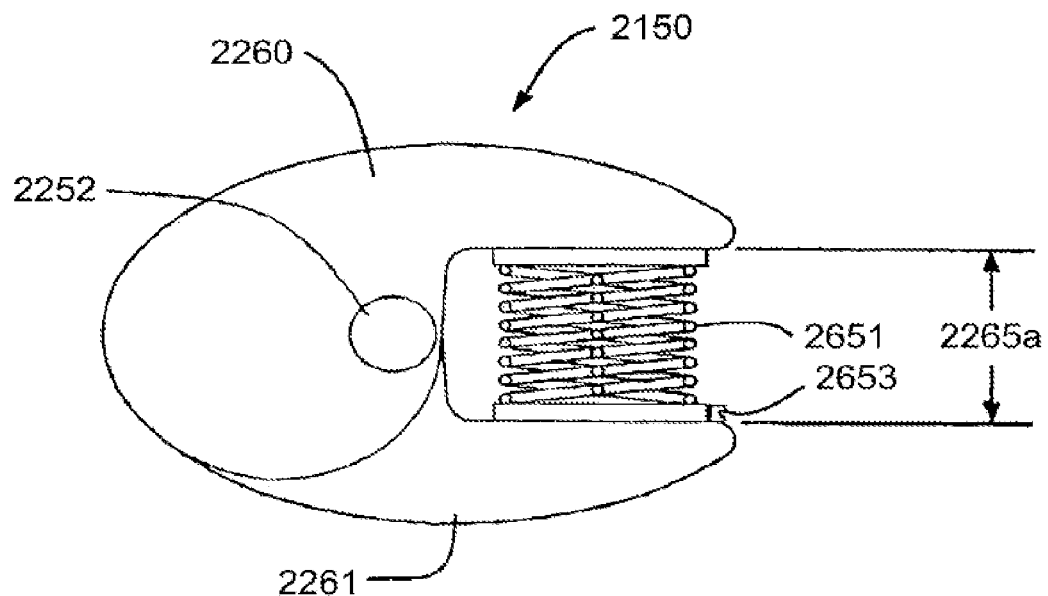
FIG. 135A is a right side view of an alternative embodiment of the selectably expandable spacer with a jack expansion mechanism in an unexpanded position.
Figure 135B:
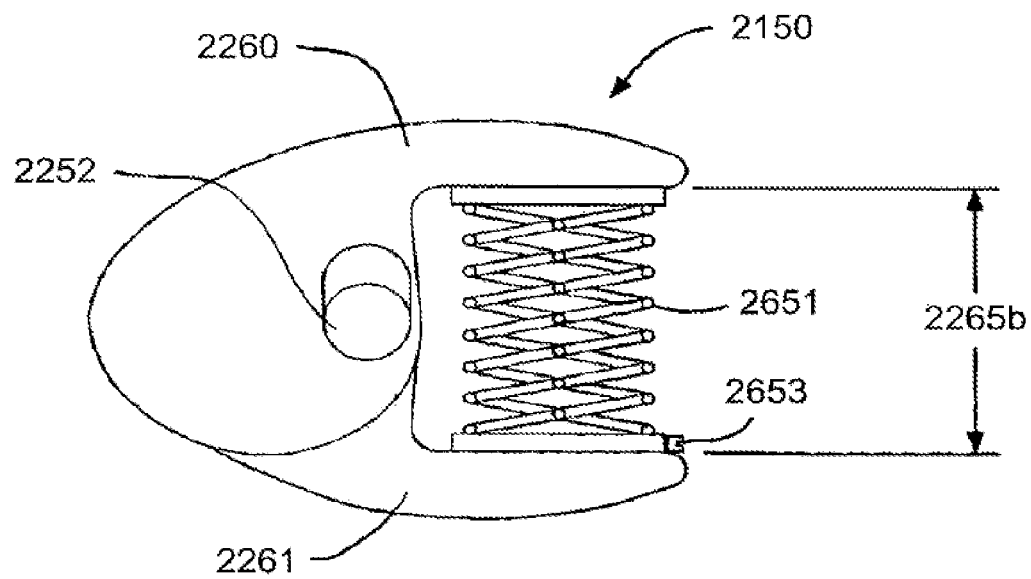
FIG. 135B is a right side view of an alternative embodiment of the selectably expandable spacer with a jack expansion mechanism in a fully expanded position.

One of skill in the art can also appreciate the different expansion mechanisms that can be employed to expand the spacer 2150. For example, an expansion mechanism could include: pistons, ratchets, cams, jacks, or other machines. FIGS. 135A and 135B illustrate one alternative embodiment in which a jack 2651 is used to expand the spacer 2150. The jack 2651 is expanded or collapsed by rotating a slotted screw 2653, thereby increasing or decreasing the gap 2665. FIG. 135A shows the spacer 2150 in an unexpanded position with a narrow gap 2665a.

FIG. 135B illustrates another alternative embodiment utilizing a jack, whereby the hinge 2462 can allow for translation of the first and second portions in the y-direction as well as for rotation about the hinge 2462, thereby reducing the stresses on the side of the jack closest to the hinge caused by uneven compression when the gap 2665b expands. For the embodiment in FIGS. 135A and 135B any of the above devices for allowing the first portion of the spacer to move relative to the second portion of the spacer can be employed, as well as other known methods, and be within the spirit and scope of the invention.

Figure 136:
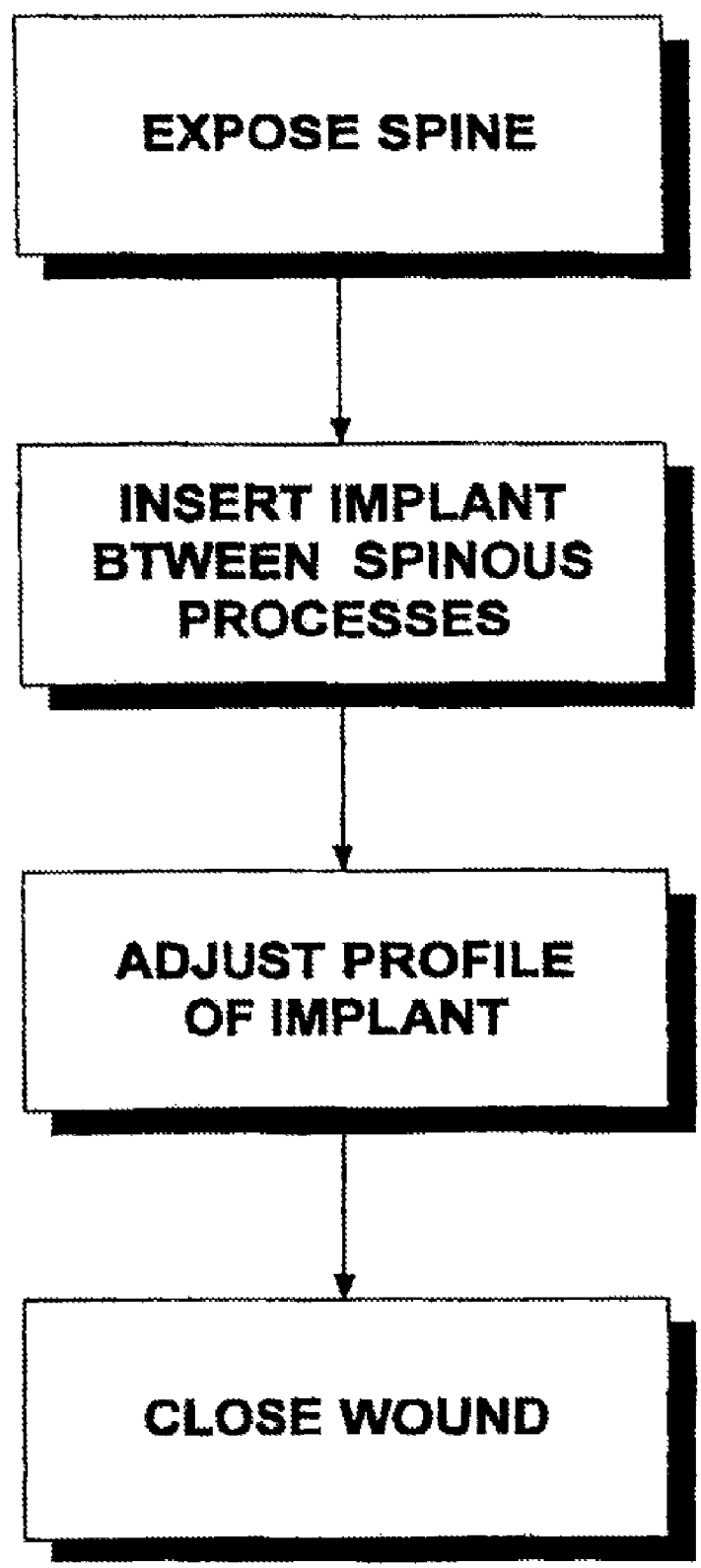
FIG. 136 is a block diagram demonstrating the steps for performing the method.

The preferred method for inserting the implant between adjacent vertebrae is block-diagramed in FIG. 136. The method requires that the spine be surgically exposed. The implant is then inserted between the spinous processes, with the wedge shape of the guide forcing tissue apart to create room for the implant. Once the implant is in place, with the spacer between adjacent vertebrae, the profile of the implant is adjusted by expanding or collapsing the spacer using a tool for operating the expansion mechanism. The wound is then closed.

The implant can subsequently be readjusted with the insertion of a cannula through which a tool is inserted for operating the expansion mechanism.

Embodiments of the present invention relate to an interspinous process implant including a first wing for implant retention after placement, a spacer for maintaining and/or causing additional distraction, and a tissue expander for converting from a first position for insertion to a second position for retention of the implant after placement between adjacent spinous processes. In the second position, the tissue expander acts like a second wing to prevent displacement of the implant. The disclosed invention further claims a method for lateral insertion of the disclosed implant of the invention.

Figure 137:
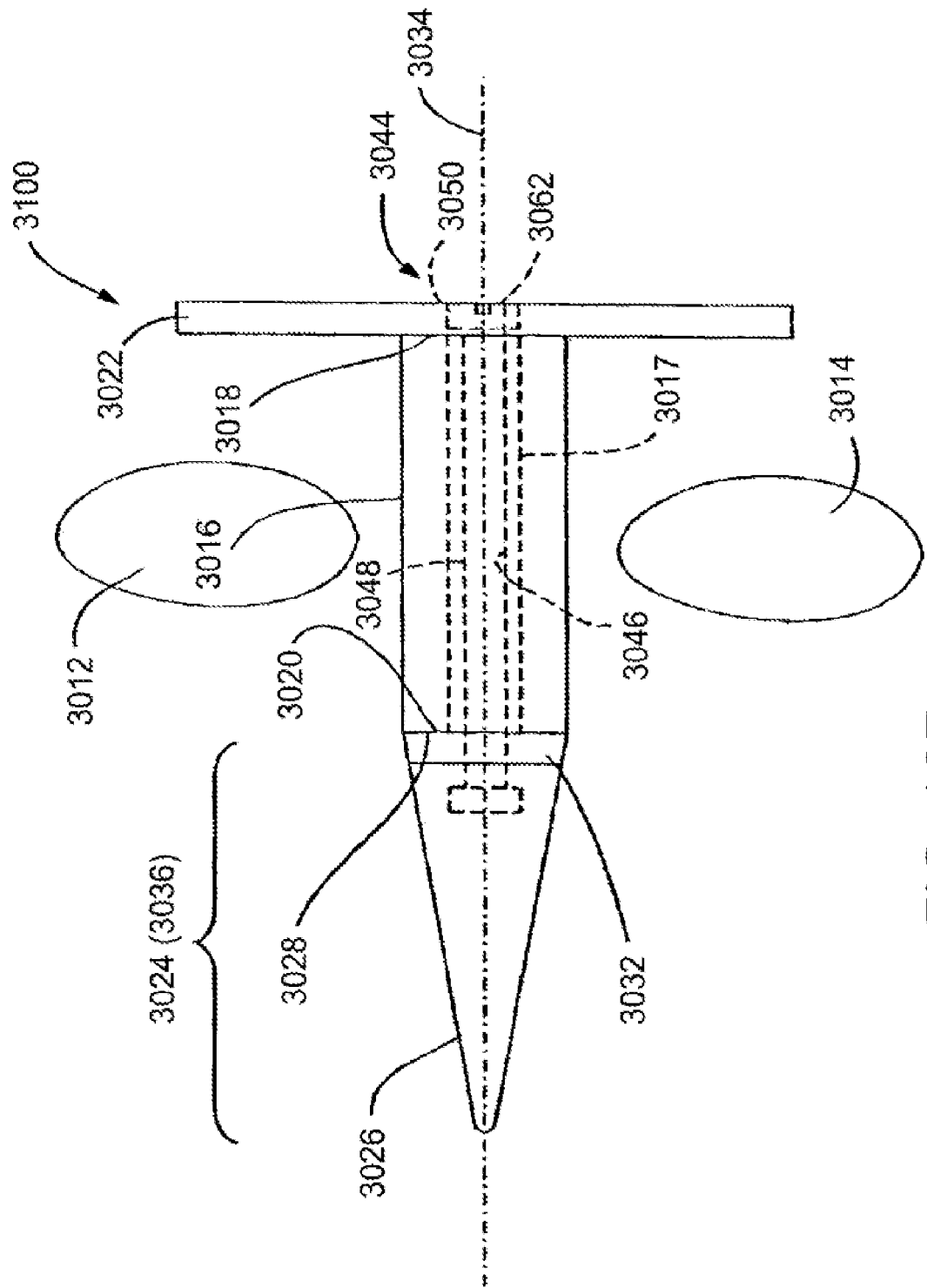
FIG. 137 depicts a side view of an embodiment of the implant of the invention, in a first insertion position.

FIG. 137 shows a side view of an embodiment of an implant 3100 of the disclosed invention. The implant 3100 comprises a spacer 3016 that maintains the distraction of the spinous processes of adjacent vertebrae, once the spacer 3016 is positioned between the spinous processes 3012, 3014. The spacer 3016 can have various shapes including, by way of example only, a cylindrical shape, an elliptical shape, or teardrop shape when viewed in cross-section substantially perpendicular to a longitudinal or elongated axis 3034 of the spacer 3016. The longitudinal axis 3034 is oriented from the left lateral to right lateral spine, when the implant 3100 is positioned in the spine.

The spacer 3016 has a first or proximal end 3018 and a second or distal end 3020. At the first end 3018, the spacer 3016 is connected with a first wing 3022. The first wing 3022 functions as a first retaining unit. That is, the first wing 3022 prevents displacement of the implant 3100 once the implant 3100 is positioned in the spine, with the spacer 3016 between adjacent spinous processes. From the first wing 3022 extends a shaft 3017 upon which the rotatable spacer 3016 is rotatably mounted, so that the spacer 3016 can rotate independently from the first wing 3022 for positioning of both elements of the implant 3100. Alternatively, the first wing 3022 can be fixedly connected with, or integral to the spacer 3016.

The second end 3020 of the spacer 3016 is located adjacent to a tissue expander 3024. The tissue expander 3024 has a wedge-shaped first end 3026 that is distal to the spacer 3016, and a second end 3028 that is adjacent the spacer 3016. As discussed below, the tissue expander 3024 can be rotated about the axis 3034. When the tissue expander 3024 is rotated about the rotation axis 3034, it is converted from a first insertion position 3036 (shown in FIGS. 137 and 138) to a second retention position 3042 (shown in FIGS. 139 and 140).

Figure 138:
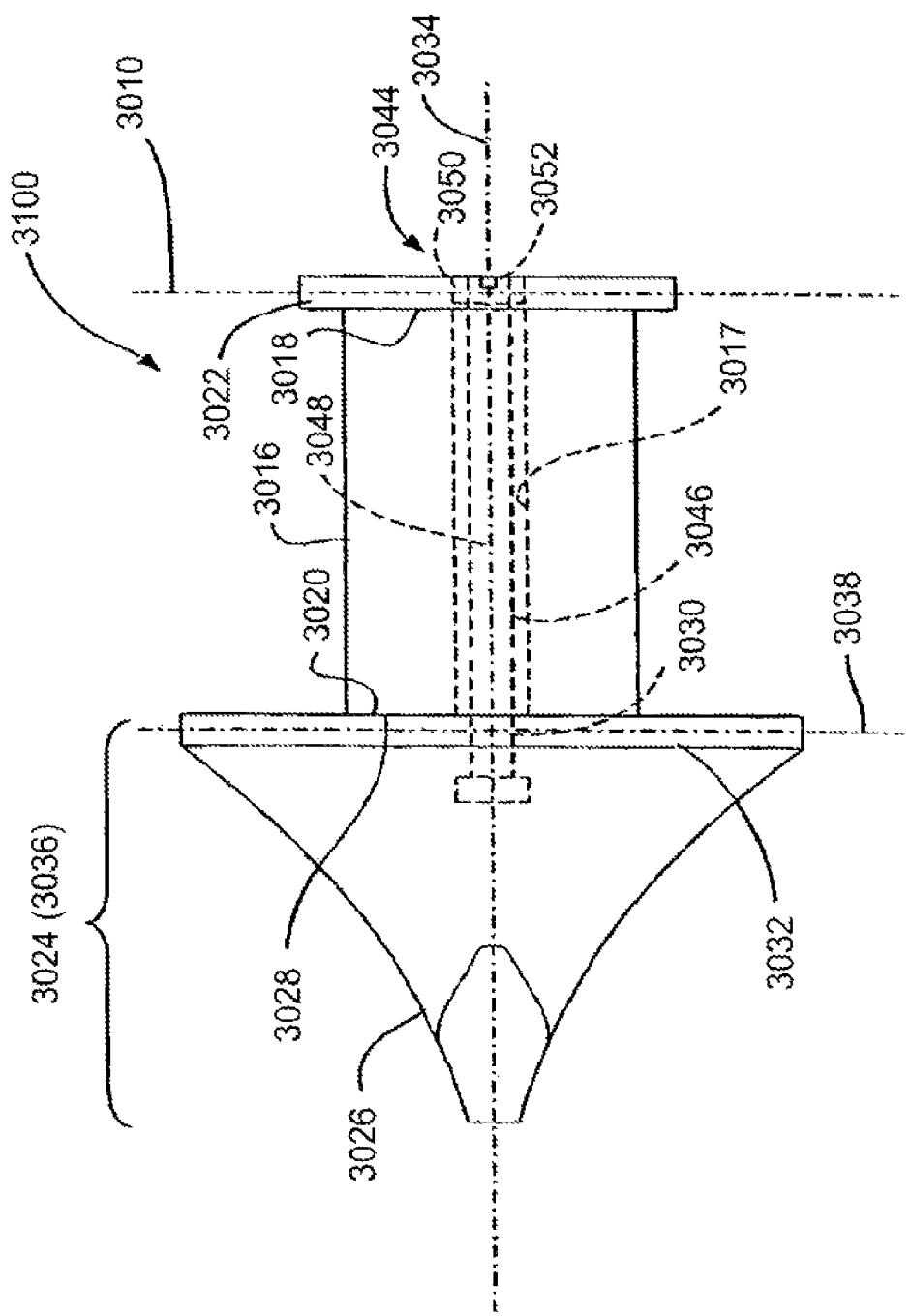
FIG. 138 is a top-down view of the embodiment of the implant of the invention depicted in FIG. 137 in the first insertion position.

In FIGS. 137 and 138, the tissue expander 3024 is in the first insertion position 3036, where FIG. 137 is a side view of an embodiment of the implant of the invention, and FIG. 138 is a top-down view of an embodiment of the implant 3100 of the invention, in the same first insertion position 3036 as the implant 3100 depicted in FIG. 137. The first end 3026 of the tissue expander 3024 is wedge-shaped in the direction of insertion, where the implant 3100 is inserted laterally. That is, where the implant 3100 is to be inserted laterally, the wedge-shaped first end 3026 is narrowest at the point of insertion and broadens along the length of the tissue expander 3024 toward the second end 3028 of the tissue expander 3024 that is located adjacent to the second end 3020 of the spacer 3016. The wedge shape of the tissue expander 3024 facilitates insertion of the implant 3100 by initiating distraction, if no other method is used during implantation, or by adding to or maintaining distraction created by another source, if any other such source is employed.

FIG. 138 shows a top-down view of the implant 3100, with the tissue expander 3024 in the first insertion position 3036. The elongated base element 3032 of the tissue expander 3024 in the first insertion position 3036, where insertion is from a lateral direction, is oriented in an anterior-posterior direction relative to a patient. In contrast, as discussed in greater detail below, the elongated base element 3032 of the tissue expander 3024 in the second retention position 3042 is oriented substantially perpendicular to the first insertion position 3036, in a direction that is substantially perpendicular to the anterior-posterior direction relative to the patient. In this embodiment, the elongated base element 3032 in the first insertion position 3036 can further be described as substantially perpendicular to the orientation of the first wing 3022, the first wing 3022 being at about a 90° angle from the anterior-posterior direction relative to the patient, substantially parallel to the axial plane of the patient.

Figure 139:
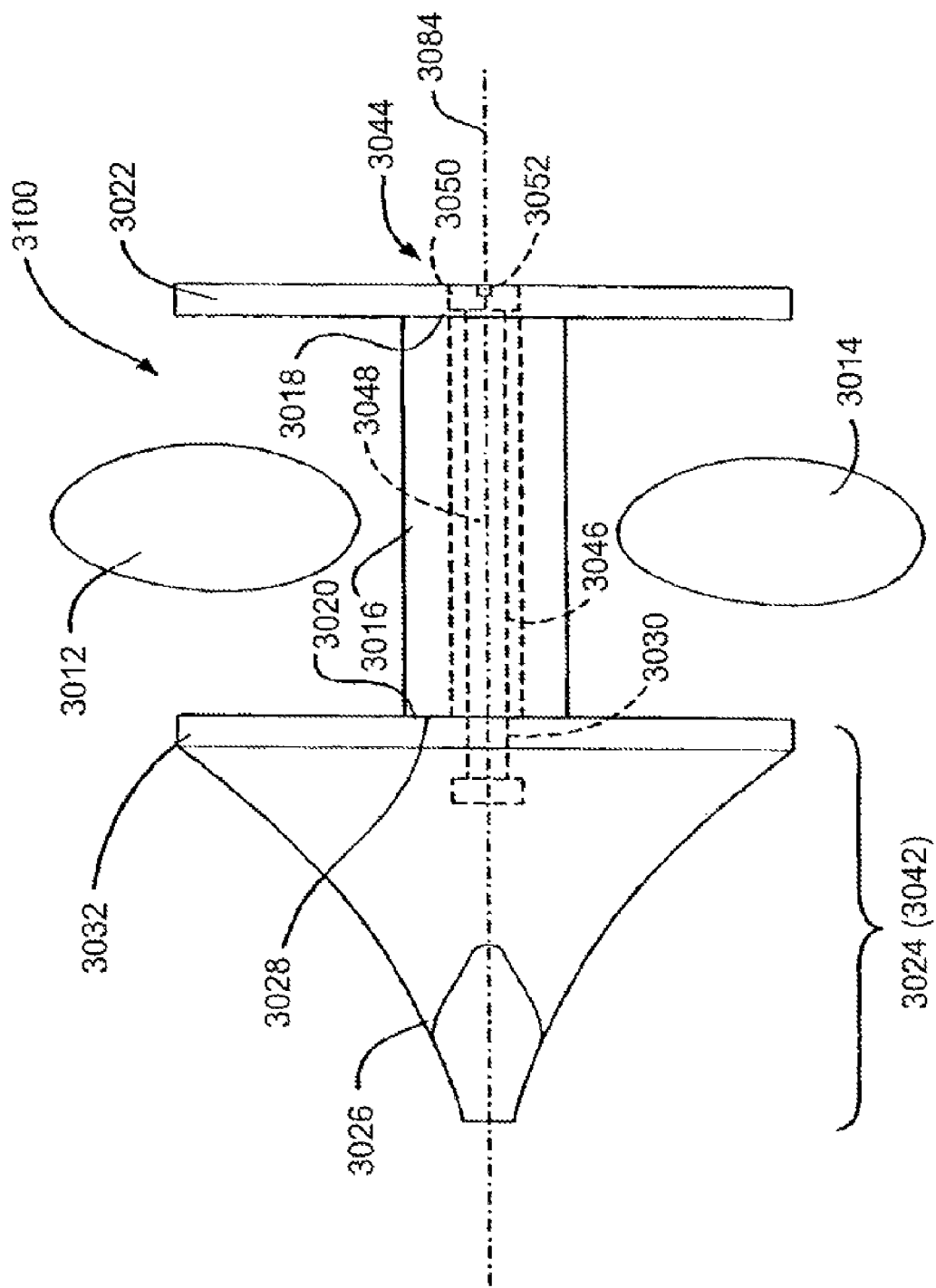
FIG. 139 is a side view of the embodiment of the implant of the invention depicted in FIG. 137 in a second retention position.

FIG. 139 depicts a side view of the implant 3100 with the tissue expander 3024 rotated to the second retention position 3042. The tissue expander 3024 in the second retention position 3042 can prevent displacement of the implant 3100 after insertion in the spine of a patient. The tissue expander 3024, including the wedge-shaped first end 3026, and the elongated element 3032, can rotate from the first insertion position 3036 (FIG. 137) adapted to facilitate insertion, to the second retention position 3042 (FIG. 139) after insertion and positioning of the implant 3100.

In one embodiment, the tissue expander 3024 rotates about 90° to be reconfigured into the second retention position 3042, which alters the orientation of the wedge-shaped first end 3026 of the tissue expander 3024 and the elongated base element 3032. In the second retention position 3042, the tissue expander 3024 is rotated about 90° so that the elongated element 3032 (FIG. 139) is substantially perpendicular to the anterior-to-posterior direction of a patient. In other words, instead of being oriented with the axis 3038 of the elongated element 3032 from anterior to posterior (FIGS. 137 (side view) and 138 (top-down view)), the elongated base element 3032 is rotated about the elongated axis 3034 of the spacer 3016, so that the elongated base element 3032 is oriented generally parallel to the first wing 3022 (FIG. 139). It will be understood by those of ordinary skill in the art that the shift need not be 90° and could be by way of example of 45° or 60°.

Figure 140:
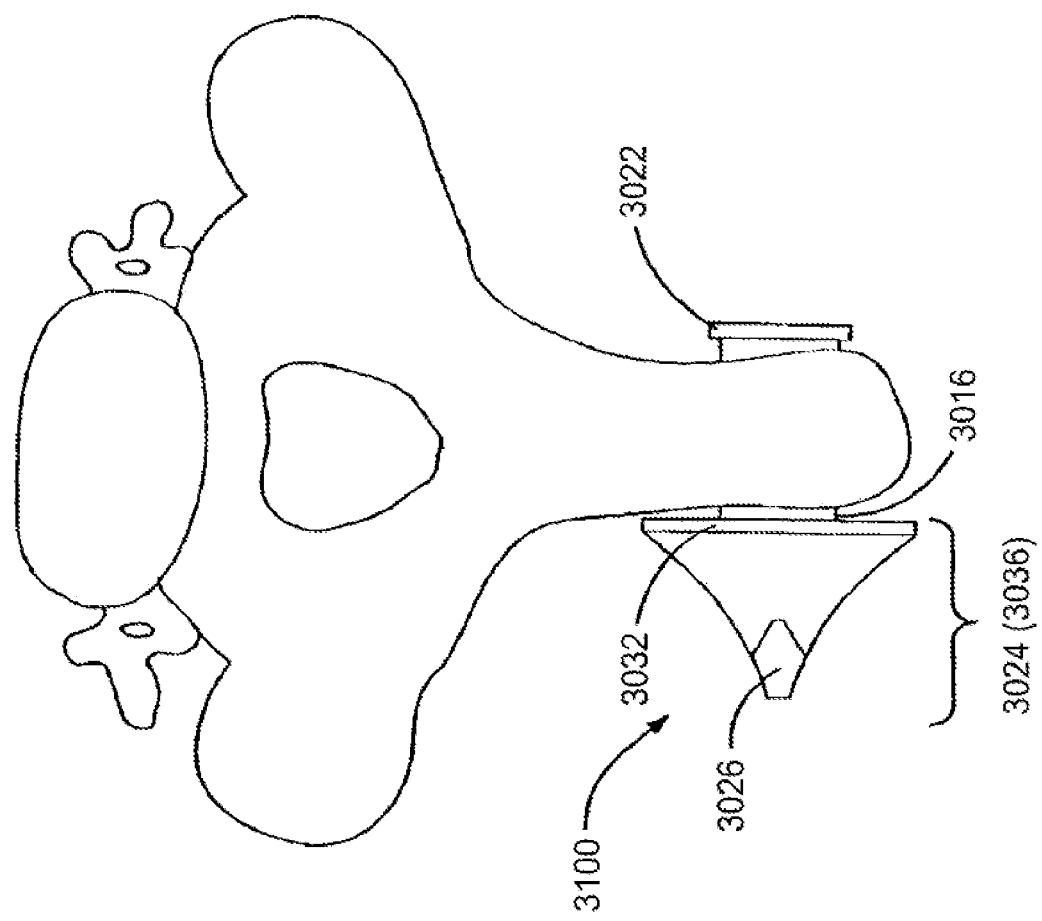
FIG. 140 illustrates a top-down view of an embodiment of the implant of the invention, the implant positioned under a spinous process of the spine with the tissue expander in the second retention position.

FIG. 140 depicts the embodiment of the implant 3100, positioned between adjacent spinous processes, upon initial insertion and in the configuration of FIGS. 137 and 138.

The tissue expander 3024 can be locked into the second retention position 3042, as depicted in FIGS. 137-139. In this embodiment, the shaft 3017 has a bore 3046 extending completely therethrough, which bore 3046 has the same longitudinal axis 3034 as does shaft 3017. Positioned in bore 3046 is a shaft 3048 which can rotate in bore 3046, and which is connected to tissue expander 3024. Shaft 3048 includes a head 3050 which has a slot 3052 that can accept a rotation tool, such as a screwdriver. Rotation of the shaft 3048 causes the tissue expander 3024 to rotate. Thus once the implant 3100 is positioned between spinous processes, a screwdriver can be used to rotate the tissue expander 3024 from the insertion position as seen in FIGS. 137 and 138 to the retention position shown in FIG. 139. In a preferred embodiment the shaft 48 can rotate the tissue expander 3024 about 90°. Alternatively, different amounts of rotation can be accomplished. Although the patient's tissue will hold the tissue expander 3024 in the rotated position, if desired, a mechanism can be included to fix the shaft 3048 in the rotated position. Such mechanism can include a detent extending from head 3050 which can lock into a recess in the first wing 3022 as the shaft 3048 is rotated. Another mechanism can include ridges extending from the head 3050 of the shaft 3048 which can lock into recesses in the first wing 3022. One of ordinary skill in the art can appreciate that other lock-and-key mechanisms, or other mechanism that allows rotation and locking into the desired second retention position 3042, can also be employed to secure the second retention position 3042 for implant 3100.

Figure 141:
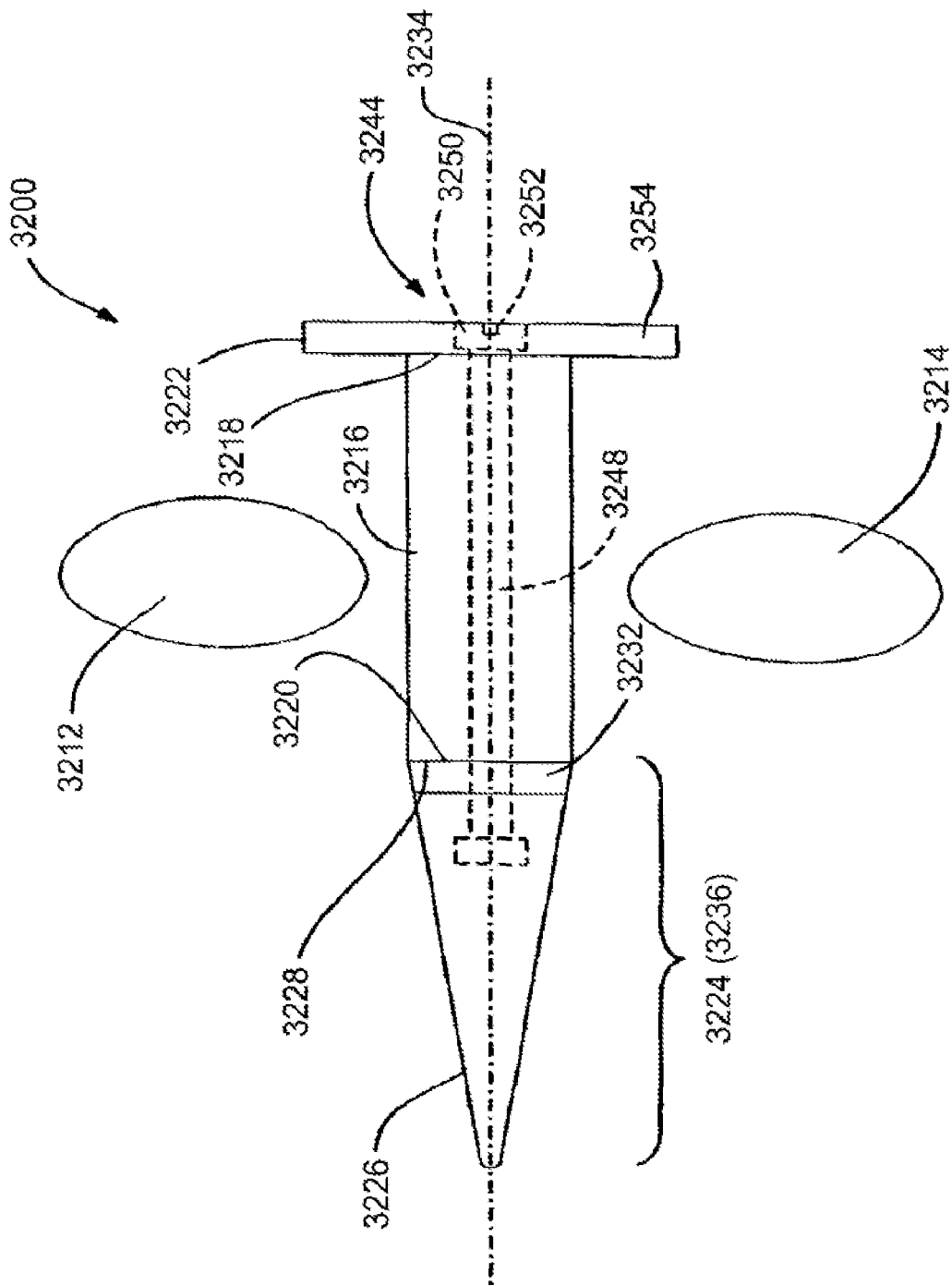
FIG. 141 depicts a side view of an alternative embodiment of the implant of the invention in a first insertion position.
Figure 142:
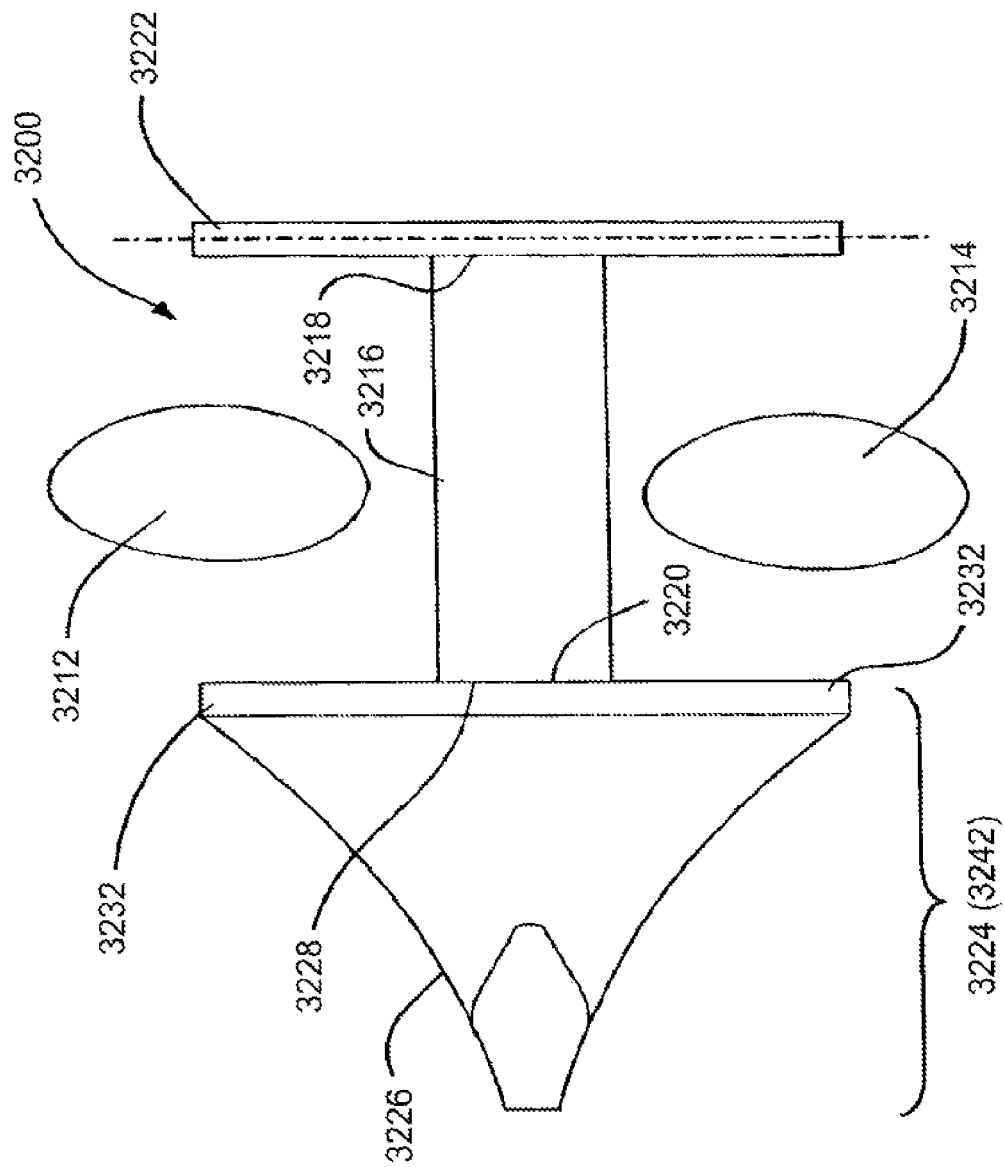
FIG. 142 depicts a side view of the alternative embodiment of the implant of the invention illustrated in FIG. 141, in a second retention position.

FIGS. 141 and 142 depict an alternative embodiment of the implant 3200 of the disclosed invention. In this embodiment, both the first wing 3222 and the tissue expander 3224, are secured to shaft 3248 and can rotate together, from a first insertion position 3236 (FIG. 141) to a second retention position 3242, (FIG. 142) once the implant 3200 is positioned between the adjacent spinous processes. In the first insertion position 3236, the first wing 3222 and an elongated base element 3232 of the tissue expander 3224 are oriented for ease of insertion in an anterior-to-posterior direction of the patient. In the second retention position 3242, for second wing 3226 (FIG. 142) the elongated base element 3232 of the tissue expander 3224 and the first wing 3222 are oriented about 90° from the first insertion position 3236, or in other words, substantially perpendicular to the anterior-to-posterior direction of the first insertion position 3236.

The implant 3200 has a tissue expander 3224 having a wedge-shaped distal end 3226 and a proximal end 3228 that is located adjacent to rotatable spacer 3216 at a second distal end 3220 of a rotatable spacer 3216. A first wing 3222 is located adjacent to a proximal first end 3218 of spacer 3216. Focusing first on the tissue expander 3224, the wedge-shaped distal end 3226 is oriented in the first insertion position 236 to accommodate insertion between spinous processes 3212, 3214, with the flat distal part of the wedge 3226 oriented in an anterior-to-posterior direction in a patient. Also in the first insertion position 3236, the elongated base element 3232 of the tissue expander 3224, located adjacent to the spacer 3216, is oriented so that it is elongated in a direction that is anterior-to-posterior when the implant 3200 is implanted laterally in a patient.

With respect to the first wing 3222, when the tissue expander 3224 is oriented in the first insertion position 3236, the first wing 3222 is oriented, like the tissue expander 3224, in an anterior-to-posterior direction relative to a patient. As with the tissue expander 3226 rotation of the shaft 3248 causes the first wing 3222 to rotate so that is about perpendicular to an anterior-posterior direction.

In this embodiment, as indicated above, the first wing 3222 and the tissue expander 3224 are joined together by the shaft 3248 which has a longitudinal axis 3234. The spacer 3216 can rotate upon shaft 3248. Shaft 3248 includes a head 3250 which has a slot 3252 that can accept a rotation tool such as a screwdriver. Rotation of the shaft 3248 causes the first wing 3222 as well as the tissue expander 3224 to rotate. Thus, once the implant 3200 is positioned between spinous processes, a screwdriver can be used to rotate the tissue expander 3224 and the first wing 3222 from the insertion position 3236 as seen in FIG. 141 to the retention position 3242 shown in FIG. 142. In a preferred embodiment, the shaft 3248 can rotate the first wing 3222 as well as the tissue expander 3224 about 90°. Alternatively, different amounts of rotation can be accomplished.

Although the patient's tissue will hold the first wing 3222 and the tissue expander 3224 in the rotated position, if desired, a mechanism can be included to fix the shaft 3248 in the rotated position. Such mechanism can include a detent extending from the shaft 3248 which can lock into a recess in the spacer 3216. Accordingly, in the second retention position 3242, both the first wing 3222 and the tissue expander 3224 are rotated about 90° and can be locked into place.

Figure 143:
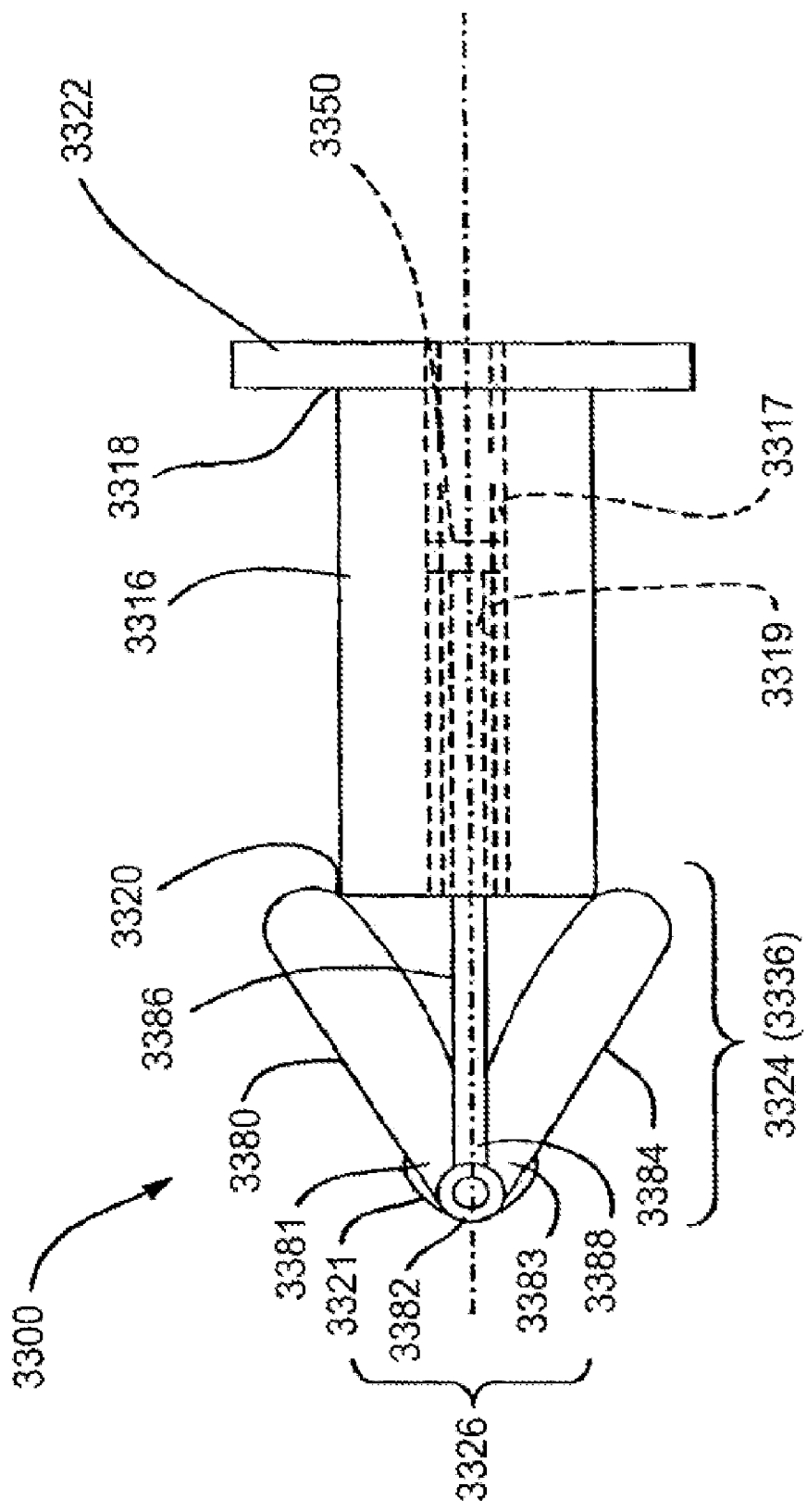
FIG. 143 depicts a top view of yet another embodiment of the implant of the invention, in a first insertion position.
Figure 144:
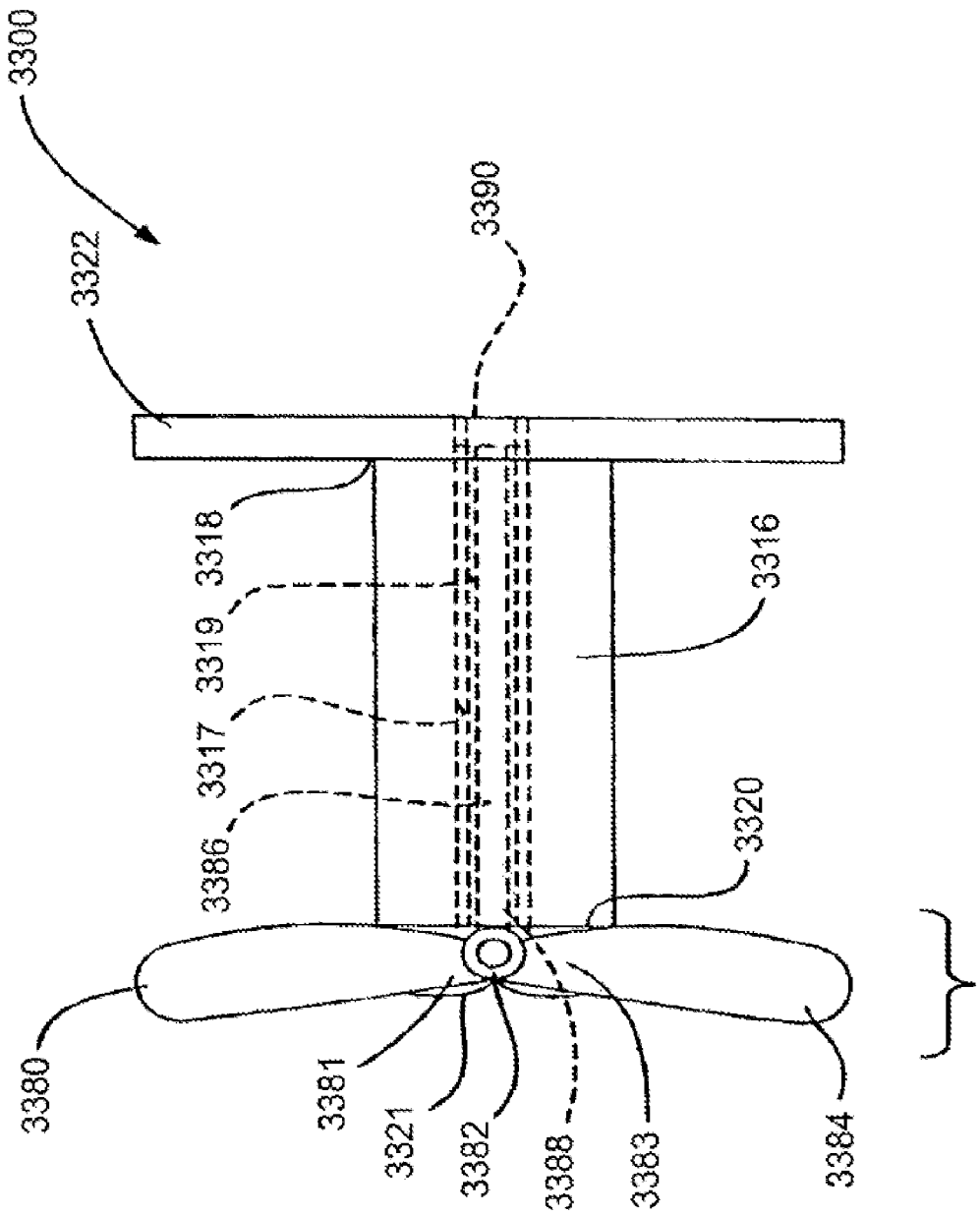
FIG. 144 depicts a side view of the embodiment shown in FIG. 145 of the implant of the invention, in a second retention position.

FIGS. 143 and 144 depict yet another embodiment 3300 of the implant of the invention. In this embodiment 3300, the tissue expander 3324 has a first insertion position 3336 (FIG. 143 being a view looking down on the spinal column), and a second retention position 3342 (FIG. 3144 being a view looking from posterior to anterior into the spinal column). The tissue expander 3324 converts between the first insertion position 3336 and the second retention 3342 position through a pivoting motion, that may also include a rotation motion.

In this embodiment 3300, the first wing 3322 is positioned adjacent to a spacer 3316 at a first end 3318 of the spacer. As above with the implants 3100 and 3200, the spacer 3316 is rotatably mounted over a hollow spacer-mounting shaft 3317 extending from the first wing 3322. The spacer 3316 can be cylindrical, or it can have other shapes, including but not limited to elliptical or tear-drop shape in cross-section.

The tissue expander 3324 of implant 3300 comprises an upper segment 3380 that is pivotally connected via a pivoting joint 3382, or other pivoting means, with a lower segment 3384. That is, a second end 3381 of the upper segment 3380 meets a second end 3383 of the lower segment 3384 via the pivoting joint 3382. A coiled spring 3321 is provided around pivoting joint 3382 and biases both the upper segment 3380 and the lower segment 3384 of the tissue expander 3324 against the spacer 3316. The pivoting joint 3382 is connected with a first end 3388 of a rod 3386. Rod 3386 is slidably disposed in a bore 3319 which runs the entire length of the spacer 316, and is located within hollow spacer-mounting shaft 3317.

The pivoting joint 3382 and the rod 3386 provide the mechanism whereby the tissue expander 3324 is converted from the first insertion position 3336 to the second retention position 3342. In the first insertion position 3336, depicted in FIG. 143, the first end 3388 of the rod 3386 extends outside the spacer 3316. The pivoting joint 3382, functionally connected with the first end 3388 of the rod 3386, is not in contact with the second end 3320 of the spacer 3316, but instead is separated by a segment of the rod 3386 from the second end 3320 of the spacer 3316. The upper segment 3380 of the tissue expander 3324 and the lower segment 3384 of the tissue expander 3324 meet at the pivoting joint 3382 to form a wedge-shaped first end 3326 of the tissue expander 3324 that is not in contact with the second end 3320 of the spacer 3316 when the tissue expander 3324 is in the first insertion position 3336. In one embodiment, wedge-shaped first end 3326 of the tissue expander 3324 can be wedge-shaped in the lateral direction of insertion, i.e., perpendicular to an anterior-to-posterior direction of a patient. The wedge-shaped first end 3326 is useful for inserting the implant 3300 between adjacent spinous processes.

Rod 3386 includes a head 3350 at the end of the rod 3386 distal from the tissue expander 3324. The head 3350 has a slot 3352 that can accept a tool adapted to be used to rotate and pull the rod 3386 through a bore 3319 of shaft 3317 toward the first wing, causing the upper segment 3380 and lower segment 3384 of the tissue expander 3324 to become aligned, such that the tissue expander 3324 is no longer wedge-shaped in the first insertion position 3336 (FIG. 143). Instead, the tissue expander 3324 adopts the form of a second wing (FIG. 144). In this embodiment, the tissue expander 3324 is wedge-shaped in the direction of lateral insertion in the first insertion position 3336, and the tissue expander in the second retention position is oriented substantially vertical, or substantially perpendicular to the anterior-to-posterior direction of the patient.

In contrast, in another embodiment, the tissue expander 3324 in the first insertion position 3336 is not wedge-shaped in a top view during lateral insertion, as discussed above. Instead, the wedge-shape of the tissue expander 3324 in the first insertion position 3336 is wedge-shaped looking into the spine from a posterior to anterior direction. As such, merely pulling without rotating rod 3386 causes upper segment 3380 of the tissue expander 3324 and the lower segment 3384 of the tissue expander 3324 to pivot about the pivoting joint 3382, as above. Thus without rotating the tissue expander 3324, the tissue expander 3324 after reconfiguration will be oriented as depicted in FIG. 144.

Figure 145:
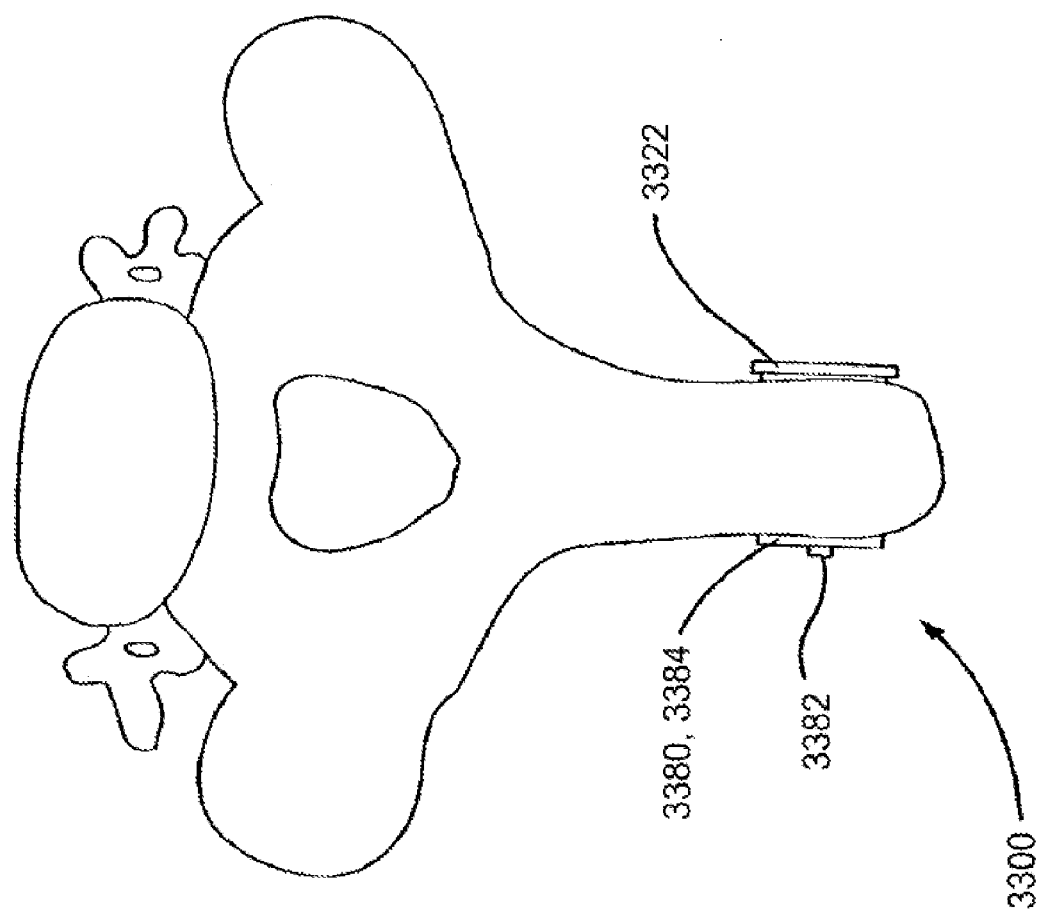
FIG. 145 depicts a top view of the embodiment of FIG. 143 in a deployed position between spinous processes.

FIG. 145 depicts the embodiment of FIGS. 143 and 144 deployed between spinous processes from a top view.

A rotating tool, such as a hook mounted on the end of a rod, can be used to pull the rod 3386 through the bore 3319, and can be used to rotate the tissue expander 3324 so that it is generally parallel to the first wing 3322. In a preferred embodiment, the rod 3386 can rotate the tissue expander about 90°. Alternatively, different amounts of rotation can be accomplished as needed to adapt to the anatomical structure of a patient.

Although the patient's tissue will hold the tissue expander 3324 in the rotated position 3242, if desired, a mechanism can be included to fix the rod 3386 in the rotated position. Such mechanism can include a detent extending from head 3350 which can lock into a recess in the first wing 3322 as the rod 3386 is pulled toward the first wing 3322 and rotated when the head 3350 is adjacent to the first wing 3322. Another mechanism can include ridges extending from the head 3350 of the rod 3386 which can lock into recesses in the first wing 3322.

One of ordinary skill in the art will appreciate that the locking components need not be limited to a detent and recess. The invention contemplates any locking mechanism that can secure the implant 3300 in a second retention position 3342 with the tissue expander 3324 reconfigured to a second wing.

Figure 146:
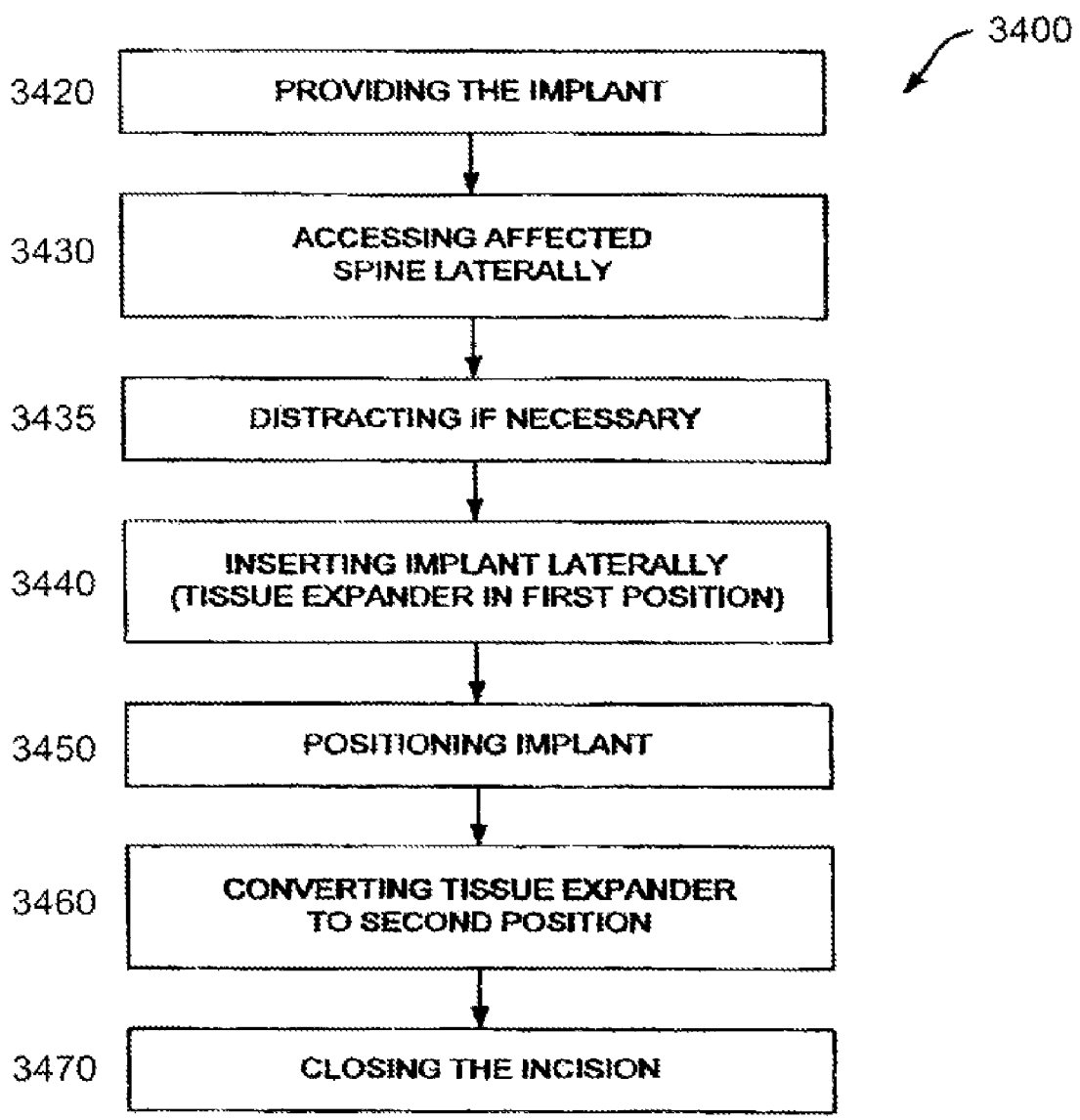
FIG. 146 depicts a flow diagram of a method of insertion of an implant of the invention.

FIG. 146 depicts a method 3400 of insertion of an embodiment of the invention from a lateral or posterolateral approach. Using the disclosed method, any of implants 3100, 3200, and 3300 can be implanted.

First, an implant as in, by way of example only, embodiment 3100, is provided 3420, and the spine is accessed 3430. Access can be accomplished laterally or postero-laterally. The implant with the tissue expander 3034 in the first insertion position 3036 then is inserted 3440 between the spinous processes, either from the right lateral side, or the left lateral side.

The tissue expander 3024 is wedge-shaped in the first insertion position 3036, as described above, and is used to distract the vertebrae somewhat to facilitate the lateral insertion of the spacer 3016 between the adjacent spinous processes. This level of distraction may suffice to fully insert the implant 3100. However, if additional distraction is necessary prior to insertion of the tissue expander, distraction can be added prior to insertion 3435, by methods already well-known in the art.

Once the implant 3100 is positioned 3450 with the spacer maintaining distraction of the adjacent spinous processes, the tissue expander 3024 is moved from the first insertion position to the second retention position 3460. For implant 2100, moving the tissue expander 3024 involves rotating 3470 the tissue expander 3024 to the second retention position 3042. The rotation in one embodiment is preferably about 90°. However, varying degrees of rotation are also possible. The tissue expander 3024 locks into the second retention position 3042, as described above. The base element 3032 in the second retention position 3042 is parallel to the first wing 3022, which also serves to retain the implant 2100 in position and prevent displacement.

For an implant as in embodiment 3200, both the first wing 3222 and the tissue expander 3224 are rotated together 3470, because in embodiment 3200, the spacer 3216 is connected with the first wing 3222.

For an implant as in embodiment 3300, the tissue expander 3324 is moved 3460 from a wedge-shaped first insertion position 3336 to a retaining arm or second wing second retention position 3342.

After the converting step 3460 the incision is closed 3470.

Figure 147:
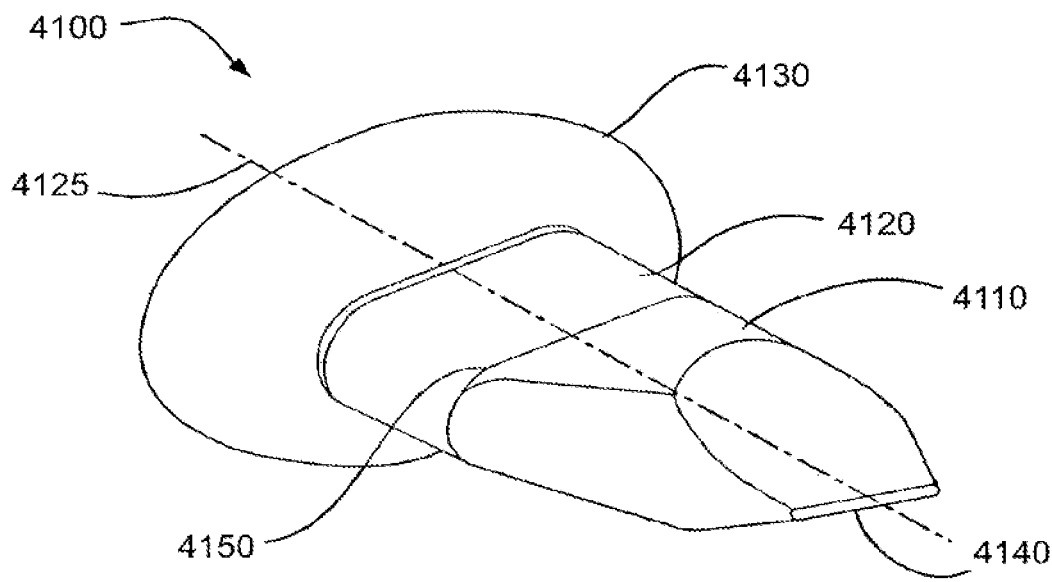
FIG. 147 is a perspective view of an embodiment of an implant in accordance with the present invention having a spacer, a distraction guide, and a wing with an elliptical cross-section.
Figure 148:
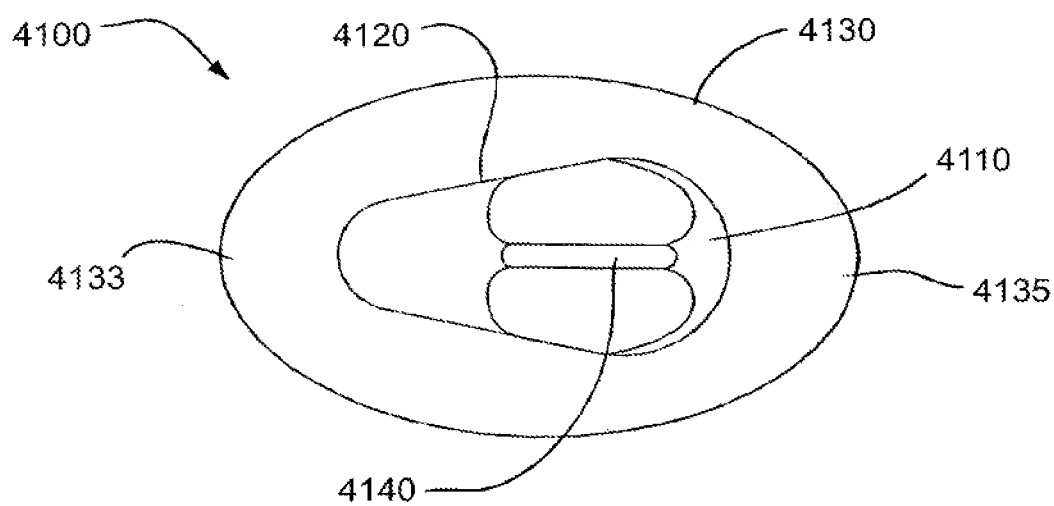
FIG. 148 is an end view of the implant of FIG. 147.

FIGS. 147 and 148 illustrate an implant 4100 in accordance with an embodiment of the present invention. The implant 4100 comprises a wing 4130, a spacer 4120, and a lead-in tissue expander (also referred to herein as a distraction guide) 4110. The distraction guide 4110 in this particular embodiment is wedge-shaped, i.e., the implant has an expanding cross-section from a distal end of the implant 4102 to a region 4104 where the guide 4110 joins with the spacer 4120 (referencing for the figures is based on the point of insertion of the implant between spinous processes). As such, the distraction guide functions to initiate distraction of the soft tissue and the spinous processes when the implant 4100 is surgically inserted between the spinous processes. It is to be understood that the distraction guide 4110 can be pointed and the like, in order to facilitate insertion of the implant 4100 between the spinous processes of adjacent cervical vertebrae. It is advantageous that the insertion technique disturb as little of the bone and surrounding tissue or ligaments as possible in order to reduce trauma to the site and promote early healing, and prevent destabilization of the normal anatomy. In the embodiment of FIGS. 147 and 148, there is no requirement to remove any of the bone of the spinous processes and no requirement to sever or remove from the body ligaments and tissues immediately associated with the spinous processes. For example, it is unnecessary to sever the ligamentum nuchae (supraspinous ligament), which partially cushions the spinous processes of the upper cervical vertebrae.

As can be seen in FIGS. 147-148, the spacer 4120 can be teardrop-shaped in cross-section perpendicular to a longitudinal axis 4125 of the implant 4100. In this way, the shape of the spacer 4120 can roughly conform to a wedge-shaped space, or a portion of the space, between adjacent spinous processes within which the implant 4100 is to be positioned. In other embodiments, the spacer 4120, can have alternative shapes such as circular, wedge, elliptical, ovoid, football-shaped, and rectangular-shaped with rounded corners and other shapes, and be within the spirit and scope of the invention. The shape of the spacer 4120 can be selected for a particular patient so that the physician can position the implant 4100 as close as possible to the anterior portion of the surface of the spinous process. The shape selected for the spacer 4120 can affect the contact surface area of the implant 4100 and the spinous processes that are to be subject to distraction. Increasing the contact surface area between the implant 4100 and the spinous processes can distribute the force and load between the spinous frame and the implant 4100.

Figure 149:
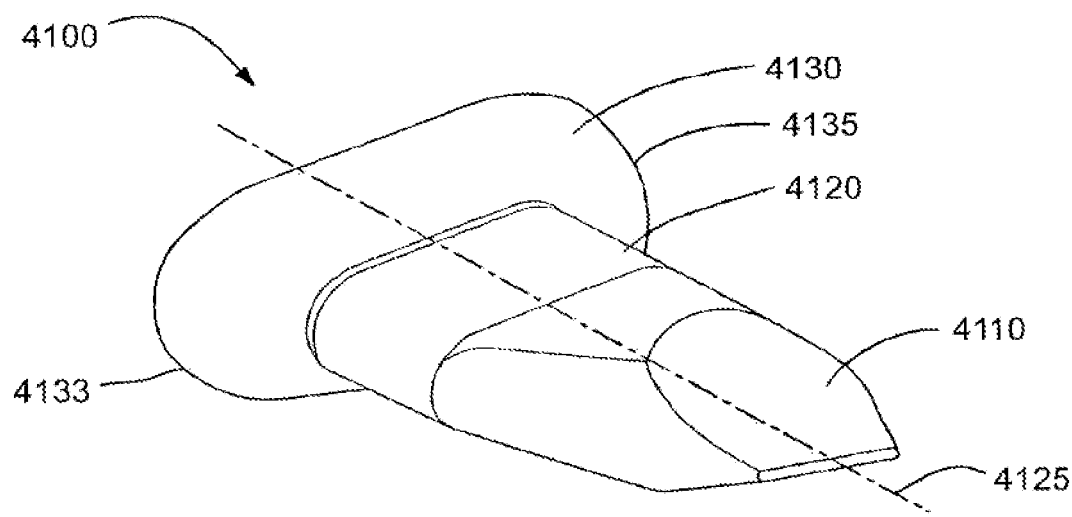
FIG. 149 is a perspective view of another embodiment of an implant in accordance with the present invention having a wing with a teardrop-shaped cross-section.

As can be seen in FIGS. 147 and 148, the wing 4130 in an embodiment can be elliptically shaped in cross-section perpendicular to the longitudinal axis 4125. The dimensions of the wing 4130 can be larger than that of the spacer 4120, particularly along the axis of the spine, and can limit or block lateral displacement of the implant 4100 in the direction of insertion along the longitudinal axis 4125. As illustrated in the embodiment of FIG. 149, the wing 4130 can alternatively have other cross-sectional shapes, such as teardrop, wedge, circular, ovoid, football-shaped, and rectangular-shaped with rounded corners and other shapes, and be within the spirit and scope of the invention. The wing 4130 has an anterior portion 4138 and a posterior portion 4136.

In other embodiments, the implant 4100 can include two wings, with a second wing 4160 (shown in FIG. 150) separate from the distraction guide 4110, spacer 4120 and first wing 4130. The second wing 4160 can be connected to the distal end of the spacer 4120. The second wing 4160, similar to the first wing 4130, can limit or block lateral displacement of the implant 4100, however displacement is limited or blocked in the direction along the longitudinal axis 4125 opposite insertion. When both the first wing 4130 and the second wing 4160 are connected with the implant 4100 and the implant 4100 is positioned between adjacent spinous processes, a portion of the spinous processes can be sandwiched between the first wing 4130 and the second wing 4160, limiting any displacement along the longitudinal axis 4125.

Figure 150:
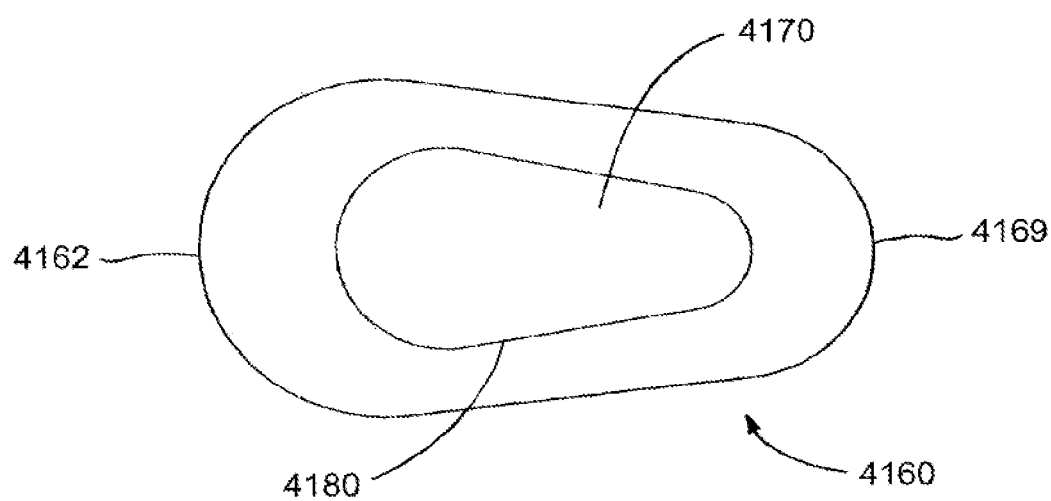
FIG. 150 is an end view of a second wing for use with the implant of FIG. 149.

As can be seen in FIG. 150, the second wing 4160 can be teardrop-shaped in cross-section. The wider end 4166 of the second wing 4160 is the posterior end and the narrower end 4168 of the second wing 4160 is the anterior end. Unlike the first wing 4130, however, an opening 4164 is defined within the second wing 4160, the opening 4164 being at least partially circumscribed by a lip 4162 that allows the second wing 4160 to pass over the distraction guide 4110 to meet and connect with the spacer 4120. The second wing 4160 can be secured to the spacer 4120 once the second wing 4160 is properly positioned. The second wing 4160 can be connected with the implant after the implant 4100 is positioned between the spinous processes.

It is to be understood that the implant can be made in two pieces. The first piece can include the first wing 4130, the spacer 4120, and the distraction guide 4110. The second piece can include the second wing 4160. Each piece, can be manufactured using technique known in the art (e.g., machining, molding, extrusion). Each piece, as will be more fully discussed below, can be made of a material that is bio-compatible with the body of the patient. An implant can be formed with multiple pieces and with the pieces appropriately joined together, or alternatively, an implant can be formed as one piece or joined together as one piece.

Figure 151:
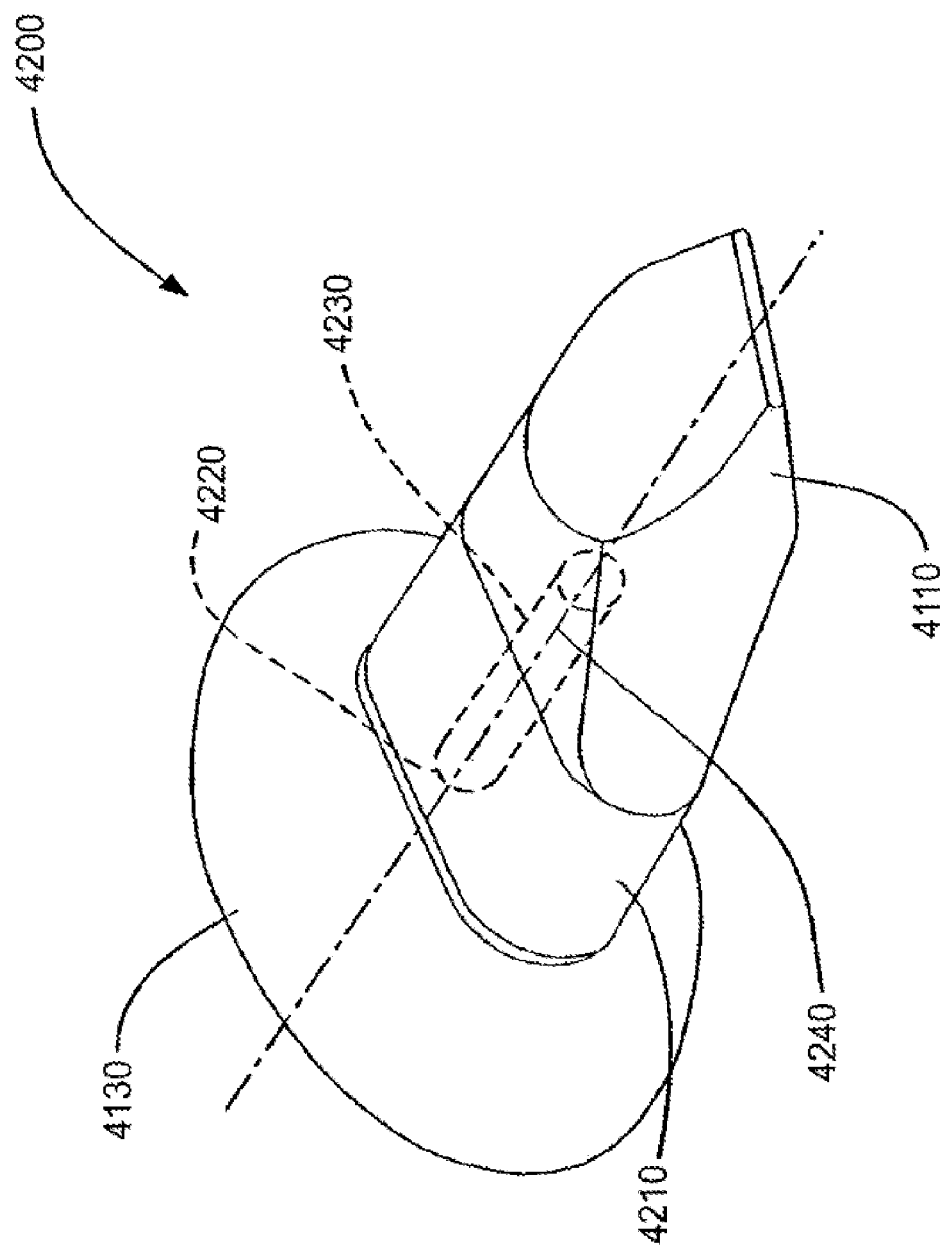
FIG. 151 is a perspective view of an embodiment of an implant in accordance with the present invention having a rotatable spacer and a wing with an elliptical cross-section.
Figure 152:
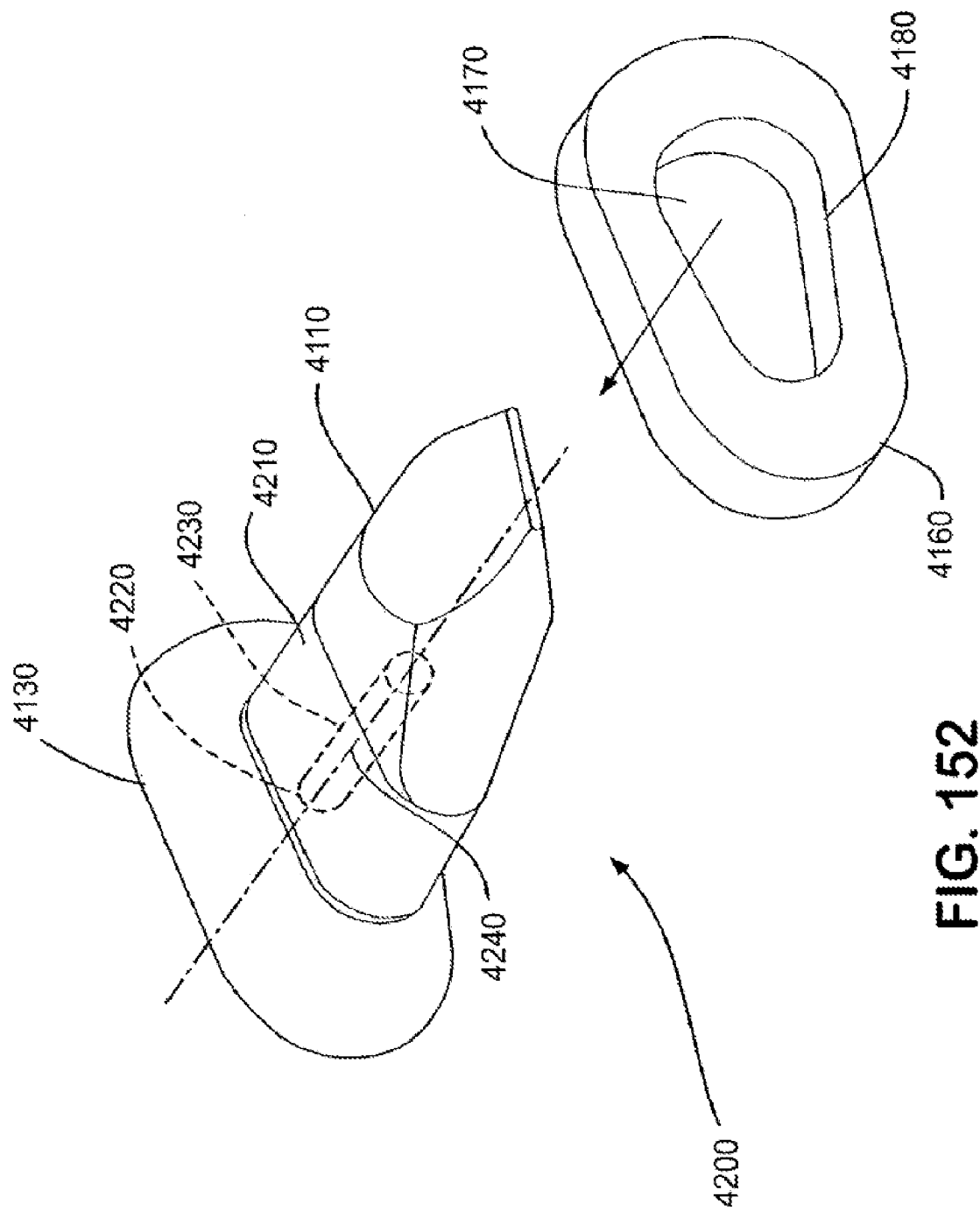
FIG. 152 is a perspective view of an embodiment of an implant in accordance with the present invention having a rotatable spacer with two wings that are teardrop-shaped in cross-section.
Figure 153:
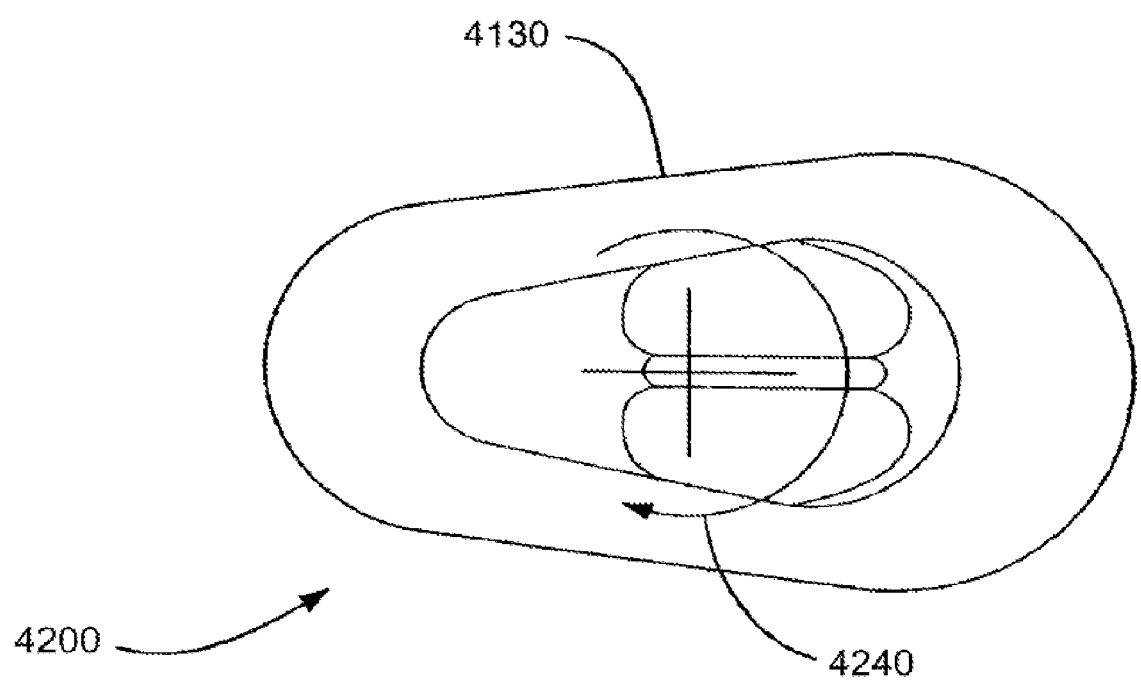
FIG. 153 depicts the axis of rotation of the implant of FIG. 152 as seen from an end view.

Further embodiments of implants in accordance with the present invention are depicted in FIGS. 151-153. In such embodiments, the spacer 4220 can be rotatable about the longitudinal axis 4225 relative to the first wing 4130, or relative to the first wing 4130 and a second wing 4160 where two wings are used. The spacer 4220 can be rotatable or fixed relative to the distraction guide 4110. Where the spacer 4220 is rotatable relative to the distraction guide 4110, the spacer 4220 can include a bore 4222 running the length of the longitudinal axis 4225, and a shaft 4224 inserted through the bore 4222 and connecting the distraction guide 4110 with the first wing 4130. It can be advantageous to position any of the implants taught herein as close as possible to the vertebral bodies. The rotatable spacer 4220 can rotate to conform to or settle between adjacent spinous processes as the implant 200 is inserted and positioned during implantation, so that on average the contact surface area between the spacer 4220 and the spinous processes can be increased over the contact surface area between a fixed spacer 4120 and the spinous processes. Thus, the rotatable spacer 4220 can improve the positioning of the spacer 4220 independent of the wings 4130, 4160 relative to the spinous processes. The embodiment of FIG. 6 includes a teardrop-shaped first wing 4130, and a teardrop-shaped second wing 4160, similar to the second wing 4160 depicted in the embodiment of FIG. 149. As discussed below, the shape of the wings 4130, 4160 in FIGS. 149 and 152 is such that the implants 4100, 4200 accommodate the twisting of the cervical spine along its axis, for example, as the head of a patient turns from side-to-side.

Figure 154:
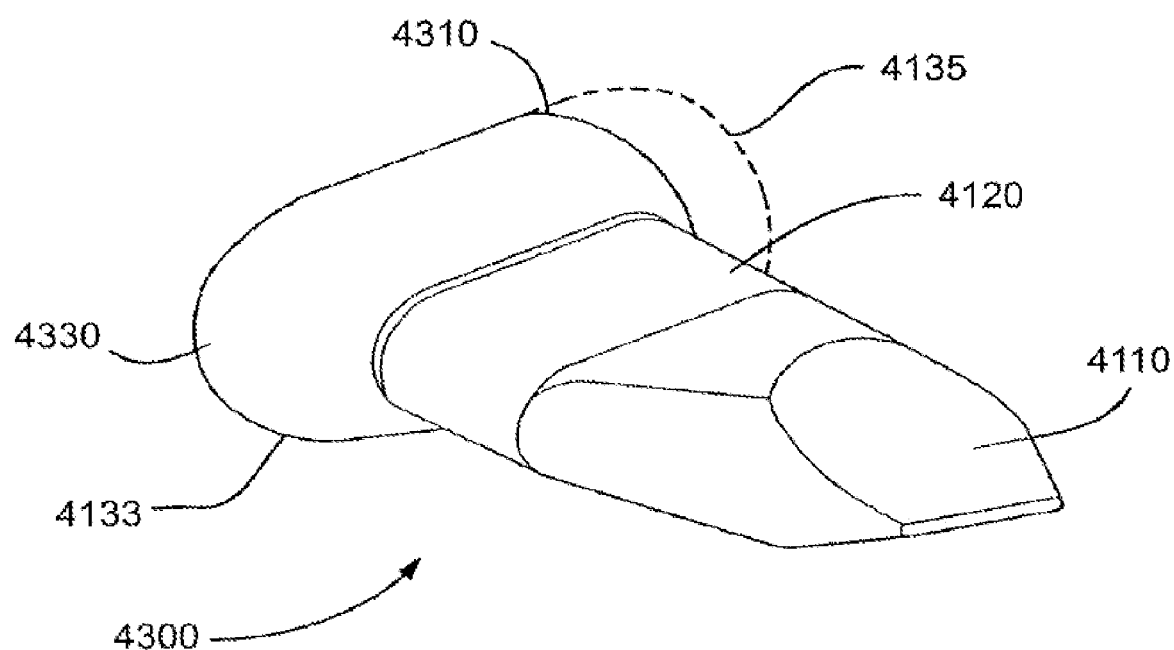
FIG. 154 is a perspective view of an embodiment of an implant in accordance with the present invention having a wing that is truncated at a posterior end.
Figure 155A:
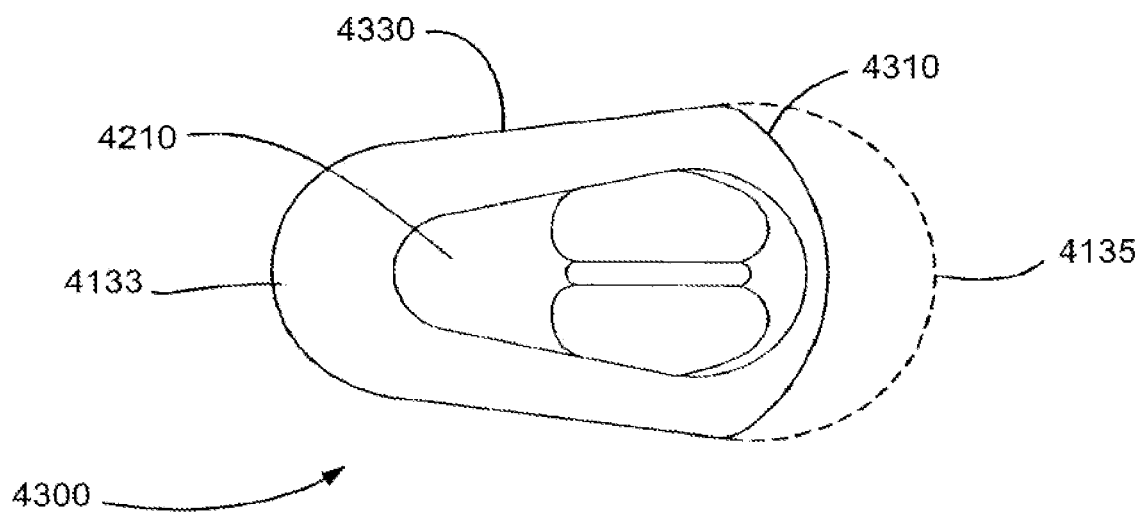
FIG. 155A is an end view of the implant of FIG. 154.
Figure 155B:
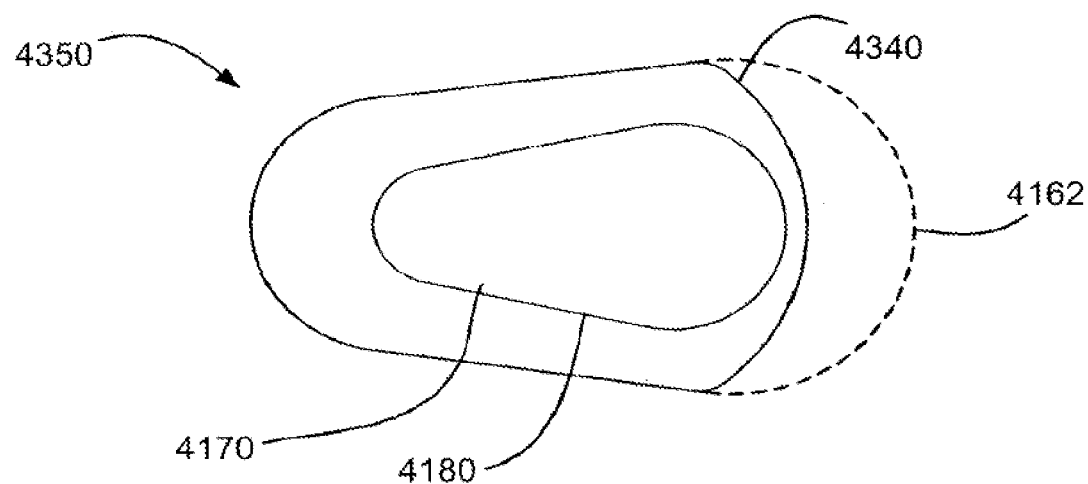
FIG. 155B is a truncated second wing for use with the implant of FIG. 155A.

FIG. 154 is a perspective view and FIG. 155A is an end view of still another embodiment of an implant in accordance with the present invention, wherein the posterior portion 4336 of the teardrop-shaped first wing 4330 is truncated, making the first wing 4330 more ovoid in shape. In this configuration, the anterior portion 4138 of the first wing 4330 can be longer than the truncated posterior end 4336 of the first wing 4330. As in previous embodiments, the spacer 4120 can alternatively be a rotatable spacer rather than a fixed spacer. FIG. 155B illustrates a second wing 4360 for use with such implants 4300, the second wing 4360 having a truncated posterior end 4366. Truncation of the posterior ends 4336, 4366 of the first and second wings 4330, 4360 can reduce the possibility of interference of implants 4300 having such first and second wings 4330, 4360 positioned between spinous processes of adjacent pairs of cervical vertebrae, e.g., implants between cervical vertebrae five and six, and between cervical vertebrae six and seven. During rotation of the neck, the spinous process move past each other in a scissor-like motion. Each cervical vertebra can rotate relative to the next adjacent cervical vertebra in the general range of about 6°-12°. In addition, about 50 percent of the rotational movement of the neck is accomplished by the top two neck vertebrae. Thus, such embodiments can accommodate neck rotation without adjacent embodiments interfering with each other.

Figure 156:
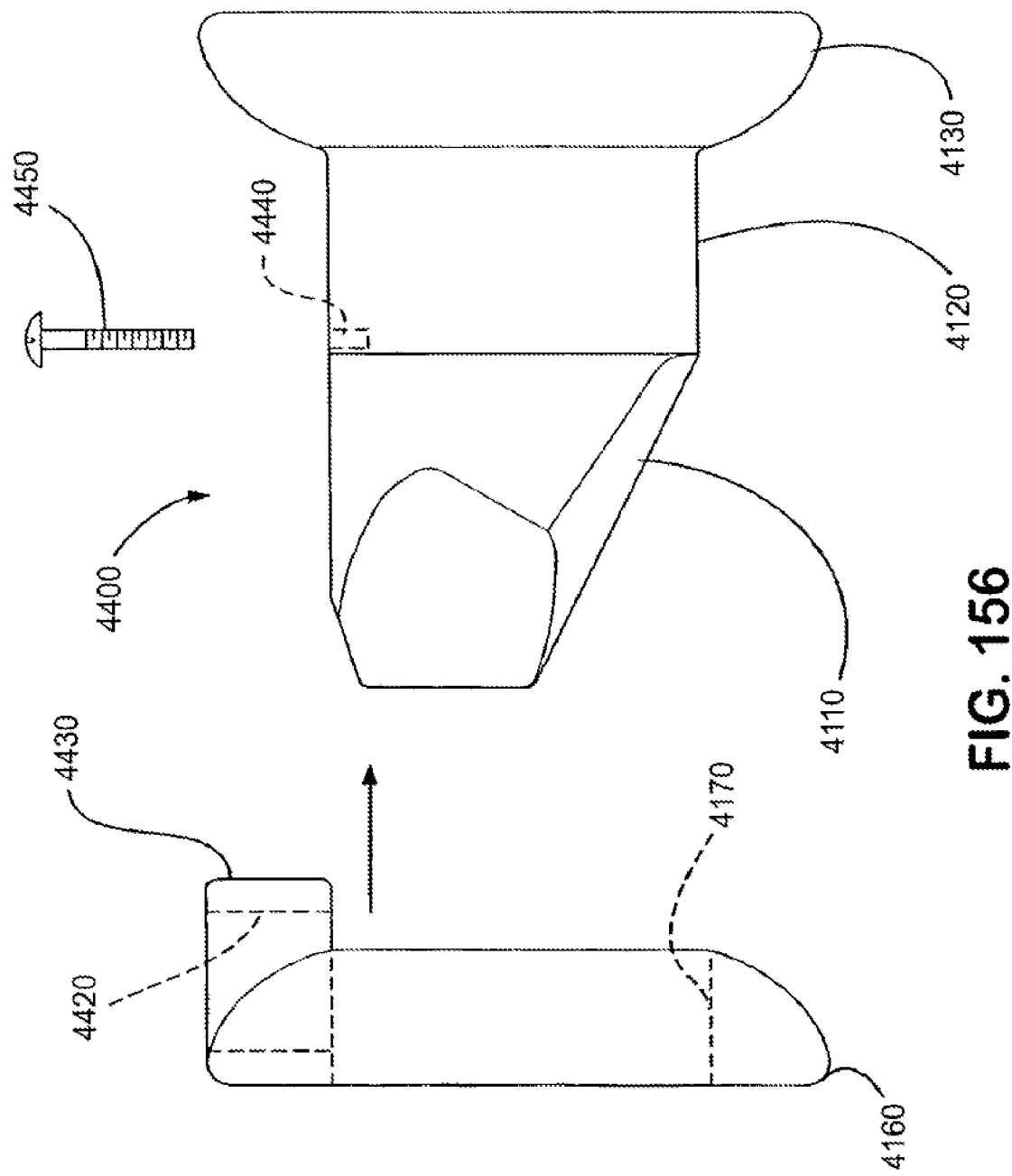
FIG. 156 is a plan view of an embodiment of an implant in accordance with the present invention wherein a screw is used to secure a second wing to the spacer.
Figure 157:
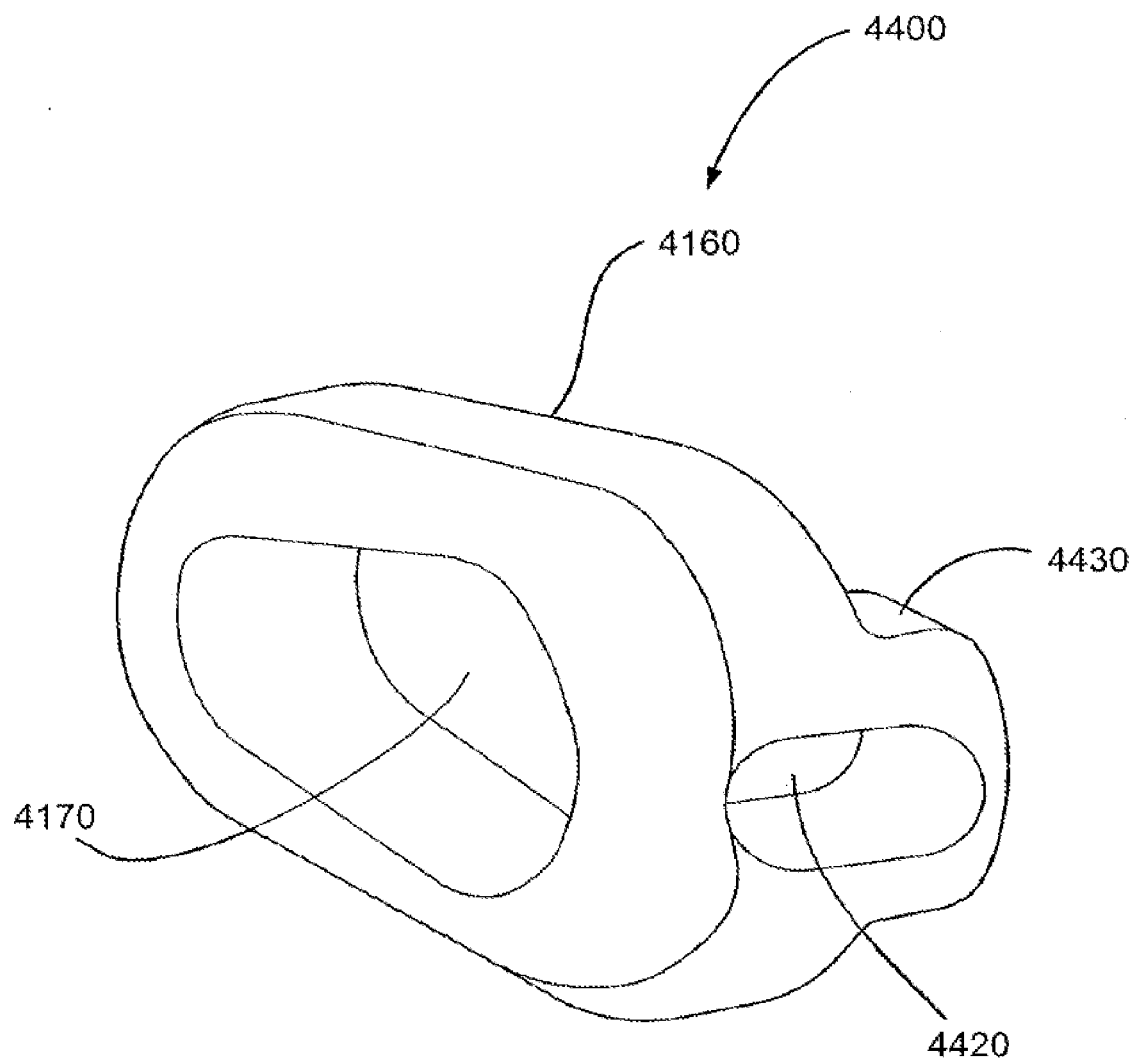
FIG. 157 is a perspective view of the second wing of FIG. 156.
Figure 158:
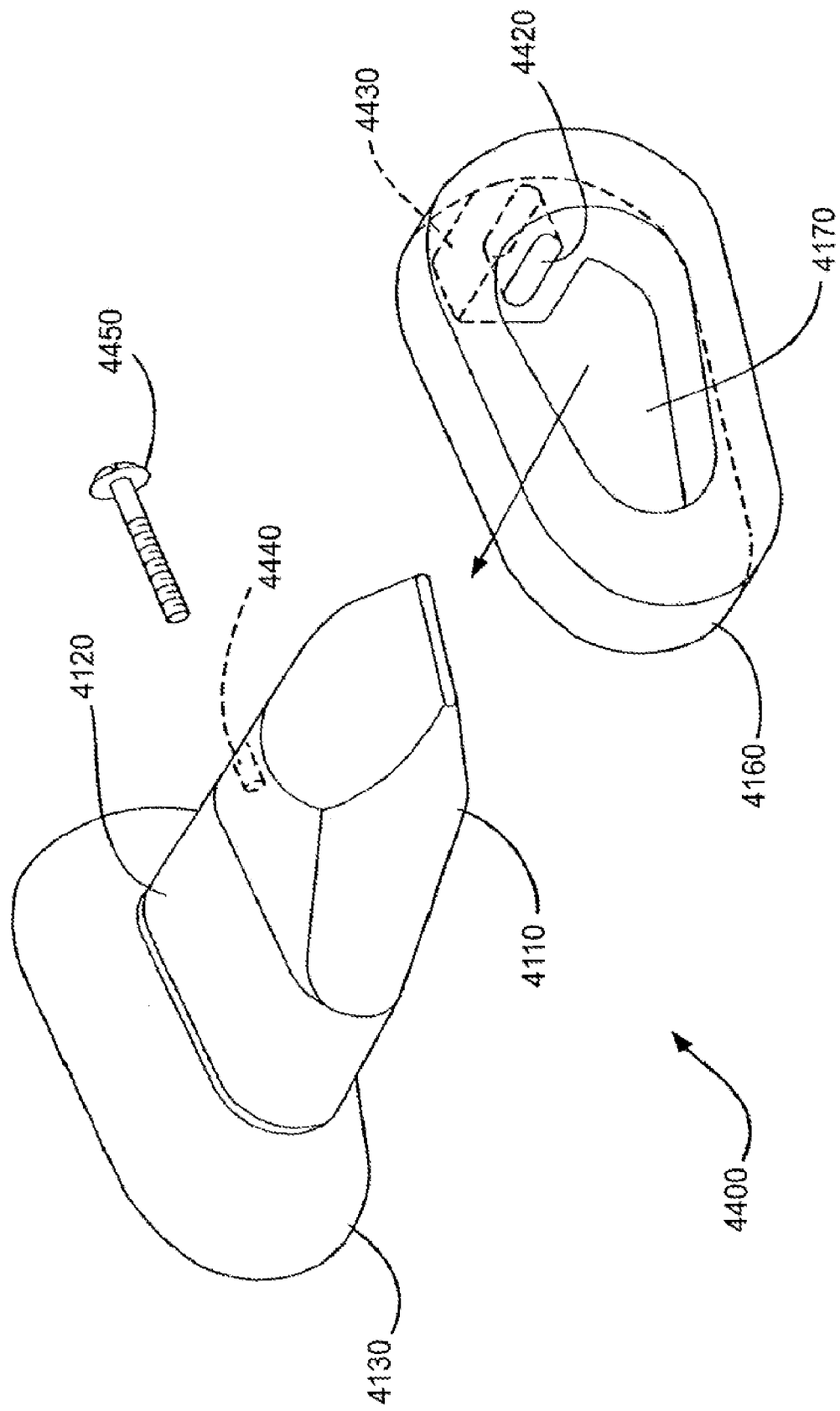
FIG. 158 is a perspective view of the implant of FIG. 156.

With respect to the prior embodiments which have first and second wings 4130, 4160, the second wing 4160, can be designed to be interference-fit onto the spacer 4120 (where the spacer is fixed) or a portion of the distraction guide 4110 adjacent to the spacer 4120 (where the spacer is rotatable). Where the second wing 4160 is interference-fit, there is no additional attachment device to fasten the second wing 4160 relative to the remainder of the implant. Alternatively, various fasteners can be used to secure the second wing relative to the remainder of the implant. For example, FIGS. 156-158 illustrate an embodiment of an implant 4400 including a teardrop-shaped second wing 4460 having a bore 4463 through a tongue 4461 at the posterior end of the second wing 4460. The bore 4463 is brought into alignment with a corresponding bore 4440 on the spacer 4120 when the second wing 4460 is brought into position by surgical insertion relative to the rest of the implant 4400. A threaded screw 4442 can be inserted through the aligned bores 4463, 4440 in a posterior-anterior direction to secure the second wing 4460 to the spacer 4120. The direction of insertion from a posterior to an anterior direction has the screw 4442 engaging the bores 4463, 4440 and the rest of the implant 4400 along a direction that is generally perpendicular to the longitudinal axis 4125. This orientation is most convenient when the surgeon is required to use a screw 4442 to secure the second wing 4460 to the rest of the implant 4400. Other securing mechanisms using a member inserted into corresponding bores 4463, 4440 on the spacer 4120 and second wing 4460 are within the spirit of the invention. It should be understood that a rotatable spacer 4220 also can be accommodated by this embodiment. With a rotatable spacer 4220, the second wing 4460 would be attached to a portion of the distraction guide 4110 that is located adjacent to the rotatable spacer 4220.

Figure 159A:
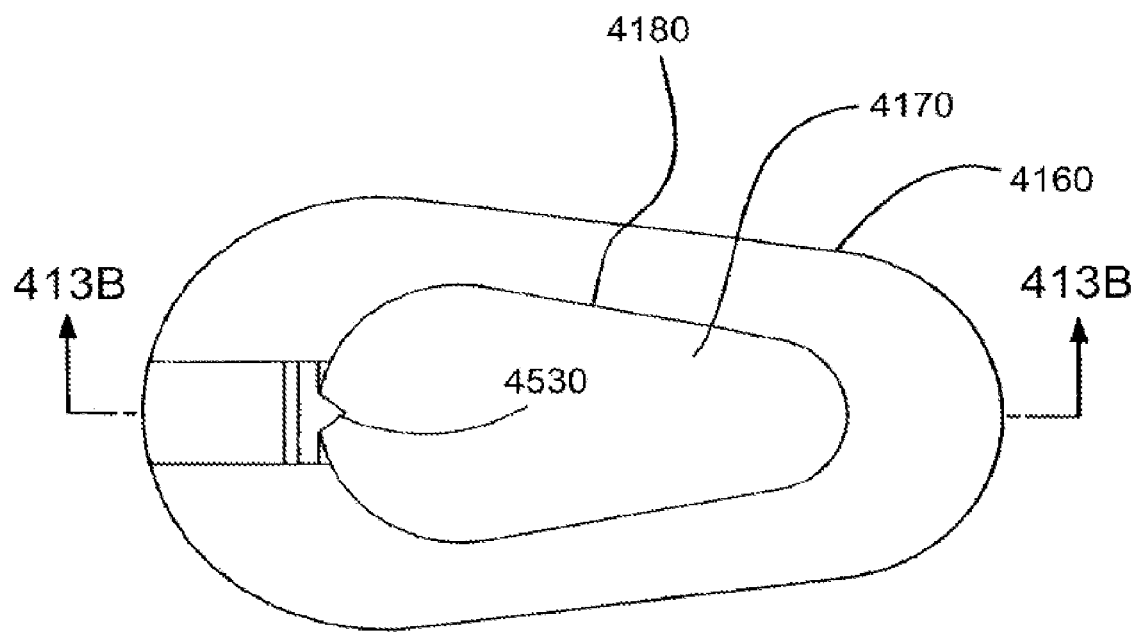
FIG. 159A is a front view of a second wing for use with some embodiments of implants of the present invention having a flexible hinge mechanism for securing the second wing to an implant.
Figure 159B:
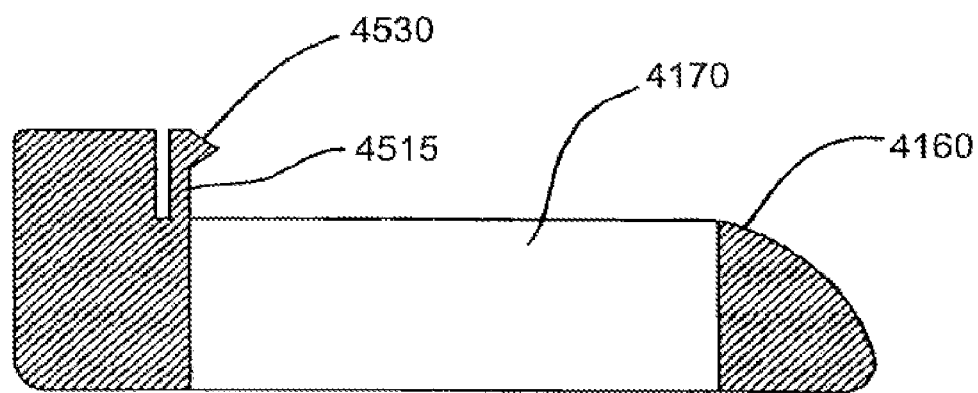
FIG. 159B is a side-sectional view of the second wing of FIG. 159A.
Figure 160A:
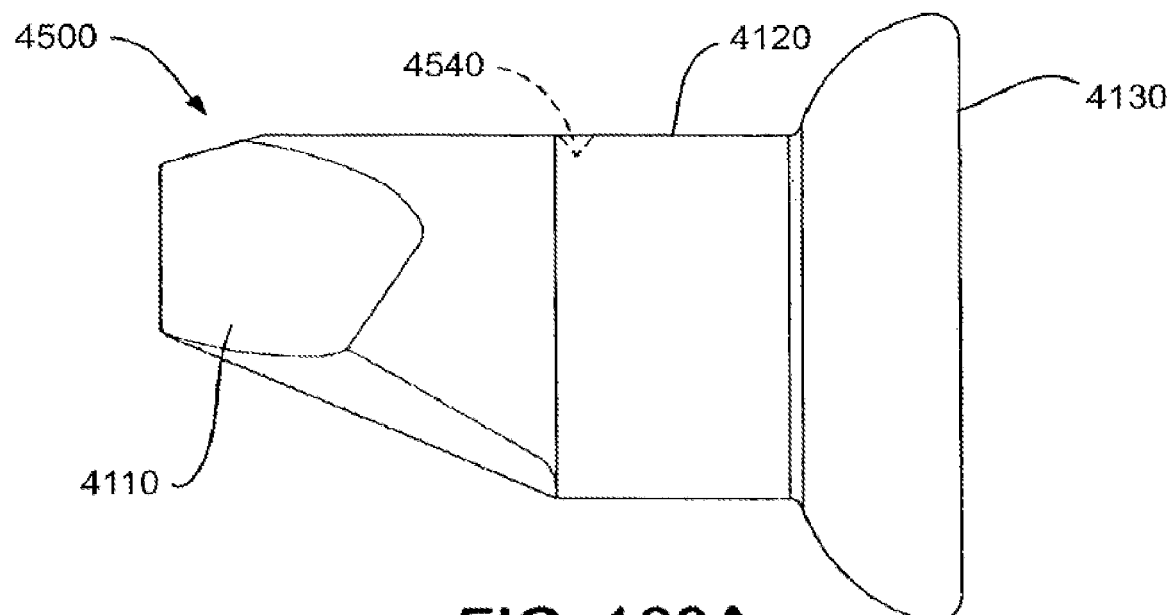
FIG. 160A is a plan view of an embodiment of an implant for use with the second wing of FIGS. 159A and 159B.
Figure 160B:
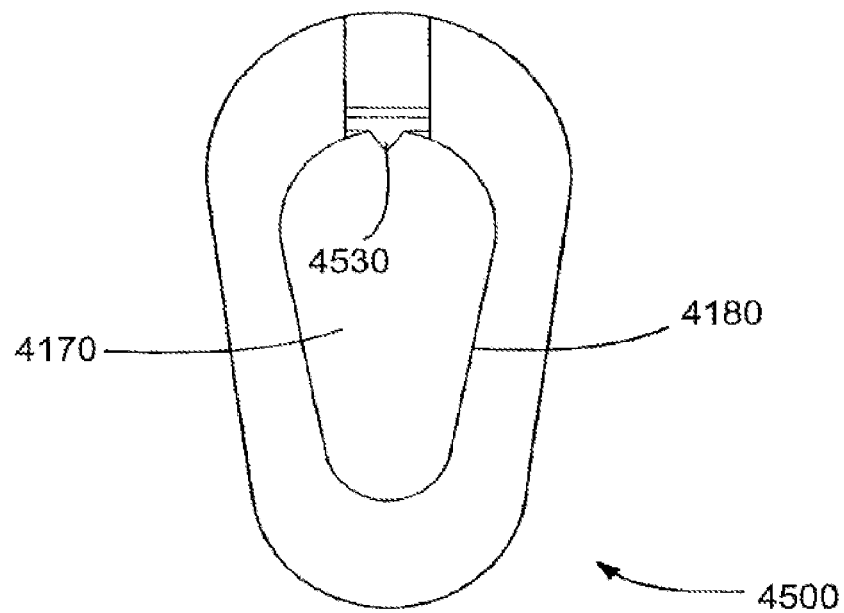
FIG. 160B is a front view of the second wing of FIGS. 159A and 159B.

FIGS. 159A-159B depict a further embodiment 4500 wherein the second wing 4560 is secured to the spacer 4120 by a mechanism including a flexible hinge 4565, with a protrusion 4561 on the end of the hinge 4565 adjacent to the lip 4562 of the opening 4564 defined by portions of the second wing 4560. The securing mechanism also encompasses an indentation 4540 on the spacer 4120, wherein the indentation 4540 accommodates the protrusion 4561 on the end of the flexible hinge 4565. During surgery, after insertion of the distraction guide 4110, spacer 4120, and first wing 4130, the second wing 4560 is received over the distraction guide 4110 and the spacer 4120. As the second wing 4560 is received by the spacer 4120, the flexible hinge 4565 and its protrusion 4561 deflect until the protrusion 4561 meets and joins with the indentation 4540 in the spacer 4120, securing the second wing 4560 to the spacer 4120. Again in embodiments where the spacer can rotate, the indentation 4540 is located on an end of the distraction guide 4110 that is adjacent to the rotatable spacer 4220. With respect to the flexible hinge 4565, this hinge is in a preferred embodiment formed with the second wing 4560 and designed in such a way that it can flex as the hinge 4565 is urged over the distraction guide 4110 and the spacer 4120 and then allow the protrusion 4561 to be deposited into the indentation 4540. Alternatively, it can be appreciated that the indentation 4540 can exist in the second wing 4560 and the flexible hinge 4565 and the protrusion 4561 can exist on the spacer 4120 in order to mate the second wing 4560 to the spacer 4120. Still alternatively, the flexible hinge 4565 can be replaced with a flexible protrusion that can be flexed into engagement with the indentation 4540 in the embodiment with the indentation 4540 in the spacer 4120 or in the embodiment with the indentation 4540 in the second wing 4560. One of ordinary skill in the art will appreciate the myriad different ways with which the second wing can be mated with the implant.

Figure 161A:
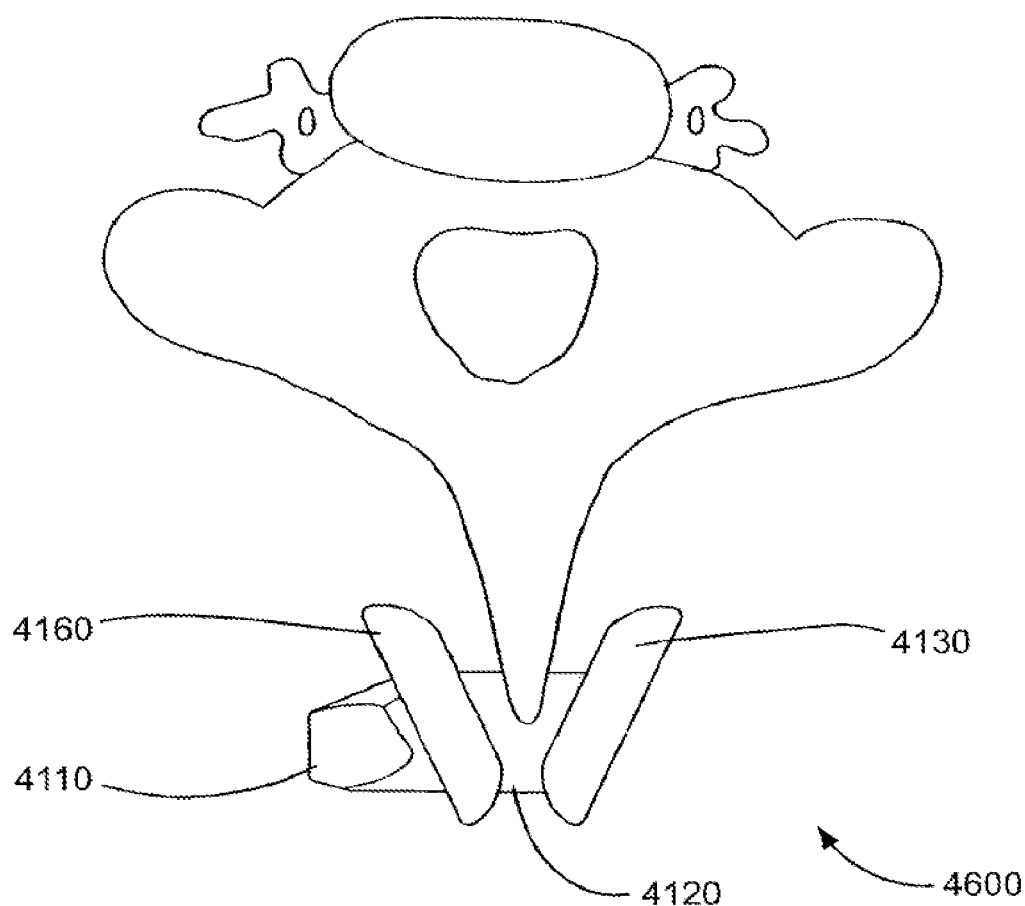
FIG. 161A is a top view of an embodiment of an implant in accordance with the present invention positioned between spinous processes of adjacent cervical vertebrae.
Figure 161B:
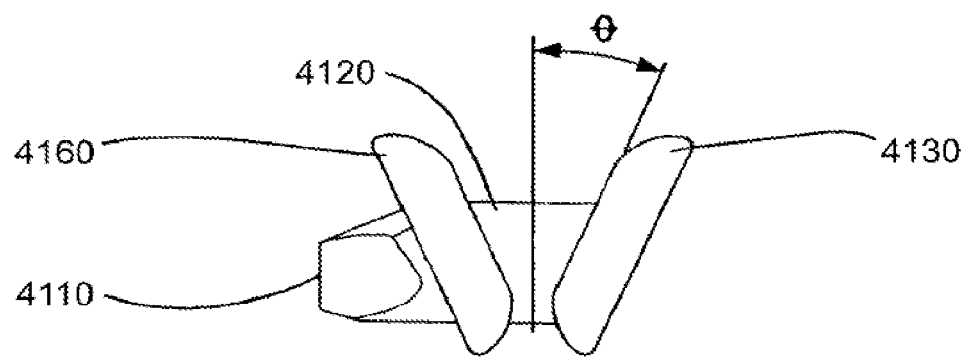
FIG. 161B is a top view of the implant of FIG. 161A showing wing orientation.
Figure 162:
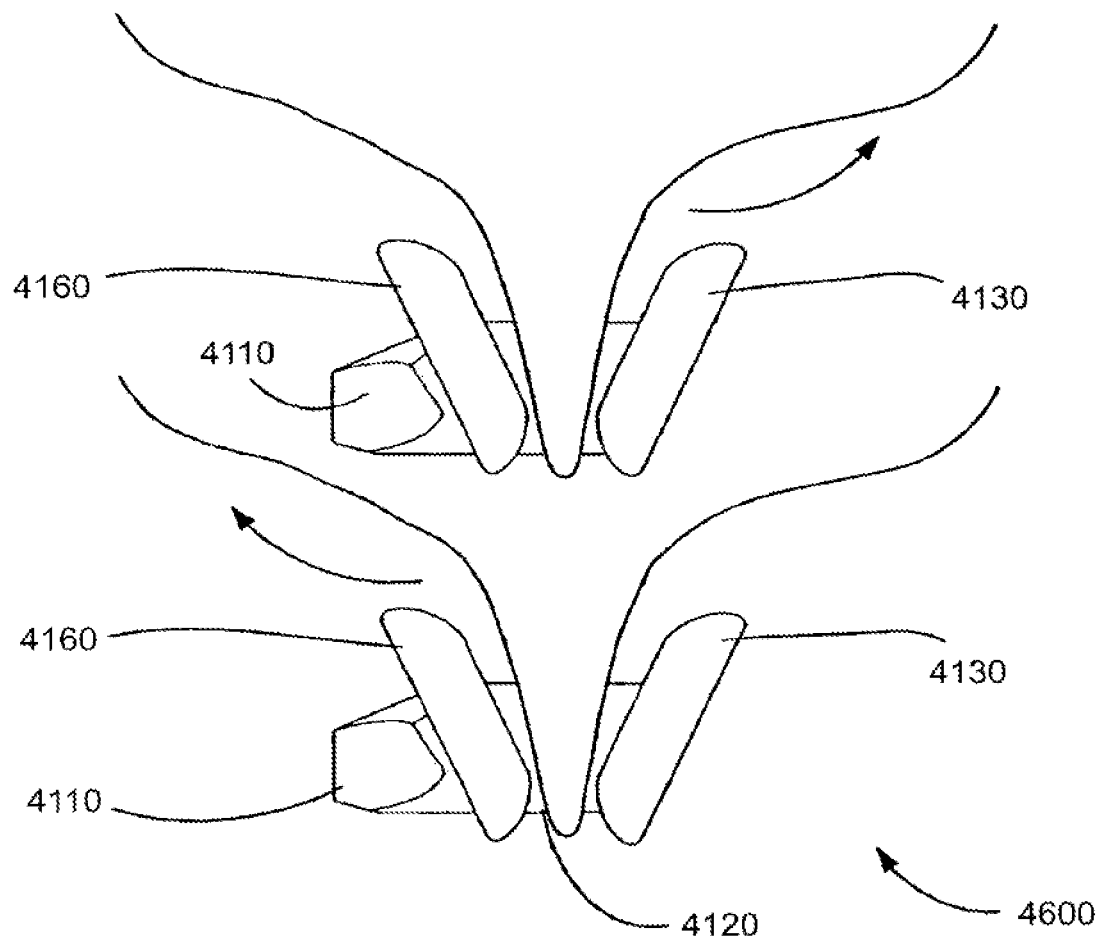
FIG. 162 is a top view of two such implants of the invention of FIGS. 161A and 161B, positioned in the cervical spine.

FIGS. 161A-162 illustrate an embodiment of an implant 4600 wherein anterior ends of a first wing and second wing 4660 flare out at an angle away from the spacer 4120 and away from each other. The cervical spinous processes are themselves wedge-shaped when seen from a top view. The first wing 4630 and second wing 4660 flare out so that the implant 4600 can roughly conform with the wedge shape of the spinous processes, allowing the implant 4600 to be positioned as close as possible to the vertebral bodies of the spine where the load of the spine is carried. The first and second wings 4630, 4660 are positioned relative to the spacer, whether the spacer is fixed 4120 or rotatable 4220, so that the wings flare out as the wings approach the vertebral body of the spine. FIG. 161B is a top view of the implant 4600 of FIG. 161A removed from proximity with the spinous processes. The first wing 4630 is aligned at an angle with respect to an axis along the spinous processes perpendicular to the longitudinal axis (also referred to herein as the plane of symmetry). In one embodiment, the angle is about 30°, however, the angle θ can range from about 15° to about 45°. In other embodiments, other angles outside of this range are contemplated and in accordance with the invention. Likewise, the second wing 4660 can be aligned along a similar, but oppositely varying range of angles relative to the plane of symmetry.

As described above in reference to FIG. 150, the second wing 4660 defines an opening which is outlined by a lip. As is evident, the lip can be provided at an angle relative to the rest of the second wing 4660 so that when the lip is urged into contact with the spacer 4120, the second wing 4660 has the desired angle relative to the spacer 4120. As discussed above, there are various ways that the second wing 4660 is secured to the spacer 4120. FIG. 161A depicts a top view of one such implant 4600 placed between the spinous processes of adjacent cervical vertebrae. FIG. 162 is a top view illustrating two layers of distracting implants 4600 with flared wings 4630, 4660.

Figure 163:
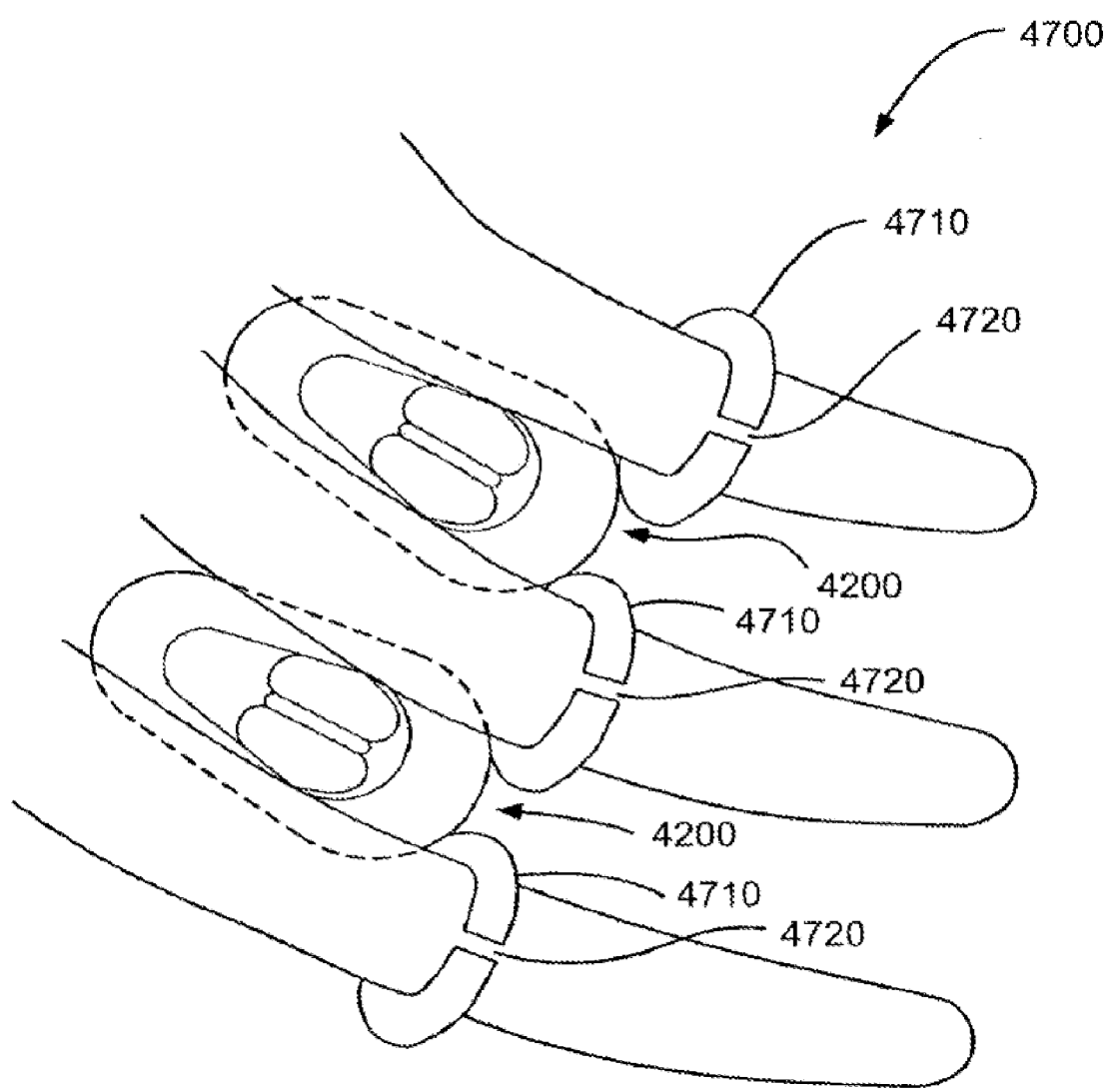
FIG. 163 is a side view of two implants of the invention positioned in the cervical spine, with stops or keeps at the proximal ends of the spinous processes.

Systems and methods in accordance with the present invention can include devices that can be used in cooperation with implants of the present invention. FIG. 163 illustrates "stops" (also referred to herein as "keeps") 4656, which are rings of flexible biocompatible material, which can be positioned around the spinous processes of adjacent cervical vertebrae and located posteriorly to the implant 4600. The keeps 4656 can prevent posterior displacement of implants. In one embodiment, the keeps can include a ring having a slit 4658. The keeps 4656 can be somewhat sprung apart, so that the keep 4656 can be fit over the end of the spinous process and then allowed to spring back together in order to hold a position on the spinous process. The keep 4656 can act as a block to the spacer 4120 in order to prevent the implant 4600 from movement in a posterior direction.

Implants Having Deployable Wings

Figure 164A:
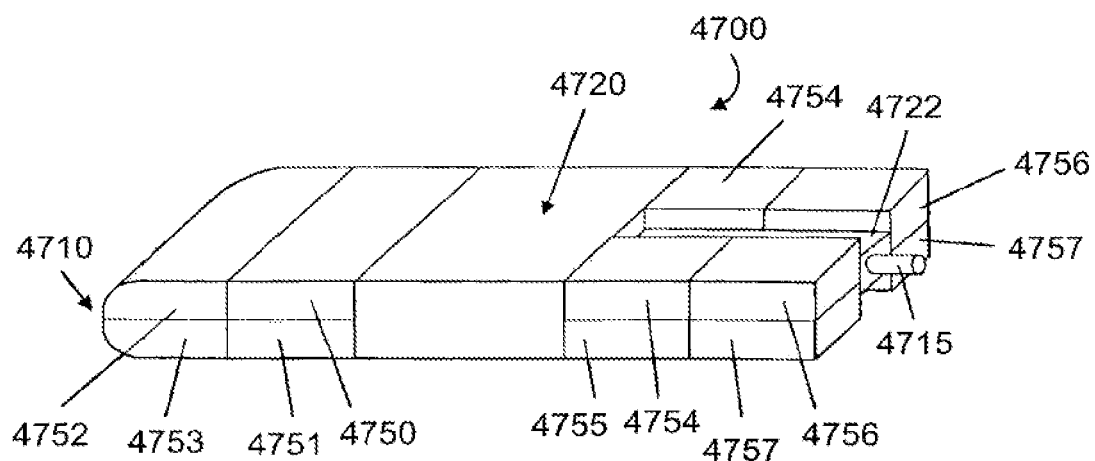
FIG. 164A is a perspective view of an alternative embodiment of an implant in accordance with the present invention having a first wing and a second wing that can be deployed after arranging the implant between adjacent spinous processes.
Figure 164B:
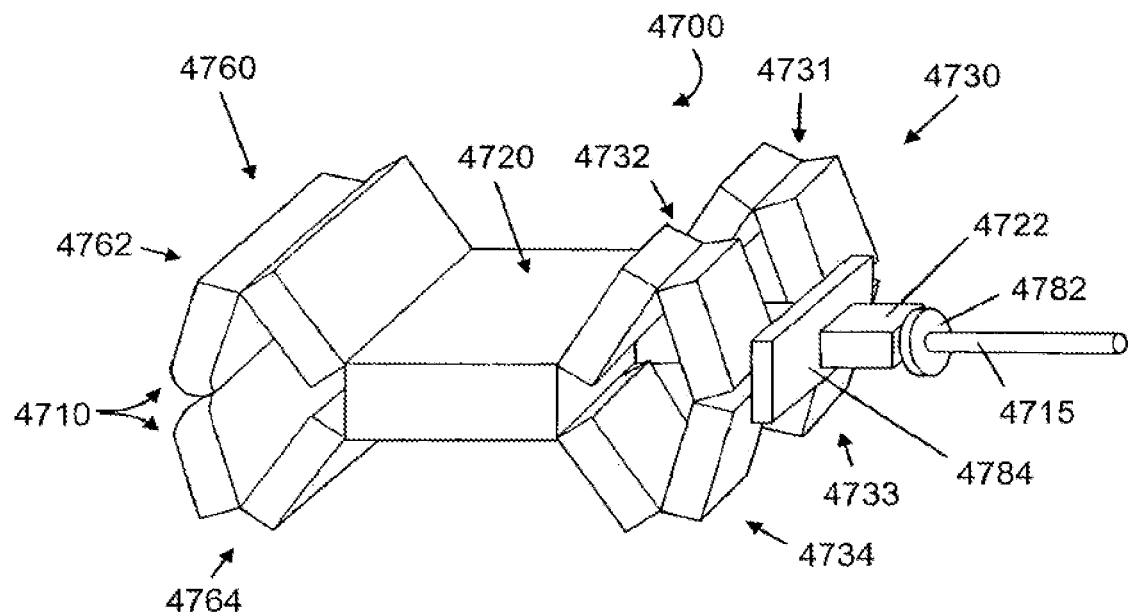
FIG. 164B is a perspective view of the implant of FIG. 164B in a deployed configuration.

In other embodiments, implants in accordance with the present invention can comprise a "matchbox"-like structure having a first configuration (as shown in FIG. 164A) and a second, deployed configuration (as shown in FIG. 164B). Arranged in the first configuration, such implants 4700 can have a substantially flat profile having an approximately uniform thickness. The uniform thickness approximates the thickness of a spacer 4720 of the implant 4700. The implant 4700 can comprise a distraction guide 4710 at a proximal end of the implant, the distraction guide 4710 having a slightly rounded or tapered shape to pierce and/or distract a space between adjacent spinous processes. The implant 4700 can further comprise a plurality of hinged structures 4750-4757, the hinged structures 4750-4757 being collapsed so as to facilitate the substantially flat profile. The hinged structures 4750-4757 are pivotally connected with the spacer 4720 and extend from both sides of the spacer 4720. As shown in FIG. 164A, a support structure 4722 extends from the spacer 4720 toward the distal end of the implant 4700. A rod 4715 (or alternatively some other mechanism such as a tab) can be connected with the proximal end of the implant 4700 and can extend through the hinged structures 4750-4753, through the spacer 4720, and through the support structure 4722 so that the rod 4715 is accessible.

Referring to FIG. 164B, once the implant 4700 is positioned as desired between adjacent spinous processes, the rod 4715 can be drawn in a direction opposite the direction of insertion along the longitudinal axis 4725 so that the hinged structures 4750-4757 fold outward to form a first wing 4730 and a second wing 4760 between which is arranged the spacer 4720 and a portion of the spinous processes. As the hinged structures 4750-4757 fold outward, the height of the first and second wings 4730, 4760 increases from approximately the same as the thickness of the spacer 4720 to a height such that the first and second wing 4730, 4760 can limit or block movement of the implant 4700 along the longitudinal axis 4725 when positioned between adjacent spinous processes.

As can be seen, the second wing 4760 includes four hinged structures 4750-4753: an upper first structure 4750 connected by a hinge to an upper second structure 4752, and a lower first structure 4751 connected by a hinge to a lower second structure 4753. The hinged structures 4750-4753 pivot outward to form an upper end 4762 of the second wing and a lower end 4764 of the second wing. Likewise, the first wing 4730 includes four hinged structures 754-4757: an upper first structure 4754 connected by a hinge to an upper second structure 4756, and a lower first structure 4755 connected by a hinge to a lower second structure 4757. However, unlike the second wing 4760, the first wing 4730 is (effectively) bisected by the support structure 4722 so that the first wing 4730 comprises four winglets 4731-4734. The hinged structures 4754-4757 pivot outward to form upper winglets 4731, 4732 of the first wing and lower winglets 4733, 4734 of the first wing.

As mentioned above, the support structure 4722 extends from the spacer 4720 toward the distal end of the implant 4700. The spacer 4720 and the support structure 4722 include a bore or other cavity through which the rod 4715 can travel. Applying resistive force to the support structure 4722 can fix the spacer 4720 in place between spinous processes when drawing the rod 4715 through the bore. As the rod 4715 is drawn through the bore, the hinged structures 4752, 4753 with which the proximal end of the rod 4715 is connected are drawn with the rod 4715. As the rod 4715 is drawn through the spacer 4720, the hinged structures 4752,4753 are drawn toward the spacer 4720. The hinged structures 4750-4753 pivot outward to accommodate the relative movement between the rod 4715 and the spacer 4720. Accordingly, the second wing 4760 has been satisfactorily deployed.

The hinged structures 4756, 4757 of the first wing 4730 can cause deployment of the first wing 4730 by applying resistive force to the hinged structures 4756, 4757 while drawing the spacer 4720 (via the support structure 4722), or by urging the hinged structures 4756, 4757 toward the spacer 4720. The resistive force or urging can be applied by a second stop 4784 that can fit around the support structure 4722 and can be interference fit or otherwise selectively fixed with the support structure 4722. As the second stop 4784 is pushed along the longitudinal axis 4725, along the support structure 4722, the hinged structures 4754-4757 pivot outward to accommodate the relative movement between the second stop 4784 and the spacer 4720. Accordingly, the first wing 4730 has been satisfactorily deployed.

Figure 165A:
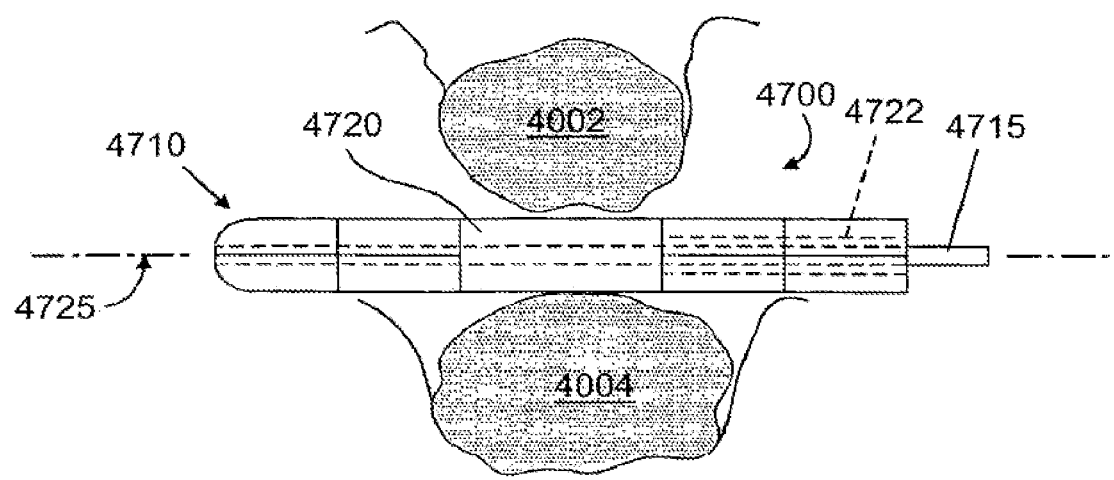
FIG. 165A is a posterior view of the implant of FIGS. 164A and 164B positioned between adjacent spinous processes in an undeployed configuration.
Figure 165B:
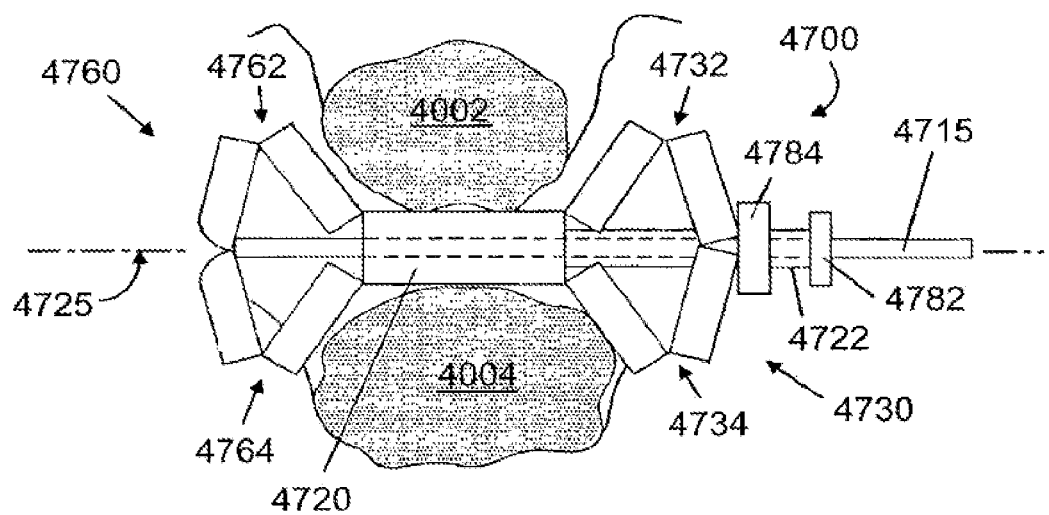
FIG. 165B is a posterior view of the implant of FIGS. 164A and 164B positioned between adjacent spinous processes in a deployed configuration.

FIGS. 165A and 165B are posterior views of the implant 4700 positioned between adjacent spinous processes 4002, 4004 demonstrating an embodiment of a method for deploying the implant 4700 between the spinous processes 4002, 4004. The implant 4700 can be positioned so that a distraction guide 4710 of the implant 4700 is arranged at a space between the spinous processes 4002, 4004. The implant 4700 can then be urged between the spinous processes 4002, 4004 so that the spacer 4720 is positioned as desired. The substantially flat profile of the implant 4700 can ease positioning of the spacer 4720 by reducing potential obstructing surfaces that can resist movement of the implant 4700 during implantation. The second wing 4760 and the first wing 4730 can then be deployed to limit movement of the implant 4700. To deploy the second wing 4760 the rod 4715 is drawn in a direction opposite the direction of insertion along the longitudinal axis 4725. The upper end 4762 and lower end 4764 of the second wing extend outward as described above. Once the second wing 4760 is deployed, the rod 4715 can be fixed in position relative to the spacer 4720. This can be accomplished using myriad different mechanisms. For example, as shown a first stop 4782 can be interference fit to the rod 4715 and positioned against the support structure 4722 along the rod 4715. The first stop 4782 can grip the rod 4715, as with a friction fit between the first stop 4782 and the rod 4715, so that the rod 4715 is prevented from moving through the bore of the support structure 4722 by interference between the first stop 4782 and the support structure 4722. In other embodiments, some other mechanism can be used, such as a pin (e.g., a cotter pin), a latch system, etc. One of ordinary skill in the art will appreciate the myriad different mechanisms for fixing a rod 4715 in position relative to the spacer 4720. The upper second structure 4756 and the lower second structure 4757 can be urged toward the spacer 4720 in the direction of insertion along the longitudinal axis 4725 using a second stop 4784 as described above, causing the upper winglets 4731, 4732 and lower winglets 4733, 4734 to extend outward to form the first wing 4730. Once the first wing 4730 is deployed, the hinged structures 4754-4757 can be fixed in position using the second stop 4784 or some other mechanism. The second stop 4784 can grip the support structure 4722, as with a friction fit or pin, and resist movement of the hinged structures 4754-4757, thereby preventing collapse. As above, one of ordinary skill in the art will appreciate the myriad different mechanisms for fixing the first wing 4730 in a deployed position. With the first wing 4730 and the second wing 4760 deployed, movement of the implant 4700 along the longitudinal axis 4725 can be limited or blocked, thereby resisting undesirable displacement of the implant 4700.

It should be noted that with implants as described above in reference to FIGS. 164A-167 the rod 4715 can optionally be trimmed or otherwise partially detached to decrease a space required to accommodate the implant 4700, 4800 within the patient's spine. For example, the structure of the rod 4715 can be beveled or otherwise weakened near a distal end of the rod 4715 to allow the rod 4715 to be snapped off when the first and second wings 4730, 4760, 4830, 4860 are deployed and the rod 4715 is fixed in place. In other embodiments, a tool (not shown) can be used to cut the rod 4715 after the first and second wings 4730, 4760, 4830, 4860 are deployed and the rod 4715 is fixed in place. Still further, the rod 4715 need not comprise a rigid structure, but rather alternatively can include a tether, string, or similarly flexible structure that can be placed in tension to retain the second wing 4760, 4860 and/or first wing 4730, 4830 in a deployed position.

Figure 166A:
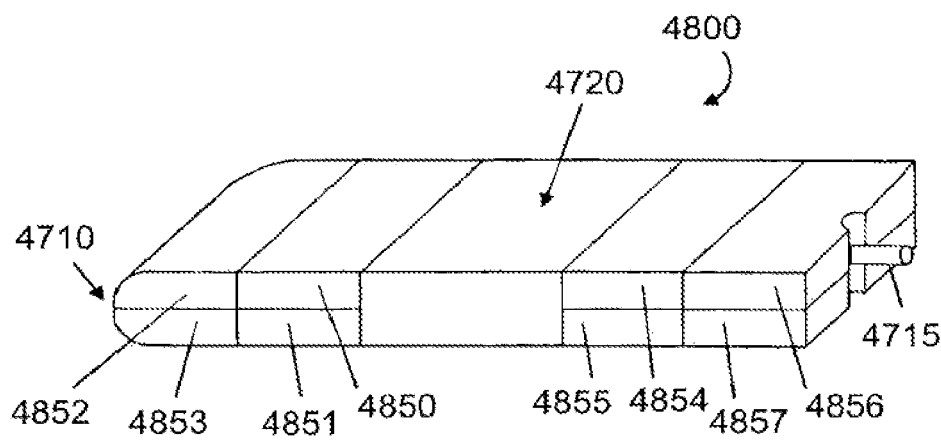
FIG. 166A is a perspective view of still another embodiment of an implant in accordance with the present invention having a first wing and a second wing that can be deployed after arranging the implant between adjacent spinous processes.
Figure 166B:
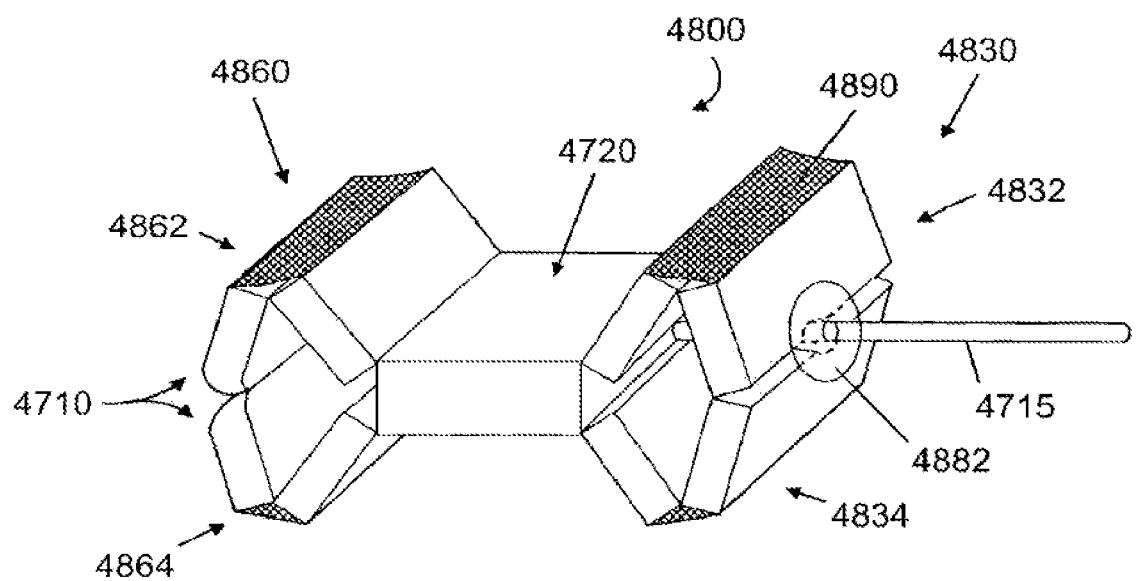
FIG. 166B is a perspective view of the implant of FIG. 166A in a deployed configuration.

Referring to FIGS. 166A and 166B, a still further embodiment of an implant 4800 in accordance with the present invention is shown. In such an embodiment, a flexible strap 4890 can be connected between pairs of hinged structures (i.e., 4850 and 4852, 4851 and 4853, 4854 and 4856, 4855 and 4857). The flexible strap 4890 can limit the relative movement of the hinged structures 4850-4857 so that first wing 4830 and second wing 4860 have increased rigidity when fully deployed. The implant 800 need not include the support structure 4722 of the previous embodiment. A resistive force can be applied to the hinged structures 4856, 4857 so that as the rod 4715 is drawn in a direction opposite the direction of insertion along the longitudinal axis 4825 the resistive force causes the hinged structures 4854-4857 to extend outward to form the first wing 4830. As the hinged structures 4854-4857 extend outward the flexible strap 4890 connected opposite the hinge unfolds. Once the hinged structures 4854-4857 reach a maximum extension, the flexible strap 4890 becomes taut and resists further extension, locking the first wing 4830 in place. The flexible straps 4890 can provide the first wing 4830 with sufficient rigidity to resist movement of the spacer 4720, so that as the rod 4715 is further drawn the rod 4715 moves through the spacer 4720 and the hinged structures 4852, 4853 connected with the rod 4715 are drawn toward the spacer 4720. As the hinged structures 4852, 4853 connected with the rod 4715 are drawn toward the spacer 4720, all of the hinged structures 4850-4853 extend outward to deploy the second wing 4860. The flexible strap 4890, connected opposite the hinge, unfolds. Once the hinged structures 4854-4857 reach a maximum extension the flexible strap 4890 becomes taut and resists further extension, locking the first wing 4830 in place. A stop 4882 (or alternatively some other mechanism such as a pin) can be fixed to the rod 4715 to create interference between the stop 4882 and the hinged structures 4832, 4834 of the first wing 4830 that resists movement of the rod 4715.

The flexible straps 4890 can be made from a biocompatible material. In an embodiment, the flexible straps 4890 can be made from a braided polyester suture material. Braided polyester suture materials include, for example, Ethibond, Ethiflex, Mersilene, and Dacron, and are non-absorbable, having high tensile strength, low tissue reactivity and improved handling. In other embodiments, the flexible straps 4890 can be made from stainless steel (i.e., surgical steel), which can be woven into a strap, for example. In still other embodiments, flexible straps 4890 can be made from some other material (or combination of materials) having similar properties.

Figure 167:
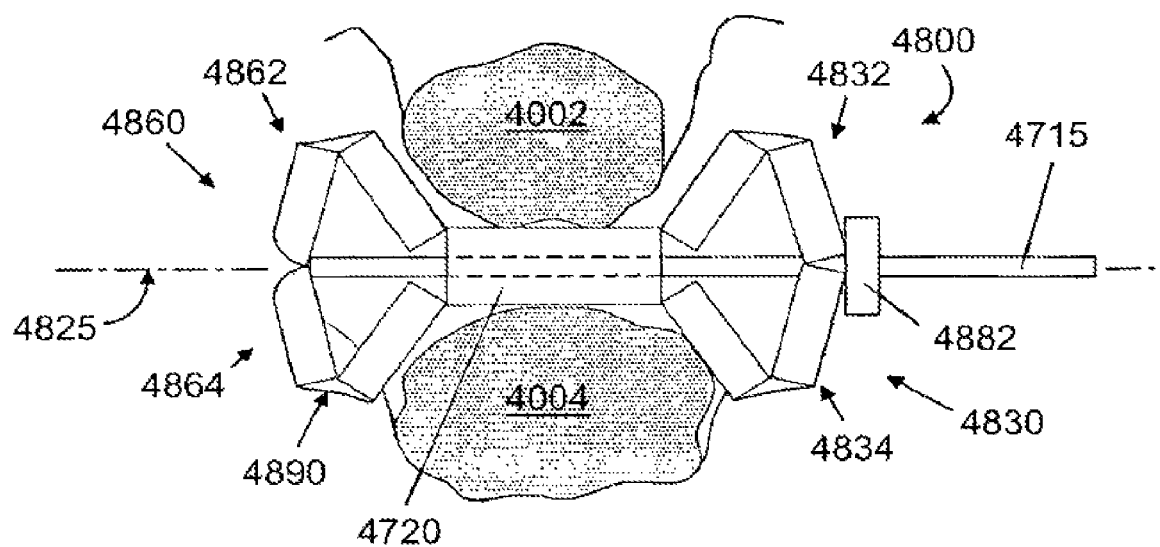
FIG. 167 is a posterior view of the implant of FIGS. 166A and 166B positioned between adjacent spinous processes in a deployed configuration.

FIG. 167 is a posterior view of the implant 4800 positioned between adjacent spinous processes 4002, 4004 demonstrating an embodiment of a method for deploying the implant 4800 between the spinous processes 4002, 4004. The first wing 4830 can be deployed to limit movement of the implant 4800 relative to the spinous processes 4002, 4004. To deploy the first wing 4830 the rod 4715 can be held fixed in position or urged in a direction opposite the direction of insertion along the longitudinal axis 4825 while a force is applied to the hinged structures 4854-4857 (FIG. 166A) of the first wing 4830 to cause the upper end 4832 of the first wing and the lower end 4834 of the first wing to extend away from the rod 4715, thereby deploying the first wing 4830. The rod 4715 can be further urged in the direction opposite the direction of insertion so that the proximal end of the rod 4715 pivotably connected with the hinged structures 4852, 4853 that comprise the distraction guide 4710, is drawn toward the spacer 4720, causing the upper end 4862 of the spacer, and the lower end 864 of the spacer to extend away from the rod 4715. Once the second wing 4860 and the first wing 4830 are deployed, the rod 4715 can be fixed in position relative to the spacer 4720. As above, this can be accomplished using myriad different mechanisms. For example, as shown a first stop 4882 can be interference fit to the rod 4715 and positioned against the first wing 4830 along the rod 4715. The first stop 4882 can grip the rod 4715 so that the rod 4715 is prevented from moving by a friction fit between the first stop 4882 and the rod 4715. In other embodiments, some other mechanism can be used, such as a pin (e.g., a cotter pin), a latch system, etc. One of ordinary skill in the art will appreciate the myriad different mechanisms for fixing a rod 4715 in position relative to the spacer 4720. With the first wing 4830 and the second wing 4860 deployed, movement of the implant 4800 along the longitudinal axis 4825 can be limited or blocked, thereby resisting undesirable displacement of the implant 4800.

Figure 168A:
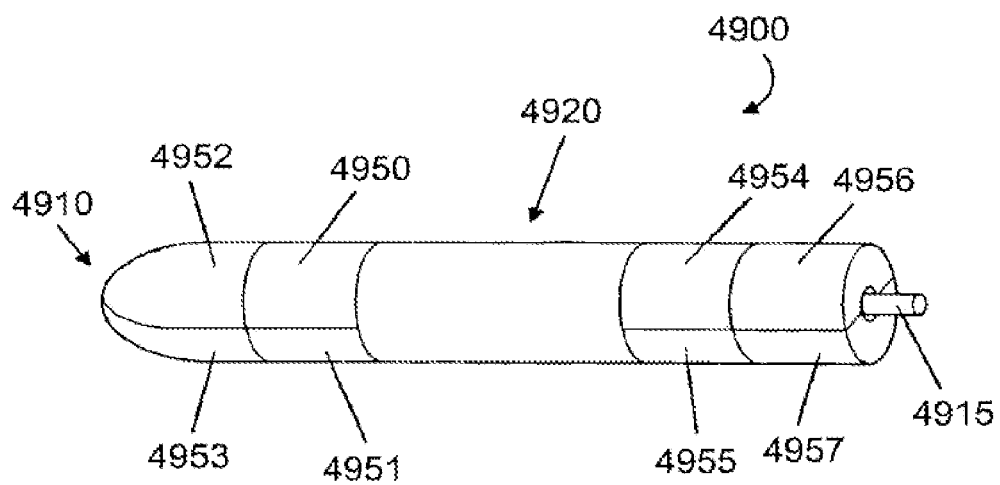
FIG. 168A is a perspective view of an alternative embodiment of an implant in accordance with the present invention having a first wing and a second wing that can be deployed after arranging the implant between adjacent spinous processes.
Figure 168B:
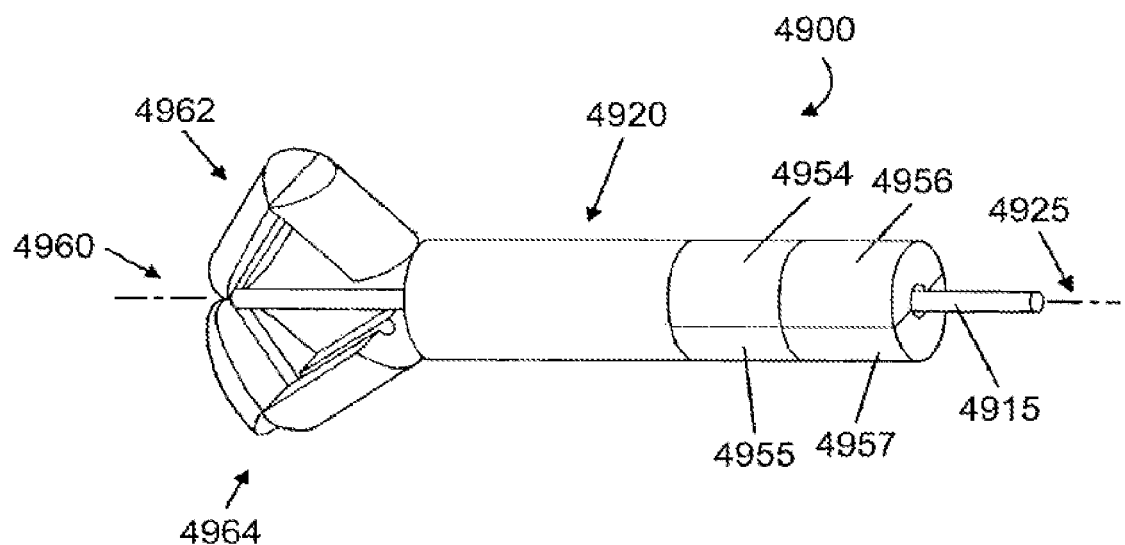
FIG. 168B is a perspective view of the implant of FIG. 168A in a partially deployed configuration.

Referring to FIGS. 168A and 168B, in still other embodiments, implants in accordance with the present invention can comprise a "matchbox"-like structure having a rounded, collapsed first configuration and a second, deployed configuration. Arranged in the first configuration, such implants 4900 can have a shape allowing the implant 4900 to be more naturally inserted through a cannula. As shown, such a shape includes a substantially circular cross-section, though in other embodiments the implant can have an ovoid or elliptical cross-section, thereby allowing a spacer shape to be employed that generally accommodates a space between adjacent spinous processes. However, it will be appreciated that an implant 4900 having a circular cross-section can most efficiently use the space of a cannula, where the cannula includes a circular cross-section; therefore, it may be preferable to employ an implant 4900 having a circular cross-section where a physician desired to minify the diameter of the cannula inserted into the surgical site.

The cross-section of the implant 4900 in a first configuration is generally consistent along the implant's length, having a diameter generally the thickness of a spacer 4920 of the implant 4900. The implant 4900 can comprise a distraction guide 4910 at a proximal end of the implant 4900, the distraction guide 4910 having a rounded (as shown) or tapered shape to pierce and/or distract a space between adjacent spinous processes. However, where a cannula is employed to deliver an implant to a surgical site, the implant 4900 can optionally include a distraction guide 4910 at the proximal end. The surgical site, and associated tissues and structures can be distracted and repositioned by the cannula, allowing substantially unobstructed access to the surgical site by the implant 4900. In such circumstance a distraction guide 4910 may not be necessary.

The implant 4900 can further comprise a plurality of hinged structures 4950-4957, the hinged structures 4950-4957 being collapsed so as to facilitate the substantially collapsed profile.

The hinged structures 4950-4957 are pivotally connected with the spacer 4920 and extend from both sides of the spacer 4920. A rod 4915 (or alternatively some other mechanism such as a tab) can be connected with the proximal end of the implant 4900 and can extend through the hinged structures 4950-4953, and through the spacer 4920 so that the rod 4915 is accessible to a physician.

Figure 168C:
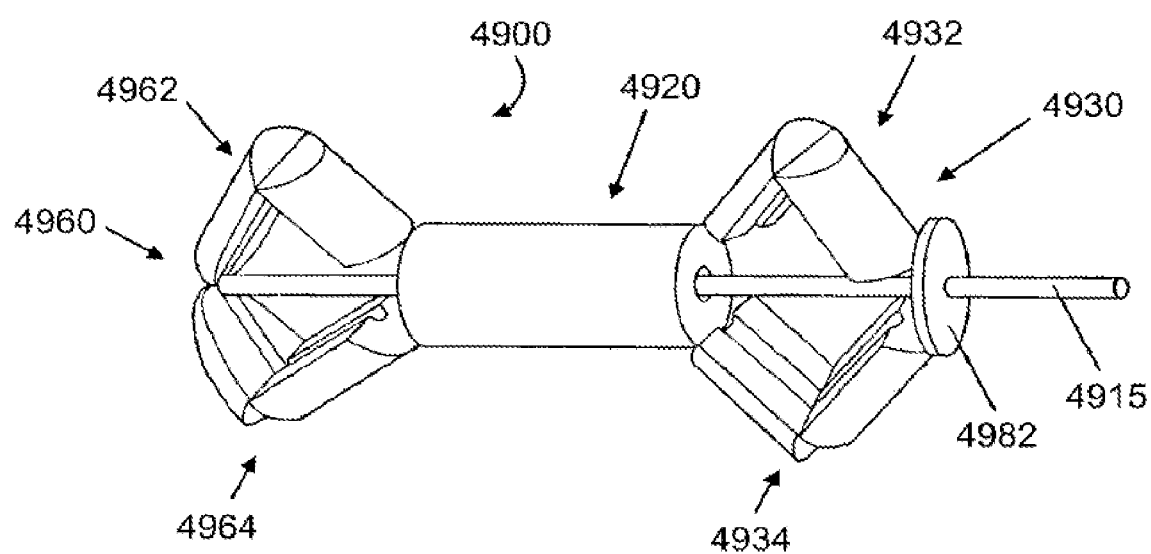
FIG. 168C is a perspective view of the implant of FIG. 168A in a fully deployed configuration.

Referring to FIGS. 168B and 168C, once the implant 4900 is positioned as desired between adjacent spinous processes, the rod 4915 can be drawn in a direction opposite the direction of insertion along the longitudinal axis 4925 so that the hinged structures 4950-4957 fold outward to form a first wing 4930 and a second wing 4960 between which is arranged the spacer 4920 and a portion of the spinous processes. As the hinged structures 4950-4957 fold outward, the height of the first and second wings 4930, 4960 increases from approximately the same as the thickness of the spacer 4920 to a height such that the first and second wing 4930, 4960 can limit or block movement of the implant 4900 along the longitudinal axis 4925 when positioned between adjacent spinous processes. As can be seen, the second wing 4960 includes four hinged structures 4950-4953: an upper first structure 4950 connected by a hinge to an upper second structure 4952, and a lower first structure 4951 connected by a hinge to a lower second structure 4953. The hinged structures 4950-4953 pivot outward to form an upper end 4962 of the second wing and a lower end 4964 of the second wing. Likewise, the first wing 4930 includes four hinged structures 4954-4957: an upper first structure 4954 connected by a hinge to an upper second structure 4956, and a lower first structure 4955 connected by a hinge to a lower second structure 4957.

Figure 169A:
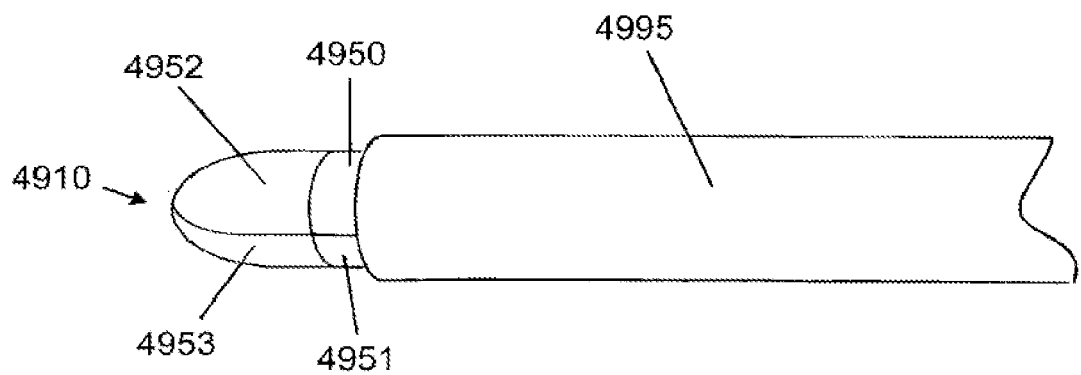
FIG. 169A is a perspective view of the implant of FIG. 168A including a cannula within which the implant is disposed for insertion into desired location between adjacent spinous processes.
Figure 169B:
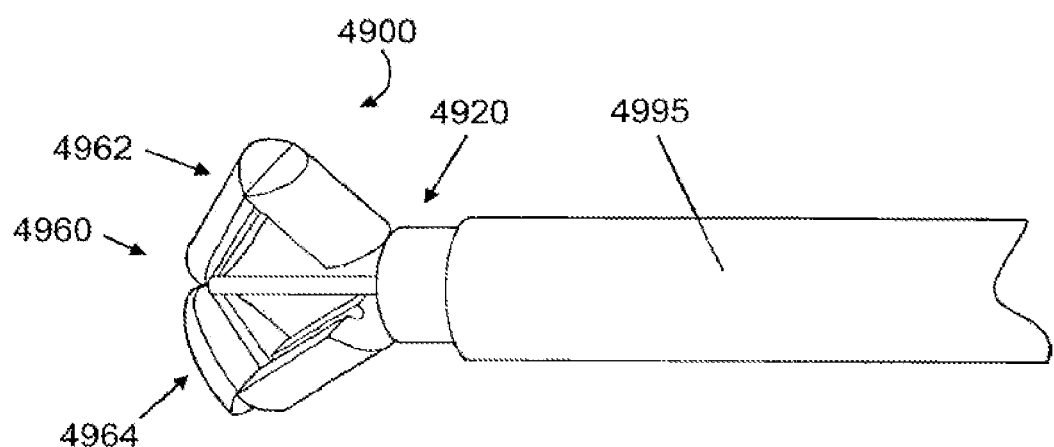
FIG. 169B is a perspective view of the implant of FIG. 168A in a partially deployed configuration.
Figure 169C:
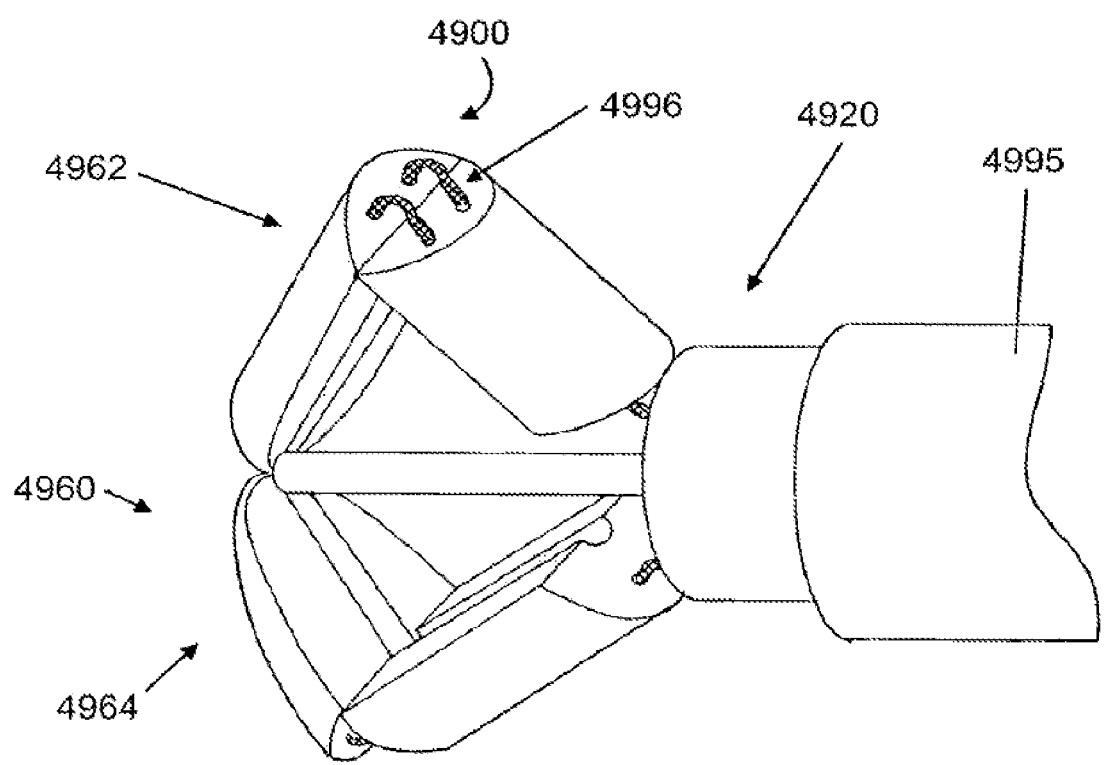
FIG. 169C is a perspective close-up view of the implant of FIG. 168A showing hinged structures connected by cords.

Embodiments as described above in reference to FIGS. 164A and 164B included a support structure 4722 extending from the spacer 4720. Likewise, a support structure can optionally extend from the spacer 4920 of the cannula delivered implant 4900. However, such a structure need not be necessary where the first wing 4930 is prevented from deploying during deployment of the second wing 4960 by the cannula 995 itself (see FIG. 169B). Referring to FIGS. 169A and 169B, once the cannula is positioned at the surgical site, the implant 4900 can be urged through the cannula so that the hinged structures 4950-4953 are clear of the cannula. The rod 4915 can then be urged in an opposite direction (relative to insertion) along the longitudinal axis 4925 to deploy the second wing 4960. As the rod 4915 is drawn through the spacer 4920, the hinged structures 4952, 4953 are drawn toward the spacer 4920. The hinged structures 4950-4953 pivot outward to accommodate the relative movement between the rod 4915 and the spacer 4920. Accordingly, the second wing 4960 has been satisfactorily deployed.

Once the second wing 4960 is deployed, the cannula 995 can be retracted from the surgical site, thereby allowing the hinged structures 956, 4957 of the first wing 4930 to deploy by urging the hinged structures 4956, 4957 toward the spacer 4920. The urging can be applied by a stop 4982 that can fit around the rod 4915 and can be interference fit or otherwise selectively fixed with the rod 4915. As the stop 982 is pushed along the longitudinal axis 4925, along the rod 4915, the hinged structures 4954-4957 pivot outward to accommodate the relative movement between the stop 4982 and the spacer 4920. Accordingly, the first wing 4930 has been satisfactorily deployed.

Once the second wing 4960 and the first wing 4930 are deployed, the rod 4915 can be fixed in position relative to the spacer 4920. As above, this can be accomplished using myriad different mechanisms. For example, as shown a stop 4982 can be interference fit to the rod 4915 and positioned against the first wing 4930 along the rod 4915. The stop 4982 can grip the rod 4915 so that the rod 4915 is prevented from moving by a friction fit between the stop 4982 and the rod 4915. In other embodiments, some other mechanism can be used, such as a pin (e.g., a cotter pin), a latch system, etc. One of ordinary skill in the art will appreciate the myriad different mechanisms for fixing a rod 4915 in position relative to the spacer 4920. With the first wing 4930 and the second wing 4960 deployed, movement of the implant 4900 along the longitudinal axis 4925 can be limited or blocked, thereby resisting undesirable displacement of the implant 4900.

It should be noted that with implants as described above in reference to FIGS. 168A-169B the rod 4915 can optionally be trimmed or otherwise partially detached to decrease a space required to accommodate the implant 4900 within the patient's spine. For example, the structure of the rod 4915 can be beveled or otherwise weakened near a distal end of the rod 4915 to allow the rod 4915 to be snapped off when the first and second wings 4930, 4960 are deployed and the rod 4915 is fixed in place. In other embodiments, a tool (not shown) can be used to cut the rod 4915 after the first and second wings 4930, 4960 are deployed and the rod 4915 is fixed in place. Still further, the rod 4915 need not comprise a rigid structure, but rather alternatively can include a tether, string, or similarly flexible structure that can be placed in tension to retain the second wing 4960 and/or first wing 4930 in a deployed position.

Referring to FIGS. 168B, 168C and 169B, the implant 4900 is shown having operably connected "hinged" structures 4950-4957. Such structures can be hinged in any way that permits relative movement. For example, the structures may be hinged by way of flexible straps, for example as described above in reference to FIG. 167B. Alternatively, the structures can be hinged using some other technique. For example, referring to FIG. 169C, one or a pair of cords 4996 can connect pairs of hinged structures so that relative movement is restricted, thereby permitting hinging motion, while resisting separation of the structures. In still other embodiments, some other mechanism can be employed to define a range of movement of the hinged structures 4950-4957. One of ordinary skill in the art will appreciate the myriad different techniques for defining a range of motion of two mechanical parts.

As with the flexible straps 4890 above, the cord 4996 can be made from a biocompatible material. In an embodiment, the cord 4996 can be made from a braided polyester suture material. Braided polyester suture materials include, for example, Ethibond, Ethiflex, Mersilene, and Dacron, and are non-absorbable, having high tensile strength, low tissue reactivity and improved handling. In other embodiments, the cords 4996 can be made from stainless steel (i.e., surgical steel), which can be woven into a strap, for example. In still other embodiments, the cords 4996 can be made from some other material (or combination of materials) having similar properties.

Materials for Use in Implants of the Present Invention

In some embodiments, the implant can be fabricated from medical grade metals such as titanium, stainless steel, cobalt chrome, and alloys thereof, or other suitable implant material having similar high strength and biocompatible properties. Additionally, the implant can be at least partially fabricated from a shape memory metal, for example Nitinol, which is a combination of titanium and nickel. Such materials are typically radiopaque, and appear during x-ray imaging, and other types of imaging. Implants in accordance with the present invention, and/or portions thereof can also be fabricated from somewhat flexible and/or deflectable material. In these embodiments, the implant and/or portions thereof can be fabricated in whole or in part from medical grade biocompatible polymers, copolymers, blends, and composites of polymers. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer. Many polymers, copolymers, blends, and composites of polymers are radiolucent and do not appear during x-ray or other types of imaging. Implants comprising such materials can provide a physician with a less obstructed view of the spine under imaging, than with an implant comprising radiopaque materials entirely. However, the implant need not comprise any radiolucent materials.

One group of biocompatible polymers are the polyaryl ester ketones which has several members including polyetheretherketone (PEEK), and polyetherketoneketone (PEKK). PEEK is proven as a durable material for implants, and meets the criterion of biocompatibility. Medical grade PEEK is available from Victrex Corporation of Lancashire, Great Britain under the product name PEEK-OPTIMA. Medical grade PEKK is available from Oxford Performance Materials under the name OXPEKK, and also from CoorsTek under the name BioPEKK. These medical grade materials are also available as reinforced polymer resins, such reinforced resins displaying even greater material strength. In an embodiment, the implant can be fabricated from PEEK 450G, which is an unfilled PEEK approved for medical implantation available from Victrex. Other sources of this material include Gharda located in Panoli, India. PEEK 450G has the following approximate properties: TABLE-US-00001 Property Value Density 1.3 g/cc Rockwell M 99 Rockwell R 126 Tensile Strength 97 MPa Modulus of Elasticity 3.5 GPa Flexural Modulus 4.1 GPa PEEK 450G has appropriate physical and mechanical properties and is suitable for carrying and spreading a physical load between the adjacent spinous processes. The implant and/or portions thereof can be formed by extrusion, injection, compression molding and/or machining techniques.

It should be noted that the material selected can also be filled. Fillers can be added to a polymer, copolymer, polymer blend, or polymer composite to reinforce a polymeric material. Fillers are added to modify properties such as mechanical, optical, and thermal properties. For example, carbon fibers can be added to reinforce polymers mechanically to enhance strength for certain uses, such as for load bearing devices. In some embodiments, other grades of PEEK are available and contemplated for use in implants in accordance with the present invention, such as 30% glass-filled or 30% carbon-filled grades, provided such materials are cleared for use in implantable devices by the FDA, or other regulatory body. Glass-filled PEEK reduces the expansion rate and increases the flexural modulus of PEEK relative to unfilled PEEK. The resulting product is known to be ideal for improved strength, stiffness, or stability. Carbon-filled PEEK is known to have enhanced compressive strength and stiffness, and a lower expansion rate relative to unfilled PEEK. Carbon-filled PEEK also offers wear resistance and load carrying capability.

As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. As mentioned, the implant can be comprised of polyetherketoneketone (PEKK). Other material that can be used include polyetherketone (PEK), polyetherketoneetherketoneketone (PEKEKK), polyetheretherketoneketone (PEEK K), and generally a polyaryletheretherketone. Further, other polyketones can be used as well as other thermoplastics. Reference to appropriate polymers that can be used in the implant can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials." Other materials such as Bionate®., polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

As described above, the binder can be made from a biocompatible material. In an embodiment, the binder can be made from a braided polyester suture material. Braided polyester suture materials include, for example, Ethibond, Ethiflex, Mersilene, and Dacron, and are nonabsorbable, having high tensile strength, low tissue reactivity and improved handling. In other embodiments, the binder can be made from stainless steel (i.e., surgical steel), which can be braided into a tether or woven into a strap, for example. In still other embodiments, the binder can be made from some other material (or combination of materials) having similar properties.

Figure 170:
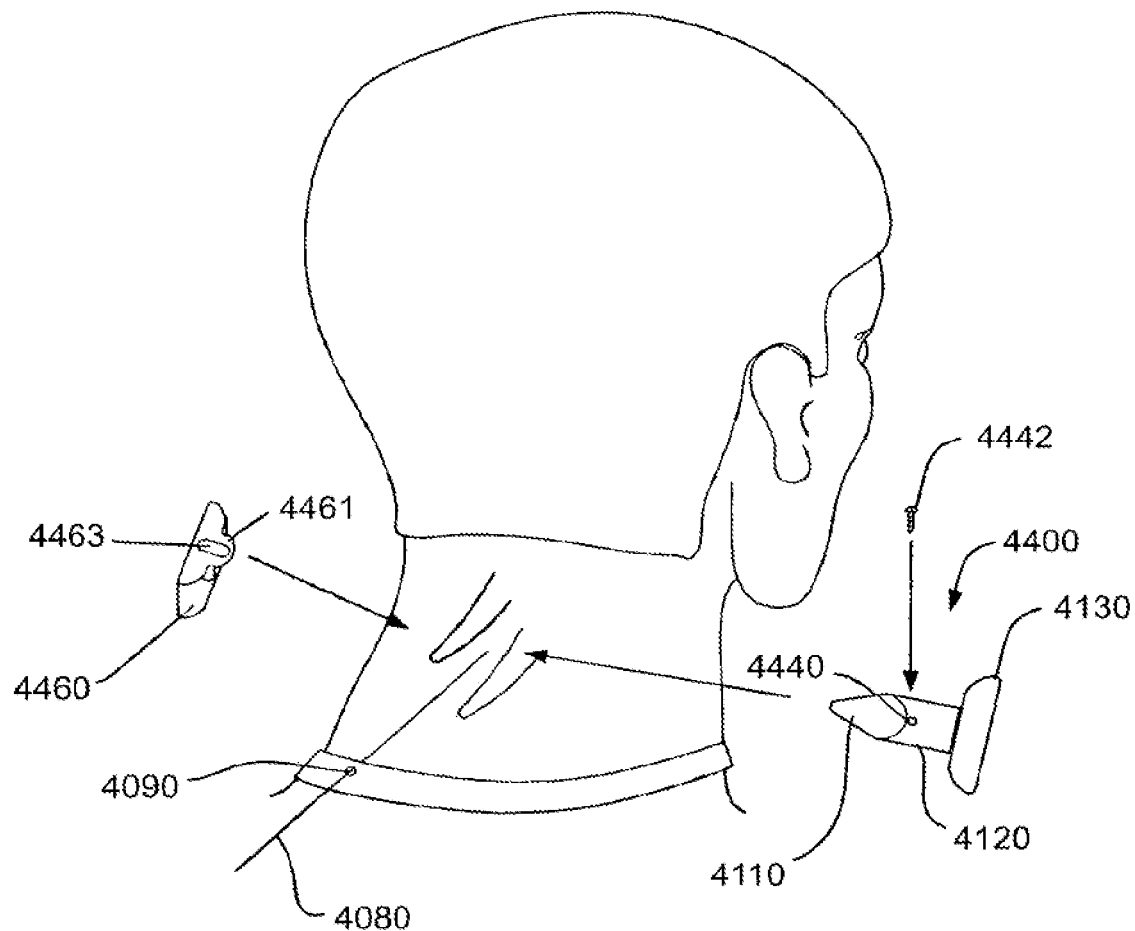
FIG. 170 illustrates an embodiment of a method for implanting an interspinous implant as shown in FIGS. 147-163 in accordance with the present invention.

It is to be understood that embodiments in accordance with the present invention can be constructed without a pliant material. It is also to be understood that the embodiments in accordance with the present invention can have other dimensions Methods for Implanting Interspinous Implants A minimally invasive surgical method for implanting an implant 4400 in the cervical spine is disclosed and taught herein. In this method, as shown in FIG. 170, preferably a guide wire 4080 is inserted through a placement network or guide 90 into the neck of the implant recipient. The guide wire 4080 is used to locate where the implant is to be placed relative to the cervical spine, including the spinous processes. Once the guide wire 4080 is positioned with the aid of imaging techniques, an incision is made on the side of the neck so that an implant in accordance with an embodiment of the present invention, can be positioned in the neck thorough an incision and along a line that is about perpendicular to the guide wire 4080 and directed at the end of the guide wire 4080. In one embodiment, the implant can be a sized implant 4400 (i.e., having a body that is not distractible), such as described above in FIGS. 147-163 and including a distraction guide 4110, a spacer 4120, and a first wing 4130. The implant 4400 is inserted into the neck of the patient. Preferably during insertion, the distraction guide 4110 pierces or separates the tissue without severing the tissue.

Once the implant 4400 is satisfactorily positioned, a second wing 4460 can be optionally inserted along a line that is generally co-linear with the line over which the implant 4400 is inserted but from the opposite side of the neck. The anatomy of the neck is such that it is most convenient and minimally invasive to enter the neck from the side with respect to the implant 4400 and the second wing 4460. The second wing 4460 is mated to the implant and in this particular embodiment, the second wing 4460 is attached to the implant 4400 by the use of a fastener, for example by a screw 4442. Where a screw is used, the screw 4442 can be positioned using a screw driving mechanism that is directed along a posterior to anterior line somewhat parallel to the guide wire 4080. This posterior to anterior line aids the physician in viewing and securing the second wing 4460 to the implant. The second wing 4460 is positioned so that a bore 4463 formed in a lip 4461 of the second wing 4460 is aligned with a bore 4440 of the implant 4400, as described above. The screw 4442 is positioned within both bores and secured, at least, to the bore 4440 of the implant 4400. In other embodiments, the second wing can be interference fit with the implant, as described above, or fastened using some other mechanism, such as a flexible hinge and protrusion.

Figure 171:
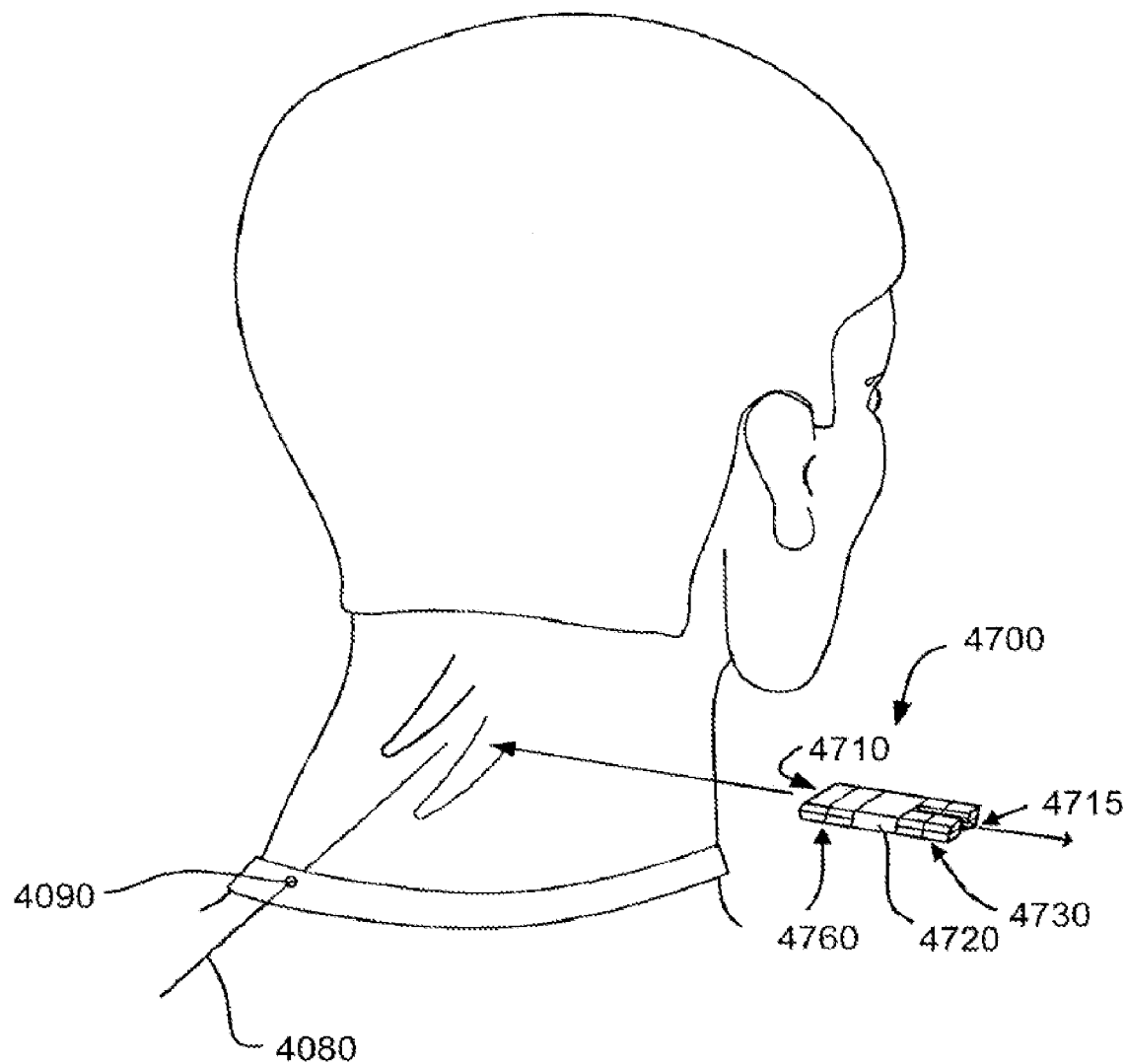
FIG. 171 illustrates an embodiment of a method for implanting an interspinous implant as shown in FIGS. 164A-167 having deployable first and second wings in accordance with the present invention.

A minimally invasive surgical method for implanting an alternative embodiment of an implant 4700 in the cervical spine is disclosed and taught herein. In this method, as shown in FIG. 171, preferably a guide wire 4080 is inserted through a placement network or guide 4090 into the neck of the implant recipient. The guide wire 4080 is used to locate where the implant 4700 is to be placed relative to the cervical spine, including the spinous processes. Once the guide wire 4080 is positioned with the aid of imaging techniques, an incision is made on the side of the neck so that an implant 4700 in accordance with an embodiment of the present invention, can be positioned in the neck thorough an incision and along a line that is about perpendicular to the guide wire 4080 and directed at the end of the guide wire 4080. In an embodiment, the implant 4700 can include a distraction guide 4710, a spacer 4720, a rod 4715 extending through the spacer 4720, and deployable first and second wings 4730, 4760. The implant 4700 can have a substantially flat profile to ease implantation, as described above. The implant 4700 is inserted into the neck of the patient. Preferably during insertion, the distraction guide 4710 pierces or separates the tissue without severing the tissue.

Once the implant 4700 is satisfactorily positioned, the first wing 4730 and the second wing 4760 can be deployed. As described above, the second wing 4760 can be deployed by urging the rod 4715 in a direction opposite the direction of insertion along the longitudinal axis 4725. As the rod 4715 travels through the spacer 4720, hinged structures 4750-4753 contact the spacer 4720, buckle and extend away from the rod 4715 two form an upper end 4762 of the second wing and a lower end 4764 of the second wing. When second wing 4760 is satisfactorily deployed, the rod 4715 can be fixed in place relative to the spacer 4720 using a first stop 4782, a pin, or some other mechanism. The first wing 4730 can be deployed by urging the hinged structures 4754-4757 toward the spacer 4720, causing the hinged structures 4754-4757 to buckle and extend away from one another to form an upper end 4732 of the second wing and a lower end 4734 of the second wing. The anatomy of the neck is such that it is most convenient and minimally invasive to enter the neck from the side with respect to the implant 4700.

Figure 172:
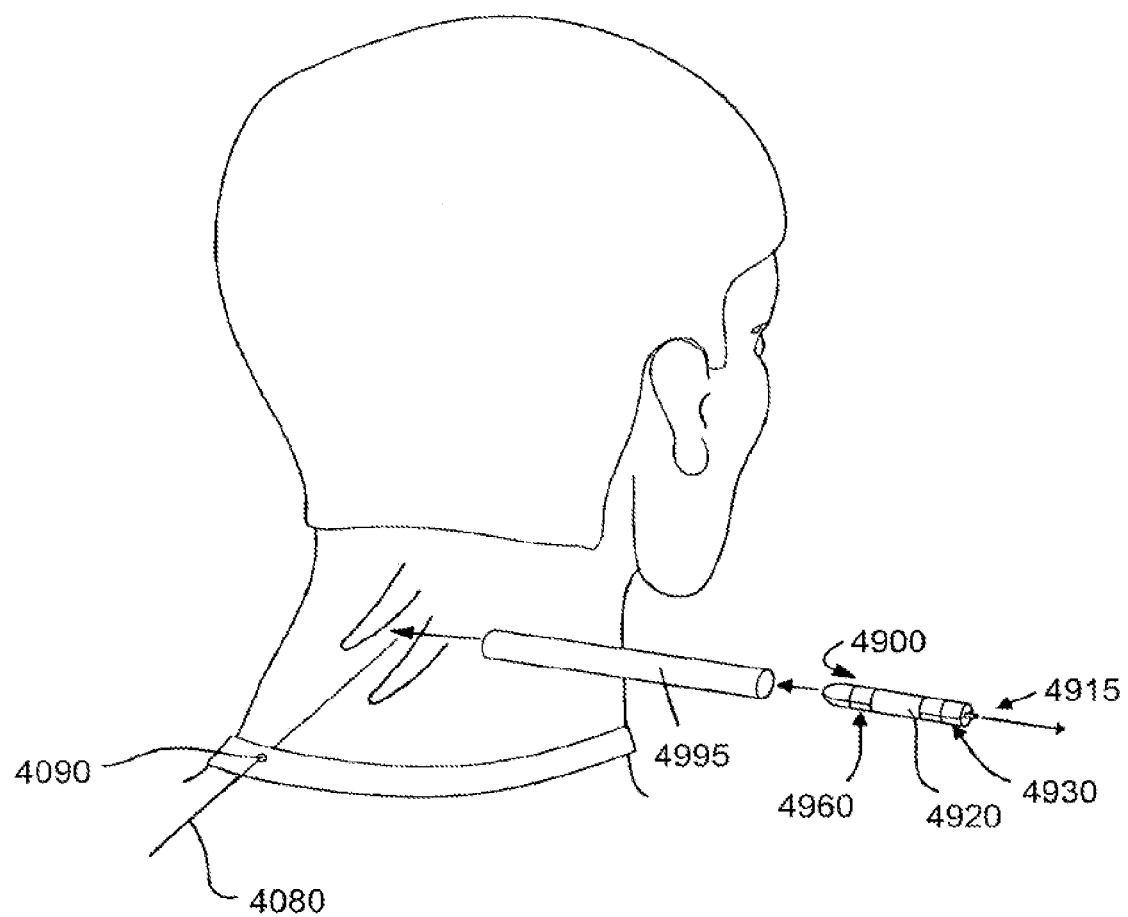
FIG. 172 illustrates an alternative embodiment of a method for implanting an interspinous implant as shown in FIGS. 168A-169B having deployable first and second wings by way of a cannula inserted between adjacent spinous processes in accordance with the present invention.

A minimally invasive surgical method for implanting an alternative embodiment of an implant 4900 in the cervical spine is disclosed and taught herein. In this method, as shown in FIG. 172, preferably a guide wire 4080 is inserted through a placement network or guide 4090 into the neck of the implant recipient. The guide wire 4080 is used to locate where the implant 4900 is to be placed relative to the cervical spine, including the spinous processes. Once the guide wire 4080 is positioned with the aid of imaging techniques, an incision is made on the side of the neck along a line that is about perpendicular to the guide wire 4080 and directed at the end of the guide wire 4080. The cannula 4995 is fed through the incision and positioned between the targeted adjacent spinous processes. In an embodiment, the implant 4900 can include a distraction guide 4910, a spacer 4920, a rod 4915 extending through the spacer 4920, and deployable first and second wings 4930, 4960. The implant 4900 can have a substantially circular cross-section to roughly conform with an inside surface of the cannula 4995. The implant 4900 is urged through the cannula 4995 and into position between the adjacent spinous processes so that the second wing 4960 hinge structures are clear of the cannula 4995, as described above in reference to FIG. 169B. The second wing 4960 is then deployed by urging the rod 4915 in a direction opposite the direction of insertion along the longitudinal axis 4925. As the rod 4915 travels through the spacer 4920, hinged structures 4950-4953 contact the spacer 4920, buckle and extend away from the rod 4915 two form an upper end 4962 of the second wing and a lower end 4964 of the second wing. When second wing 4960 is satisfactorily deployed, the cannula 4995 can be retracted to expose the hinged structures 4954-4957 of the first wing 4930. The first wing 4930 can be deployed by urging the hinged structures 4954-4957 toward the spacer 4920, causing the hinged structures 4954-4957 to buckle and extend away from one another to form an upper end 4932 of the second wing and a lower end 4934 of the second wing. Once the first wing 4930 is deployed, the rod 4915 can optionally be shortened, and the cannula 4995 can be withdrawn from the incision. The incision can then be closed.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims and their equivalence.

Additional aspects, objects and advantages of the invention can be obtained through a review of the appended claims and figures.

What is claimed is:

1. A method for stabilizing at least one spinal motion segment comprising a superior vertebra and an inferior vertebra, the method comprising:

inserting an expandable spacer in a collapsed state into the interspinous space between the superior and inferior vertebrae such that the spacer extends through the sagittal plane defined by the spinous processes of the superior and inferior vertebrae; the spacer having a flexible membrane defining an interior cavity;

with the spacer disposed in the interspinous space, expanding the spacer to an expanded state by forcing a fill material in a fluid state into the cavity;

thereafter, solidifying the fill material to a solid state in the cavity.

2. The method of claim 1 wherein the forcing the fill material in the fluid state into the cavity causes the first and second vertebrae to be distracted.

3. The method of claim 1 wherein the spacer presses against the superior and inferior vertebrae in the expanded state.

4. The method of claim 1 wherein the steps of inserting and expanding are performed through a percutaneous penetration in the patient's skin.

* * * * *